US010301254B2

(12) United States Patent
Wuest et al.

(10) Patent No.: US 10,301,254 B2
(45) Date of Patent: May 28, 2019

(54) SUBSTITUTED POLYCATIONIC MULTI-QUATERNARY AMMONIUM SALTS AS ANTIMICROBIAL AGENTS

(71) Applicants: Temple University—Of The Commonwealth System of Higher Education, Philadelphia, PA (US); Villanova University, Villanova, PA (US)

(72) Inventors: William M. Wuest, Wallingford, PA (US); Kevin P. C. Minbiole, Media, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 15/568,555

(22) PCT Filed: Apr. 22, 2016

(86) PCT No.: PCT/US2016/028781
§ 371 (c)(1),
(2) Date: Oct. 23, 2017

(87) PCT Pub. No.: WO2016/172436
PCT Pub. Date: Oct. 27, 2016

(65) Prior Publication Data
US 2018/0111893 A1    Apr. 26, 2018

Related U.S. Application Data

(60) Provisional application No. 62/151,806, filed on Apr. 23, 2015, provisional application No. 62/151,811, (Continued)

(51) Int. Cl.
| | | |
|---|---|---|
| C07D 295/02 | (2006.01) |
| C07C 211/63 | (2006.01) |
| A61K 31/13 | (2006.01) |
| A61K 31/16 | (2006.01) |
| A61K 45/06 | (2006.01) |
| C08G 73/00 | (2006.01) |
| C07D 401/04 | (2006.01) |
| C07D 453/02 | (2006.01) |
| C07D 255/02 | (2006.01) |
| C07D 257/02 | (2006.01) |
| C07D 295/037 | (2006.01) |
| C07D 213/36 | (2006.01) |
| A01N 33/12 | (2006.01) |
| A01N 43/40 | (2006.01) |
| A01N 43/60 | (2006.01) |
| A01N 43/64 | (2006.01) |
| A01N 43/90 | (2006.01) |
| C07C 211/64 | (2006.01) |

C07D 295/13    (2006.01)
C08F 8/32    (2006.01)
(Continued)

(52) U.S. Cl.
CPC ............. *C07C 211/63* (2013.01); *A01N 33/12* (2013.01); *A01N 43/40* (2013.01); *A01N 43/60* (2013.01); *A01N 43/64* (2013.01); *A01N 43/90* (2013.01); *A61K 31/13* (2013.01); *A61K 31/16* (2013.01); *A61K 45/06* (2013.01); *C07C 211/64* (2013.01); *C07D 213/36* (2013.01); *C07D 255/02* (2013.01); *C07D 257/02* (2013.01); *C07D 295/037* (2013.01); *C07D 295/13* (2013.01); *C07D 401/04* (2013.01); *C07D 453/02* (2013.01); *C08F 8/32* (2013.01); *C08F 112/14* (2013.01); *C08F 120/34* (2013.01); *C08G 73/00* (2013.01); *C09D 5/14* (2013.01)

(58) Field of Classification Search
CPC ................................................... C07D 295/02
USPC ....................................................... 544/404
See application file for complete search history.

(56) References Cited

U.S. PATENT DOCUMENTS 3,875,174 A    4/1975  Edwards
5,744,453 A    4/1998  Mintz et al.
(Continued)

FOREIGN PATENT DOCUMENTS

WO    9937635    7/1999
WO    2016007821    1/2016

OTHER PUBLICATIONS

Eckenhoff, et al. Dalton Transactions, 40(18), 2011, 4909-4917.*
(Continued)

*Primary Examiner* — Douglas M Willis
(74) *Attorney, Agent, or Firm* — Riverside Law LLP

(57) ABSTRACT

The present invention includes polycationic amphiphilic compounds of formula VII useful as antimicrobial agents.

formula VII $$R^1_{\phantom{1}}\!\!\!\overset{\oplus}{\underset{R^2}{N}}\!\!\!-\!\!\!\overset{R^6}{\underset{\phantom{N}}{\bigcirc}}\!\!\!\overset{\oplus}{N}\!\!\!-\!X^1\!-\!\overset{R^3}{\underset{R^5}{\overset{\oplus}{N}}}\!\!\!-\!R^4 \cdot 3Z^-$$

The present invention further includes novel polymers of polycationic amphiphilic compounds useful as antimicrobial agents. The present invention further includes methods useful for removing microorganisms and/or biofilm-embedded microorganisms from a surface. The present invention further includes compositions and methods useful for preventing or reducing the growth or proliferation of microorganisms and/or biofilm-embedded microorganisms on a surface.

9 Claims, 69 Drawing Sheets

Related U.S. Application Data filed on Apr. 23, 2015, provisional application No. 62/302,520, filed on Mar. 2, 2016, provisional application No. 62/302,530, filed on Mar. 2, 2016.

(51) Int. Cl.
  *C08F 112/14* (2006.01)
  *C08F 120/34* (2006.01)
  *C09D 5/14* (2006.01)

(56) References Cited

U.S. PATENT DOCUMENTS

| | | | |
|---|---|---|---|
| 6,251,381 | B1 | 6/2001 | Kourai et al. |
| 7,410,981 | B2 | 8/2008 | Kamiyama et al. |
| 8,865,909 | B2 | 10/2014 | Srebnik et al. |
| 2013/0224258 | A1 | 8/2013 | Baker |
| 2014/0148487 | A1 | 5/2014 | Minbiole et al. |
| 2016/0262384 | A1 | 9/2016 | Wuest et al. |
| 2016/0278375 | A1 | 9/2016 | Wuest et al. |

OTHER PUBLICATIONS

Weldes in Industrial & Engineering Chemistry Product Research and Development, 9(2), 1970, 243-248.*

Paniak et al., "The antimicrobial activity of mono-, bis-, tris-, and tetracationic amphiphiles derived from simple polyamine platforms". 2014, Bioorganic & Medicinal Chemistry Letters, 24:5824-5828.

Jennings et al., "Biofilm-Eradicating Properties of Quaternary Ammonium Amphiphiles: Simple Mimics of Antimicrobial Peptides". 2014, ChemBioChem, 15:2211-2215.

Barbero et al., "Synthesis, Physicochemical Characterization, and Interaction with DNA of Long-Alkyl-Chain Gemini Pyridinium Surfactants". 2015, ChemPlusChem, 80:952-962.

Goswami et al., "Biocompatible Nanocarrier Fortified with a Dipyridinium-Based Amphiphile for Eradication of Biofilm". 2014, ACS Appl. Mater. Interlaces, 6:16384-16394.

Wimley, "Describing the mechanism of antimicrobial peptide action with the interfacial activity model". 2010, ACS Chem. Biol., 5:905-917.

Hugo, "The Mode of Action of Antibacterial Agents". 1967, J. Appl. Bacteriol., 30:17-50.

Bragg et al. "Bacterial Resistance to Quaternary Ammonium Compounds (QAC) Disinfectants". 2014, Infectious Diseases and Nanomedicine II, Springer India pp. 1-13.

Jennings et al., "Bioorganic Investigation of Multicationic Antimicrobials to Combat QAC-Resistant *Staphylococcus aureus*". 2015, ACS Inf. Dis., 1:304-309.

Poole, "Efflux-mediated antimicrobial resistance". 2005, J. Antimicrob. Chemother., 56:20-51.

Holdsworth et al., "The major facilitator superfamily transporter MdtM contributes to the intrinsic resistance of *Escherichia coli* to quaternary ammonium compounds". 2013, J. Antimicrob. Chemother., 68:831-839.

Buffet-Bataillon et al., "Emergence of resistance to antibacterial agents: the role of quaternary ammonium compounds—a critical review". 2012, Int. J. Antimicrob. Agents, 39:381-389.

Raggi et al., "Methicillin resistance, biofilm formation and resistance to benzalkonium chloride in *Staphylococcus aureus* clinical isolates". 2013, Clin. Microbiol., 2:1000121.

Sidhu et al., "Frequency of Disinfectant Resistance Genes and Genetic Linkage with β-Lactamase Transposon Tn552 among Clinical Staphylococci". 2002, Antimicrob. Agents Chemother., 46:2797-2803.

Martin et al., "Alkaloids from the Chinese Vine *Gnetum montanum*". 2011, J. Nat. Prod., 74:2425-2430.

Čerňáková et al., "Antimicrobial activity of berberine—a constituent of Mahonia aquifolium". 2002, Folia Microbiol., 47:375-378.

Panarin et al., "Synthesis and antimicrobial properties of polymers containing quaternary ammonium groups". 1971, Khim.-Farm. Zh., 5:24-28 (English translation attached).

Tashiro, "Antibacterial and bacterium adsorbing macromolecules". 2001, Macromol. Mater. Eng., 286:63-87.

Tew et al., "De novo design of antimicrobial polymers, foldamers, and small molecules: from discovery to practical applications". 2010, Acc. Chem. Res., 43:30-39.

Kenawy et al., "The chemistry and applications of antimicrobial polymers: a state-of-the-art review". 2007, Biomacromolecules, 8:1359-1384.

Mintzer et al., "Exploiting dendrimer multivalency to combat emerging and re-emerging infectious diseases". 2012, Mol. Pharmaceutics, 9:342-354.

Liu et al., "Nylon-3 Polymers Active against Drug-Resistant Candida albicans Biofilms". 2015, J. Am. Chem. Soc. 137:2183-2186.

Kenawy et al., "Biologically active polymers. V. Synthesis and antimicrobial activity of modified poly(glycidyl methacrylate-co-2-hydroxyethyl methacrylate) derivatives with quaternary ammonium and phosphonium salts". 2002, J. Polym. Sci. Part A Polym. Chem., 40:2384-2393.

Dizman et al., "Synthesis and antimicrobial activities of new water-soluble bis-quaternary ammonium methacrylate polymers". 2004, J. Appl. Polym. Sci., 94:635-642.

Ayfer et al., "Synthesis and antibacterial activities of new quaternary ammonium monomers". 2005, Des. Monomers Polym., 8:437-451.

Ladow et al., "Bicephalic amphiphile architecture affects antibacterial activity". 2011, Eur. J. Med. Chem., 46:4219.

Black et al., "TMEDA-derived biscationic amphiphiles: An economical preparation of potent antibacterial agents". 2014, Bioorg. Med. Chem. Lett., 24:99-102.

Ator et al., "Beyond paraquats: Dialkyl 3, 3'-and 3, 4'-bipyridinium amphiphiles as antibacterial agents". 2014, Bioorg. Med. Chem. Lett. 24:3706-3709.

Grenier et al., "The antibacterial activity of 4, 4'-bipyridinium amphiphiles with conventional, bicephalic and gemini architectures". 2012, Bioorg. Med. Chem. Lett., 22:4055-4058.

Mitchell et al., "QacA Multidrug Efflux Pump from*Staphylococcus aureus*: Comparative Analysis of Resistance to Diamidines, Biguanidines, and Guanylhydrazones". 1998, Antimicrob. Agents Chemother., 42:475-477.

Paniak et al., "The antimicrobial activity of mono-, bis-, tris-, and tetracationic amphiphiles derived from simple polyamine platforms". 2014, Bioorg. Med. Chem. Lett., 24:5824-5828.

Jennings et al., "Quaternary ammonium compounds: an antimicrobial mainstay and platform for innovation to address bacterial resistance". 2015, ACS Inf. Dis., 1:288-303.

Ignatova et al., "Synthesis of copolymer brushes endowed with adhesion to stainless steel surfaces and antibacterial properties by controlled nitroxide-mediated radical polymerization.". 2004, Langmuir, 20:10718-10726.

McCormic et al., "Aqueous RAFT polymerization: recent developments in synthesis of functional water-soluble (co) polymers with controlled structures". 2004, Acc. Chem. Res., 37:312-325.

Lee et al., "Permanent, nonleaching antibacterial surfaces. 1. Synthesis by atom transfer radical polymerization". 2004, Biomacromolecules, 5:877-882.

Ravikumar et al., "Surface-active antifungal polyquaternary amine". 2006, Biomacromolecules, 7:2762-2769.

Zhang et al., "Synthesis and antibacterial characterization of gemini surfactant monomers and copolymers". 2012, Polym. Chem., 3:907-913.

Palermo et al., "Chemical structure of cationic groups in amphiphilic polymethacrylates modulates the antimicrobial and hemolytic activities". 2009, Biomacromolecules, 10:1416-1428.

Alvaerz-Paino et al., "Effect of glycounits on the antimicrobial properties and toxicity behavior of polymers based on quaternized DMAEMA". 2015, Biomacromolecules,16:295-303.

Ganewatta et al., "Bio-inspired resin acid-derived materials as anti-bacterial resistance agents with unexpected activities". 2014, Chem. Sci., 5:2011-2016.

(56) References Cited

OTHER PUBLICATIONS

Dizman et al., "Synthesis and characterization of antibacterial and temperature responsive methacrylamide polymers". 2006, Macromolecules, 39:5738-5746.

Ng et al., "Antimicrobial polycarbonates: Investigating the impact of nitrogen-containing heterocycles as quaternizing agents". 2014, Macromolecules, 47:1285-1291.

Lv et al., "Synthesis and evaluation of amphiphilic cationic quinine-derived for antibacterial activity against methicillin-resistant *Staphylococcus aureus*". 2007, Bioorg. Med. Chem. Lett., 17:4102-4106.

Bottcher et al., "Synthesis and activity of biomimetic biofilm disruptors". 2013, J. Am. Chem. Soc., 135:2927-2930.

\* cited by examiner

|  | MIC (µM) | | | | | |
|---|---|---|---|---|---|---|
| Compound | SA | CA-MRSA | HA-MRSA | EF | EC | PA |
| TET-10,0,0 | N.T. | N.T. | N.T. | N.T. | N.T. | N.T. |
| TET-10,1,1 | 2 | 32 | 8 | 8 | 8 | 125 |
| TET-11,0,0 | 4 | 32 | 2 | 2 | 63 | 125 |
| TET-11,1,1 | 1 | 4 | 2 | 4 | 4 | 63 |
| TET-12,0,0 | 2 | 125 | 1 | 1 | 125 | 125 |
| TET-12,1,1 | 1 | 4 | 2 | 2 | 4 | 16 |
| TET-14,0,0 | 1 | 125 | 1 | 2 | 63 | 250 |
| TET-14,1,1 | 0.5 | 2 | 1 | 1 | 4 | 16 |
| TET-16,0,0 | 2 | 250 | 4 | 4 | 63 | 500 |
| TET-16,1,1 | 1 | 0.5 | 1 | 1 | 1 | 8 |
| TET-18,0,0 | 8 | 125 | 8 | 16 | 63 | 500 |
| TET-18,1,1 | 1 | 0.5 | 0.5 | 1 | 1 | 8 |
| TET-20,0,0 | N.T. | N.T. | N.T. | N.T. | N.T. | N.T. |
| TET-20,1,1 | 1 | 2 | 1 | 1 | 4 | 16 |
| LCV-1,1,1 | >500 | >500 | >500 | >500 | >500 | >500 |
| LCV-10,0,0 | 1 | 16 | 1 | 1 | 8 | 32 |
| LCV-10,1,1 | 4 | 125 | 16 | 32 | 16 | 125 |
| LCV-11,0,0 | 0.5 | 16 | 0.5 | 0.5 | 16 | 32 |
| LCV-11,1,1 | 4 | 125 | 16 | 32 | 16 | 125 |
| LCV-12,0,0 | 0.25 | 16 | 0.5 | 0.5 | 8 | 32 |
| LCV-12,1,1 | 4 | 125 | 16 | 32 | 16 | 125 |
| LCV-14,0,0 | 2 | 32 | 2 | 2 | 63 | 125 |
| LCV-14,1,1 | 4 | 1 | 2 | 4 | 4 | 32 |
| LCV-16,0,0 | 4 | 125 | 2 | 2 | 63 | 250 |
| LCV-16,1,1 | 1 | 1 | 2 | 2 | 1 | 16 |
| LCV-18,0,0 | 16 | 250 | 8 | 8 | 500 | 500 |
| LCV-18,1,1 | 1 | 0.5 | 0.5 | 1 | 0.5 | 4 |
| TET-1,1,0 | 4 | 125 | 32 | 32 | 250 | >500 |
| TET-1,1,1 | 500 | >500 | >500 | 250 | >500 | >500 |

FIGURE 66

| Compound | MIC (μM) | | | | | |
|---|---|---|---|---|---|---|
| | SA | CA-MRSA | HA-MRSA | EF | EC | PA |
| LMG-1,1 | >500 | >500 | >500 | >500 | >500 | >500 |
| LMG-10,0 | 1 | 8 | 0.5 | 0.5 | 4 | 8 |
| LMG-10,1 | 2 | 63 | 8 | 8 | 8 | 63 |
| LMG-10,10 | 0.5 | 1 | ≤0.25 | 0.25 | 1 | 2 |
| LMG-11,0 | ≤0.25 | 4 | ≤0.25 | ≤0.25 | 4 | 8 |
| LMG-11,1 | 1 | 32 | 4 | 4 | 2 | 32 |
| LMG-11,11 | 0.5 | 1 | 0.5 | 0.5 | 1 | 2 |
| LMG-12,0 | 2 | 32 | 0.5 | ≤0.25 | 32 | 32 |
| LMG-12,1 | 0.5 | 16 | 1 | 1 | 1 | 16 |
| LMG-12,12 | 1 | 1 | 0.5 | 0.5 | 2 | 1 |
| LMG-14,0 | 2 | 32 | 4 | 2 | 32 | 63 |
| LMG-14,1 | 0.5 | 2 | 0.5 | 0.5 | 1 | 8 |
| LMG-14,14 | 2 | 8 | 1 | 2 | 8 | 63 |
| LMG-16,0 | 4 | 32 | 4 | 4 | 32 | 125 |
| LMG-16,1 | 0.5 | 1 | ≤0.25 | 0.5 | 1 | 2 |
| LMG-16,16 | 1 | 4 | 1 | 2 | 4 | 16 |
| LMG-18,0 | 8 | 32 | 16 | 8 | 32 | 250 |
| LMG-18,1 | 0.5 | 2 | 0.5 | 0.5 | 2 | 8 |
| LMG-18,18 | 8 | 32 | 4 | 8 | 16 | 250 |
| LMGS-10,0 | 8 | 125 | 2 | 2 | 125 | 500 |
| LMGS-11,0 | 8 | 125 | 2 | 8 | 63 | 500 |
| LMGS-12,0 | 16 | 125 | 16 | 16 | 63 | 500 |
| LMGS-14,0 | 125 | 125 | 32 | 32 | 125 | 500 |
| LMGS-16,0 | 8 | 125 | 32 | 32 | 63 | 500 |
| LMGS-18,0 | 63 | 125 | 250 | 250 | 250 | 500 |

FIGURE 66 (Continued)

|  |  | MIC, micromolar | | | | | |
|---|---|---|---|---|---|---|---|
| Compound | Yield | S. aureus | MRSA 1 | MRSA 2 | E. faecalis | E. coli | P. aeruginosa |
| (-)-Quinine | N/A | >500 | >500 | >500 | >500 | >500 | 500 |
| Q-10,0 | 93% | 4 | 16 | 8 | 8 | 16 | 250 |
| Q-11,0 | 98% | 2 | 16 | 4 | 4 | 16 | 63 |
| Q-12,0 | 91% | 1 | 4 | 2 | 2 | 8 | 32 |
| Q-14,0 | 91% | 0.5 | 2 | 4 | 1 | 8 | 8 |
| Q-16,0 | 100% | 1 | 8 | 1 | 2 | 8 | 16 |
| Q-18,0 | 100% | 2 | 63 | 2 | 4 | 63 | 125 |
| Q-1,1 | 77% | >500 | >500 | >500 | >500 | >500 | >500 |
| Q-10,1 | 96% | 8 | 16 | 16 | 8 | 16 | 125 |
| Q-11,1 | 100% | 4 | 32 | 16 | 8 | 16 | 125 |
| Q-12,1 | 97% | 2 | 63 | 16 | 16 | 16 | 125 |
| Q-14,1 | 76% | 0.5 | 8 | 2 | 2 | 2 | 16 |
| Q-16,1 | 97% | 1 | 1 | 2 | 1 | 2 | 8 |
| Q-18,1 | 100% | 1 | 1 | 1 | 2 | 2 | 8 |
| (-)-Nicotine | N/A | >500 | >500 | >500 | >500 | >500 | 500 |
| N-10,0 | 98% | 32 | 63 | 32 | 32 | 63 | 250 |
| N 11,0 | 99% | 8 | 32 | 8 | 8 | 16 | 63 |
| N 12,0 | 99% | 4 | 32 | 8 | 8 | 16 | 63 |
| N 14,0 | 99% | 1 | 16 | 4 | 1 | 8 | 125 |
| N 16,0 | 99% | 1 | 4 | 2 | 1 | 4 | 63 |
| N-18,0 | 77% | 1 | 8 | 1 | 1 | 8 | 63 |
| N-20,0 | 99% | 2 | 63 | 4 | 2 | 32 | 63 |
| N-1,1 | 90% | >500 | >500 | >500 | >500 | >500 | >500 |
| N-10,1 | 83% | 16 | 250 | 32 | 32 | 125 | 250 |
| N-11,1 | 97% | 32 | 32 | 16 | 16 | 32 | 125 |
| N-12,1 | 99% | 8 | 32 | 32 | 16 | 32 | 125 |
| N-14,1 | 87% | 4 | 32 | 16 | 16 | 16 | 250 |
| N-16,1 | 76% | 1 | 4 | 8 | 4 | 4 | 63 |
| N-18,1 | 97% | 1 | 4 | 2 | 2 | 4 | 32 |
| N-20,1 | 100% | 0.5 | 16 | 1 | 1 | 16 | 32 |
| BAC | N/A | 8 | 32 | 8 | 8 | 32 | 63 |

FIGURE 67

| Compound | SA | CA-MRSA | HA-MRSA | EF | EC | PA |
|---|---|---|---|---|---|---|
| Benzalkonium Chloride | 8 | 8 | 32 | 8 | 32 | 63 |
| sT-8,8,0 | 4 | 2 | 32 | 32 | 32 | 125 |
| sT-10,10,0 | 0.5 | 0.5 | 0.5 | 0.5 | 1 | 2 |
| sT-11,11,0 | 0.5 | 0.5 | 0.5 | 0.5 | 0.5 | 1 |
| sT-12,12,0 | 0.5 | 0.5 | 1 | 1 | 1 | 4 |
| sT-13,13,0 | 1 | 0.5 | 1 | 1 | 1 | 8 |
| sT-14,14,0 | 1 | 0.5 | 2 | 2 | 4 | 16 |
| sT-16,16,0 | 8 | 4 | 16 | 16 | 16 | 32 |
| sT-18,18,0 | 8 | 4 | 32 | 16 | 32 | 63 |
| sT-8,8,1 | 0.5 | 1 | 16 | 16 | 4 | 250 |
| sT-10,10,1 | 0.5 | 0.5 | 0.5 | 0.5 | 0.5 | 2 |
| sT-11,11,1 | 0.5 | ≤0.25 | 0.5 | ≤0.25 | ≤0.25 | 1 |
| sT-12,12,1 | 1 | 0.5 | 2 | 1 | 1 | 4 |
| sT-13,13,1 | 2 | 0.5 | 1 | 1 | 1 | 4 |
| sT-14,14,1 | 4 | 2 | 2 | 2 | 4 | 32 |
| sT-8,8,3A | 1 | 1 | 8 | 16 | 4 | 125 |
| sT-10,10,3A | 0.5 | ≤0.25 | 0.5 | 0.5 | 0.5 | 1 |
| sT-11,11,3A | 0.5 | 0.5 | 1 | 1 | 0.5 | 1 |
| sT-12,12,3A | 1 | ≤0.25 | 0.5 | 1 | 0.5 | 2 |
| sT-13,13,3A | 2 | 1 | 1 | 1 | 1 | 4 |
| sT-14,14,3A | 2 | 2 | 2 | 2 | 4 | 32 |
| sT-16,16,3A | 4 | 4 | 16 | 8 | 16 | 63 |
| sT-18,18,3A | 2 | 2 | 16 | 32 | 32 | 125 |
| sT-11,11,Bn | 0.25 | ≤0.25 | ≤0.25 | 0.5 | 0.5 | 1 |
| sT-12,12,Bn | 1 | 0.5 | 0.5 | 0.5 | 0.5 | 2 |

FIGURE 68

SUBSTITUTED POLYCATIONIC MULTI-QUATERNARY AMMONIUM SALTS AS ANTIMICROBIAL AGENTS

CROSS-REFERENCE TO RELATED APPLICATIONS

The present application is the U.S. National Stage Application filed under 35 U.S.C. § 371 of International Patent Application No. PCT/US2016/028781, filed Apr. 22, 2016, which is entitled to priority under 35 U.S.C. § 119(e) from U.S. Provisional Application Ser. Nos. 62/151,806, filed on Apr. 23, 2015, 62/151,811, filed on Apr. 23, 2015, 62/302,520, filed on Mar. 2, 2016, and 62/302,530, filed on Mar. 2, 2016, all of which applications are incorporated by reference herein in their entireties.

BACKGROUND OF THE INVENTION

Bacterial infections cause a tremendous burden to human health. One would be hard-pressed to avoid news about disease outbreaks, multi-drug resistant (MDR) bacteria, and the lack of new drugs in development pipelines. While some consider there to be a modest resurgence in antibiotic development, transmission of pathogenic bacteria is still a cause for great concern. The CDC estimates that one in every 20 hospitalizations will result in an acquired infection (Bragg et al., 2014, Infect. Dis. Nanomed., 808:1-13).

Bacterial biofilms cause perhaps even greater risks to health. Biofilms are established communities of bacteria that form a protective matrix composed of extracellular materials to defend the population against environmental threats (Fletcher et al., 2014, Tetrahedron 70:6373-6383). Due in part to inhibition of diffusion through this physical barrier (Bridier et al., 2011, Biofouling 27:1017-1032), antibiotic and antiseptic treatments can be 100-1000 times less effective against established biofilms. This directly affects settings that rely on routine treatments with disinfectants to prevent the spread of bacteria (i.e., hospitals, food manufacturing plants, residential settings). Biofilms are associated with over 80% of microbial infections (NIH Program Announcement for Research on Microbial Biofilms: http://grants.nih.gov/grants/guide/pa-files/PA-03-047.html), including periodontitis, endocarditis, and chronic lung infections such as those in cystic fibrosis (Goswami et al., 2014, ACS Applied Materials & Interfaces 6:16384-16394). Furthermore, biofilms are often associated with indwelling medical devices such as catheters and joint replacements. This results in tremendous health ramifications; hospital-acquired infections are estimated to affect up to 2M patients per year and ultimately cause up to 100,000 deaths per year in the United States alone (Bragg et al., 2014, Infect Dis. Nanomed. 1-13).

One of the most routine methods to combat bacteria is the use of quaternary ammonium compounds (QAC) in antiseptics (Goswami et al., 2014, ACS Applied Materials & Interfaces 6:16384-16394). QACs, including those in Lysol and Microban® formulations, are ubiquitous and have been employed for decades, being used for pre-operative hand-cleaning as early as 1935 (Domagk, 1935, Dtsch. Med. Wiss. 61:829-832, Noguchi et al., 2005, J. Med. Microbiol. 557-565); today, approximately 500,000 tons of QACs are used annually (Tezel and Pavlostathis, 2011, Role of Quaternary Ammonium Compounds On Antimicrobial Resistance In The Environment. In Antimicrobial Resistance in the Environment, First Edition. John Wiley & Sons, Inc, p 349). Quaternary ammonium compounds work by targeting and disrupting the barrier function of bacterial membranes, which leads to death of the microbe (Wimley, 2010, ACS Chem Biol 905-917). QACs are initially attracted to the predominantly anionic bacterial surface due to coulombic interactions. Structurally, there is significant similarity amongst these compounds, although direct activity comparisons of the antimicrobials against panels of bacteria (and MRSA in particular) are not readily available. Common QACs generally have a single cation, and a long-chained alkyl group, which provides a non-polar "arm" with which the bacterial membrane is disrupted (Hugo, 1967, J. Appl. Bacteriol. 30:17). While these QAC structures are regarded as reasonably non-toxic, as many can be directly applied to human skin or even used in oral therapies, it is now recognized that all of these structures are likely to be susceptible to bacterial resistance, and little antibiofilm activity is reported for these compounds.

An alarming trend that has garnered surprisingly little public attention is the diminishing effectiveness of mono- and bis-cationic QACs over time due to bacterial resistance (Bragg et al., 2014, Infect Dis. Nanomed. 1-13). Multiple genes that code for QAC resistance (such as qacA, qacB, and qacC, as well as the norA promoter) have been identified over the past decade (Bragg et al., 2014, Infect Dis. Nanomed. 1-13); these genes encode efflux pumps that can expel QACs. Such qac genes are found on easily transferrable plasmids that typically contain several other putative gene products, including teichoic acid translocation permease and various surface proteins designed to aid the bacterial cell in evading QACs (Jensen et al., 2010, Plasmid 64:135-42).

Over the past thirty years the identification of bacterial isolates with QAC resistance genes has risen dramatically (Jennings et al., 2015, ACS Inf. Dis. 1:288-303) and, as a result, there have been efforts to better understand the mechanisms by which antiseptics can lose efficacy (Schumacher et al., 2001, Science 294:2158-2163; Jennings et al., 2015, ACS Inf. Dis. 1:304-309). Resistance to traditional disinfectants such as benzalkonium chloride (BAC) and didecyldimethylammonium chloride (DDAC) has been identified in both Gram-positive and Gram-negative bacteria (Costa et al., 2013, Open Micro. J. 7:59-71; Poole, 2004, Clin. Microbiol. Infect. 10:12-26) and has presumably arisen through overuse and prolonged sub-lethal exposure. These compounds can in fact activate numerous resistance mechanisms, including physiological changes to bacterial cell membranes, as well as the production of transporter proteins, which efflux antibacterial agents (Poole, 2005, J. Antimicrob. Chemo. 56:20-51). More specifically, the qacAB/R system is one of the primary methods by which Gram-positive bacteria, specifically S. aureus, minimizes exposure to QAC compounds. Although QACs are lytic to cell membranes, they are capable of entering the cell at sub-MIC concentrations by passive diffusion. The compounds can then either be exported by the basal level of QacA (a transmembrane efflux pump) that is present, or bind with QacR, a negative transcriptional regulator of qacA. Following the binding of QAC compounds to the recognition site, QacR disassociates, allowing for the transcription of the gene, qacA. This leads to the increased production of QacA and the rapid efflux of the antimicrobial compounds from the cell. Other efflux proteins in Gram-positive bacteria include NorA (Jennings et al., 2015, ACS Inf. Dis. 1:288-303; Marchi et al., 2015, Microbiol. Res. 170:184-194); an analogous system has also been observed in Gram-negative bacteria through the efflux pumps AcrAB-TolC in *E. coli* (EC) and MexAB-OprM in *P. aeruginosa* (PA) (Costa et al., 2013, Open Micro. J. 7:59-71; Poole, 2004, Clin. Microbiol.

Infect. 10:12-26; Holdsworth and Law, 2013, J. Antimicrob. Chemother. 68:831-839; Li et al., 1995, Antimicrob. Agents Chemother. 39:1948-1953).

It has been posited that efflux pumps are in fact multidrug transporters with alternate primary functions, having evolved to recognize and export a wide range of antibacterial and biocidal scaffolds (Schumacher et al., 2001, Science 294:2158-2163; Poole, 2005, J. Antimicrob. Chemo. 56:20-51). The evolutionary origins of some of these resistance mechanisms have been attributed to the recognition of natural product QACs such as berberine, sanguinarine, and chelerythrine produced by plants (Schumacher et al., 2001, Science 294:2158-2163; Jennings et al., 2015, ACS Inf. Dis. 1:304-309). This is evidenced by the crystal structure of berberine bound to QacR, which highlights the key electrostatic (acidic amino acid residues) and π-π (aromatic residues) interactions. Brennan et al. demonstrated that commercially available dyes—crystal violet and malachite green—fit neatly into the binding site for berberine; they noted, however, that this recognition motif was limited to mono- and biscationic QACs (Schumacher et al., 2001, Science 294:2158-2163).

Furthermore, QAC-resistance genes are often transferred with multidrug-resistance genes, further promoting the spread of these debilitating strains (Bragg et al., 2014, Infect Dis. Nanomed. 1-13; Noguchi et al., 2005, J. Med. Microbiol. 557-565; Buffet-Bataillon et al., 2012, Int J Antimicrob Agents 39:381-389; Zhang et al., 2011, J. Hosp. Infection 78:113-117; Muller et al., 2013, PLOS ONE 8:e76835; Raggi et al., 2013, Clinical Isolates. Clin Microbial 2:1000121). This can also be attributed to a plasmid containing multiple sets of resistance genes, shown to readily transfer in biofilms (Taitt et al., 2014, Antimicrob Agents Chemother. 58:767-781). And this association has been rising—the proportion of methicillin-resistant *S. aureus* (MRSA) strains bearing QAC resistance genes has increased sharply in a short period of time (Buffet-Bataillon et al., 2012, Int J Antimicrob Agents 39:381-389; Sidhu et al., 2002, Antimicrob. Agents Chemother. 46:2797). A review from the Sep. 12, 2014 issue of Science starkly announced: "The widespread use of biocides [which include quaternary ammonium compounds] coselects for antibiotic resistance genes and could promote the spread of multidrug resistance plasmids" (Laxminarayan, 2014, Science 345:1299-1301).

Amphiphiles—compounds with both polar and non-polar sections—represent one of the longest-serving and most effective classes of antimicrobial agents. Anionic amphiphiles have been protecting human health since the advent of soaps; exciting recent developments are represented by polyanionic dendritic structures (Meyers et al., 2008, J. Am. Chem. Soc. 130:14444-14445; Williams et al., 2007, J. Amtimicrob. Chemother. 59:451-458; Macri et al., 2009, Bioorg. Med. Chem. 17:3162-3168; Maisuria et al., 2011, Bioorg. Med. Chem. 19:2918-2926; Lu et al., 2013, Biomacromolecules 14:3589-3598). Cationic amphiphiles are likewise of great importance (Walker and Paulson, 2002, Quaternary Ammonium Compounds, Marcel Dekker, New York); while nearly every class of living organism employs cationic antimicrobial peptides in a host of defensive applications (Guani-Guerra et al., 2010, Clin. Immunol. 135:1-11), laboratory-derived quaternary ammonium compounds (QACs) have been used to defend human health for about a century (Jacobs, 1916, J. Exp. Med. 23:563-568; Jacobs, 1916, J. Exp. Med. 23:569-576; Jacobs, 1916, J. Exp. Med. 23:577-599; Domagk, 1935, Dtsch. Med. Wiss. 61:829-832).

QACs bearing long alkyl chains are classical examples of amphiphiles, displaying a variety of interesting physical properties, such as the capacity for micelle formation and gelation (Steichen, 2002, in Handbook of Applied Surface and Colloid Chemistry, ed. Holmberg, K. 310-347 John Wiley & Sons, Ltd., New York). QACs also enjoy extensive precedent and applications in bacterial cell membrane disruption, leading to their widespread use as antiseptics (Walker and Paulson, 2002, Quaternary Ammonium Compounds, Marcel Dekker, New York). Both synthetic QACs and peptide-based amphiphiles (notably, antimicrobial peptides or AMPs (Guani-Guerra et al., 2010, Clin. Immun. 135:1-11) are prevalent. However, aside from modified peptides, there are relatively few QACs in scaffolds of natural products.

Amongst the examples of natural products with permanent cationic charges based at nitrogen are a series of tetrahydroisoquinolinium structures isolated from the Chinese vine *Gnetum montanum*, including magnocurarine, cyclized derivatives thereof, and the latifolians (Rochfort et al., 2005, J. Nat. Prod. 68:1080-1082). Latifolian A demonstrated modest antimicrobial activity, with a MIC of 35 μm against *Pseudomonas aeruginosa* (Martin et al., 2011, J. Nat. Prod. 74:2425-2430). However, it only demonstrated 55% inhibition of methicillin-resistant *Staphylococcus aureus* (MRSA) at 350 μm while magnocuraine and its tetracyclic derivatives showed no effectiveness at this concentration, which perhaps correlates to the lack of an alkyl chain.

Related isoquinolinium structures bearing additional aromatic rings include chelerythrine, sanguinarine and berberine. Berberine, also identified from a Chinese herb, has shown micromolar activity against *P. aeruginosa* (Čerňáková, M. and Košt'álová, 2002, Folia Microbiol. 47:375-378). Other quinolinium natural products with a quaternary ammonium center include tabouensinium chloride (Wabo et al., 2005, Nat. Prod. Res. 19:591-595) and the quinocitrines (Kozlovsky et al., 2005, Appl. Biochem. Microbiol. 41:499-502). Finally, ageloxime D (Hertiani et al., 2010, Bioorg. Med. Chem. 18:1297-1311) and dehydroevodiamine (Park et al., 1996, Planta Med. 62:405-409) diversify this structural class and present a positive charge delocalized over two nitrogens.

While the preparation and testing of QAC-derived polymers has been pursued with increasing intensity over the past three decades (Panarin et al., 1971, Khim.-Farm. Zh. 5:24-28; Jaeger et al., 2010, Progress Polym. Sci. 35:511-577; Tahiro, 2001, Macromol. Mater. Eng. 286:63-87; Tew et al., 2010, Acc. Chem. Res. 43:30-39; Kenawy et al., 2007, Biomacromolecules 8:1359-1384; Mintzer et al., 2012, Mol. Pharmaceuticals 9:342-354; Munoz-Bonilla and Fernandez-Garcia, 2012, Prog. Polym. Sci. 37:281-339; Munoz-Bonilla et al., 2014, Polymeric Materials with Antimicrobial Activity: From Synthesis to Applications, RSC Publishing; Liu et al., 2015, J. Am. Chem. Soc. 137:2183-2186) the incorporation of multicationic QACs and corresponding antimicrobial testing of these polymers has received scarce attention; literature reports of multicationic QAC polymers often present little to no bioactivity or characterization data (Kenawy et al., 2002, J. Polym. Sci. Part Polym. Chem. 40:2348-2393; Dizman et al., 2004, J. Appl. Polym. Sci. 94:635-642; Ayfer et al., Des. Monomers Polym. 8:437-451; Gong et al., 2001, Sens. Actuators B 73:185-191). Results suggest that mono- and bis-QAC-derived polymers not only possess superior antimicrobial properties in comparison to their small molecular counterparts, but may also possess lower toxicity (Tahiro, 2001, Macromol. Mater. Eng. 286:63-87; Ganewatta et al., 2014, Chem. Sci. 5:2011-2016).

There is a continuing need in the art for novel antimicrobial agents with low toxicity profiles that also demonstrate activity against resistant bacterial strains. The present invention addresses this unmet need in the art.

BRIEF SUMMARY OF THE INVENTION

The present invention includes a compound selected from the group consisting of formula I-XII, XXVI, and XXVII:

formula I
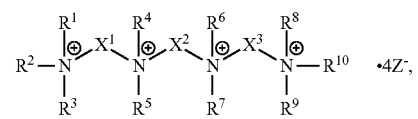

formula II
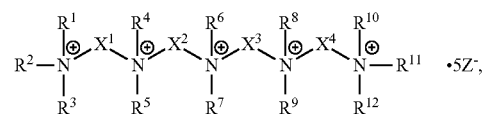

formula III
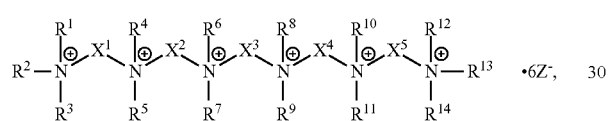

formula IV
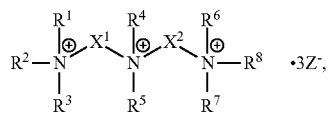

formula V
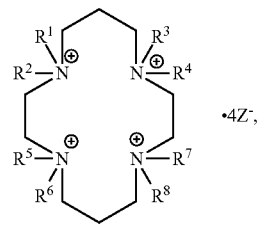

formula VI
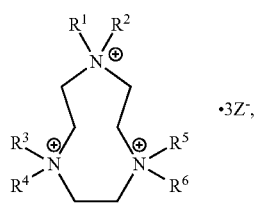

formula VII
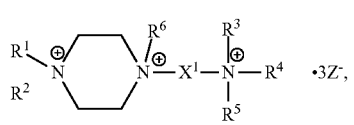

formula VIII
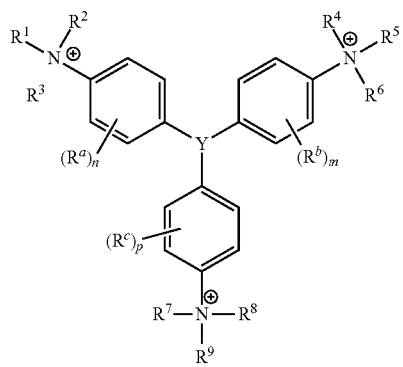

formula VIIIa
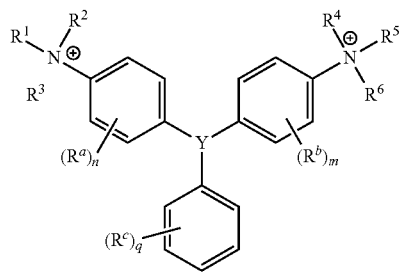

formula IX
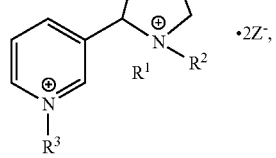

formula X
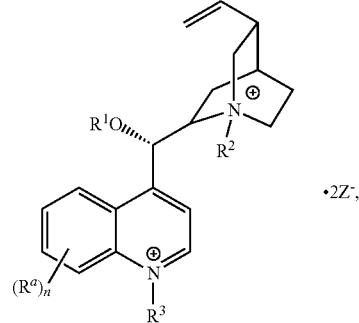

formula XI
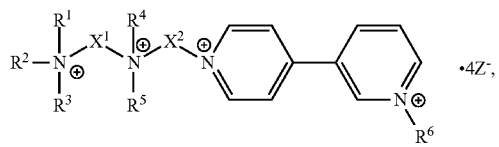

formula XII
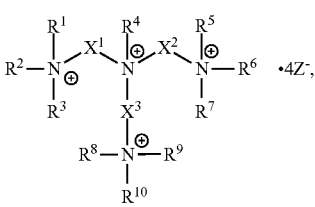

-continued

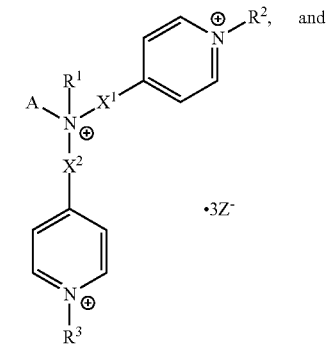

formula XXVI

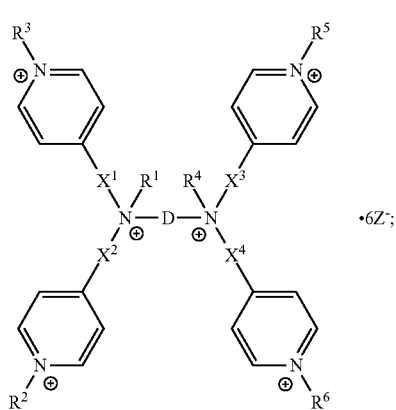

formula XXVII wherein in formula I-XII, XXVI, and XXVII:

$R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ are each independently selected from the group consisting of null, H or $C_1$-$C_{25}$ alkyl, wherein the alkyl group may be optionally substituted with —OR', —NR'$_2$, —NR'—C(O)R', —C(O)NR'$_2$, —NR'—C(O)CR'=CR', —SR', —O—C(O)R', —C(O)OR', —C(O)R', —CF$_3$, —OCF$_3$, halogen, benzyl, o-vinylbenzyl, m-vinylbenzyl, p-vinylbenzyl, phenyl, allyl, and substituted allyl;

each occurrence of $R^a$, $R^b$, and $R^c$ is independently selected from the group consisting of H, $C_1$-$C_6$ alkyl, —OR', —CN, —NO$_2$, —NR'$_2$, —N—C(O)R', —C(O)NR'$_2$, —N—C(O)CR'=CR', —SR', —O—C(O)R', —C(O)OR', —C(O)R', —CF$_3$, —OCF$_3$, and halogen;

each occurrence of R' is independently selected from the group consisting of H and $C_{1-4}$ alkyl;

$X^1$, $X^2$, $X^3$, $X^4$, and $X^5$ are each independently selected from the group consisting of $C_1$-$C_6$ alkyl, $C_1$-$C_6$ alkyl-OC(O)O—$C_1$-$C_6$ alkyl, $C_1$-$C_6$ alkyl-O—$C_1$-$C_6$ alkyl-O—$C_1$-$C_6$ alkyl, $C_1$-$C_6$ alkyl-S—S—$C_1$-$C_6$ alkyl, $C_1$-$C_6$ alkyl-NC(O)O—$C_1$-$C_6$ alkyl, $C_1$-$C_6$ alkyl-S—$C_1$-$C_6$ alkyl, $C_1$-$C_6$ alkyl-NC(S)N—$C_1$-$C_6$ alkyl, and $C_1$-$C_6$ alkyl-NC(O)N—$C_1$-$C_6$ alkyl, wherein the alkyl group may be optionally substituted;

Y is N or CR";

A is selected from the group consisting of $C_1$-$C_{25}$ alkyl and

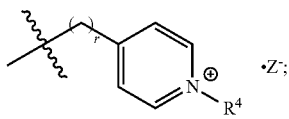

D is selected from the group consisting of $C_1$-$C_6$ alkyl and

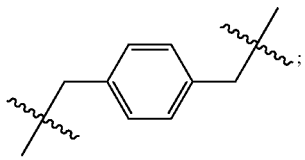 [SMILES: *Cc1ccc(C*)cc1]

each occurrence of Z is independently a counterion;
R" is H or $C_1$-$C_6$ alkyl, wherein the alkyl group may be optionally substituted and may combine with any of $R^a$, $R^b$, and $R^c$ to form a ring;
m is an integer from 0 to 4;
n is an integer from 0 to 4;
p is an integer from 0 to 4;
q is an integer from 0 to 5; and
r is an integer from 1 to 6.

The present invention also includes a composition comprising a compound of the invention. In one embodiment, the composition is an antimicrobial composition.

The present invention also includes a method for preventing or reducing the growth or proliferation of microorganisms or biofilm-embedded microorganisms on at least one surface. The method includes the steps of providing at least one surface, providing a composition comprising at least one compound of the invention, and contacting the at least one surface with the composition in an amount sufficient to prevent or reduce the growth or proliferation of microorganisms or biofilm-embedded microorganisms on the at least one surface.

The present invention also a method for removing at least a portion of or reducing the number of microorganisms or biofilm-embedded microorganisms attached to at least one surface. The method includes the steps of providing at least one surface, wherein the microorganisms or biofilm-embedded microorganisms are attached to the at least one surface, providing a composition comprising at least one compound of the invention, and contacting the composition with the at least one surface in an amount sufficient to remove at least a portion of or reduce the number of microorganisms or biofilm-embedded microorganisms attached to the at least one surface.

The present invention also includes a polymer comprised of at least one monomer of formula XVIII:

formula XVIII

PM
|
L
|
PA;

wherein in formula XVIII:
PM is a polymerizable moiety attached to a polycationic amphiphile (PA) via a linker L.

The present invention also includes a method for preventing or reducing the growth or proliferation of microorganisms or biofilm-embedded microorganisms on at least one surface. The method includes the steps of providing at least one surface, providing a composition comprising at least one polymer of the invention, and contacting the at least one surface with the composition in an amount sufficient to prevent or reduce the growth or proliferation of microorganisms or biofilm-embedded microorganisms on the at least one surface.

The present invention also includes a method for removing at least a portion of or reducing the number of microorganisms or biofilm-embedded microorganisms attached to at least one surface. The method includes the steps of providing at least one surface, wherein the microorganisms or biofilm-embedded microorganisms are attached to the at least one surface, providing a composition comprising a polymer of the invention, and contacting the composition with the at least one surface in an amount sufficient to remove at least a portion of or reduce the number of microorganisms or biofilm-embedded microorganisms attached to the at least one surface.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 18A-18B, depicts QAC resistance mechanism and the overlay of QAC structures bound to QacR. FIG. 18A is an image of a QAC resistance mechanism: QACs (red circles) penetrate the membrane and associate with QacR (dark blue), causing dissociation from DNA and allowing transcription of qacA. The resulting QacA proteins in the membrane (light blue) facilitate efflux of QACs. FIG. 18B is an image of the overlay of QAC structures (bottom) bound to QacR: berberine (light gray), crystal violet (medium gray), malachite green (dark gray). Residues with proposed importance are structurally highlighted in beige (E57, E58, W61, E90, Y93, Y103, E170, F162).

FIGS. 19A-19B, depicts natural products and their derivatives. FIG. 19A depicts the structures of examples of quaternary ammonium natural products. FIG. 19B depicts the structures of quinine and nicotine, and alkylation thereof.

FIGS. 20A-20B, depicts the synthesis of quinine- (FIG. 20A) and nicotine-derived (FIG. 20B) quaternary ammonium compounds.

FIGS. 21A-21B, depicts amphiphiles of the present invention. FIG. 21A depicts polyamine starting "core" structures, based on previous core 7: the P-series (8, Piperazine), the C-series (9, Cyclononyl), and the T-series (10, T-shaped tetramine). FIG. 21B depicts chimera-produced models of sample amphiphile structures, where blue=non-polar, and red=polar.

FIG. 23 depicts a table of experimental data of the full biological results including MIC, MBEC, and Lysis20 (in µM) for each QAC against a panel of Gram-positive and Gram-negative bacteria. MBEC is defined by regrowth assays that result in OD values under 0.1 (denoted in bold). MBEC values in italics denote significant eradication (OD<0.5). Lysis20 indicates the concentration of compound (in µM) at which less than 20% of red blood cells are lysed. insol.=insoluble compound.

FIGS. 26A-26B, depicts the $^1$H NMR (FIG. 26A) and $^{13}$C NMR (FIG. 26A) spectra of compound P-10,0,10.

FIGS. 27A-27B, depicts the $^1$H NMR (FIG. 27A) and $^{13}$C NMR (FIG. 27A) spectra of compound P-11,0,11.

FIGS. 28A-28B, depicts the $^1$H NMR (FIG. 28A) and $^{13}$C NMR (FIG. 28A) spectra of compound P-12,0,12.

FIGS. 29A-29B, depicts the $^1$H NMR (FIG. 29A) and $^{13}$C NMR (FIG. 29A) spectra of compound P-13,0,13.

FIGS. 30A-30B, depicts the $^1$H NMR (FIG. 30A) and $^{13}$C NMR (FIG. 30A) spectra of compound P-14,0,14.

FIGS. 33A-33B, depicts the $^1$H NMR (FIG. 33A) and $^{13}$C NMR (FIG. 33A) spectra of compound C-10,0,0.

FIGS. 34A-34B, depicts the $^1$H NMR (FIG. 34A) and $^{13}$C NMR (FIG. 34A) spectra of compound C-11,0,0.

FIGS. 35A-35B, depicts the $^1$H NMR (FIG. 35A) and $^{13}$C NMR (FIG. 35A) spectra of compound C-12,0,0.

FIGS. 35A-35B, depicts the $^1$H NMR (FIG. 36A) and $^{13}$C NMR (FIG. 36A) spectra of compound C-13,0,0.

FIGS. 37A-37B, depicts the $^1$H NMR (FIG. 37A) and $^{13}$C NMR (FIG. 37A) spectra of compound C-14,0,0.

FIGS. 38A-38B, depicts the $^1$H NMR (FIG. 38A) and $^{13}$C NMR (FIG. 38A) spectra of compound C-16,0,0.

FIGS. 39A-39B, depicts the $^1$H NMR (FIG. 39A) and $^{13}$C NMR (FIG. 39A) spectra of compound C-18,0,0.

FIGS. 40A-40B, depicts the $^1$H NMR (FIG. 40A) and $^{13}$C NMR (FIG. 40A) spectra of compound C-20,0,0.

FIGS. 41A-41B, depicts the $^1$H NMR (FIG. 41A) and $^{13}$C NMR (FIG. 41A) spectra of compound C-10,1,1.

FIGS. 42A-42B, depicts the $^1$H NMR (FIG. 42A) and $^{13}$C NMR (FIG. 42A) spectra of compound C-11,1,1.

FIGS. 43A-43B, depicts the $^1$H NMR (FIG. 43A) and $^{13}$C NMR (FIG. 43A) spectra of compound C-12,1,1.

FIGS. 44A-44B, depicts the $^1$H NMR (FIG. 44A) and $^{13}$C NMR (FIG. 44A) spectra of compound C-13,1,1.

FIGS. 45A-45B, depicts the $^1$H NMR (FIG. 45A) and $^{13}$C NMR (FIG. 45A) spectra of compound C-14,1,1.

FIGS. 46A-46B, depicts the $^1$H NMR (FIG. 46A) and $^{13}$C NMR (FIG. 46A) spectra of compound C-16,1,1.

FIGS. 47A-47B, depicts the $^1$H NMR (FIG. 47A) and $^{13}$C NMR (FIG. 47A) spectra of compound C-18,1,1.

FIGS. 48A-48B, depicts the $^1$H NMR (FIG. 48A) and $^{13}$C NMR (FIG. 48A) spectra of compound C-20,1,1.

FIGS. 49A-49B, depicts the $^1$H NMR (FIG. 49A) and $^{13}$C NMR (FIG. 49A) spectra of compound T-8,8,8.

FIGS. 50A-50B, depicts the $^1$H NMR (FIG. 50A) and $^{13}$C NMR (FIG. 50A) spectra of compound T-10,10,10.

FIGS. 51A-51B, depicts the $^1$H NMR (FIG. 51A) and $^{13}$C NMR (FIG. 51A) spectra of compound T-11,11,11.

FIGS. 52A-52B, depicts the $^1$H NMR (FIG. 52A) and $^{13}$C NMR (FIG. 52A) spectra of compound T-12,12,12.

FIGS. 53A-53B, depicts the $^1$H NMR (FIG. 53A) and $^{13}$C NMR (FIG. 53A) spectra of compound T-14,14,14.

FIGS. 56A-56B, depicts the structures of T-shaped tetramines of the present invention. FIG. 56A depicts the structure of tris(2-dimethylaminoethyl)amine. FIG. 56B depicts the structure of N,N-bis[3-(dimethylamine)propyl]-N,N'-dimethylpropane-1,3-diamine (Super T).

FIGS. 58A-58B, depicts strategies for cleavage of "self-destructing" multiQACs of the present invention. FIG. 58A depicts a scheme for both "Edge-destruct" multiQACs and "Center-destruct" multiQACs of the present invention. FIG. 58B depicts a scheme for chemical moieties allowing for the indicated cleavage strategies for "self-destruct" multiQACs of the present invention.

FIGS. 60A-60B, depicts strategies for "Center-destruct" multiQACs of the present invention. FIG. 60A depicts a scheme of preparations of Center-destruct multiQAC structures of the present invention. FIG. 60B depicts a scheme of commercially available precursors.

FIGS. 61A-61B, depicts schemes of the preparation of multiQAC structures of the present invention. FIG. 61A depicts a scheme of a synthesis of acid-labile multiQAC structures of the present invention. FIG. 61B depicts a scheme of a synthesis of reduction-labile multi-QAC structures of the present invention.

FIGS. 62A-62B, depicts schemes of a preparation of multiQAC structures of the present invention. FIG. 62A depicts a scheme of a synthesis of photo-labile multiQAC structures of the present invention. FIG. 62B depicts a scheme of a synthesis of thermally-labile multiQAC structures of the present invention.

FIG. 66 is a table depicting the Minimum Inhibitory Concentrations (MIC) in M of QAC dye analogs. N.T.=not tested, due to solubility. MonoQACs (gray) are grouped with their corresponding multiQACs.

FIG. 67 is a table depicting yields for the synthesis of quinine- and nicotine-derived quaternary ammonium compounds, with antimicrobial activity. Results from two MRSA strains are shaded.

FIG. 68 is a table depicting the MIC in μM of multiQAC analogs.

DETAILED DESCRIPTION

Figure 1:
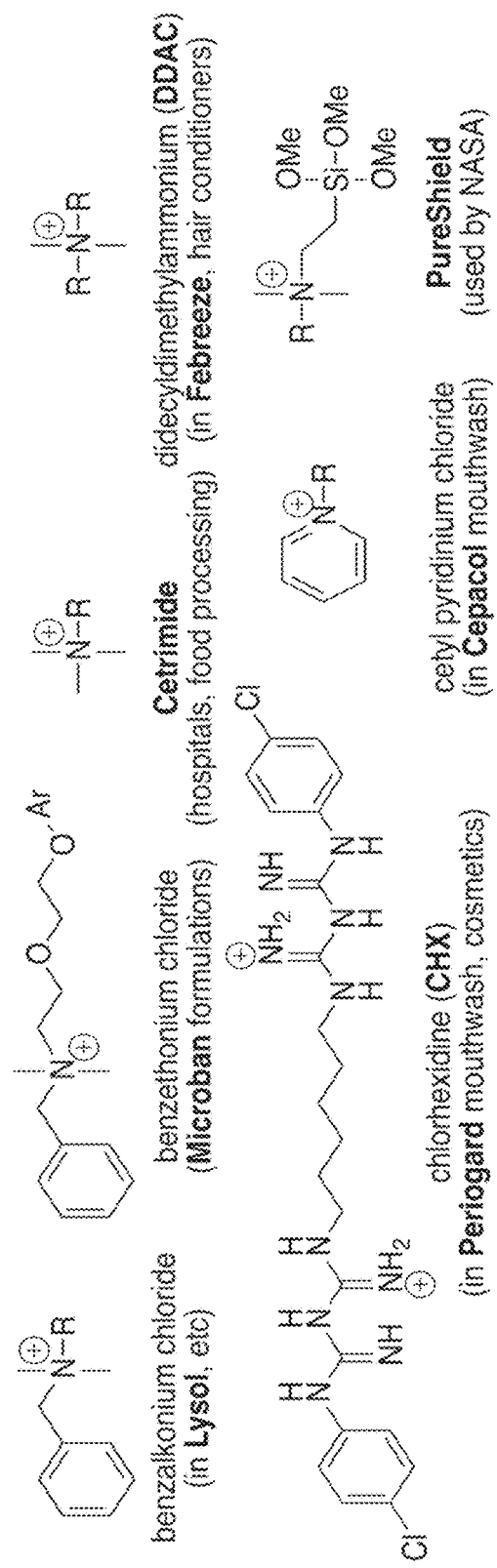
FIG. 1 is an illustration of common amphiphilic antiseptic compounds. R=alkyl chain.

The present invention includes novel polycationic amphiphilic compounds that are useful as antimicrobial agents. In one embodiment, the compounds are quaternary ammonium compounds (QACs). The present invention also includes novel polymers of polycationic amphiphilic compounds that are useful as antimicrobial agents. In one embodiment, the polycationic amphiphilic compounds are quaternary ammonium compounds (QACs). The present invention also includes methods of using the compounds and/or polymers of the invention for preventing or reducing the growth or proliferation of microorganisms or biofilm-embedded microorganisms on at least one surface. The present invention also includes a method for removing at least a portion of or reducing the number of microorganisms or biofilm-embedded microorganisms attached to at least one surface using the compounds and/or polymers of the invention.

Definitions

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated, or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

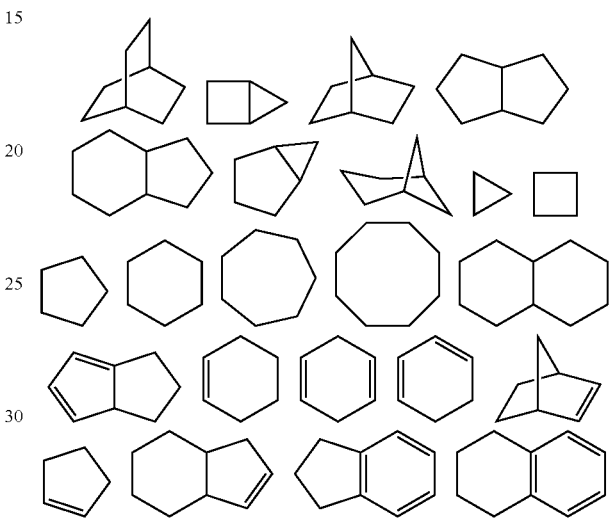

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "aromatic" refers to a carbocycle or heterocycle with one or more polyunsaturated rings and having aromatic character, i.e. having (4n+2) delocalized π (pi) electrons, where n is an integer.

The terms "aryl" or "arylene" are used interchangeably herein, and when employed alone or in combination with other terms, mean, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is one of aryl-$CH_2$—, aryl-$CH(CH_3)$—, and aryl-$CH_3$. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "benzylic hydrogen" refers to a hydrogen atom bound to a carbon atom that is directly bound to an aromatic ring. In one embodiment, the polymer of the present invention comprises at least one of the arylene group having a benzylic hydrogen. Benzylic methyl, benzylic methylene, and benzylic methine all contain at least one benzylic hydrogen.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C($NH_2$)[substituted or unsubstituted alkyl]$_2$. In another embodiment, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —S(=O)$_2$—$CH_3$, —C(=O)$NH_2$, —C(=O)—$NHCH_3$, —NHC(=O)$NHCH_3$, —C(=O)$CH_3$, and —C(=O)OH. In yet one embodiment, the substituents are independently selected from the group consisting of $C_{1-6}$ alkyl, —OH, $C_{1-6}$ alkoxy, halo, amino, acetamido, oxo and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

As used herein, the term "antimicrobial" refers to an ability to kill or inhibit the growth of microorganisms, including but not limited to bacteria, viruses, yeast, fungi, and protozoa, or to attenuate the severity of a microbial infection. The antimicrobial compounds or compositions of the present invention are compounds or compositions that may be used for cleaning or sterilization, or may be used in the treatment of disease and infection. The applications may include both in vitro and in vivo antimicrobial uses. "Applying" an antimicrobial composition may include administrating a composition into a human or animal subject.

As used herein, a "microorganism" refers to any microorganism that may colonize or proliferate on the surface including, but not limited to, gram-positive bacteria (such as *Staphylococcus epidermidis*), gram-negative bacteria (such as *Pseudomonas aeruginosa*), mycobacteria (such as *Mycobacterium tuberculosis*), fungi (such as *Candida albicans*), or virus.

As used herein, the term "biofilm" refers to a film formed by a group of microorganisms adhered together. The term "antibiofilm" as used herein refers to an ability to kill, disperse and/or eradicate a pre-established biofilm.

As used herein, the term "contacting" includes, but is not limited to, impregnating, compounding, mixing, integrating, coating, rubbing, painting, spraying, immersing, rolling, smearing and dipping.

As used herein, the term "treatment" or "treating," is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of medicine or pharmacology. In one embodiment, the condition is selected from the group consisting of a bacterial infection, fungal infection, mycobacterial infection, viral infection, and a combination thereof.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "pharmaceutical composition" refers to a mixture of at least one compound useful within the invention with a pharmaceutically acceptable carrier. The pharmaceutical composition facilitates administration of the compound to a patient or subject, or use of the compound within the methods of the invention. Multiple techniques of administering a compound exist in the art including, but not limited to, intravenous, oral, aerosol, parenteral, ophthalmic, pulmonary and topical administration.

As used herein, the terms "effective amount," "pharmaceutically effective amount" and "therapeutically effective amount" refer to a non-toxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Effective amount" also refers to a sufficient amount of the polycationic amphiphile to prevent or reduce the growth or proliferation of microorganisms and/or biofilm-embedded microorganisms on a surface, in the case of the composition being a coating. "Effective amount" also refers to a sufficient amount of the polycationic amphiphile to penetrate, or break-up, at least a portion of the biofilm on a surface, thereby facilitating access of polycationic amphiphile, antimicrobial agent, and/or antifungal agent to the microorganisms embedded in the biofilm, thus removing at least a portion of or reducing the number of microorganisms attached to a surface. The amount may vary for each compound considered within the compositions of the invention, and upon known factors such as the pharmaceutical characteristics, type of surface, degree of biofilm-embedded microorganism contamination, and the use and length of use. It is within the ability of a person of ordinary skill in the art to relatively easily determine an effective concentration for each compound considered within the compositions of the invention.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, a "biofilm-embedded microorganism" refers to any microorganism that forms or nests within a biofilm during colonization and proliferation on a surface, including, but not limited to, gram-positive bacteria (such as *Staphylococcus epidermidis*), gram-negative bacteria (such as *Pseudomonas aeruginosa*), mycobacteria (such as *Mycobacterium tuberculosis*), fungi (such as *Candida albicans*), or virus.

As used herein, the term "minimum inhibitory concentration (MIC)" refers to the lowest concentration of an antimicrobial agent that will inhibit the visible growth of a microorganism after overnight incubation. MIC values against bacteria, for example, the Gram-positive *Staphylococcus aureus* and *Enterococcus faecalis* and the Gram-negative *Escherichia coli* and *Pseudomonas aeruginosa* were determined by standard methods. See also P. A. Wayne, Methods for Dilution Antimicrobial Tests for Bacteria that Grow Aerobically; Approved Standard, Ninth Edition, 2012, CLSI Document M07-A9, Vol. 32 No. 2, which is incorporated by reference herein in its entirety.

As used herein, the term "the minimum biofilm eradication concentration (MBEC)" of a compound refers to the lowest concentration of compound dosed against a previously established bacterial biofilm that leads to a clear well (optical density of less than 0.1) when the treated biofilm is regrown in fresh media, indicating >95% clearance of bacteria. A regrowth assay was used to establish the MBEC of a compound to evaluate the antibiofilm activity. See also H. Ceri, M. Olson, D. Morck, D. Storey, R. Read, A. Buret, B. Olson, *Methods Enzymol.* 2001, 337, 377, which is incorporated by reference herein in its entirety.

As used herein, the term "organic solvent" refers to solvents including, but not limited to, alcohols (e.g., methanol and ethanol), ketones (e.g., acetone and methylethylketone), ethers (e.g., tetrahydrofuran), aldehydes (e.g., formaldehyde), acetonitrile, carboxylic acids (e.g., formic acid and acetic acid), methylene chloride, chloroform, alkyl carbonates, and hydrocarbons (e.g., hexane and heptane, and xylene), esters (e.g., ethyl acetate, propyl acetate, butyl acetate, amyl acetate, and combination thereof) or similar solvents.

As used herein, the term "alkalinizing agent" refers to an organic and inorganic base, including sodium hydroxide, potassium hydroxide, alkyl hydroxides, ammonia in water (27% ammonium hydroxide), diethylamine and triethylamine.

As used herein, the term "high ionic strength salt" refers to a salt exhibiting high ionic strength, such as sodium chloride, potassium chloride, or ammonium acetate. These salts may act both as an alkalinizing agent and as a penetrating agent to enhance the reactivity of the surface. Therefore, in one specific embodiment, high ionic strength salts may also be used in the step of forming the biofilm-penetrating composition.

As used herein, the term "base material" refers to any material that effectively disperses the polycationic amphiphile at an effective concentration to contact the microorganisms and/or penetrate or disrupt the biofilm. The base material thus facilitates access of the polycationic amphiphile, antimicrobial agent, and/or antifungal agent to the microorganisms on the surface and/or embedded in the biofilm, thus removing at least a portion of or reducing the number of microorganisms attached to the a surface. The term "base material" also includes any solution that effectively disperses the polycationic amphiphile at an effective concentration to form a composition coating for a surface, which prevents or reduces the growth or proliferation of microorganisms and/or biofilm-embedded microorganisms on a surface. In the case of the composition coating, the base material may also facilitate the adhesion of the composition to a surface, thus preventing the composition coating from being easily removed from the surface.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This definition applies regardless of the breadth of the range.

DESCRIPTION

The present invention is based in part on the discovery that novel multi-quaternary ammonium compounds (QACs) do not show diminished activity against QAC-resistant bacterial strains, and are in fact equipotent against both sensitive and resistant strains. These compounds are also extremely efficient at eradicating biofilms, show toxicity profiles advantageous to that of commercial QACs, and have been designed for extension to polymeric materials. Thus, the present invention provides novel polycationic compounds that may be useful as antimicrobial agents and methods of use thereof. In one embodiment, the QAC contains two, three, or four cations. The present invention also includes a composition comprising at least one compound of the invention.

Examples of common QACs, which generally have a single cation, are shown in FIG. 1; in each structure, R represents a long-chained alkyl group, which provides a non-polar "arm" with which the bacterial membrane is disrupted (Hugo, 1967, J. Appl. Bacteriol. 30:17). Structurally, there is significant similarity amongst these compounds, although direct activity comparisons of the antimicrobials against panels of bacteria (and MRSA in particular) are not readily available. While these QAC structures are regarded as reasonably non-toxic, as many can be directly applied to human skin or even used in oral therapies, it is now recognized that all of these structures are likely to be susceptible to bacterial resistance, and little antibiofilm activity is reported for these compounds.

Figure 2:
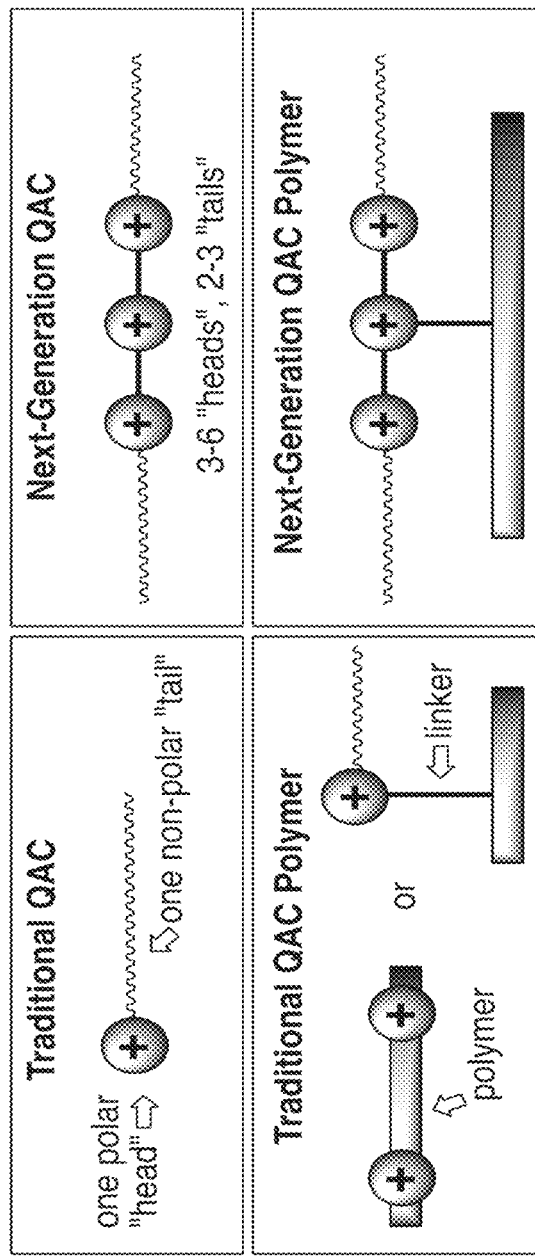
FIG. 2 is an illustration comparing traditional quaternary ammonium compounds (QACs) to compounds of the present invention.

The compounds of the invention are structurally distinct from commercialized QACs. While traditional QACs bear one or occasionally two cations, and thus are vulnerable to QAC resistance genes, the compounds of the invention may contain bis-, tris-, tetra-, and hexacationic structures (FIG. 2). Despite numerous reports of the antimicrobial activity of biscationic amphiphiles, no investigations correlating antimicrobial activity to amphiphiles with three or four quaternary ammonium groups were found. This stood in stark contrast to the wide variety of bioactive natural products (and derivatives thereof) incorporating multiple primary, secondary, and tertiary amines.

In another aspect, the present invention also includes QACs generated from natural products, such as quinine or nicotine. In contrast to natural products that are themselves quaternary ammonium compounds (FIG. 20A), these natural products, which are not in their own right antibacterial agents, can be converted into QACs and thus exhibit antimicrobial or antiseptic activity.

Polymeric materials comprising such QACs possess superior antimicrobial properties to their small molecular counterparts, and may also possess lower toxicity. Thus, in another aspect, the present invention provides novel polymers comprising polycationic compounds that may be useful as antimicrobial agents and methods of use thereof. The compounds described herein exhibit several advantages in addition to low MIC values and simple synthetic pathways, such as excellent biofilm disruption capabilities, as well as negligible susceptibility to resistance.

In one embodiment, the compounds and polymers of the invention demonstrate biofilm eradication against both Gram-positive and Gram-negative bacteria. In another embodiment, the compounds and polymers of the invention contain a wide array of architectures of polycationic structures, and can be prepared by straightforward synthetic routes. In another embodiment, the compounds and polymers of the invention demonstrate "resistance to resistance" in MRSA multi-generational tests. In another embodiment, the compounds and polymers of the invention demonstrate effectiveness against the ESKAPE bacteria, which are pathogens of highest clinical concern.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is at least one compound selected from the group consisting of formula I-XII, XXVI, and XXVII:

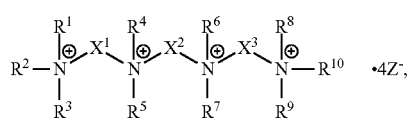

formula I

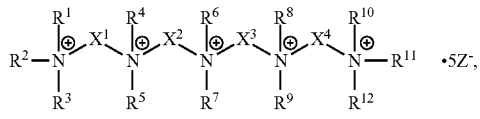

formula II

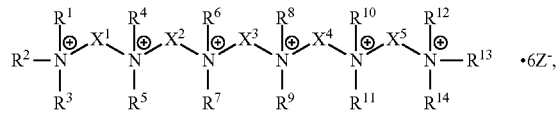

formula III

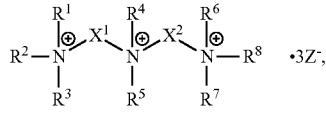

formula IV

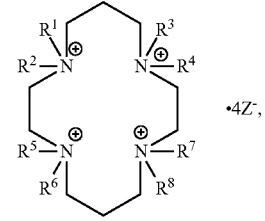

formula V

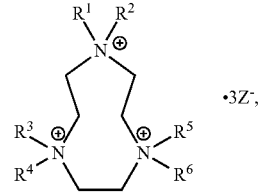

formula VI

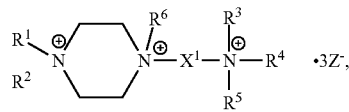

formula VII

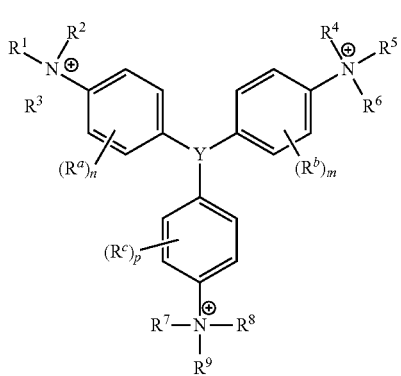

formula VIII

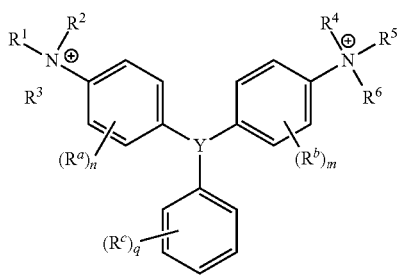

formula VIIIa formula IX

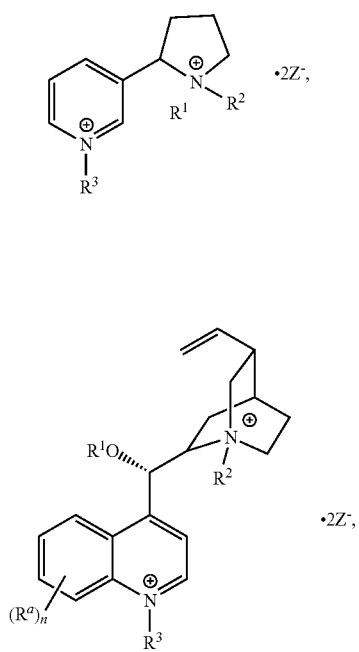

formula X formula XI

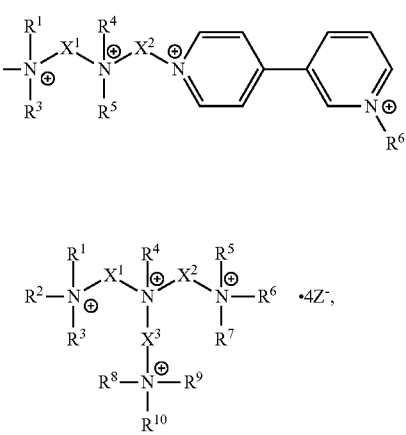

formula XII formula XXVI

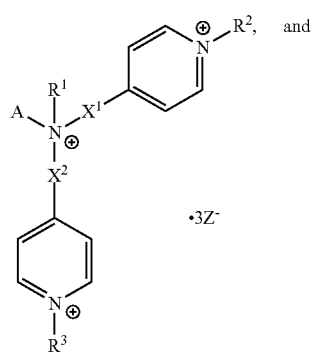

formula XXVII

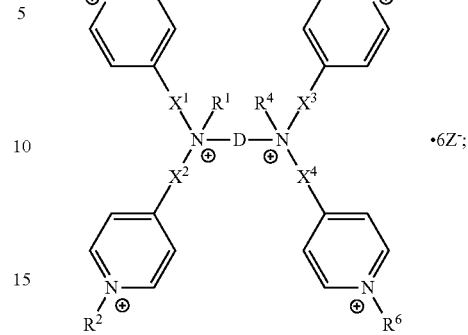

wherein in formula I-XII, XXVI, and XXVII:

$R^1, R^2, R^3, R^4, R^5, R^6, R^7, R^8, R^9, R^{10}, R^1, R^{12}, R^{13}$, and $R^{14}$ are each independently selected from the group consisting of null, H or $C_1$-$C_{25}$ alkyl, wherein the alkyl group may be optionally substituted with —OR', —NR'$_2$, —NR'—C(O)R', —C(O)NR'$_2$, —NR'—C(O)CR'=CR', —SR', —O—C(O)R', —C(O)OR', —C(O)R', —CF$_3$, —OCF$_3$, halogen, benzyl, o-vinylbenzyl, m-vinylbenzyl, p-vinylbenzyl, phenyl, allyl, and substituted allyl;

each occurrence of $R^a$, $R^b$, and $R^c$ is independently selected from the group consisting of H, $C_1$-$C_6$ alkyl, —OR', —CN, —NO$_2$, —NR'$_2$, —N—C(O)R', —C(O)NR'$_2$, —N—C(O)CR'=CR', —SR', —O—C(O)R', —C(O)OR', —C(O)R', —CF$_3$, —OCF$_3$, and halogen;

each occurrence of R' is independently selected from the group consisting of H and $C_{1-4}$ alkyl;

$X^1, X^2, X^3, X^4$, and $X^5$ are each independently selected from the group consisting of $C_1$-$C_6$ alkyl, $C_1$-$C_6$ alkyl-OC(O)O—$C_1$-$C_6$ alkyl, $C_1$-$C_6$ alkyl-O—$C_1$-$C_6$ alkyl, $C_1$-$C_6$ alkyl-S—S—$C_1$-$C_6$ alkyl, $C_1$-$C_6$ alkyl-NC(O)O—$C_1$-$C_6$ alkyl, $C_1$-$C_6$ alkyl-S—$C_1$-$C_6$ alkyl, $C_1$-$C_6$ alkyl-NC(S)N—$C_1$-$C_6$ alkyl, and $C_1$-$C_6$ alkyl-NC(O)N—$C_1$-$C_6$ alkyl, wherein the alkyl group may be optionally substituted;

Y is N or CR";

A is selected from the group consisting of $C_1$-$C_{25}$ alkyl and

D is selected from the group consisting of $C_1$-$C_6$ alkyl and

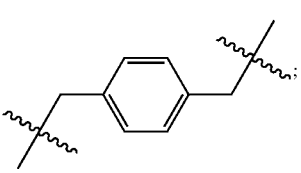 [SMILES: *Cc1ccc(C*)cc1]

each occurrence of Z is independently a counterion;

R" is H or $C_1$-$C_6$ alkyl, wherein the alkyl group may be optionally substituted and may combine with any of $R^a$, $R^b$, and $R^c$ to form a ring;

m is an integer from 0 to 4;

n is an integer from 0 to 4;

p is an integer from 0 to 4;

q is an integer from 0 to 5; and r is an integer from 1 to 6.

In one embodiment, the compound is a compound of formula I. In another embodiment, the compound is a compound of formula II. In another embodiment, the compound is a compound of formula III. In another embodiment, the compound is a compound of formula IV. In another embodiment, the compound is a compound of formula V. In another embodiment, the compound is a compound of formula VI. In another embodiment, the compound is a compound of formula VII. In another embodiment, the compound is a compound of formula VIII. In another embodiment, the compound is a compound of formula VIIIa. In another embodiment, the compound is a compound of formula IX. In another embodiment, the compound is a compound of formula X. In another embodiment, the compound is a compound of formula XI. In another embodiment, the compound is a compound of formula XII. In another embodiment, the compound is a compound of formula XXVI. In another embodiment, the compound is a compound of formula XXVII.

In one embodiment, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is $C_1$ alkyl. In another embodiment, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is $C_{12}$ alkyl. In another embodiment, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is $C_{10}$ alkyl. In another embodiment, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is benzyl.

In one embodiment, at least one of $X^1$, $X^2$, $X^3$, $X^4$, and $X^5$ is $C_2$ alkyl. In another embodiment, at least one of $X^1$, $X^2$, $X^3$, $X^4$, and $X^5$ is $C_3$ alkyl. In another embodiment, at least one of $X^1$, $X^2$, $X^3$, $X^4$, and $X^5$ is selected from the group consisting of $C_1$-$C_6$ alkyl-OC(O)O—$C_1$-$C_6$ alkyl, $C_1$-$C_6$ alkyl-NC(O)O—$C_1$-$C_6$ alkyl, $C_1$-$C_6$ alkyl-S—$C_1$-$C_6$ alkyl, $C_1$-$C_6$ alkyl-NC(S)N—$C_1$-$C_6$ alkyl, and $C_1$-$C_6$ alkyl-NC(O)N—$C_1$-$C_6$ alkyl, wherein the alkyl group may be optionally substituted. In another embodiment, at least one of $X^1$, $X^2$, $X^3$, $X^4$, and $X^5$ is $C_2$ alkyl-OC(O)O—$C_2$ alkyl.

In one embodiment, Z is selected from the group consisting of a halogen ion, a mesylate ion, a tosylate ion, triflate ion, an acetate ion, a propionate ion, and a stearate ion. In one embodiment, Z is a halogen ion.

In one embodiment, the compound is a compound of formula I, and at least one of $X^1$, $X^2$, and $X^3$ is selected from the group consisting of $C_1$-$C_6$ alkyl-OC(O)O—$C_1$-$C_6$ alkyl, $C_1$-$C_6$ alkyl-NC(O)O—$C_1$-$C_6$ alkyl, $C_1$-$C_6$ alkyl-S—$C_1$-$C_6$ alkyl, $C_1$-$C_6$ alkyl-NC(S)N—$C_1$-$C_6$ alkyl, and $C_1$-$C_6$ alkyl-NC(O)N—$C_1$-$C_6$ alkyl, wherein the alkyl group may be optionally substituted.

In one embodiment, the compound of formula I is a compound of formula XIII:

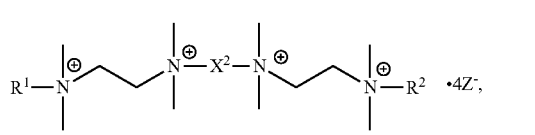

formula XIII wherein in formula XIII:

$R^1$, $R^2$, and Z have the same meaning as in formula I;

$X^2$ is selected from the group consisting of $C_1$-$C_6$ alkyl-OC(O)O—$C_1$-$C_6$ alkyl, $C_1$-$C_6$ alkyl-O—$C_1$-$C_6$ alkyl-O—$C_1$-$C_6$ alkyl, $C_1$-$C_6$ alkyl-S—S—$C_1$-$C_6$ alkyl, $C_1$-$C_6$ alkyl-NC(O)O—$C_1$-$C_6$ alkyl, $C_1$-$C_6$ alkyl-NC(S)N—$C_1$-$C_6$ alkyl, and $C_1$-$C_6$ alkyl-NC(O)N—$C_1$-$C_6$ alkyl.

In one embodiment, $X^2$ is selected from the group consisting of $C_2$ alkyl-OC(O)O—$C_2$ alkyl, $C_2$ alkyl-O—$CH_2$—O—$C_2$ alkyl, and $C_3$ alkyl-S—S—$C_3$ alkyl.

In one embodiment, the compound is a compound of formula IV, and at least one of $R^1$, $R^2$, and $R^3$ and at least one of $R^6$, $R^7$, and $R^8$ is independently $C_1$-$C_{25}$ alkyl substituted with at least one substitutent selected from the group consisting of —OR', —NR'$_2$, —N—C(O)R', —N—C(O)CR'=CR', —SR', —O—C(O)R', —C(O)OR', —C(O)R', —CF$_3$, —OCF$_3$, halogen, benzyl, o-vinylbenzyl, m-vinylbenzyl, p-vinylbenzyl, phenyl, allyl, and substituted allyl.

In one embodiment, the compound of formula IV is a compound of formulae XIV-XVa:

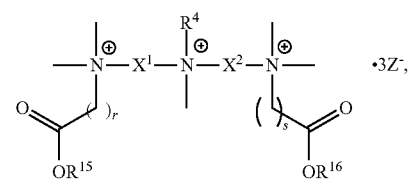

formula XIV

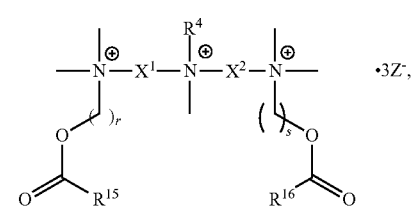

formula XV

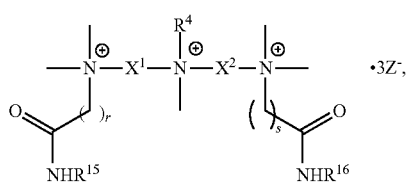

formula XIVa

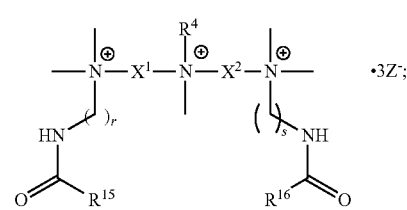

formula XVa wherein in formula XIV-XVa:

$R^4$ and Z have the same meaning as in formula IV;

$R^{15}$ and $R^{16}$ are each independently $C_1$-$C_{25}$ alkyl, wherein the alkyl group may be optionally substituted;

$X^1$ and $X^2$ are each independently $C_1$-$C_6$ alkyl;

r is an integer from 1 to 25; and s is an integer from 1 to 25.

In one embodiment, $X^1$ and $X^2$ are each $C_3$ alkyl. In another embodiment, $R^4$ is ethyl.

In one embodiment, the compound of formula I is selected from the group consisting of:

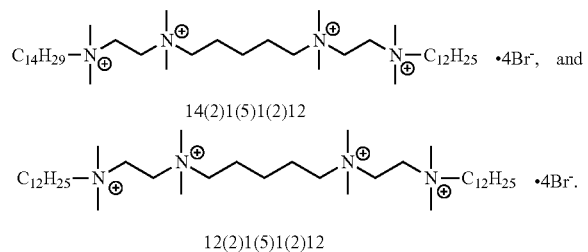

14(2)1(5)1(2)12

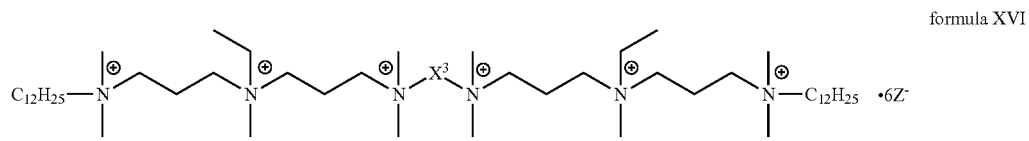

12(2)1(5)1(2)12

In one embodiment, the compound of formula III is a compound of formula XVI:

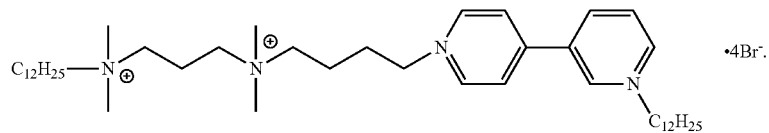

formula XVI wherein $X^3$ and Z have the same meaning as in formula III.

In one embodiment, the compound of formula XI is

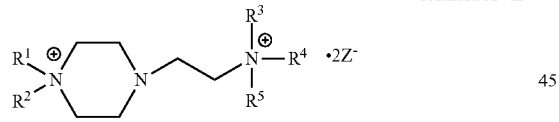

In one embodiment, the compound is a compound of formula VII. In another embodiment, $R^6$ is null. In another embodiment, X is $C_2$ alkyl. In one embodiment, the compound of formula VII is a compound of formula XVII:

formula XVII $$R^1 \overset{\oplus}{\underset{R^2}{N}} \diagup \diagdown N - CH_2CH_2 - \overset{R^3}{\underset{R^5}{\overset{|}{\underset{|}{N^\oplus}}}} - R^4 \cdot 2Z^-$$

wherein in formula XVII:

$R^1$, $R^2$, $R^3$, $R^4$, $R^5$, and Z have the same meaning as in formula VII.

In one embodiment, the compound of formula XVII is P-12,0,12:

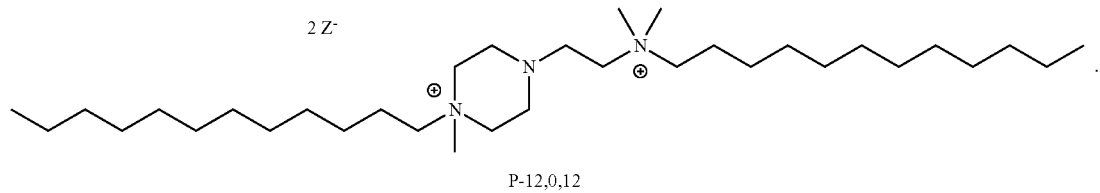 [SMILES: CCCCCCCCCCCC[N+](C)(C)CCN1CC[N+](C)(CCCCCCCCCCCC)CC1]

P-12,0,12

In another embodiment, the compound of formula XVII is P-12,0,12, wherein each Z is Br⁻:

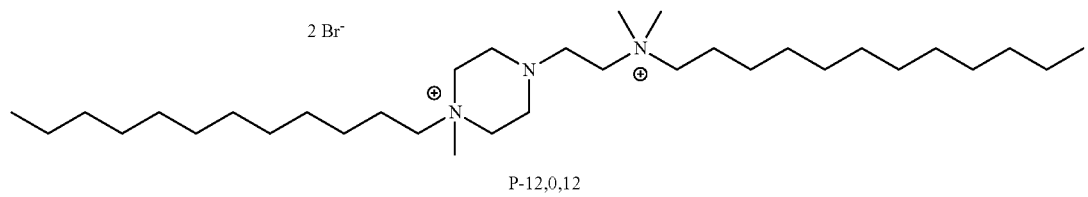 [SMILES: CCCCCCCCCCCC[N+](C)(C)CCN1CC[N+](C)(CCCCCCCCCCCC)CC1]

P-12,0,12

In one aspect, the compound of the invention is a compound of formula XXIII:

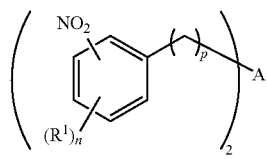

formula XXIII wherein in formula XXIII:
each occurrence of $R^1$ is independently selected from the group consisting of H, $C_1$-$C_6$ alkyl, —OR', —CN, —$NO_2$, —$NR'_2$, —N—C(O)R', —N—C(O)CR'=CR', —SR', —O—C(O)R', —C(O)OR', —C(O)R', —$CF_3$, —$OCF_3$, $C_1$-$C_6$ alkyl-OC(O)R', and halogen;
A is:

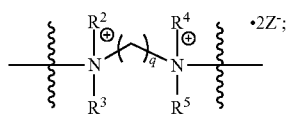

$R^2$, $R^3$, $R^4$, and $R^5$ are each independently selected from the group consisting of null, H or $C_1$-$C_{25}$ alkyl, wherein the alkyl group may be optionally substituted with —OR', —$NR'_2$, —N—C(O)R', —N—C(O)CR'=CR', —SR', —O—C(O)R', —C(O)OR', —C(O)R', —$CF_3$, —$OCF_3$, halogen, benzyl, o-vinylbenzyl, m-vinylbenzyl, p-vinylbenzyl, phenyl, allyl, and substituted allyl;
each occurrence of R' is independently selected from the group consisting of H and $C_{1-30}$ alkyl;
each occurrence of Z is independently a counterion;
n is an integer from 0 to 4;
p is an integer from 0 to 4; and
q is an integer from 0 to 4.

In one aspect, the compound of the invention is a compound of formula XXIV:

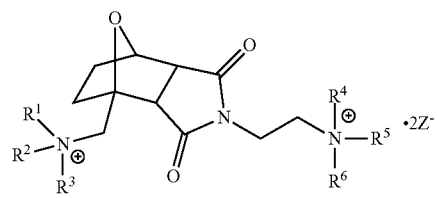

formula XXIV wherein in formula XXIV:
$R^1$, $R^2$, $R^3$, $R^4$, and $R^5$ are each independently selected from the group consisting of null, H or $C_1$-$C_{25}$ alkyl, wherein the alkyl group may be optionally substituted with —OR', —$NR'_2$, —N—C(O)R', —N—C(O)CR'=CR', —SR', —O—C(O)R', —C(O)OR', —C(O)R', —$CF_3$, —$OCF_3$, halogen, benzyl, o-vinylbenzyl, m-vinylbenzyl, p-vinylbenzyl, phenyl, allyl, and substituted allyl;
each occurrence of R' is independently selected from the group consisting of H and $C_{1-30}$ alkyl; and
each occurrence of Z is independently a counterion.

In one embodiment, the compound of the invention is selected from the group consisting of:

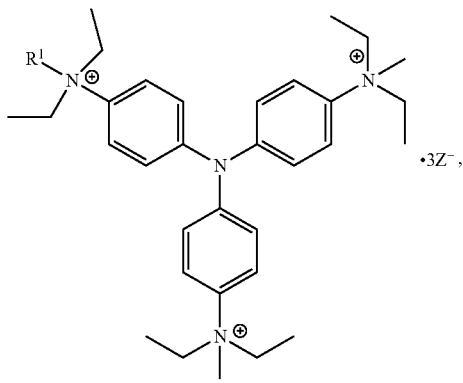

TET-10,0,0 - $R^1$ = $C_{10}H_{21}$
TET-11,0,0 - $R^1$ = $C_{11}H_{23}$
TET-12,0,0 - $R^1$ = $C_{12}H_{25}$
TET-14,0,0 - $R^1$ = $C_{14}H_{29}$
TET-16,0,0 - $R^1$ = $C_{16}H_{33}$
TET-18,0,0 - $R^1$ = $C_{18}H_{37}$
TET-20,0,0 - $R^1$ = $C_{20}H_{41}$

TET-10,1,1 - $R^1$ = $C_{10}H_{21}$
TET-11,1,1 - $R^1$ = $C_{11}H_{23}$
TET-12,1,1 - $R^1$ = $C_{12}H_{25}$
TET-14,1,1 - $R^1$ = $C_{14}H_{29}$
TET-16,1,1 - $R^1$ = $C_{16}H_{33}$
TET-18,1,1 - $R^1$ = $C_{18}H_{37}$
TET-20,1,1 - $R^1$ = $C_{20}H_{41}$

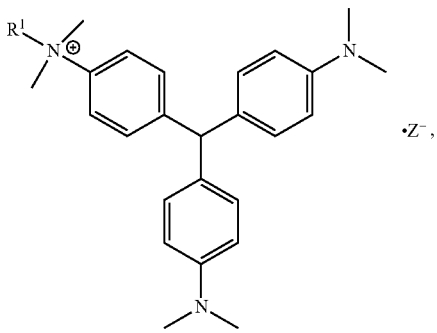

LCV-10,0,0 - R¹ = $C_{10}H_{21}$
LCV-11,0,0 - R¹ = $C_{11}H_{23}$
LCV-12,0,0 - R¹ = $C_{12}H_{25}$
LCV-14,0,0 - R¹ = $C_{14}H_{29}$
LCV-16,0,0 - R¹ = $C_{16}H_{33}$
LCV-18,0,0 - R¹ = $C_{18}H_{37}$
LCV-20,0,0 - R¹ = $C_{20}H_{41}$

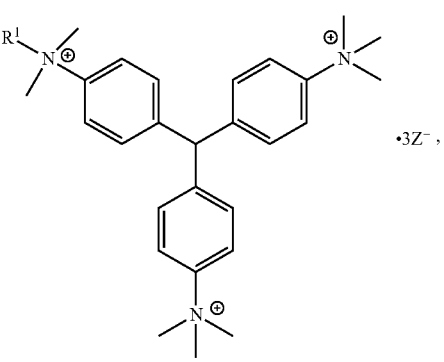

LCV-10,1,1 - R¹ = $C_{10}H_{21}$
LCV-11,1,1 - R¹ = $C_{11}H_{23}$
LCV-12,1,1 - R¹ = $C_{12}H_{25}$
LCV-14,1,1 - R¹ = $C_{14}H_{29}$
LCV-16,1,1 - R¹ = $C_{16}H_{33}$
LCV-18,1,1 - R¹ = $C_{18}H_{37}$
LCV-20,1,1 - R¹ = $C_{20}H_{41}$

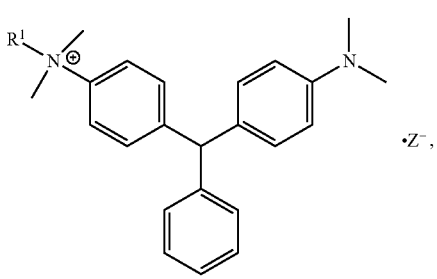

LMG-10,0 - R¹ = $C_{10}H_{21}$
LMG-11,0 - R¹ = $C_{11}H_{23}$
LMG-12,0 - R¹ = $C_{12}H_{25}$
LMG-14,0 - R¹ = $C_{14}H_{29}$
LMG-16,0 - R¹ = $C_{16}H_{33}$
LMG-18,0 - R¹ = $C_{18}H_{37}$

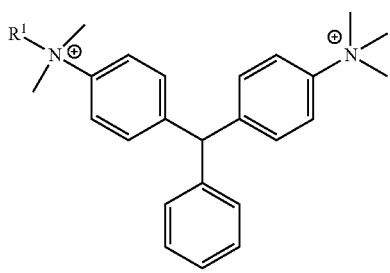

LMG-10,1 - R¹ = $C_{10}H_{21}$
LMG-11,1 - R¹ = $C_{11}H_{23}$
LMG-12,1 - R¹ = $C_{12}H_{25}$
LMG-14,1 - R¹ = $C_{14}H_{29}$
LMG-16,1 - R¹ = $C_{16}H_{33}$
LMG-18,1 - R¹ = $C_{18}H_{37}$

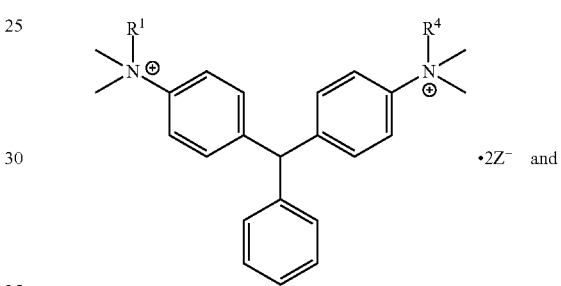

LMG-10,10 - R¹, R⁴ = $C_{10}H_{21}$
LMG-11,11 - R¹, R⁴ = $C_{11}H_{23}$
LMG-12,12 - R¹, R⁴ = $C_{12}H_{25}$
LMG-14,14 - R¹, R⁴ = $C_{14}H_{29}$
LMG-16,16 - R¹, R⁴ = $C_{16}H_{33}$
LMG-18,18 - R¹, R⁴ = $C_{18}H_{37}$

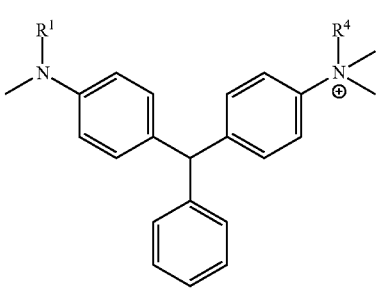

LMGS-10,0 - R¹, R⁴ = $C_{10}H_{21}$
LMGS-11,0 - R¹, R⁴ = $C_{11}H_{23}$
LMGS-12,0 - R¹, R⁴ = $C_{12}H_{25}$
LMGS-14,0 - R¹, R⁴ = $C_{14}H_{29}$
LMGS-16,0 - R¹, R⁴ = $C_{16}H_{33}$
LMGS-18,0 - R¹, R⁴ = $C_{18}H_{37}$ wherein each occurrence of Z is independently selected from the group consisting of I⁻ and Br⁻.

In one embodiment, the compound of the invention is selected from the group consisting of:

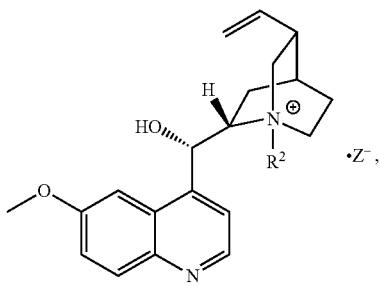

Q-10,0 - R² = C₁₀H₂₁
Q-11,0 - R² = C₁₁H₂₃
Q-12,0 - R² = C₁₂H₂₅
Q-14,0 - R² = C₁₄H₂₉
Q-16,0 - R² = C₁₆H₃₃
Q-18,0 - R² = C₁₈H₃₇

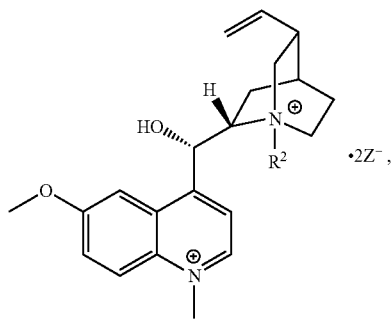

Q-10,1 - R² = C₁₀H₂₁
Q-11,1 - R² = C₁₁H₂₃
Q-12,1 - R² = C₁₂H₂₅
Q-14,1 - R² = C₁₄H₂₉
Q-16,1 - R² = C₁₆H₃₃
Q-18,1 - R² = C₁₈H₃₇

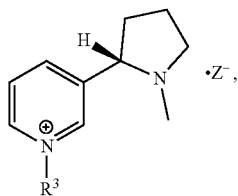

N-10,0 - R³ = C₁₀H₂₁
N-11,0 - R³ = C₁₁H₂₃
N-12,0 - R³ = C₁₂H₂₅
N-14,0 - R³ = C₁₄H₂₉
N-16,0 - R³ = C₁₆H₃₃
N-18,0 - R³ = C₁₈H₃₇
N-20,0 - R³ = C₂₀H₄₁

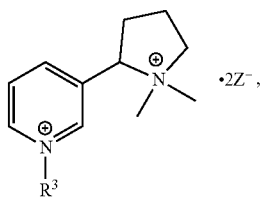

N-10,1 - R³ = C₁₀H₂₁
N-11,1 - R³ = C₁₁H₂₃
N-12,1 - R³ = C₁₂H₂₅
N-14,1 - R³ = C₁₄H₂₉
N-16,1 - R³ = C₁₆H₃₃
N-18,1 - R³ = C₁₈H₃₇
N-20,1 - R³ = C₂₀H₄₁ wherein each occurrence of Z is independently selected from the group consisting of I⁻ and Br⁻.

In one embodiment, the compound of the invention is selected from the group consisting of:

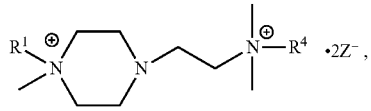

P-10,0,10 - R¹, R⁴ = C₁₀H₂₁
P-11,0,11 - R¹, R⁴ = C₁₁H₂₃
P-12,0,12 - R¹, R⁴ = C₁₂H₂₅
P-13,0,13 - R¹, R⁴ = C₁₃H₂₇
P-14,0,14 - R¹, R⁴ = C₁₄H₂₉
P-16,0,16 - R¹, R⁴ = C₁₆H₃₃
P-18,0,18 - R¹, R⁴ = C₁₈H₃₇

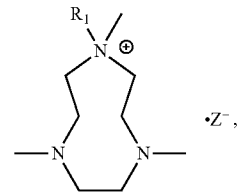

C-10,0,0 - R¹ = C₁₀H₂₁
C-11,0,0 - R¹ = C₁₁H₂₃
C-12,0,0 - R¹ = C₁₂H₂₅
C-13,0,0 - R¹ = C₁₃H₂₇
C-14,0,0 - R¹ = C₁₄H₂₉
C-16,0,0 - R¹ = C₁₆H₃₃
C-18,0,0 - R¹ = C₁₈H₃₇
C-20,0,0 - R¹ = C₂₀H₄₁

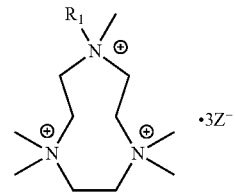

C-10,1,1 - R¹ = C₁₀H₂₁
C-11,1,1 - R¹ = C₁₁H₂₃
C-12,1,1 - R¹ = C₁₂H₂₅
C-13,1,1 - R¹ = C₁₃H₂₇
C-14,1,1 - R¹ = C₁₄H₂₉
C-16,1,1 - R¹ = C₁₆H₃₃
C-18,1,1 - R¹ = C₁₈H₃₇
C-20,1,1 - R¹ = C₂₀H₄₁

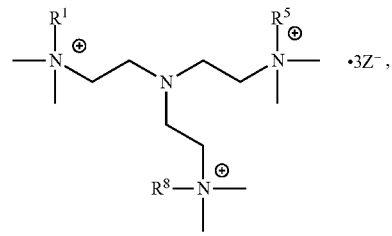

T-8,8,8 - R¹, R⁵, R⁸ = C₈H₁₇
T-10,10,10 - R¹, R⁵, R⁸ = C₁₀H₂₁
T-11,11,11 - R¹, R⁵, R⁸ = C₁₁H₂₃
T-12,12,12 - R¹, R⁵, R⁸ = C₁₂H₂₅
T-14,14,14 - R¹, R⁵, R⁸ = C₁₄H₂₉
T-16,16,16 - R¹, R⁵, R⁸ = C₁₆H₃₃
T-18,18,18 - R¹, R⁵, R⁸ = C₁₈H₃₇ wherein each occurrence of Z is independently selected from the group consisting of I⁻ and Br⁻.

In one embodiment, the compound of the invention is selected from the group consisting of:

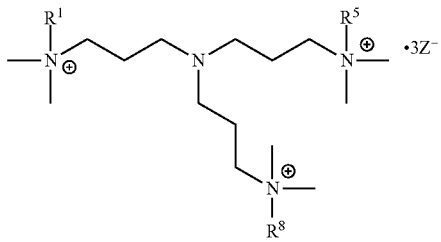

sT-8,8,8,0 - $R^1, R^5, R^8 = C_8H_{17}$
sT-10,10,10,0 - $R^1, R^5, R^8 = C_{10}H_{21}$
sT-11,11,11,0 - $R^1, R^5, R^8 = C_{11}H_{23}$
sT-12,12,12,0 - $R^1, R^5, R^8 = C_{12}H_{25}$
sT-13,13,13,0 - $R^1, R^5, R^8 = C_{13}H_{27}$
sT-14,14,14,0 - $R^1, R^5, R^8 = C_{14}H_{29}$
sT-16,16,16,0 - $R^1, R^5, R^8 = C_{16}H_{33}$
sT-18,18,18,0 - $R^1, R^5, R^8 = C_{18}H_{37}$

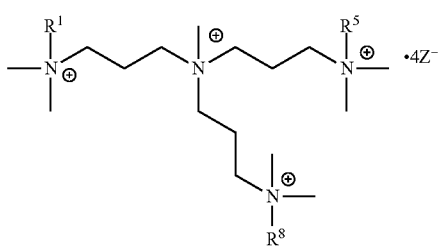

sT-8,8,8,1 - $R^1, R^5, R^8 = C_8H_{17}$
sT-10,10,10,1 - $R^1, R^5, R^8 = C_{10}H_{21}$
sT-11,11,11,1 - $R^1, R^5, R^8 = C_{11}H_{23}$
sT-12,12,12,1 - $R^1, R^5, R^8 = C_{12}H_{25}$
sT-13,13,13,1 - $R^1, R^5, R^8 = C_{13}H_{27}$
sT-14,14,14,1 - $R^1, R^5, R^8 = C_{14}H_{29}$

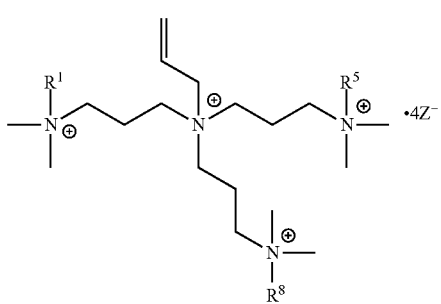

sT-8,8,8,3A - $R^1, R^5, R^8 = C_8H_{17}$
sT-10,10,10,3A - $R^1, R^5, R^8 = C_{10}H_{21}$
sT-11,11,11,3A - $R^1, R^5, R^8 = C_{11}H_{23}$
sT-12,12,12,3A - $R^1, R^5, R^8 = C_{12}H_{25}$
sT-13,13,13,3A - $R^1, R^5, R^8 = C_{13}H_{27}$
sT-14,14,14,3A - $R^1, R^5, R^8 = C_{14}H_{29}$
sT-16,16,16,3A - $R^1, R^5, R^8 = C_{16}H_{33}$
sT-18,18,18,3A - $R^1, R^5, R^8 = C_{18}H_{37}$

-continued

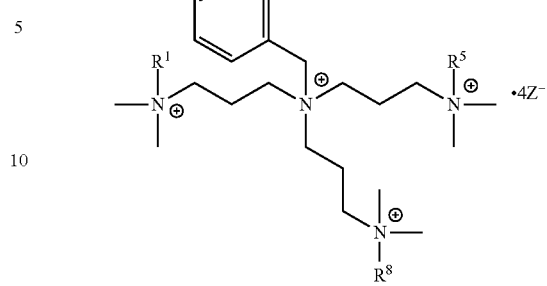

sT-11,11,11,Bn - $R^1, R^5, R^8 = C_{11}H_{23}$
sT-12,12,12,Bn - $R^1, R^5, R^8 = C_{12}H_{25}$ wherein each occurrence of Z is independently selected from the group consisting of I⁻ and Br⁻.

In one embodiment, the compound of formula XXVI is a compound selected from the group consisting of formula XXVIa-XXVId:

formula XXVIa

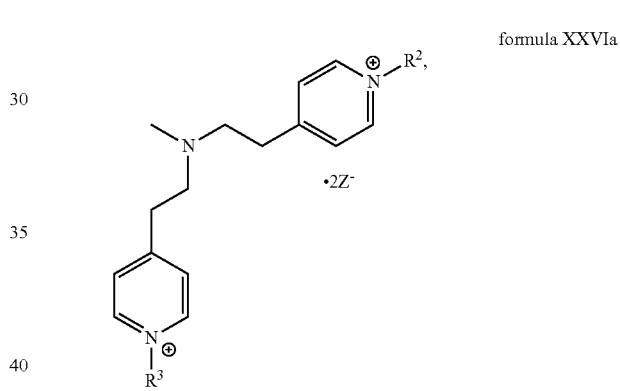

formula XXVIb

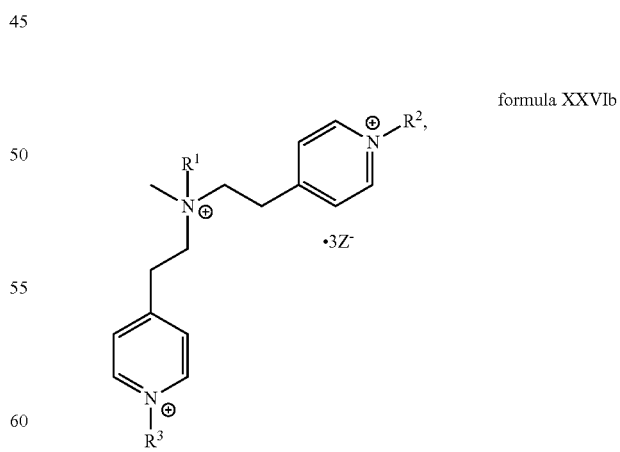

formula XXVIc

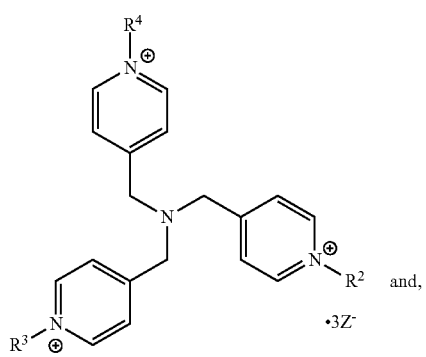

•3Z⁻ and, formula XXVId

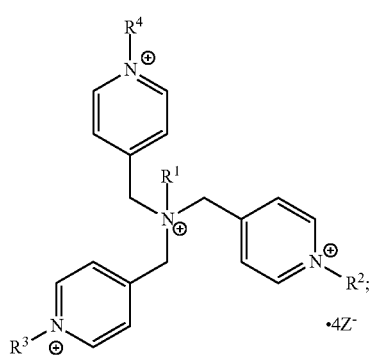

Figure 64:
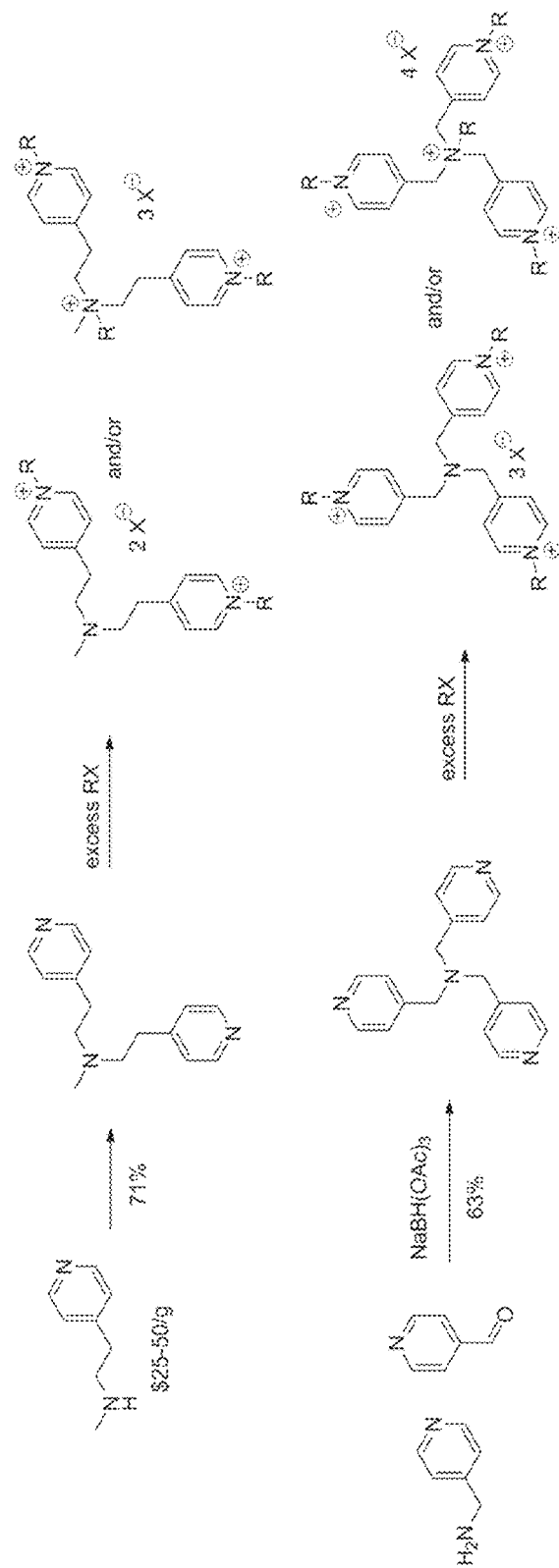
FIG. 64 is a scheme depicting a synthesis of compounds of the present invention.

•4Z⁻;

wherein $R^1$, $R^2$, $R^3$, $R^4$, and Z have the same meaning as in formula XXVI. See FIG. 64 for examples of the synthesis of compound of formula XXVI.

In one embodiment, the compound of formula XXVII is a compound selected from the group consisting of formula XXVIIa-XXVIId:

formula XXVIIa

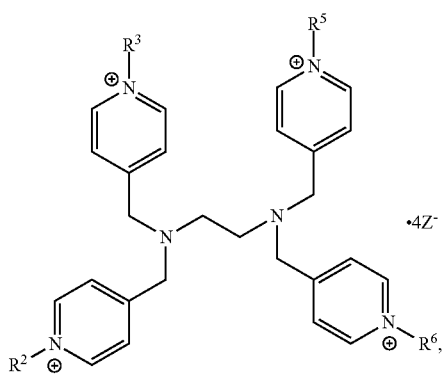

•4Z⁻, formula XXVIIb

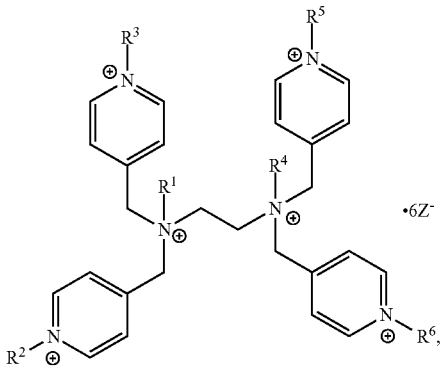

•6Z⁻ formula XXVIIc

[Structure with $R^3$, $R^5$, $R^1$, $R^2$, $R^4$, $R^6$] •4Z⁻ and, formula XXVIId

Figure 65:
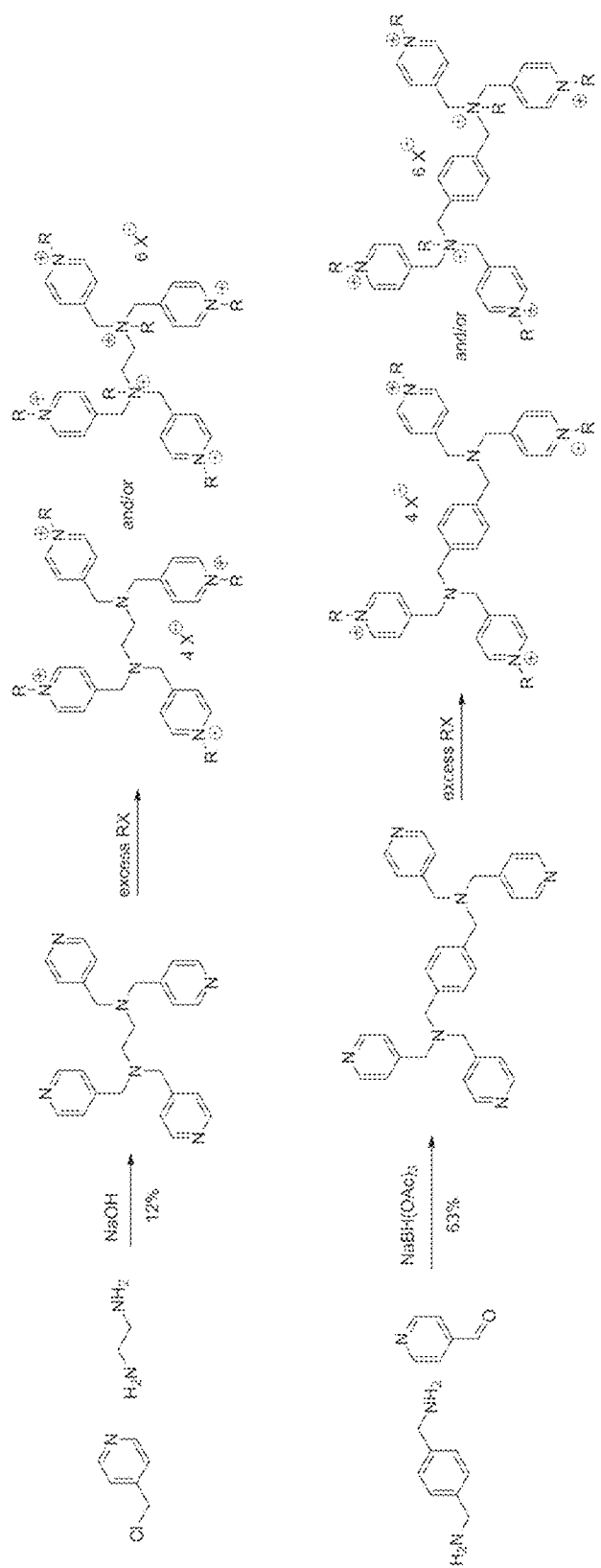
FIG. 65 is a scheme depicting a synthesis of compounds of the present invention.

[Structure with $R^3$, $R^5$, $R^1$, $R^2$, $R^4$, $R^6$] •6Z⁻;

wherein $R^1$, $R^2$, $R^3$, $R^4$, $R^5$, $R^6$, and Z have the same meaning as in formula XXVII. See FIG. 65 for examples of the synthesis of compound of formula XXVI. See also Tamamura et al., 2006, J. Med. Chem. 49:3412-3415, which is incorporated by reference herein in its entirety.

In one aspect, the compound of the invention is a polycationic (e.g., biscationic, triscationic, tetracationic or the like) amphiphile. As used herein, the terms "amphiphile" and "amphiphilic" refer to a compound which has at least one hydrophilic moiety and at least one hydrophobic moiety. In one embodiment, the compound is monocationic. In one embodiment, the compound is a quaternary ammonium compound, or QAC, comprising at least one tetrasubstituted nitrogen atom. In some embodiments, the compound is comprised of two, three, four, five, six, seven, eight, nine, or ten tetrasubstituted nitrogen atoms. In one embodiment, the compound is comprised of three tetrasubstituted nitrogen atoms (triscationic). In another embodiment, the compound is comprised of four tetrasubstituted nitrogen atoms (tetracationic). In another embodiment, the compound is comprised of five tetrasubstituted nitrogen atoms (pentacationic). In another embodiment, the compound is comprised of six tetrasubstituted nitrogen atoms (hexacationic). In one embodiment, the compounds of the invention also comprise at least one amine, wherein the amine is a monosubstituted, disubstituted, or trisubstituted amine. The amine may be protonated or it may not be protonated. In a non-limiting example, the compound comprises two cations and an amine, wherein the amine is protonated or unprotonated. In another non-limiting example, the compound comprises two cations and two amines, and the amines are independently protonated or unprotonated.

In some embodiments, a substituent may be null. As used herein, the term "null" refers to the group being absent. Accordingly, the number of substitutents on the nitrogen to which the null group is attached and the number of corresponding counterions Z would each be reduced by one. In a non-limiting example, a compound of formula XVII is a compound of formula VII where $R^6$ is null, and $R^6$ is no longer present in the compound and the nitrogen atom to which $R^6$ was attached becomes a trisubstituted nitrogen that does not have a positive charge. Accordingly, the number of the counterion Z in formula XVII is reduced from $3Z^-$ to $2Z^-$.

The counterion Z may be any ion which carries a charge(s) opposite to the charge on the compound. Non-limiting examples of counterions include halogen ions, mesylate ion, tosylate ion, triflate ion, carboxylate ions such as acetate, propionate, and stearate, and any ion that forms a pharmaceutically acceptable salt with the compound, such as pharmaceutically acceptable non-toxic acids, including inorganic acids, organic acids, solvates, hydrates, or clathrates. In one embodiment, the counterion Z is selected from the group consisting of a halogen ion, a mesylate ion, a tosylate ion, triflate ion, an acetate ion, a propionate ion, and a stearate ion. In another embodiment, the counterion Z is a halogen ion. In another embodiment, the counterion Z is a bromide ion.

Hybrid Polycationic Amphiphiles

In another aspect of the invention, the polycationic amphiphile is conjugated to or attached to a second compound or moiety. Any compound or moiety which may improve the biological properties of the polycationic amphiphile is contemplated for use within the invention. Non-limiting examples include QACs, antimicrobial peptides, sugars, iron siderophores, polymerizable moieties, solid surfaces such as glass, metal, paper or poly(alkyl ethers) such as polyethylene glycol (PEG) or polypropylene glycol (PPG), and other nucleophilic residues. In a non-limiting example, a first QAC can be attached to a second dicationic QAC to form a tetracationic QAC. The second dicationic QAC may be identical to the first dicationic QAC, resulting in a symmetrical tetracationic QAC, or it may be different, providing "chimeric" compounds with 4 cations, but dissimilar substituents. In one embodiment, the polycationic amphiphile is attached to a surface. In one embodiment, the surface is a solid surface. In one embodiment, the solid surface is a glass surface, a metal surface, a paper surface, or a poly(alkyl ether). In some embodiments, the polycationic amphiphile is attached to the additional compound or moiety via a bond. In other embodiment, the polycationic amphiphile is attached to the additional compound or moiety via a linker. The linker may be any suitable linker, as would be understood by one of ordinary skill the art. Examples of linkers include, but are not limited to, an alkyl group, a benzyl group, an aryl group, a heteroaryl group, a cycloalkyl group, an amide group, an ester, an amide, a sulfonamide, a carbamate, a carbonate, a sulfone, an ether, an oxime, a hydrazine, a urea, a thiourea, a phosphate, a poly(alkyl ether), or a heteroatom, wherein the group may be optionally substituted.

Self-Destruct Polycationic Amphiphiles

In another aspect of the invention, chemical instability may be installed into the compounds, aiding in diminishing the compounds' longevity and thereby reducing the time of exposure of the compounds to bacteria in order to avoid increasing bacterial resistance. In some embodiments, decomposition-prone functional groups can be incorporated into the polycationic amphiphile, allowing the compound to break down over time. In a non-limiting example, a tetracationic compound comprising such a functional group would decompose into biscationic compounds. Examples of decomposition-prone functional groups include, but are not limited to, esters, amides, disulfides, Diels-alder adducts, carbonates, thioureas, epoxides, diazo compounds, azides, and carbamates, as well as photocleavable groups such as nitroaromatics, for example o-nitrobenzyl groups. Non-limiting examples of self-destruct polycationic amphiphiles include compounds of formula XIII, XIV, and XV, wherein the compounds include a carbonate or other moieties (formula XIII) or ester moieties (formula XIV and formula XV).

Polymers

In another aspect, the present invention provides a polymer comprised of at least one monomer of formula XVIII:

formula XVIII wherein in formula XVIII:

PM is a polymerizable moiety attached to a polycationic amphiphile (PA) via a linker L.

As used herein, the term "polymerizable moiety" or "PM" refers to any functional group that has already been polymerized or is capable of being polymerized. Any polymerizable moiety is contemplated for the invention, as would be understood by one of ordinary skill in the art. Non-limiting examples include carbonate, methacrylate, methyl (meth) acrylate, ethyl (meth)acrylate, butyl (meth)-acrylate, 2-ethylhexyl (meth)acrylate, phenyl (meth)acrylate and benzyl (meth)acrylate, hydroxyalkyl esters such as 2-hydroxyethyl (meth)acrylate and 2-hydroxypropyl (meth)acrylate; polyvalent esters such as ethylene glycol diacrylate, polyethylene glycol di(meth)acrylate, neopentyl glycol di(meth)acrylate, trimethylolpropane tri(meth)acrylate and pentaerythritol tetraacrylate; (meth)acrylonitrile, (meth) acrylamide, N-substituted (meth)acrylamide; vinyl esters such as vinyl acrylate, vinyl acetate, vinyl propionate and vinyl succinate; as well as other vinyl compounds such as vinyl ethers, styrene, halogenated styrene, divinylbenzene, vinylnaphthalene, N-vinylpyrrolidone, diallyl phthalate, diallyl malate, triallyl isocyanate triallyl phosphate. In one embodiment, the polymerizable moiety is styrene. In another embodiment, the polymerizable moiety is methacrylate. In another embodiment, the polymerizable moiety is methyl methacrylate. In another embodiment, the polymerizable moiety is acrylamide. In another embodiment, the polymerizable moiety is methacrylamide. In another embodiment, the polymerizable moiety is a carbonate.

The polycationic amphiphile may be a compound of the invention, or may be any compound comprising at least one tetrasubstituted nitrogen atom (a QAC). In one embodiment, the number of tetrasubstituted nitrogen atoms in the QAC ranges from 1 to 6. In another embodiment, the number of tetrasubstituted nitrogen atoms in the QAC ranges from 2 to 6. In another embodiment, the number of tetrasubstituted nitrogen atoms in the QAC ranges from 3 to 6. In one embodiment, the polycationic amphiphile is a QAC. In one embodiment, the QAC has at least two tetrasubstituted nitrogen atoms. In another embodiment, the QAC has at least three tetrasubstituted nitrogen atoms. In another embodiment, the QAC has one tetrasubstituted nitrogen atom. For other examples of QACs useful in the invention, see LaDow et al., 2011, Eur. J. Med. Chem. 46:4219; Black et al., 2014, Bioorg. Med. Chem. Lett. 24:99-102; Ator et al., 2014, Bioorg. Med. Chem. Lett. 24:3706-3709; and Grenier et al., 2012, Bioorg. Med. Chem. Lett. 22, 4055-4058, Jennings et al., 2014, ChemBioChem: 2211-2215, each of which is incorporated by reference in its entirety herein.

The counterion Z may be any ion which carries a charge(s) opposite to the charge on the compound. Non-limiting examples of counterions include halogen ions, mesylate ion, tosylate ion, triflate ion, carboxylate ions such as acetate, propionate, and stearate, and any ion that forms a pharmaceutically acceptable salt with the compound, such as pharmaceutically acceptable non-toxic acids, including inorganic acids, organic acids, solvates, hydrates, or clathrates. In one embodiment, the counterion Z is selected from the group consisting of a halogen ion, a mesylate ion, a tosylate ion, triflate ion, an acetate ion, a propionate ion, and a stearate ion. In another embodiment, the counterion Z is a halogen ion. In another embodiment, the counterion Z is a bromide ion.

In one embodiment, the polycationic amphiphile is a compound selected from the group consisting of formula XIX-XXa:

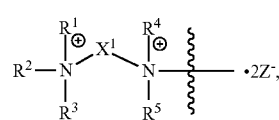

formula XIX

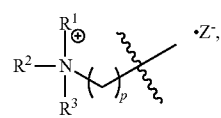

formula XIXa

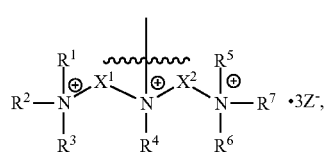

formula XX

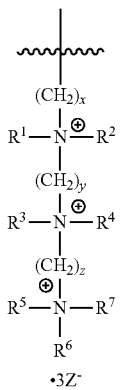

formula XXa wherein in formula XIX-XXa:
$R^1$, $R^2$, $R^3$, $R^4$, $R^5$, $R^6$, and $R^7$ are each independently selected from the group consisting of null, H or $C_1$-$C_{25}$ alkyl, wherein the alkyl group may be optionally substituted with —OR', —NR'$_2$, —N—C(O)R', —N—C(O)CR'=CR', —SR', —O—C(O)R', —C(O)OR', —C(O)R', —CF$_3$, —OCF$_3$, halogen, benzyl, o-vinylbenzyl, m-vinylbenzyl, p-vinylbenzyl, phenyl, allyl, and substituted allyl, and wherein any adjacent $R^1$, $R^2$, $R^3$, $R^4$, $R^5$, $R^6$, and $R^7$ are optionally joined to form a ring;
each occurrence of R' is independently selected from the group consisting of H and $C_{1-4}$ alkyl;
each occurrence of Z is independently a counterion;
$X^1$ and $X^2$ are each independently selected from the group consisting of $C_1$-$C_6$ alkyl, $C_1$-$C_6$ alkyl-OC(O)O—$C_1$-$C_6$ alkyl, $C_1$-$C_6$ alkyl-NC(O)O—$C_1$-$C_6$ alkyl, $C_1$-$C_6$ alkyl-S—$C_1$-$C_6$ alkyl, and $C_1$-$C_6$ alkyl-NC(O)N—$C_1$-$C_6$ alkyl, wherein the alkyl group may be optionally substituted; and
p is an integer from 1 to 25;
x is an integer from 1 to 6;
y is an integer from 1 to 6; and
z is an integer from 1 to 6.
In one embodiment, the polycationic amphiphile is selected from the group consisting of:

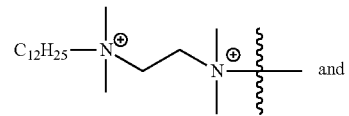

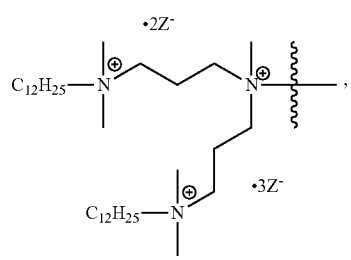

wherein each occurrence of Z is independently a counterion.

The linker L may be any suitable linker, as would be understood by one of ordinary skill the art. For example, the linker L can be a linking group that is bonded to the polymerizable moiety, the polycationic amphiphile, or both. Examples of linkers include, but are not limited to, an alkyl group, a benzyl group, an aryl group, a heteroaryl group, or a heteroatom, wherein the alkyl, benzyl, aryl, and heteroaryl groups may be optionally substituted. In one embodiment, the linker is a bond. For example, when the linker is a bond, the polymerizable moiety is bonded directly to the polycationic amphiphile. Examples of linkers include, but are not limited to, an alkyl group, a benzyl group, an aryl group, a heteroaryl group, a cycloalkyl group, an amide group, an ester, an amide, a sulfonamide, a carbamate, a carbonate, a sulfone, an ether, an oxime, a hydrazine, a urea, a thiourea, a phosphate, a poly(alkyl ether), or a heteroatom, wherein the group may be optionally substituted. In one embodiment, the linker is a $C_1$-$C_{25}$ alkyl group, wherein the alkyl group is optionally substituted. In one embodiment, the linker L is a $C_1$ alkyl group.

In one embodiment, at least one monomer is selected from the group consisting of:

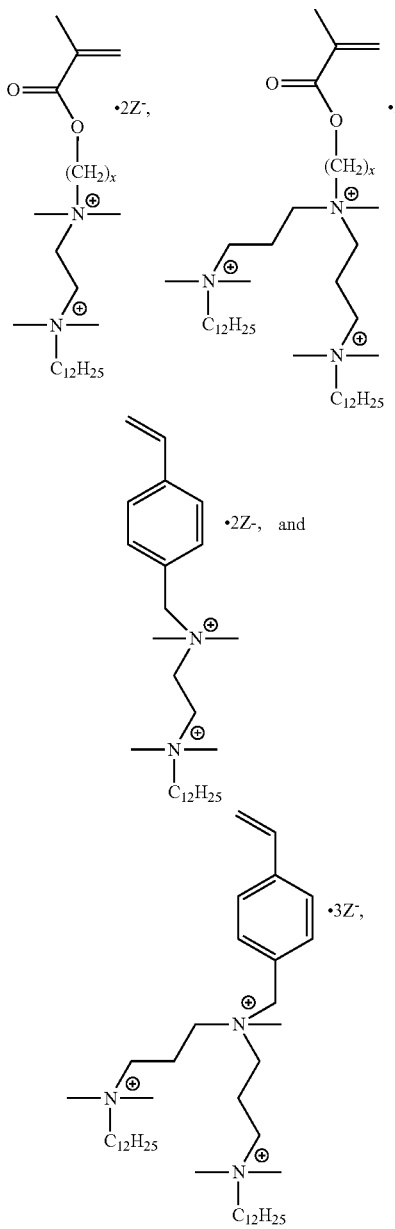

wherein:

each occurrence of Z is independently a counterion; and x is an integer from 1 to 25.

In one embodiment, the polymer is selected from the group consisting of:

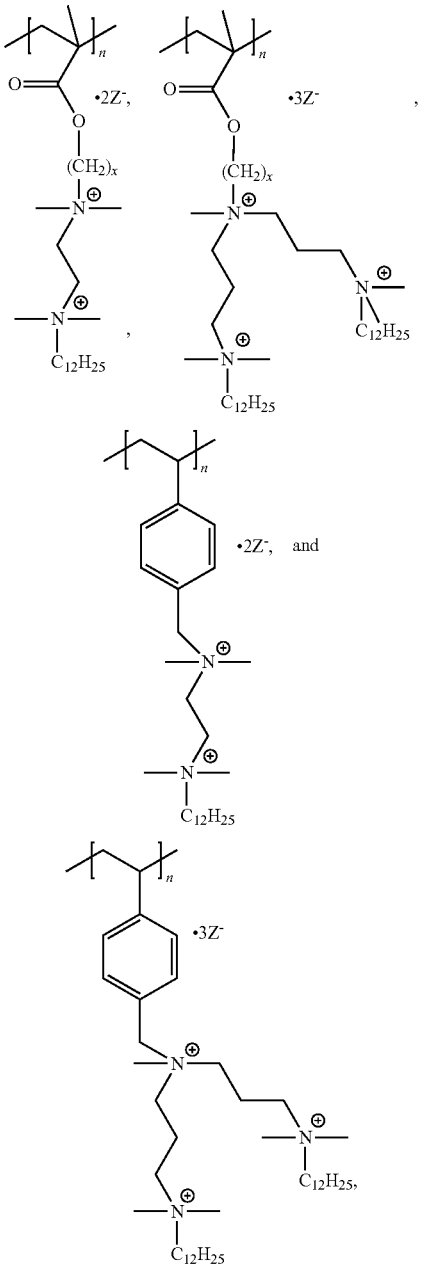

wherein:

each occurrence of Z is independently a counterion; and x is an integer from 1 to 25.

In one embodiment, the polymer is selected from the group consisting of:

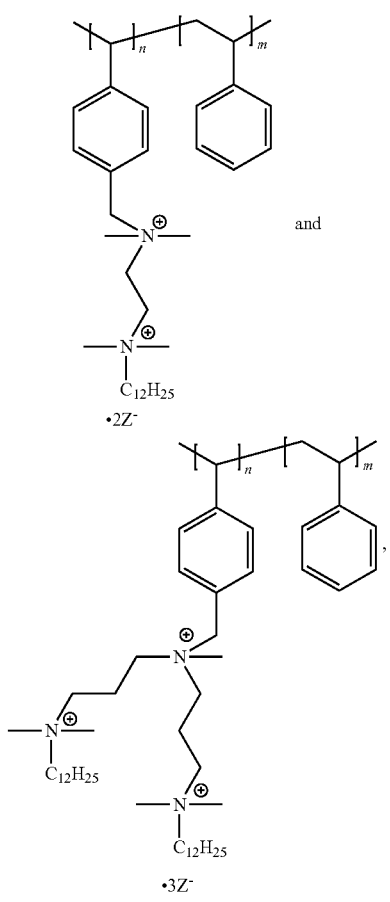

wherein each occurrence of Z is independently a counterion.

In one embodiment, the polymer is a copolymer comprised of at least one methyl methacrylate monomer and at least one methyl methacrylate monomer comprising at least one QAC with two or more tetrasubstituted nitrogens. In one embodiment, the polymer is a polymer of formula XXV:

formula XXV

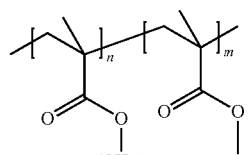

wherein in formula XXV:
$R^1$, $R^2$, $R^3$, $R^4$, $R^5$, $R^6$, and $R^7$ are each independently selected from the group consisting of null, H or $C_1$-$C_{25}$ alkyl, wherein the alkyl group may be optionally substituted with —OR', —NR'$_2$, —N—C(O)R', —N—C(O)CR'=CR', —SR', —O—C(O)R', —C(O)OR', —C(O)R', —CF$_3$, —OCF$_3$, halogen, benzyl, o-vinylbenzyl, m-vinylbenzyl, p-vinylbenzyl, phenyl, allyl, and substituted allyl;

each occurrence of R' is independently selected from the group consisting of H and $C_{1-4}$ alkyl;

each occurrence of Z is independently a counterion;

x is an integer from 1 to 6;

y is an integer from 1 to 6; and z is an integer from 1 to 6.

In one embodiment, the polymer of formula XXV is selected from the group consisting of:

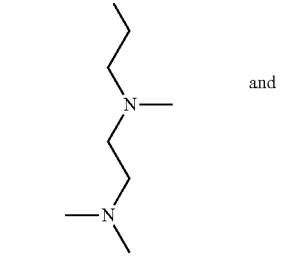

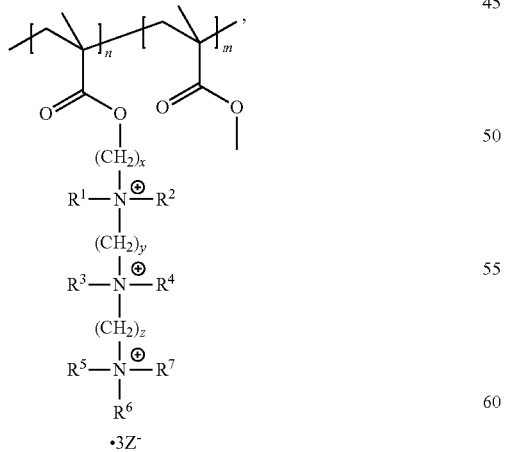

wherein $R^4$, $R^7$, Z, and x have the same meaning as in formula XXV.

In one aspect of the invention, the polymer of the invention is a multiQAC polymer based on the scaffold of a nylon polymer.

In some embodiments, the polymer is a homopolymer. As used herein, the term "homopolymer" refers to a polymer comprised of only one monomer. In other embodiments, the polymer is a copolymer. As used herein, a "copolymer" refers to a polymer comprised of at least two different monomers. In one embodiment, the copolymer is comprised of at least one styrene monomer. The copolymers may contain distinct structural units, such as alternating copolymers, periodic copolymers, block polymers, and statistical copolymers, or have monomers in a random order (random copolymer). In one embodiment, the copolymer is selected from the group consisting of statistical copolymers, random copolymers, alternating copolymers, and block copolymers. In one embodiment, the polymer may be a block polymer. As used herein, the term "block copolymer" refers to a polymer comprising two or more dissimilar polymer (e.g. homopolymer, copolymer) segments linked by covalent bonds. The union of the dissimilar segments may optionally include an intermediate non-repeat subunit, commonly referred to as a junction block. The block copolymer used in the present invention may contain any numbers of the polymeric block segments arranged in any manner (e.g. di-block, tri-block, multi-blocks, branched block, graft, linear star polymers, comb block copolymers, gradient polymers, etc.). The block copolymer may have a linear or branched structure. Non-limiting examples of applicable block copolymers are illustrated by the following formulae:

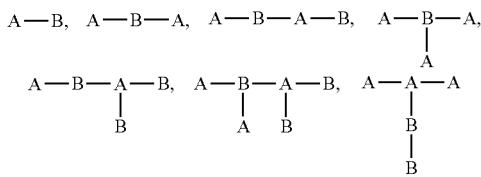

The molecular weight of these resulting polymers can be controlled as desired. In most embodiments, the molecular weight of the resulting polymers can be about 2,000 g/mol to about 1,000,000 g/mole, such as about 10,000 g/mol to about 750,000 g/mole. However, in other embodiments, the molecular weight can be larger or smaller. The molecular weight of the polymer can be determined using any method known in the art. Non-limiting examples of methods of determining molecular weight include end-group analysis ($^1$H nuclear magnetic resonance, $^1$H NMR) and gel-permeation (size exclusion) chromatography (GPC, or SEC).

The polymers of the invention can be prepared using any technique known in the art. Non-limiting examples of techniques used to prepare polymers includes reversible addition-fragmentation chain transfer polymerization (RAFT), atom transfer radical polymerization (ATRP), nitroxide-mediated polymerization (NMP), free radical polymerization, conventional ring-opening polymerization (ROP) methods such as ring-opening metathesis polymerization (ROMP), and other examples of step-growth polymerization and chain-growth polymerization.

In one embodiment, the polymer is formed by RAFT polymerization. RAFT polymerization employs a chain transfer agent that allows construction of the polymer with a well-defined molecular weight distribution and incorporates functional groups at the end of the linear polymer chains. RAFT polymerization is compatible with a wide variety of vinyl monomers.

In one embodiment, the polymer is formed by ATRP. ATRP is an example of a living free radical polymerization. The control is achieved through an activation-deactivation process, in which most of the reaction species are in dormant format, thus significantly reducing chain termination reaction. The four major components of ATRP include the monomer, initiator, ligand, and catalyst. ATRP is useful for a vinyl functional group (e.g., a (meth)acrylate group). Organic halides are particularly suitable initiators for ATRP, such as alkyl halides (e.g., alkyl bromides, alkyl chlorides, etc.). The catalyst can determine the equilibrium constant between the active and dormant species during polymerization, leading to control of the polymerization rate and the equilibrium constant. In one embodiment, the catalyst is a metal having two accessible oxidation states that are separated by one electron, and a reasonable affinity for halogens. One metal catalyst suitable for ATRP is a source of copper (I). In one embodiment, the ligands can be linear amines or pyridine-based amines.

In one embodiment, the polymer is formed by NMP. Nitroxide-mediated polymerization (NMP) is another form of controlled living polymerization utilizing a nitroxide radical, such as shown below:

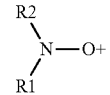

Nitroxide radical where R1 and R2 are, independently, organic groups (e.g., aryl groups such as phenyl groups, benzyl groups, etc.; alkyl groups, etc.).

The polymerization initiator, agent, or ligand used in the present invention is not especially limited. Non-limiting examples of RAFT agents include 4-cyano-4-(phenylcarbonothioylthio)-pentanoic acid, dithiocarbamates, aliphatic or aromatic dithioesters and the like. Non-limiting examples of ATRP agents include initiators such as ethyl 2-bromoisobutyrate, metal halides such as copper(I)bromide, and ligands such as 1,1,4,7,10,10-hexamethyltriethylenetetramine. Non-limiting examples of free radical initiators include persulfates, such as ammonium or alkali metal (potassium, sodium or lithium) persulfate, azo compounds such as without limitation, 2,2'-azo-bis(isobutyronitrile), 2,2'-azo-bis(2,4-dimethylvaleronitrile), and 1-t-butyl-azocyanocyclohexane), hydroperoxides such as without limitation, t-butyl hydroperoxide and cumene hydroperoxide, peroxides such as without limitation, benzoyl peroxide, caprylyl peroxide, di-t-butyl peroxide, ethyl 3,3'-di(t-butylperoxy) butyrate, ethyl 3,3'-di(t-amylperoxy) butyrate, t-amylperoxy-2-ethyl hexanoate, and t-butylperoxy pivilate, peresters such as without limitation, t-butyl peracetate, t-butyl perphthalate, and t-butyl perbenzoate, percarbonates, such as without limitation, di(1-cyano-1-methylethyl)peroxy dicarbonate, perphosphates, and the like, as well as combinations thereof. Non-limiting examples of initiators for NMP include N-tert-butyl-O-[1-[4-(chloromethyl)phenyl] ethyl]-N-(2-methyl-1-phenylpropyl)hydroxylamine, N-tert-butyl-N-(2-methyl-1-phenylpropyl)-O-(1-phenylethyl)hydroxylamine, 2,2,6,6-tetramethylpiperidine 1-oxyl (TEMPO), 4-methacryloyloxy-2,2,6,6-tetramethylpiperidine-1-oxyl (TEMPO methacrylate), and 2,2,5-trimethyl-4-phenyl-3-azahexane-3-nitroxide. Non-limiting examples of catalysts for ROP include Lewis acids such as $BF_3$ and $BF_3OEt_2$.

In one embodiment, the compositions of the present invention may further comprise crosslinking agents. Such crosslinking agents can include low molecular weight crosslinking compounds comprising ketone functionality, or another appropriate chromophore, that can absorb energy to facilitate the crosslinking of polymers of the present invention. The crosslinking agent used in the present invention is not especially limited. In one embodiment, the crosslinking agent is a photoinitiator. In another embodiment, the crosslinking agent is a thermal initiator. For non-limiting examples of thermal initiators and photoinitiators useful for crosslinking the polymers of the present invention, see The Polymer Handbook, 4th Ed., Brandrup et al., eds., John Wiley & Sons, which is incorporated by reference herein in its entirety.

Figure 15:
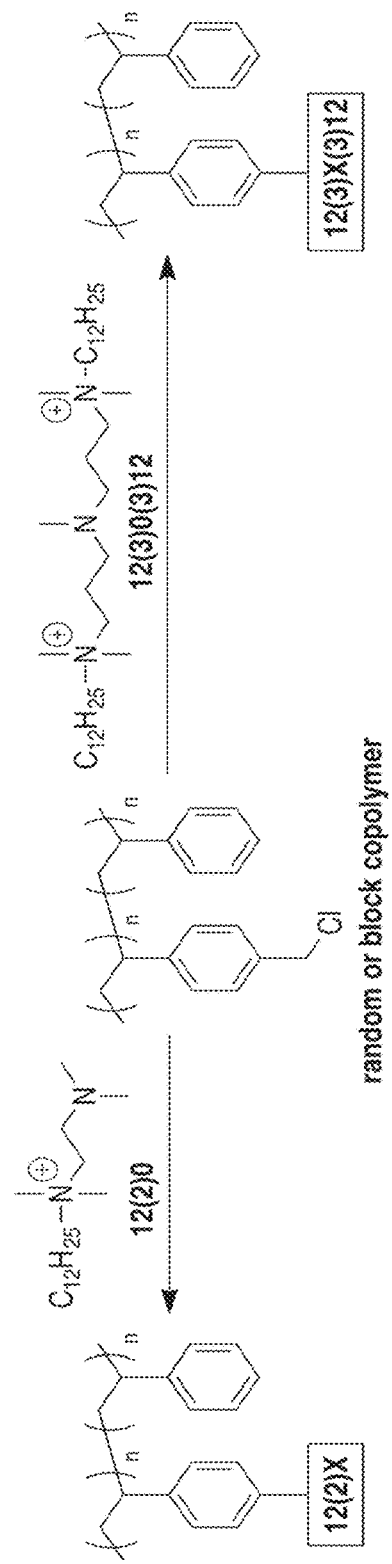
FIG. 15 is a synthetic scheme of a post-polymerization modification with bis- and tris-QACs of the present invention.

The polymers of the invention may be characterized using any methods known in the art, as would be understood by one of ordinary skill in the art. Non-limiting examples of characterization include multinuclear NMR spectroscopy, gel-permeation (size exclusion) chromatography (GPC, or SEC), infrared (IR) spectroscopy, elemental analysis, differential scanning calorimetry (DSC), thermal gravimetric analysis (TGA), and scanning electron microscopy (SEM). In one embodiment, the polymer is formed by polymerizing at least one monomer comprising the polymerizable moiety and the polycationic amphiphile. In another embodiment, the polymer is formed by first polymerizing at least one monomer comprising the polymerizable moiety but without the polycationic amphiphile, and then incorporating the polycationic amphiphile after the polymerization step. This method is known as post-polymerization modification, and may be useful to prepare homopolymers and copolymers of the invention. In a non-limiting example, the monomers 4-vinylbenzyl chloride and styrene can be polymerized to form a random copolymer, and subsequently a polycationic amphiphile can be incorporated into the polymer after the polymerization step. See FIG. 15 for a non-limiting example of post-polymerization modification with bis- and tris-QACs.

In one embodiment, the polymer is not

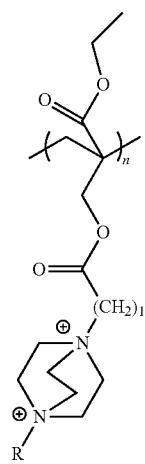

C$_4$-DAP: R = -CH$_2$(CH$_2$)$_2$CH$_3$
C$_6$-DAP: R = -CH$_2$(CH$_2$)$_4$CH$_3$

-continued

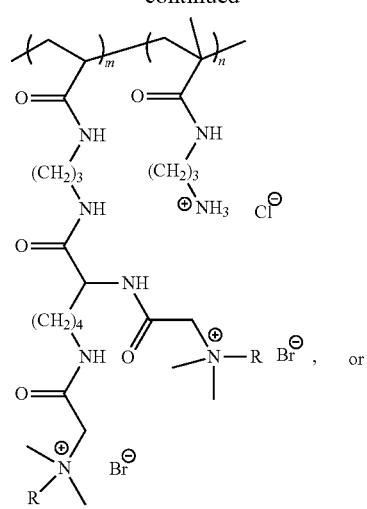

PFQ: R = C$_7$H$_{15}$
PFQ: R = C$_9$H$_{19}$

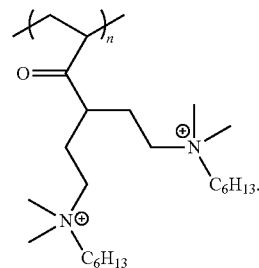

In one embodiment, the polymer is not

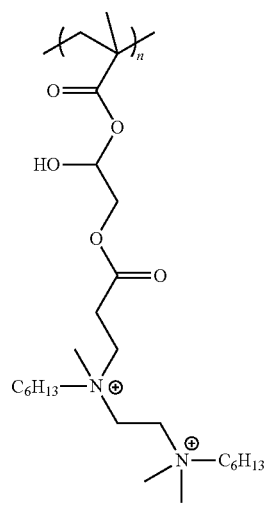

-continued

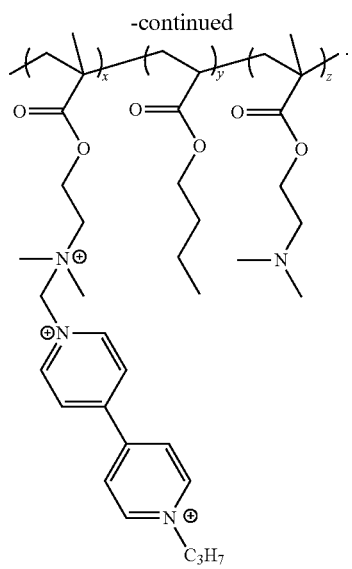

Antimicrobial Compositions

The compositions useful within the invention comprise at least one polycationic amphiphile. In one embodiment, the polycationic amphiphile is incorporated into a polymer. In one embodiment, the composition comprises at least one polymer of the invention. The compositions of the invention may be used in aqueous emulsions such as latexes, water-based paints and coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like. In one embodiment, the composition is an antimicrobial composition. In one embodiment, the composition is an antiseptic. In another embodiment, the composition is used for oil-pipeline cleaning. In another embodiment, the composition is used as an antifouling treatment for ships or other vessels used for transportation. In another embodiment, the composition is a solid-supported material.

The compositions useful within the invention may further comprise at least one additional antimicrobial agent. Non-limiting examples of the at least one additional antimicrobial agent are levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination thereof.

In one embodiment, the polycationic amphiphile and the at least one additional antimicrobial agent act synergistically in preventing, reducing or disrupting microbial growth or formation of a biofilm on a surface. A synergistic effect may be calculated, for example, using suitable methods such as, for example, the Sigmoid-Emax equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The compositions useful within the invention may further include a microbial activity indicator, which is capable of indicating the presence of microorganisms on the at least one surface.

The composition useful within the invention may further comprise an acidic solution and glycerol. The acidic solution may comprise a short chain monocarboxylic acid (e.g., formic acid, acetic acid or propionic acid). The acidic solution may further comprise ortho-phosphoric acid. In one embodiment, the acidic solution further comprises a salt, such as potassium chloride.

In one preferred embodiment, the polycationic amphiphile is present in the composition in an amount sufficient to penetrate or disrupt a biofilm and allow access of the polycationic amphiphile, and/or the at one additional antimicrobial agent to the biofilm-embedded microorganism, thereby facilitating the removal of at least a portion of the biofilm-embedded microorganisms from the at least one surface. In another preferred embodiment, the polycationic amphiphile is present in the composition in an amount sufficient to inhibit the growth or proliferation of microorganisms on the at least one surface, thereby facilitating the removal of at least a portion of the biofilm-embedded microorganisms from such surface. The polycationic amphiphile may constitute about 0.01% to about 100% (by weight) of the composition, about 0.1% to about 60% (by weight) of the composition, or about 0.5% to about 30% (by weight) of the composition.

The composition of the invention may further comprise a base material and a biofilm-penetrating agent. Non-limiting examples of suitable base materials include, but are not limited to, buffer solutions, phosphate buffered saline, saline, water, polyvinyl, polyethylene, polyurethane, polypropylene, polysiloxane (e.g., silicone elastomers and silicone adhesives), polycarboxylic acids, (e.g., polyacrylic acid, polymethacrylic acid, polymaleic acid, poly(maleic acid monoester), polyaspartic acid, polyglutamic acid, aginic acid or pectimic acid), polycarboxylic acid anhydrides (e.g., polymaleic anhydride, polymethacrylic anhydride or poly acrylic acid anhydride), polyamines, polyamine ions (e.g., polyethylene imine, polyvinylarnine, polylysine, poly-(dialkylamineoethyl methacrylate), poly(d-ialkylaminomethyl styrene) or poly-(vinylpyridine)), poly ammonium ions (e.g., poly-(2-methacryloxyethyl trialkyl ammonium ion), poly-(vinylbenzyl trialkyl ammonium ions), poly-(N-alkylypyridinium ion) or poly(dialkyloctamethylene ammonium ion) and polysulfonates (e.g. poly-(vinylsulfonate) or poly-(styrene sulfonate)), collodion, nylon, rubber, plastic, polyesters, Gortex® (polytetrafluoroethylene), Dacron® (polyethylene tetraphthalate), Teflon® polytetrafluoroethylene), latex and derivatives thereof, elastomers and Dacron® sealed with gelatin, collagen or albumin, cyanoacrylates, methacrylates, papers with porous barrier films, adhesives (e.g., hot melt adhesives, solvent based adhesives, and adhesive hydrogels), fabrics, and crosslinked and non-crosslinked hydrogels, and any other polymeric materials that facilitate dispersion of the biofilm-penetrating agent and adhesion of the biofilm-penetrating coating to the at least one surface. Linear copolymers, cross-linked copolymers, graft polymers, and block polymers, containing monomers as constituents of the above exemplified polymers may also be used.

In the case of internal or external use of the biofilm-penetrating composition on humans or animals, the polycationic amphiphile and the base material should be biocompatible with the human beings or animals on which body surface the composition is applied.

The invention further includes a coated surface, which includes a composition comprising at least one polycationic amphiphile applied to the surface. In one embodiment, the composition comprises at least one polymer of the invention. In one embodiment, the surface is coated with a polymer of the invention. In one embodiment, the surface is selected from the group consisting of a glass surface, a metal surface, a paper surface, or a polymer surface. In one embodiment, a surface may be functionalized and coated with multicationic QACs. Such surfaces are useful in medical settings (e.g., antimicrobial surfaces) and antiseptic-coated indwelling devices (e.g., antimicrobial plastics, stents, joint replacements, and the like). The invention further includes a film or coating comprising at least one polycationic amphiphile of the invention. The composition may be applied to the desired surface in any suitable manner, as described herein or as known to those skilled in the art. In one embodiment, a septum, or adhesive layer, is made of a breathable material that has small enough porosity to allow moisture to pass, but functions as a barrier to microorganisms thereby facilitating a lower incidence of microorganism colonization and resulting contamination or infection. The adhesive layer may also include a layer of gauze to facilitate a lower incidence of microorganism colonization and resulting contamination or infection.

Medical Devices

The invention contemplates applying to or coating medical devices with the compositions useful within the invention. Non-limiting examples of medical devices include disposable or permanent catheters, (e.g., central venous catheters, dialysis catheters, long-term tunneled central venous catheters, short-term central venous catheters, arterial catheters, peripherally inserted central catheters, peripheral venous catheters, pulmonary artery Swan-Ganz catheters, urinary catheters, and peritoneal catheters, drainage catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings (e.g., intravenous tubes, breathing tubes, dental water lines, dental drain tubes, and feeding tubes), fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device that may be inserted or implanted into a human being or other animal, or placed at the insertion or implantation site such as the skin near the insertion or implantation site, and that include at least one surface which is susceptible to colonization by microorganisms and/or biofilm-embedded microorganisms. Also contemplated within the invention is any other surface that may be desired or necessary to prevent microorganisms and/or biofilm-embedded microorganisms from growing or proliferating on at least one surface of the medical device, or to remove or clean microorganisms and/or biofilm-embedded microorganisms from the at least one surface of the medical device, such as the surfaces of equipment in operating rooms, emergency rooms, hospital rooms, clinics, and bathrooms. In one specific embodiment, the composition is integrated into an adhesive, such as tape, thereby providing an adhesive that may prevent or reduce growth or proliferation of microorganisms and/or biofilm embedded-microorganisms on at least one surface of the adhesive.

Implantable medical devices include orthopedic implants that may be inspected for contamination or infection by microorganisms and/or biofilm-embedded microorganisms using endoscopy. Insertable medical devices include catheters and shunts that can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex® (polytetrafluoroethylene), Dacron® (polyethylene tetraphthalate), Teflon® (polytetrafluoroethylene), latex, elastomers and Dacron® sealed with gelatin, collagen or albumin, and derivatives or combinations thereof. The medical devices include at least one surface for applying the biofilm-penetrating composition. In one embodiment, the biofilm-penetrating composition is applied to the entire medical device.

Methods

The invention includes a method of preventing or reducing the growth or proliferation of microorganisms and/or biofilm-embedded microorganisms on at least one surface. The method includes the steps of: providing at least one surface; providing a composition comprising a polycationic amphiphile, and applying the composition to the at least one surface in an amount sufficient to prevent or reduce the growth or proliferation of microorganisms or biofilm-embedded microorganisms on the at least one surface. In one embodiment, the polycationic amphiphile is incorporated into a polymer. In one embodiment, the composition comprises a polymer of the invention. In one embodiment, the surface is a subject's body. In another embodiment, the surface is at least one surface of a medical device. In another embodiment, the surface is a solid surface. In another embodiment, the surface is selected from the group consisting of a glass surface, a metal surface, a paper surface, or a polymer surface.

In one embodiment, the composition further comprises a base material. In another embodiment, preparation of the composition comprises contacting the polycationic amphiphile and the base material at room temperature and mixing the resulting mixture for a time sufficient to evenly disperse the polycationic amphiphile in the composition prior to contacting the surface with the composition. The concentration of polycationic amphiphile in the composition may be varied as desired or necessary to decrease the amount of time the composition is in contact with the surface. These variations in concentration of polycationic amphiphile are easily determined by persons skilled in the art. In another embodiment, at least one surface is contacted with the composition under conditions wherein the composition covers at least part of the surface.

In one embodiment, the composition further comprises an organic solvent or an alkalinizing agent, either of which enhances the reactivity of the surface of the medical device with the composition. In another embodiment, the organic solvent and/or alkalinizing agent facilitates adhesion of the composition to the at least one surface.

The invention also includes a method of removing at least a portion of or reducing the number of microorganisms and/or biofilm embedded microorganisms attached to at least one surface. The method comprises the steps of: providing at least one surface, wherein the at least one surface comprises microorganisms and/or biofilm-embedded microorganisms attached thereto; and contacting the least one surface with a composition comprising at least one polycationic amphiphile, whereby at least a portion of the microorganisms and/or biofilm embedded microorganisms are removed from the at least one surface or the number of microorganisms and/or biofilm embedded microorganisms attached to the at least one surface is reduced. The contact between the at least one surface and the composition should last for a period of time sufficient to remove at least a portion of the microorganisms and/or biofilm-embedded microorganisms from at least one surface or reduce the number of microorganisms and/or biofilm embedded microorganisms attached to the at least one surface. In one embodiment, the polycationic amphiphile is incorporated into a polymer. In one embodiment, the composition comprises a polymer of the invention. In one embodiment, the surface is a subject's body. In another embodiment, the surface is at least one surface of a medical device. In another embodiment, the surface is a solid surface. In another embodiment, the surface is selected from the group consisting of a glass surface, a metal surface, a paper surface, or a polymer surface.

Pharmaceutical Compositions and Formulations

The invention also encompasses the use of pharmaceutical compositions comprising a polycationic amphiphile, for inhibiting or disrupting microorganism growth or the formation of biofilms on a surface of a subject's body. Such a pharmaceutical composition may consist of the polycationic amphiphile in a form suitable for administration to a subject. The polycationic amphiphile may be present in the pharmaceutical composition in the form of a physiologically acceptable salt, such as in combination with a physiologically acceptable cation, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, topical, transdermal, ophthalmic, intrathecal or another route of administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin.

Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Administration/Dosing

The regimen of administration may affect what constitutes an effective amount. The therapeutic formulations may be administered to the patient either prior to or after the onset of pathogenic colonization, biofilm formation, and/or infection in a patient. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to prevent, reduce or disrupt pathogenic colonization, biofilm formation, and/or infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing control disorders in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

In one embodiment, the present invention is directed to a packaged pharmaceutical composition comprising a container holding a therapeutically effective amount of a compound of the invention, alone or in combination with a second pharmaceutical agent; and instructions for using the compound to prevent or reduce the growth or proliferation of microorganisms or biofilm-embedded microorganisms on at least one surface of a medical device or a subject's body.

Routes of Administration

Routes of administration of any of the compositions of the invention include rectal, transdermal, transmucosal (e.g., sublingual, lingual, (trans)buccal, (trans)urethral, vaginal (e.g., trans- and perivaginally), (trans)rectal, intravesical, and topical administration.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, gels, lotions, oil-in-water or water-in-oil emulsions such as creams, ointments or pastes, and solutions or suspensions. Topically administrable formulations may, for example, comprise from about 1% to about 10% (w/v) active ingredient in a solvent, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide (DMSO), and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1: Identification of QACs with Antimicrobial Activity

Preliminary studies have resulted in the synthesis and evaluation of ~140 unique bioactive amphiphilic compounds, providing a wealth of SAR information. A dataset for toxicity minimization and biofilm eradication ability has also been developed. In order to extend the SAR information, alternative QAC architectures, particularly those that include additional cationic residues, are developed.

Figure 3:
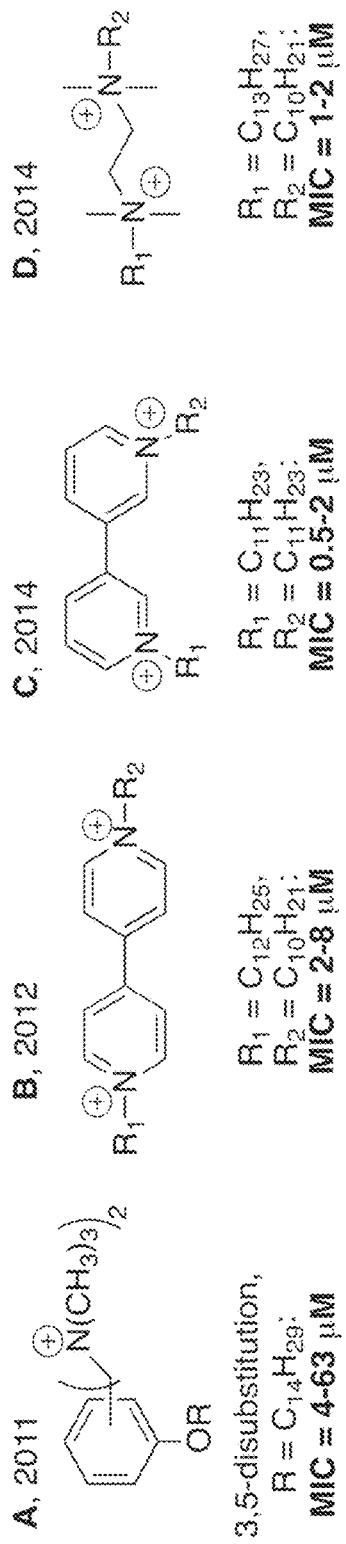
FIG. 3 is an illustration of the generic structures of QAC compounds (~105 compounds) and their associated MIC values. Bromide counterions are omitted for clarity.

Compounds with increasing efficacy in combating microbes and of decreasing complexity have been developed, as illustrated in FIG. 3 (general structures A-D). QACs have been developed based on an all-carbon core (A), bipyridine derivatives of both 4,4' (B) and other geometries (C), and an inexpensive TMEDA core (D). See LaDow et al., 2011, Eur. J. Med. Chem. 46:4219; Black et al., 2014, Bioorg. Med. Chem. Lett. 24:99; Ator et al., 2014, Bioorg. Med. Chem. Lett. 3706-3709; and Grenie et al., 2012, Bioorg. Med. Chem. Lett. 22, 4055, each of which is incorporated by reference in its entirety herein. Activity of the compounds has been increased (shown as decreasing MIC values in FIG. 2) in successive generations of structures, in addition to ease of preparation of the compounds, as synthetic procedures rely on mono- or bis-alkylation reactions, followed by filtration and recrystallization. These first-generation structures were composed of one or two cationic moieties, with an equal number of non-polar groups, designated R. Optimal alkyl chain length hovered around 12 carbons, depending on the system, with modest levels of asymmetry often being advantageous.

Figure 4:
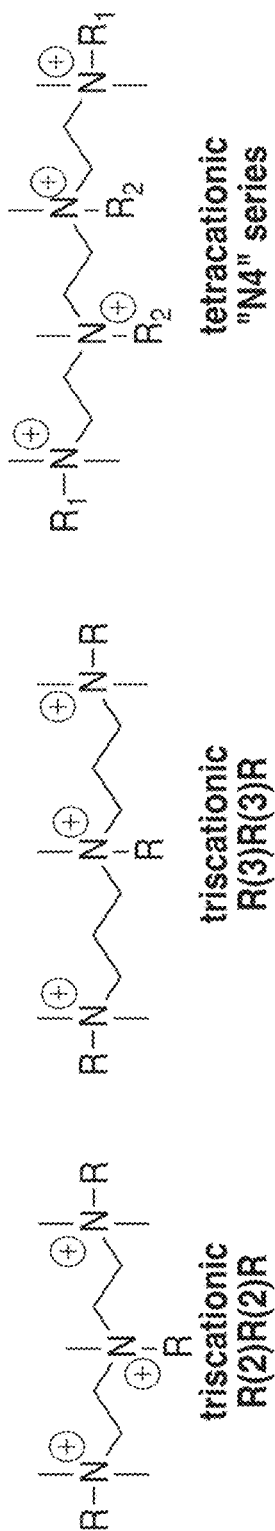
FIG. 4 is an illustration of the generic structures of QAC compounds (~35 compounds) and their associated MIC values. Compound 12(3)12(3)12 exhibited an MIC=0.5-2 µM and N4, $R_1$=$C_{12}H_{25}$ and $R_2$=allyl exhibited an MIC=1-2 µM. Numbers in parentheses reflect linker lengths; additional numbers denote alkyl substituents. "N4" is the tetraamine core shown.

The effect of additional cationic moieties on bioactivity was investigated (FIG. 4). One- or two-step synthetic routes afforded multiQACs with micromolar MICs (Table 1).

TABLE 1

Highlights of antimicrobial and antibiofilm activity

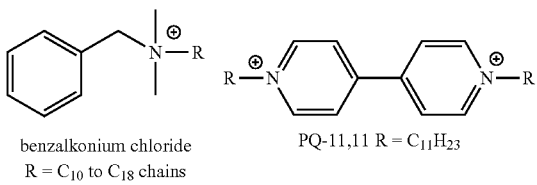

benzalkonium chloride
R = $C_{10}$ to $C_{18}$ chains

PQ-11,11 R = $C_{11}H_{23}$

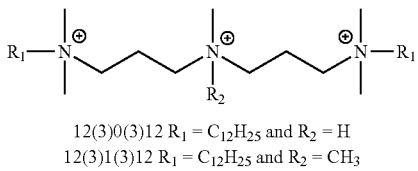

12(3)0(3)12 $R_1$ = $C_{12}H_{25}$ and $R_2$ = H
12(3)1(3)12 $R_1$ = $C_{12}H_{25}$ and $R_2$ = $CH_3$

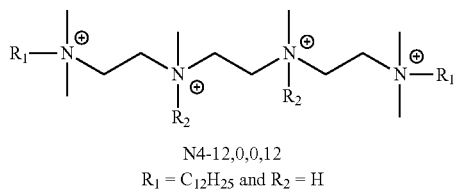

N4-12,0,0,12
$R_1$ = $C_{12}H_{25}$ and $R_2$ = H

| Antiseptic | MIC v SA | MIC v EF | MIC v EC | MIC v PA | MBEC v SA | MBEC v EF |
|---|---|---|---|---|---|---|
| Benzalkonium chloride | 8 | 8 | 32 | 63 | 200 | 200 |
| PQ-11,11 | 1 | 1 | 1 | 4 | 50 | 50 |
| 12(3)0(3)12 | 1 | 2 | 1 | 4 | 37.5 | 50 |
| 12(3)1(3)12 | 1 | 2 | 2 | 8 | 50 | 50 |
| N4-12,0,0,12 | 1 | 1 | 1 | 2 | 50 | 75 |

Values in micromolar.
MIC = minimum inhibitory concentration;
MBEC = minimum biofilm eradication concentration;
SA = *Staphylococcus aureus*;
EF = *Enterococcus faecalis*;
EC = *Escherichia coli*;
PA = *Pseudomonas aeruginosa*.

After accounting for reagents, solvents, and percent yields (which average ~70% overall for these QACs), these potent polycationic amphiphiles were prepared at relatively low cost. Furthermore, to highlight the operational simplicity of these procedures, essentially all of these compounds can be prepared as crystalline solids in ~24-36 hours in the laboratory, since the synthetic route utilizes substitution reactions followed by recrystallization.

To further investigate the utility of these QACs, their activity against established biofilms, which would require the ability to kill bacteria within this protective state. It was observed that these compounds displayed the strongest biofilm eradication values reported to date, despite their relative simplicity (Jennings et al., 2014, ChemBioChem: 2211-2215, which is incorporated by reference herein in its entirety). As examples, the biofilm eradication concentration of four of the QACs, three of which were prepared in one high-yielding step, was ~4× lower than that of benzalkonium chloride. Highlights of these results appear in Table 1.

In order to assess whether these compounds showed susceptibility to QAC-resistance genes, a qac-bearing MRSA strain (community-acquired strain USA300-0114) was obtained and compared to a non-resistant *S. aureus* strain (SH1000) against these compounds and commercially available QACs. As shown in Table 2, two commercially available QACs showed significantly reduced activity (4-32-fold) against the MRSA strain tested, yet these multicationic compounds showed no decline in activity. These compounds also demonstrated superior eradication of pre-formed MRSA biofilms. In a related experiment, it was shown that the *S. aureus* strain SH1000 did not develop resistance to triscationic compound 12(3)2(3)12 over the course of a 3-week sublethal dosing regimen. Although not wishing to be bound by any particular theory, these results suggest a potentially unique mode of antimicrobial activity. It was observed that QACs with decyl chains, which have more modest activity, see a significant drop in toxicity. Similar effects were seen for incorporated benzyl groups. When presenting a therapeutic index (TI), or ratio of $Lysis_{20}$/MIC, a distinct advantage for multiQACs over commercial QACs was observed, whose TI sharply fell. Toxicity assessments, determined as a $Lysis_{20}$ on mammalian red blood cells, initially suggested a roughly uniform dataset—for these compounds as well as commercially available QACs, lytic ability generally paralleled antimicrobial activity. Decyl or benzyl substituents led to decreased toxicity. When presenting a therapeutic index (TI), or ratio of Lysis20/MIC wherein higher values are advantageous, a distinct advantage was observed for multiQACs over commercial QACs, whose TI sharply fell against resistant organisms. At concentrations capable of killing planktonic MRSA or disrupting MRSA biofilms, these compounds show significantly less toxicity than commercial alternatives.

TABLE 2

Highlights of antimicrobial activity against resistant and non-resistant SA and biofilms, and toxicity

| Compound | # Cations | MIC v SA | MIC v MRSA | MBEC v MRSA | $Lysis_{20}$ | TI SA | TI MRSA |
|---|---|---|---|---|---|---|---|
| Benzalkonium chloride | 1 | 8 | 32 | >200 | 63 | 8 | 2 |
| Cetyl pyridinium chloride | 1 | 0.5 | 16 | 200 | 8 | 16 | 0.5 |
| 10(3)2(3)10 | 3 | 2 | 2 | 150 | 32 | 16 | 16 |
| 12(3)2(3)12 | 3 | 0.5 | 0.5 | 100 | 8 | 16 | 16 |
| 12(3)4(3)12 | 3 | 1 | 0.5 | 75 | 8 | 8 | 16 |
| N4-12,allyl,allyl,12 | 4 | 1 | 1 | 150 | 8 | 8 | 8 |

Values given in micromolar.
MIC = minimum inhibitory concentration;
SA = *Staphylococcus aureus*.
$Lysis_{20}$ = concentration at which 20% of RBCs are lysed.
TI = therapeutic index against MRSA 1, expressed as $Lysis_{20}$/MIC.

Figure 5:
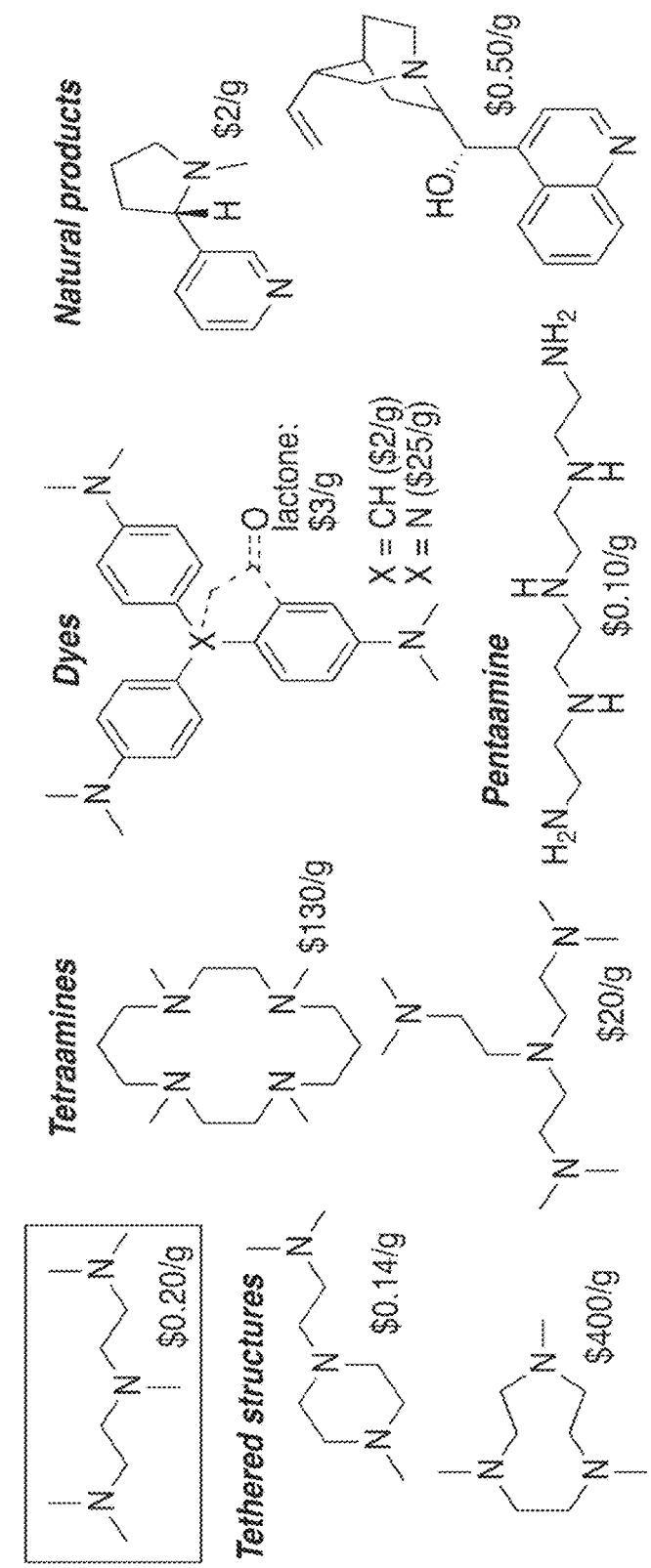
FIG. 5 is an illustration of core structures for amphiphile constructions, with associated costs of each core.
Figure 6:
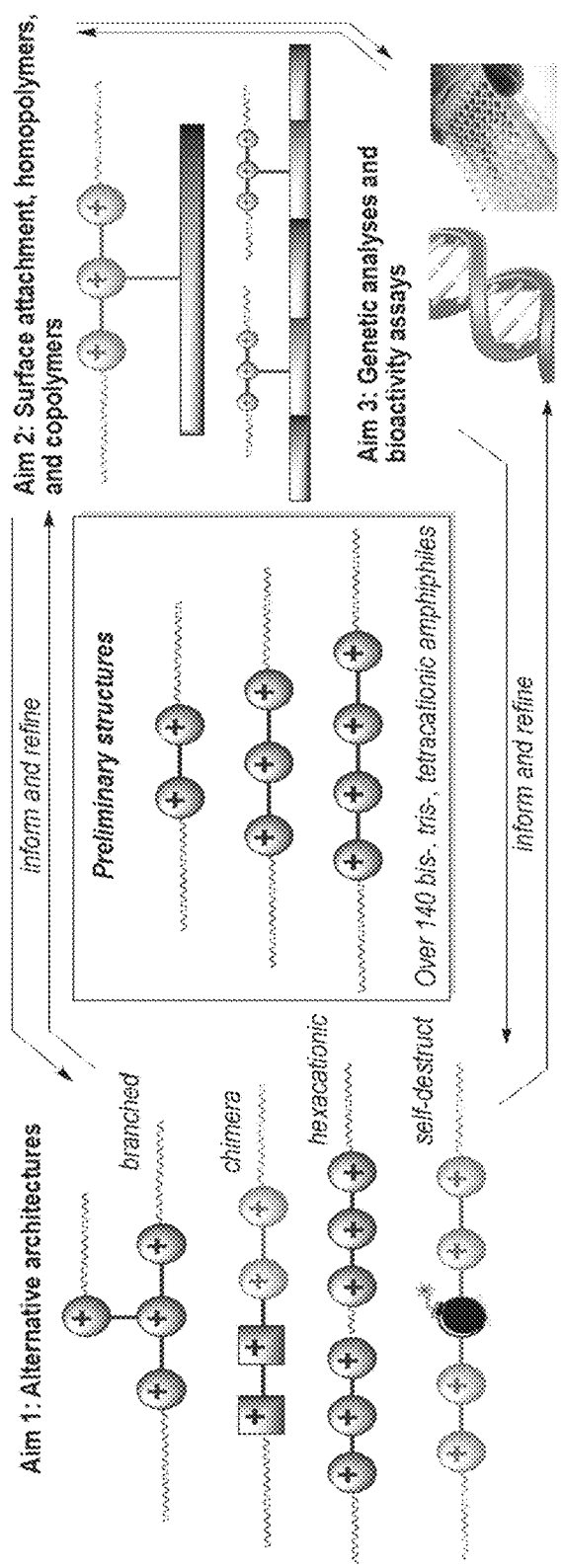
FIG. 6 is an illustration of the relationship between architectures of polycationic amphiphiles, surface attachment, homopolymers, and copolymers, and genetic analyses and bioactivity assays.

Example 2: Synthesis of Alternative QAC Architectures Including Branched, Chimera, and Self-Destruct QACs Architectural Diversification It has been observed that the most facile construction of polycationic amphiphiles can be dictated by the availability of inexpensive "core" structures, which bear multiple amines. While the tris- and tetraamine cores have been successfully employed, alternative cores are explored, such as those identified in FIG. 5. Synthetic methods are improved in regard to yield, operational simplicity, and ease of structural diversification. Dodecyl chains are incorporated in the QACs, though alternative groups suspected to minimize RBC toxicity (i.e., decyl, benzyl) are also incorporated. Exhaustive dodecyl substitution is first attempted, with NMR and mass spectrometry confirming the level of substitution from the reagent/solvent combination. To date, no bacterial resistance has been observed for triscationic QAC species (Mitchell et al., 1998, Antimicrob. Agents Chemother. 42:475-477). Therefore, the deployment of alternate amphiphilic antimicrobial structures may be useful to counter resistant bacteria (FIG. 6).

Chimera

Figure 7:
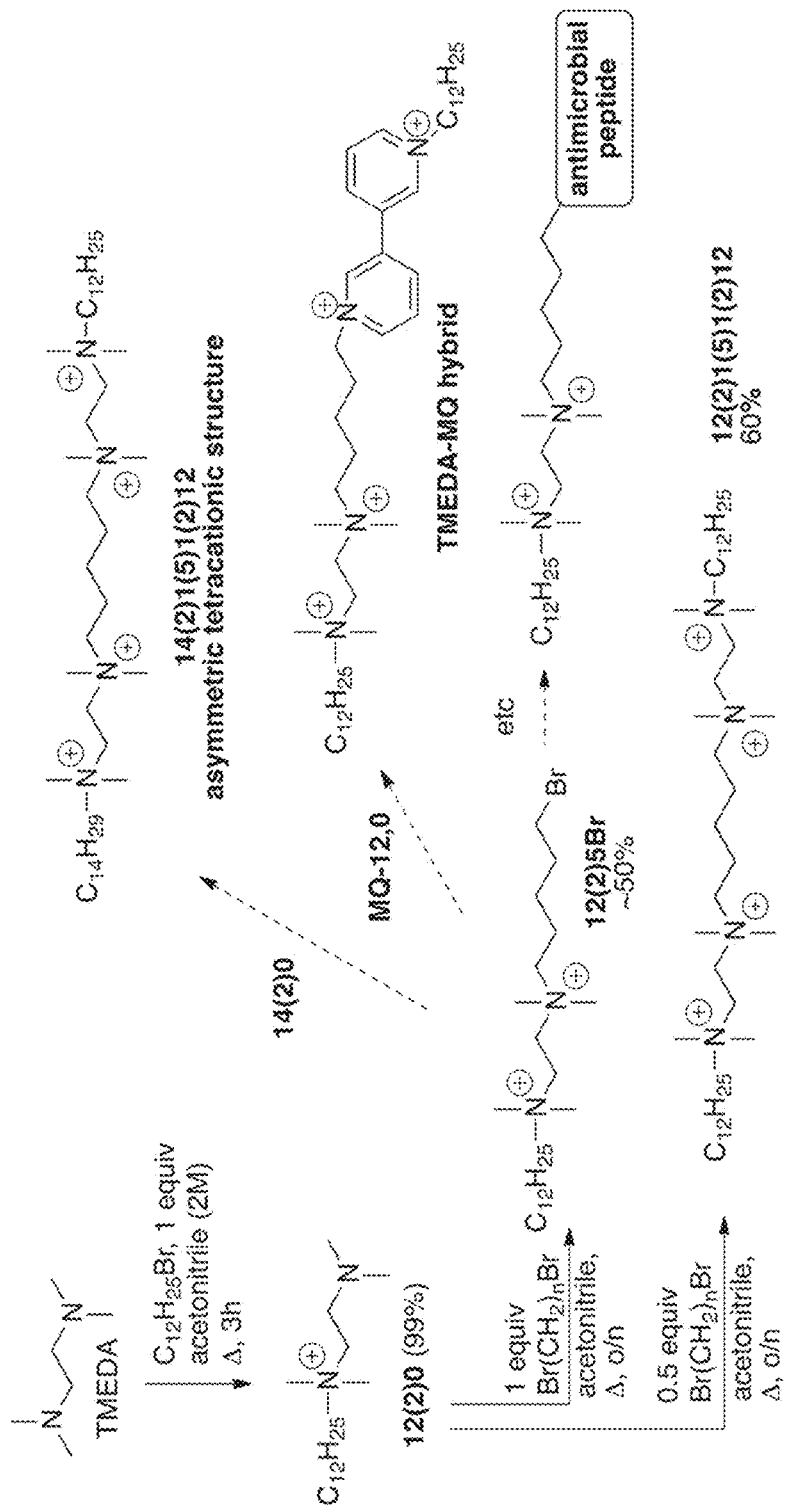
FIG. 7 is a synthetic scheme of a method for the preparation of chimeric QACs of the present invention.

The construction of complex targets from few simple synthetic steps is a hallmark of this synthetic program. Widely divergent compounds under a "chimera" label are prepared, bringing together hybrids of previously prepared compounds into larger and more complex structures. As shown in FIG. 7, standard group precursors such as 12,2,0 (prepared in 99% from TMEDA) can be monoalkylated with an α,ω-dibromide (1 equiv) to give a biscationic amphiphile with an additional handle (12,2,5Br, ~50%, unoptimized). Alternatively, incorporation of 0.5 equiv of this dibromide furnished the symmetrical tetracationic species 12,2,1,5,1, 2,12 in 60% yield. Subsequent exposure to other monocationic, amine-bearing structures provides "chimera" structures with 4 cations, but with dissimilar substituents. Markedly different moieties, such as antimicrobial peptides, sugars, iron siderophores, and other nucleophilic residues, are also incorporated into the chimeric compounds.

Figure 8:
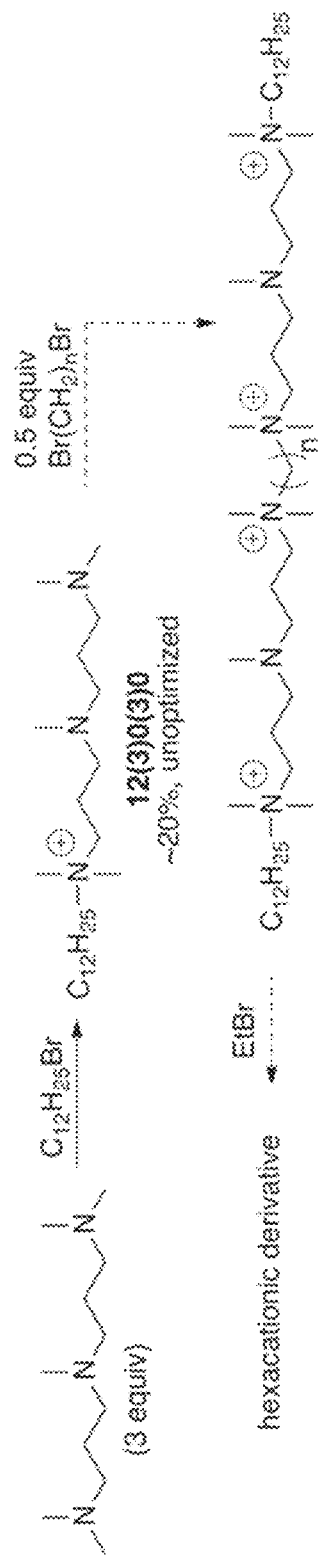
FIG. 8 is a synthetic scheme of a method for the preparation of tetra- and hexacationic QACs of the present invention.

Similar strategies are used to prepare hexacationic structures, for example, utilizing the synthetic route shown in FIG. 8. To date 12(3)0(3)0 has been prepared in modest yields; while it is the major product of alkylation, it is difficult to separate it from the bis-alkylated derivative 12(3)0(3)12. Subsequent preferential reaction at the terminal amine is expected, resulting in the tetra-QAC shown (which itself may be protonated in water), which forms a hexacationic compound upon a final alkylation reaction. It is noted that tetracationic species prepared have been soluble in CD₃OD for NMR characterization (Paniak et al., 2014, Bioorg. Med. Chem. Lett. 24:5824-5828), suggesting that polar protic solvents could be employed for final alkylations to prepare multiQACs.

Self-Destruct Compounds

Figure 9:
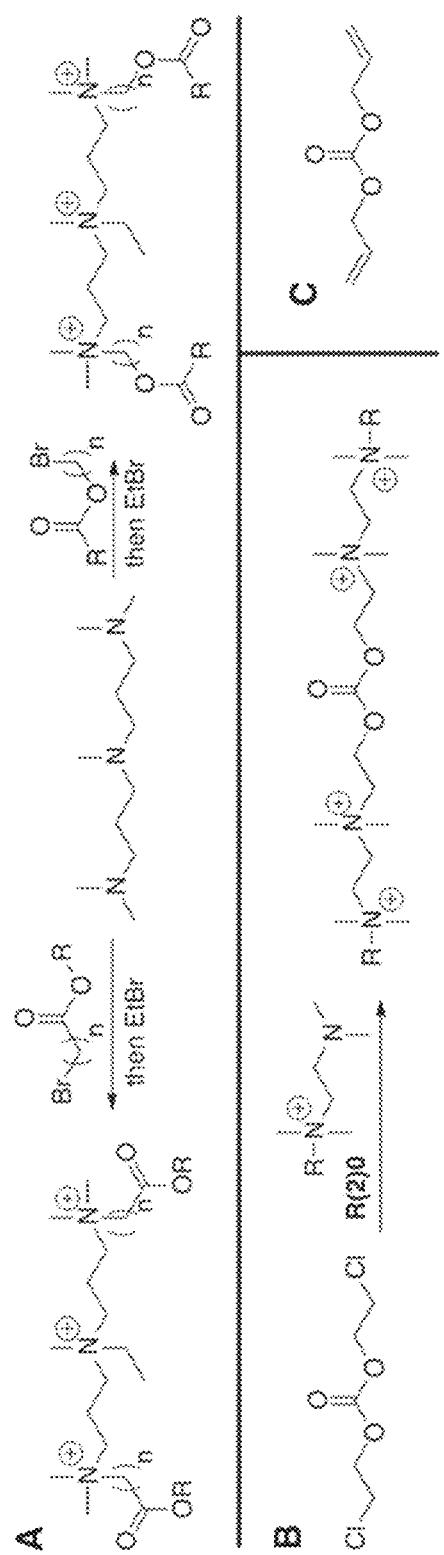
FIG. 9 is a synthetic scheme of a method for the preparation of "self-destruct" compounds of the present invention.

For antimicrobial amphiphiles to have any potential for commercial application, environmental concerns must be addressed. Specifically, it is advantageous to design chemical instability into compounds of the invention, so as to diminish their longevity after use in a hospital/household setting. Not only does this reflect ecological caution, but it also minimizes the prolonged environmental sub-MIC exposure of these compounds to bacteria, which could lead towards resistance. In this vein, analogs of alkyl chains are prepared wherein esters have been incorporated into the compounds (FIG. 9A). Additionally, tetracationic structures are developed that, over time, decompose to bis-cationic amphiphiles (FIG. 9B), whose resistance may already be unstoppable. Starting with the known dichlorocarbonate (Pierce and Adams, 1923, J. Am. Chem. Soc., 45:790-795), alkylation with a monocationic species forms a tetracationic carbonate structure (FIG. 9B). More robust carbamate analogs, as well as alkyl bromide precursors, are also be synthesized. Alternatively, diallyl carbonates (FIG. 9C) are utilized via olefin metathesis to produce QAC carbonates with an even shorter lifetime, such as allylated triscationic QAC structures. Compounds such as these are the first examples of QACs with a finite lifetime.

Synthesis of Self-Destruct Compounds

Figure 58:
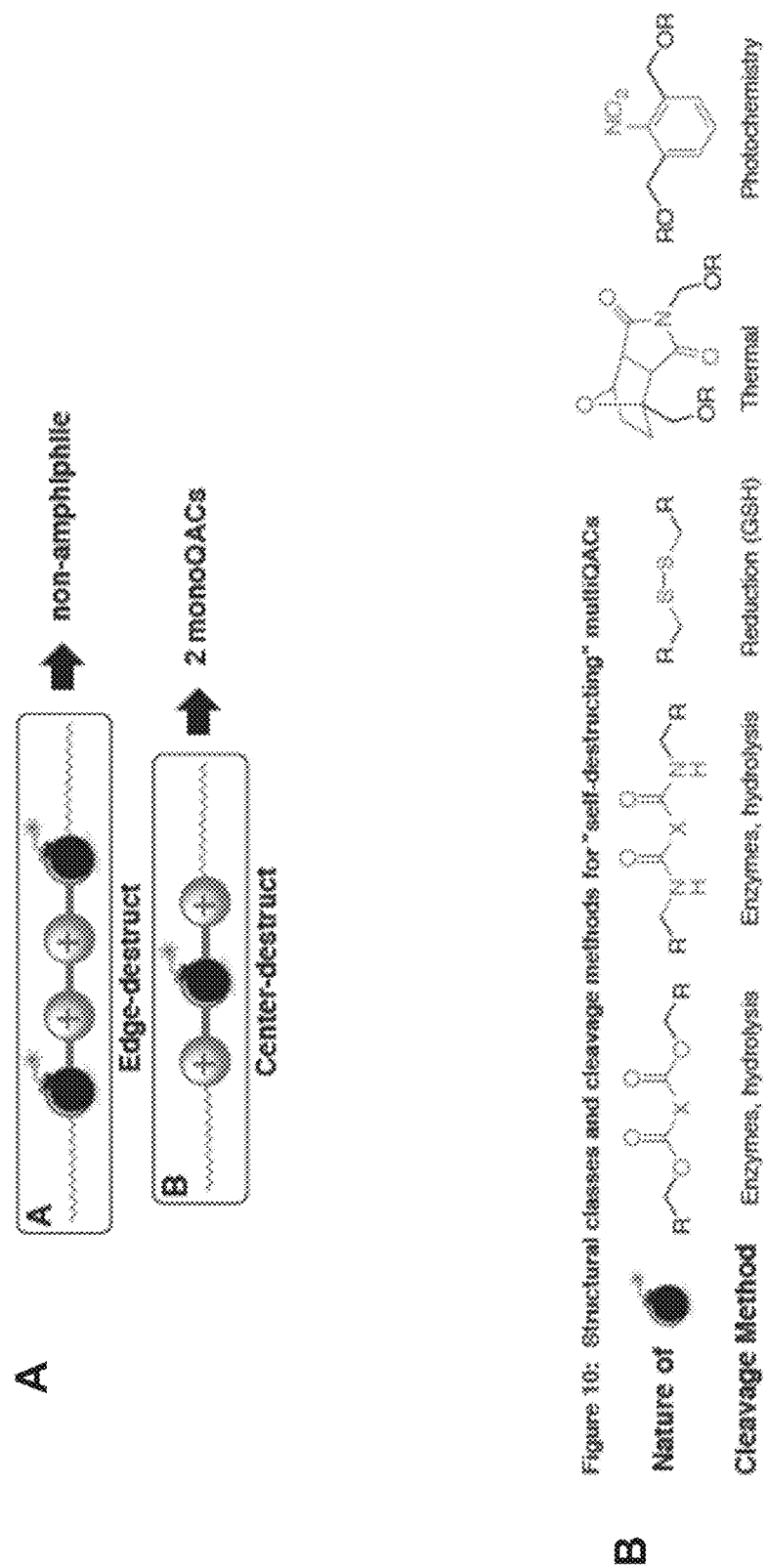
FIG. 58, comprising

Designing chemical instability into the compounds, so as to diminish their longevity after use in a hospital or household setting, is advantageous. Not only does this reflect ecological caution, but it also minimizes the prolonged environmental sub-MIC exposure of the compounds to bacteria, which could lead to resistance. While it is not known what mechanisms of resistance might occur when bacteria have the opportunity to face multiQACs over significant periods of time, such concerns could be addressed by designed decomposition. Thus, ~300 unique bioactive amphiphilic compounds were synthesized and evaluated, providing a wealth of SAR information. Two strategies of self-destructing QACs can be envisioned depending on the location of the cleavable group (FIG. 58A). The term "Edge-destruct" is used herein to describe structures that, upon decomposition, separate the polar head(s) from the nonpolar tails, rendering the compound no longer amphiphilic, which is desirable. Alternatively, "center-destruct" compounds may be envisioned that could split, for example, a bisQAC to two monoQACs. This would lead to decomposition products that would be both weaker in bioactivity and subject to existing bacterial resistance. FIG. 58B provides an overview of the nature of potential cleavable groups, including esters, amides, disulfides, Diels-Alder adducts, and o-nitrobenzyl groups.

Hydrolyzable Groups

Figure 59:
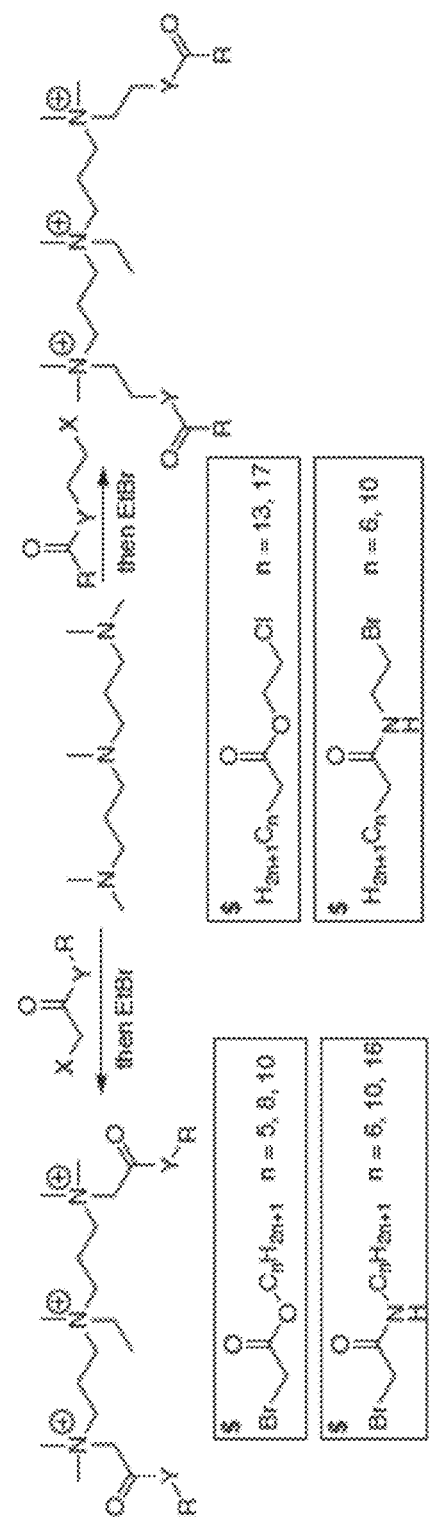
FIG. 59 is a scheme depicting a preparation of "self-destruct" compounds of the present invention, and commercially available precursors ($).

Analogs of QACs wherein alkyl chains have been edited to include simple hydrolyzable groups are prepared (FIG. 59). This route represents an attractive starting point, as any of the scaffolds can be rapidly derivatized. Furthermore, a wide variety of halogenated long-chained esters and amides are commercially available at reasonable cost (~$10/g) for preliminary investigations. Non-limiting examples of structures are shown in FIG. 59, depicted in reactions with versatile trisamine 2,6,10-trimethyl-2,6,10-triazaundecane; a variety of the esters and amides in are purchased and subjected to the standard alkylation conditions described herein. Addition of iodide is considered in order to enhance selectivity of SN2 alkylation over reaction with the ester or amide. A small library of esters and amides are prepared, with the groups facing "either direction" as indicated by the left or right side of FIG. 59. Such an approach provides for flexibility; for example, rapid enzymatic hydrolysis of esters could be avoided by installation of amide groups, and tertiary amides are available to represent even more hydrolytically-resistant structures. It should be noted that, to diminish cost and/or diversify our structures, the synthesis of the boxed alkyl halides (or analogs thereof) is relatively straightforward, and can be employed after initial bioactivity and stability screenings.

Figure 60:
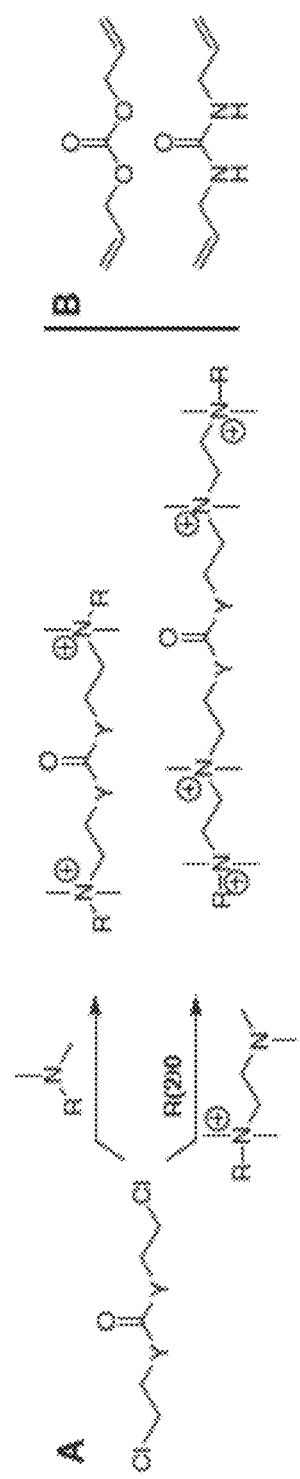
FIG. 60, comprising

All compounds described in FIG. 59 may be characterized as "Edge-destruct", as they could decompose into non-amphiphilic compounds upon complete hydrolysis. Alternatively, multicationic structures are designed such that, over time, they decompose into amphiphiles with fewer cations, to which resistance is already established. A rather straightforward approach to this plan begins with bis-2-chloroethyl carbonate or bis-2-chloroethyl urea, both commercially available, as shown in FIG. 60A (Pierce and Adams, 1945, J. Am. Chem. Soc. 45:790-795); alkylation with a tertiary amine or monocationic species rapidly furnishes a multicationic carbonate or urea structure. Alternatively, commercially available diallyl carbonate or diallyl urea (FIG. 60B) provide a launch point to shorter-lived QAC carbonates or ureas via olefin metathesis; importantly, a number of allylated QAC structures that can serve as partners have already been prepared. Click chemistry on the related alkynes may also be used.

Self-Destruct Compounds: Acid- and Reductive-Labile Groups

Figure 61:
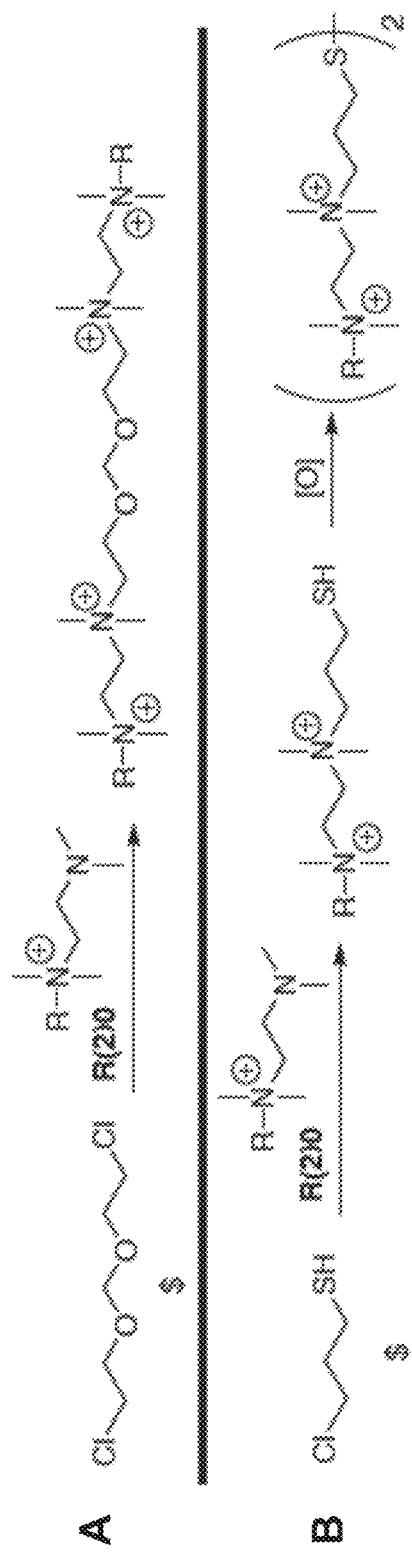
FIG. 61, comprising

While the preparation of the above-mentioned esters, amides, carbonates, and ureas are likely to be quite straightforward, QACs with other types of labile groups are examined. To explore simple acid-catalyzed hydrolysis as a decomposition pathway, derivatives of acetal-based dichloride shown in FIG. 61A are prepared. Such structures could differentiate themselves from the ester/amide moieties above, as they are stable to basic and nucleophilic conditions. In order to invoke a reductive manner of fragmentation (FIG. 61B), the installation of a pendant thiol group is explored; one related thiol, 12(3)11-SH(3)12, was previously prepared in high yield in a previous report (Jennings et al., 2015, ACS Inf. Dis. 1:288-303, which is herein incorporated by reference in its entirety). Oxidation leads to a dimeric species that is reduced for fragmentation under mild conditions, such as glutathione.

Self-Destruct Compounds: Photochemically-Labile and Other Groups

Figure 62:
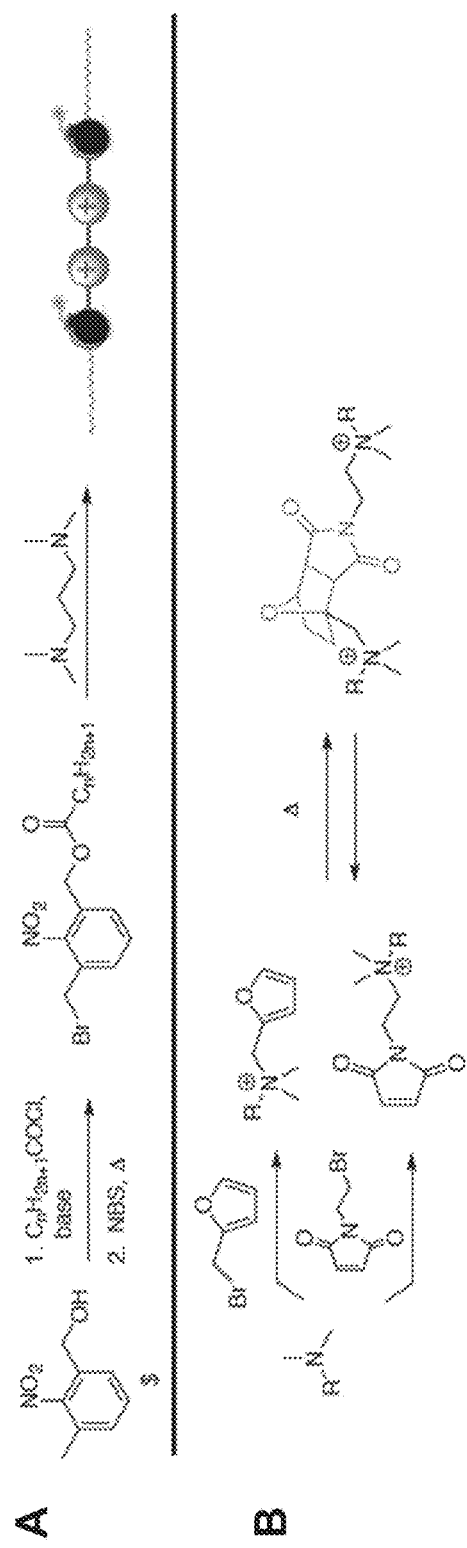
FIG. 62, comprising

There is virtually no limit to the structural variety of linking groups that could be installed into QACs. A high priority proof of concept experiment incorporates photolabile groups into a QAC structure, such as the o-nitrobenzyl alcohol functionality. (Patchornik et al., 1970, J. Am. Chem. Soc. 92:6333; bochet, 2002, J. Chem. Soc. Perkin Trans. 1:125-142). Based on the photochemically-induced photoisomerization of o-nitrobenzyl alcohol derivatives into o-nitrosobenzaldehydes, fragmentation uses light below 320 nm; additional methoxy groups are added to the ring to modify the fragmentation wavelength. To apply this strategy to QACs, a commercially available nitrobenzyl alcohol (FIG. 62A) is acylated with a variety of acyl chlorides, and then selectively brominated at the benzylic methyl group (Phattacharya et al., 2001, 42:5393-5395). Alkylation or amidation may install the long chain, though subsequent selective bromination is less precedented. Bisalkylation with an appropriate bisamine (½ equivalent) generates a bisQAC; tris- and other multiQACs are similarly prepared. Benzyl bromide and its derivatives have been shown to most rapidly react with tertiary amines in our hands, and should allow for rapid generation of the desired "Edge-destruct" structures. Also illustrated (FIG. 62B) is a Diels-Alder strategy for formation of a "Center-destruct" alternative; this is anticipated to have a slow decomposition due to retro-Diels-Alder reaction over time. (See Syrett et al., 2010, Polym. Chem. 1:102-106; Delplace and Nicolas, 2015, Nat. Chem. 7:771-784)

Anticipated Results and Alternative Approaches

Efficacy of these compounds are assessed against a panel of bacteria, including MRSA and biofilms. "Aging" experiments prior to bacterial exposure are carried out to track the loss of activity over time or via exposure to environmental conditions (pH, light, salts). Rapid decomposition of more labile "self-destruct" compounds are manifested by weak bioactivity in all experiments. Ultimately broad structure-activity-stability correlations are developed, and compounds which show the promise for good utility in home or hospital settings are presented. Bioactivity data continues to inform synthetic plans, and the permitted level of instability for these compounds will be examined. Accordingly, a variety of different synthetic routes and alternative paths have been described herein.

Preliminary Bioactivity and Toxicity

To date, synthesized compounds have been evaluated against planktonic bacteria (E. coli, S. aureus, P. aeruginosa, E. facaelis) and bacterial biofilms (E. facaelis, S. aureus, MRSA); new compounds are similarly assessed. All compounds are also evaluated via a hemolysis assay to assess their ability to lyse red blood cells (RBC) (Nagamune et al., 2000, Toxicology in Vitro 14:139-147). The assay is conducted following a known protocol to determine the concentration of compound that causes 20% of RBCs to be lysed. These data are merged to compute a therapeutic index, assessed as $Lysis_{20}$/MIC, where larger values are desired.

All compounds are benchmarked against three commercial antiseptics—benzalkonium chloride, DDAC, and CHX (FIG. 1).

Results and Alternative Approaches

A significant number of structurally diverse multiQACs is developed, with their bioactivity (both MIC and MBEC) and toxicity determined, leading to a larger picture of SAR for this emerging class of antiseptics. Syntheses of representative compounds have been highly successful due to their simplicity, and structural targets can be redesigned as informed by biological data and the availability of alternative commercially available starting materials Biological Evaluation, Resistance Determination, and Genetic Mapping of Resistance of multiQACs Preliminary data has demonstrated that representative tris- and tetracationic compounds do not show resistance profiles against strains bearing qac genes. It is hypothesized that compounds will succumb to bacterial resistance; however, the mechanism by which this resistance develops is unclear. Two potential paths to resistance are: 1) spontaneous mutations that lead to unique resistance against tris- and/or tetracationic species or 2) iterative mutations that lead to universal resistance against all QACs. Compounds of the invention are used as chemical probes to differentiate between the two potential mechanisms of resistance development in order to better understand how the process occurs in both sensitive and resistant strains of S. aureus.

Bioactivity Assays

The bioactivity of all compounds (Joynes and Sherrington, 1996, Polymer 37:1453-1462) are fully evaluated by a panel of health-specific pathogens. Other pathogens of interest include Enterobacter aerogenes, Salmonella enterica subsp. Thyphimurium, Pseudomonas aeruginosa, and vancomycin-resistant enterococci (VRE). These pathogens are of serious concern to human health as they are found in environments ranging from hospital rooms to food manufacturing plants to household bathrooms. Assays useful for identifying the Minimum Inhibitory Concentration (MIC) against planktonic bacteria (compounds/polymers) and Minimum Biofilm Eradication Concentration (MBEC) against bacterial biofilms (compounds only) are utilized. Bacterial adhesion (biofilm formation) is quantified by measuring the OD of crystal violet-stained surfaces. The compounds are benchmarked against an untreated control plate and a benzalkonium chloride-coated plate to evaluate comparative efficacies versus commercial standards.

Resistance Analysis

The development of resistance is analyzed in the resistance development assays described elsewhere herein by comparing and contrasting how resistance evolves from both the non-resistant and resistant S. aureus strains. Community-acquired MRSA (CA-MRSA) is usually of the USA300 lineage and a significant health threat. USA300-0114 is one of the MRSA strains used in preliminary experiments and is for the model pathogen for the resistance development analysis experiments. USA300-0114 contains the qacA and qacB resistance genes and norA (Tenover et al., 2006, J. Clin. Miocrobiol. 44:108-118). It has been demonstrated that tris- and tetra-QACs are unaffected by this resistance mechanism, however, it is unknown whether they too will eventually develop resistance, and if so, whether the mechanism will be directly derived from this system.

Figure 10:
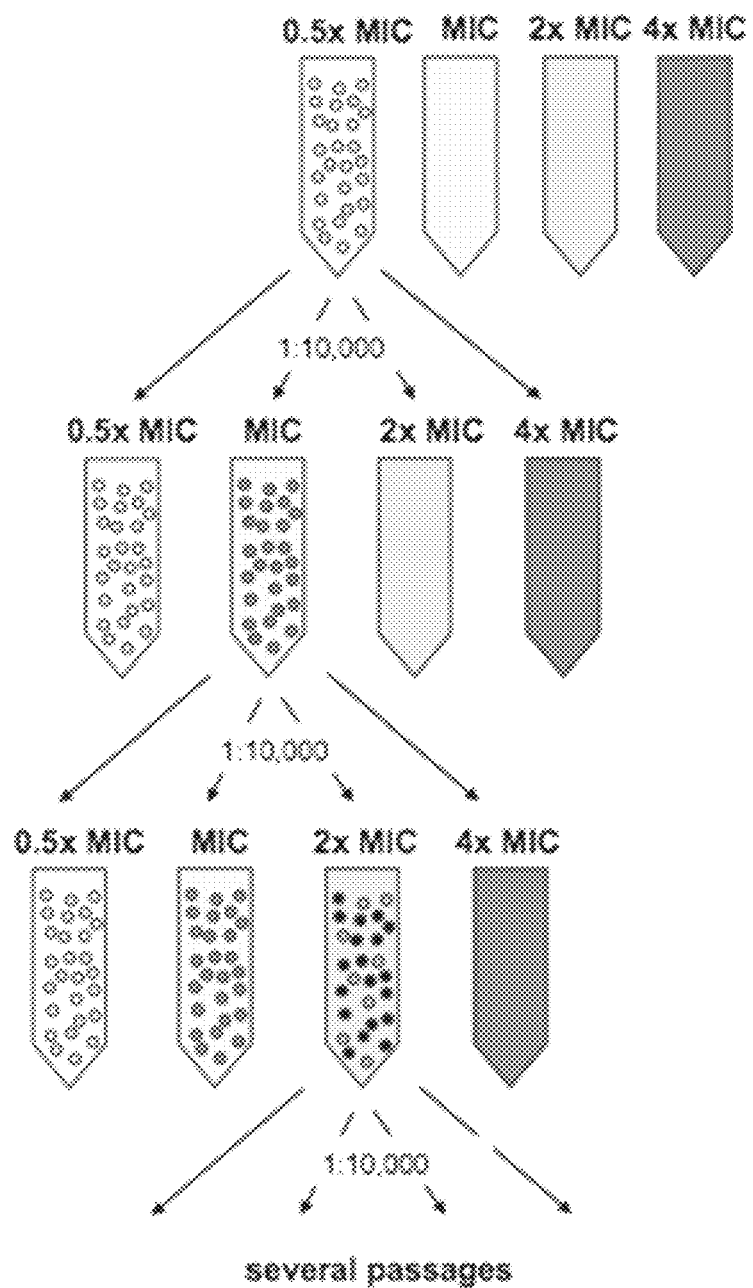
FIG. 10 is an illustration of a serial passage resistance assay. Bacteria are grown in rich media containing a sublethal dose of compound. Daily, aliquots of bacterial culture from the highest concentration allowing bacterial growth are transferred to fresh media containing higher doses of compound. Yellow=nonresistant bacteria, gray/black=resistant bacteria

Resistance development assays are based on the ability of the bacteria to accumulate random mutations in the existing efflux pumps or other chromosomal sites to develop resistance to the next generation QACs. To screen for mutations conferring resistance, a serial passage assay in broth culture is used (FIG. 10). S. aureus CA-MRSA USA300-0114 is serial passaged in rich medium (Todd-Hewitt broth) containing a sublethal concentration of antibiotic, in addition to concentrations equal to the MIC of antibiotic as well as two higher concentrations. Once the bacterial population reaches approx. $10^{10}$ S. aureus per milliliter, they are passaged by diluting 1:10,000 in fresh medium (approx. $10^4$ bacteria are passaged). Each passage represents 24 generations of bacterial growth. If resistant bacteria are present in the population, the bacteria start to grow in the higher dilutions of QAC compounds. The level of resistance is further increased by selecting for additional mutations leading to resistance to even higher levels of QAC derivatives (FIG. 10). The number of generations required to detect resistance mutants is an indicator of how easily resistance can arise by mutation. If resistance is detected within a few generations, it suggests that resistance to the compound could reduce its effectiveness. If resistance events arise only after multiple generations, it suggests resistance to the compound develops very slowly and that the compound may make be useful as a lead compound. Similar assays may be adapted for other bacteria resistant to mono-QACs to determine ease of developing resistance if these efflux pumps are present.

Genetic Resistance Mapping

Figure 11:
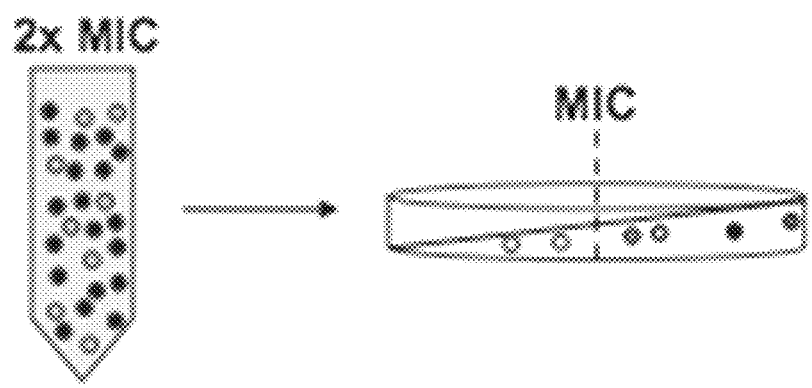
FIG. 11 is an illustration of a gradient plate resistance assay. Resistant bacteria taken from the serial passage liquid cultures are transferred to agar plates containing a gradient of compound, allowing for the isolation of individual resistant mutants. Yellow=nonresistant bacteria, gray and black=resistant bacteria.

Upon identification of resistant clones, the sites of mutation are identified in order to better understand how QAC-resistance develops. The serial dilution method permits the observance of resistance in a population of bacteria. The resistance within that population can arise from a mixed population of mutants, especially if resistance develops easily. Therefore, to characterize the types of events that give rise to resistance a gradient plate method is used for isolating resistant mutants (FIG. 11). Gradient plates contain a gradient of compound. When bacteria are plated on the gradient plates, individual mutant resistant bacteria present in the population grow and give rise to a resistant colony. Since all of the bacteria in that colony arose from a single cell, those bacteria can be grown and used for analysis to determine the site of mutation. It is hypothesized that resistance will arise within the already established suite of qac genes. Therefore, PCR primers for the qac genes and the qacR regulatory gene and norA and its promoter region are designed initially. The PCR products are sequenced and compared to the original genetic material. Because PCR can give rise to random mutations, if a mutation is detected, the experiment will be repeated to make sure the same mutation is again detected. To confirm that any detected mutations confer the resistance phenotype to the resistant bacteria, the genes are cloned into SH1000, a QAC-sensitive strain of S. aureus. The MIC of QAC compounds is then compared between the parental strain, a recombinant strain containing a nonmutated copy of qac, and a recombinant strain containing the mutated copy of qac.

Anticipated Results and Alternative Approaches

In the event that resistance mutations are not be found on the qac genes, a novel mechanism for QAC resistance may have be identified. Titanium 454 Deep Sequencing of the entire genome is then performed and in silico comparisons of parental and mutant genome sequences are used to look for putative resistance determinants (for example, genes for putative efflux pumps or changes in membrane synthesis pathway genes).

Example 3: Development of Surface-Attached multiQAC Structures, and the Generation of multiQAC Homopolymers and Copolymers The syntheses of the QAC compounds has been designed to easily accommodate polymeric attachment via a variety of possible strategies. In one embodiment, polymeric materials contain QACs with multiple (3-6) cations, easily varied architectures, and efficient synthetic preparations. Suitable polymeric scaffolds are therefore identified to append multicationic QACs, largely relying on modern controlled free-radical polymerization (CRP) methods that were unavailable in the early years of QAC-polymer development (Polyelectrolytes and Polyzwitterions: Synthesis, Properties and Applications. ACS Symposium Series. American Chemical Society, Washington, D.C., 2006).

In order to extend the utility of multiQAC structures, strategies have been developed for their incorporation into polymeric materials. Lead antimicrobial polymeric materials (either multiQAC-containing homopolymers, copolymers, or surface-attached multiQACs) are synthesized, characterized, and identified. Postpolymerization modification of homo- and copolymers with multiQACs and polymerization of multiQAC-functionalized monomers are performed, and surface-attached multiQAC efforts are also performed for antiseptic applications in medical settings.

Synthesis of a Toolbox of QAC-Functionalized Monomers for Homopolymerization

Figure 12:
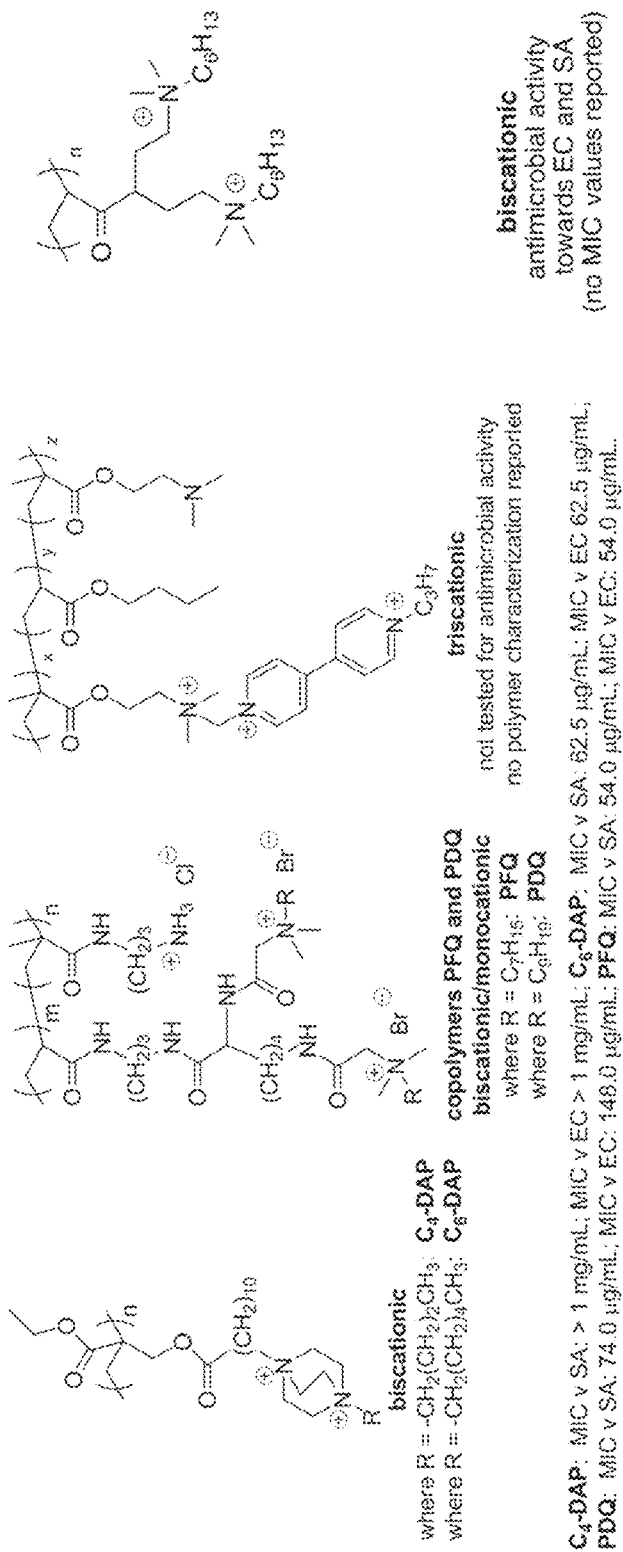
FIG. 12 is an illustration of biscationic QAC homopolymers.

Styrenic- and methacroyl-derived monomers are known to be suitable scaffolds for monocationic QACs, though the QACs are most commonly installed via post-polymerization quaternization of an amine sidechain (Ignatova et al., 2004, Langmuir 20:10718-10726). The few reported examples of homopolymers containing biscationic QACs (FIG. 12) are prepared using conventional free-radical polymerization, though such methods are often plagued by low degree of conversion and broad polymer polydispersities (non-uniform materials). With the advent of reversible addition-fragmentation chain transfer polymerization (RAFT, a subclass of CRP) and its successes in generating select examples of styrenic- and methacroyl-derived polymers with appended monocationic QACs (McCormic and Lowe, 2004, Acc. Chem. Res. 37:312-325), it is hypothesized that RAFT will be ideally suited to prepare the desired polymers with enhanced sidechain cationic density (see FIG. 13 for styrenic and FIG. 14 for methacroyl derivatives). The narrow polymer polydispersities anticipated when using RAFT will simplify polymer characterization and provide more uniform and well-defined materials for subsequent antimicrobial and toxicity testing. This strategy can be applied to form block copolymers, simply by adding the two monomers of interest sequentially to the reaction. Again, adjusting the ratio of multiQAC comonomers versus neutral comonomers will allow for fine-tuning of hydrophobic content.

Figure 13:
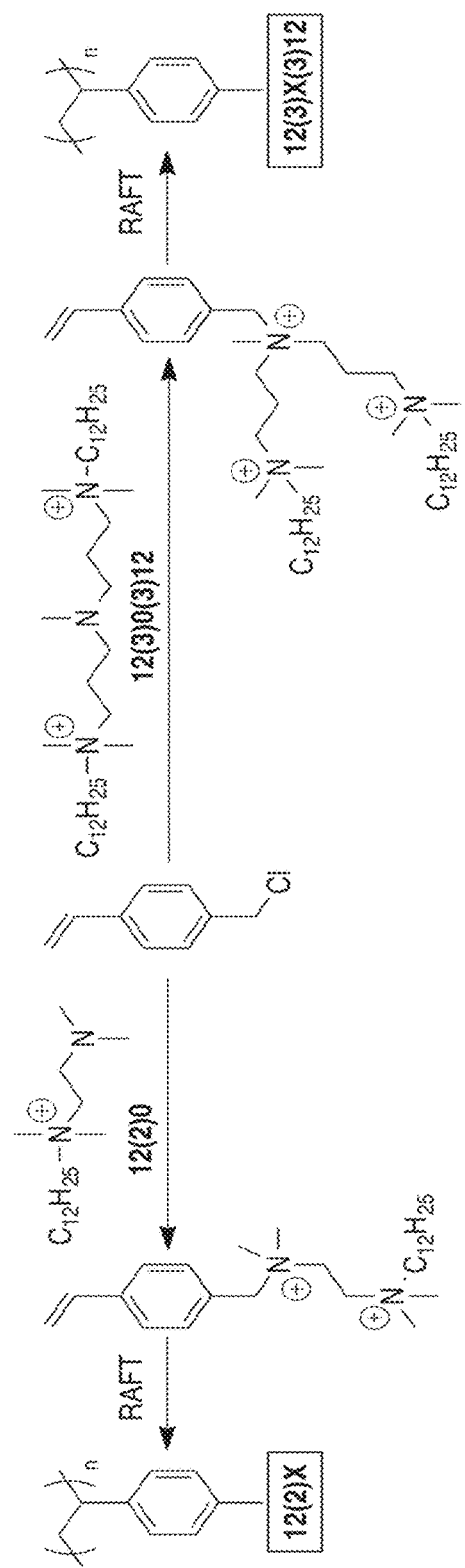
FIG. 13 is a synthetic scheme of a synthesis of bis- and tris-QACs of the present invention appended to a styrenic monomer scaffold.
Figure 14:
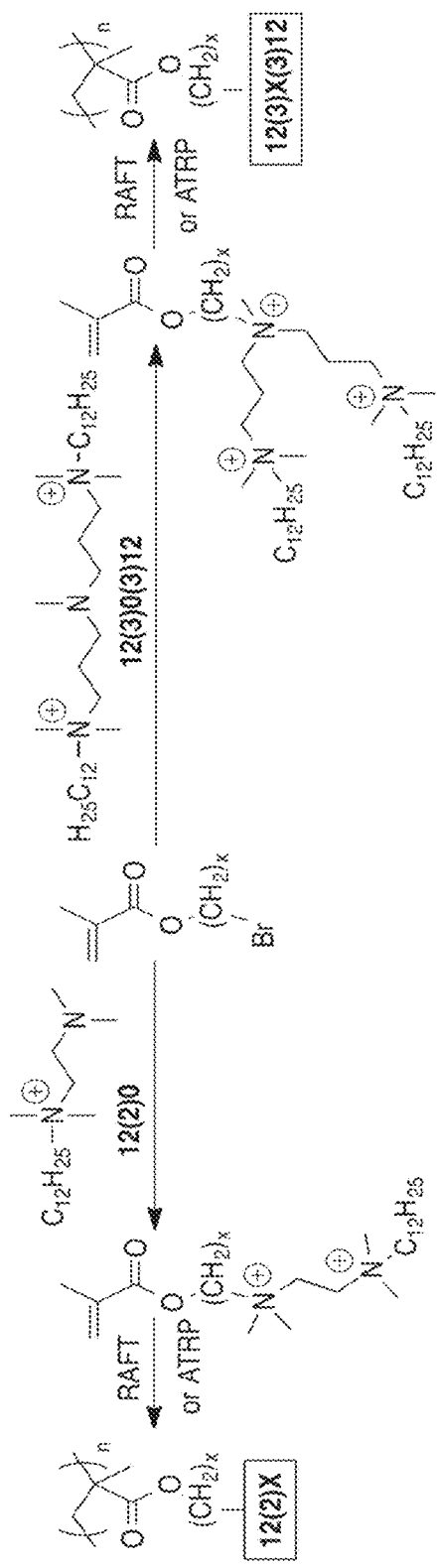
FIG. 14 is a synthetic scheme of a synthesis of bis- and tris-QACs of the present invention appended to a methacroyl monomer scaffold.

The importance of RAFT agent choice to maintain controlled polymerization is well documented, hence commercially available 4-cyano-4-(phenylcarbonothioylthio)-pentanoic acid (Mitsukami et al., 2001, Macromolecules 34:2248-2256) will be used initially before considering alternatives. The starting material 4-vinylbenzyl chloride (FIG. 13) is commercially available, and ω-bromo-alkanyl-methacrylates (FIG. 14, where x=11, and other options) is prepared using published methods (Loynes and Sherrington, 1996, Polymer 37:1453-1462). The styrenic polymer scaffold is especially attractive, as it may afford QAC-functionalized polymers in just two steps from commercial available 4-vinylbenzyl chloride and a desired QAC, such as 12(2)0 (FIG. 13). To diversify options for polymerization, the use of methacroyl monomers introduces the possibility of employing atom transfer radical polymerization (ATRP, another subclass of CRP) (Lee et al., 2004, Biomacromolecules 5:877-882; Ravidumar et al., 2006, Biomacromolecules 7:2762-2769) as an alternative to RAFT. Similar to RAFT, ATRP is expected to yield well-defined materials of uniform polymer molecular weight. Suitable ATRP initiators (ethyl 2-bromoisobutyrate), metal halides (copper(I)bromide), and ligands (1,1,4,7,10,10-hexamethyltriethylenetetramine) are commercially available.

The polymerization of multiQAC-functionalized monomers is an elegant approach for the preparation of multiQAC polymers. Homopolymers benefit from simplified polymer characterization (one type of repeat unit), yet one must consider the potential for poor polymer solubility or aggregation phenomena for polymers with high charge density (Zhang et al., 2012, Polym. Chem. 3:907-903; Palermo et al., 2009, Biomacromolecules 10:1416-1428). Copolymers provide better alternatives since hydrophobicity can be tuned by altering the ratio of charged, multiQAC comonomer versus chemically analogous neutral comonomer (Alvaerz-Paino et al., 2015, 16:295-303). However, multiQAC comonomers may be challenging to polymerize, and copolymers have added complexity for characterization.

A series of experiments is designed in which the amount of multiQAC comonomer content is based on a robust comonomer platform.

Figure 63:
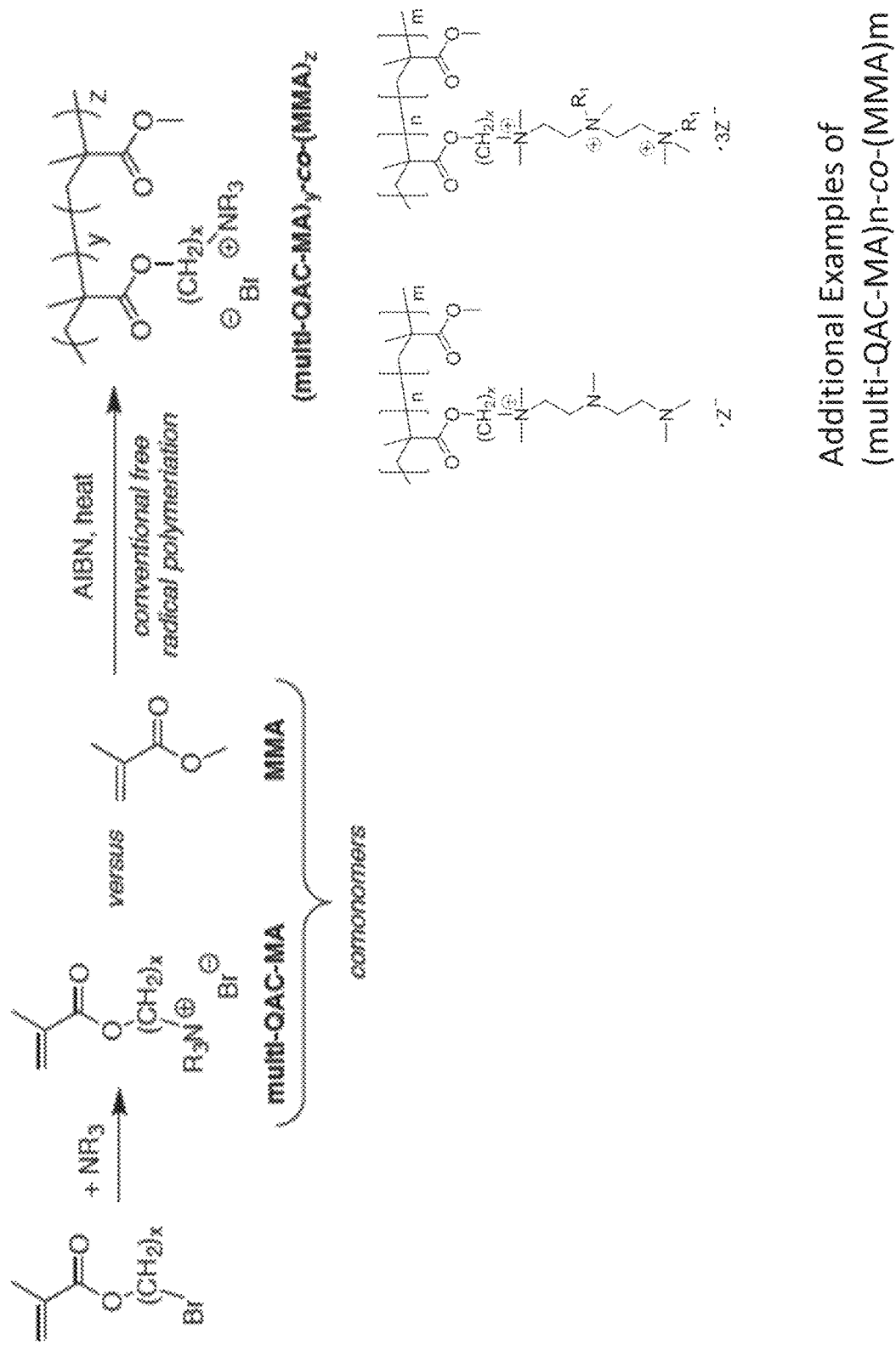
FIG. 63 is a scheme depicting the use of multiQAC-MA and MMA comonomers to form methacrylate-derived copolymers of the present invention.

Reaction conditions have been screened to prepare multiQAC methacrylate monomers (multiQAC-MA, see FIG. 63). ω-bromoundecanylmethacrylate has been previously prepared using known methods (Joynes and Sherrington, 1996, Polymer 37:1453-1462) and was then treated with 1,1,4,7,7-pentamethyldiethylenetriamine to prepare the multiQAC-MA. Next, conventional free radical copolymerization (e.g. AIBN, heat) of multiQAC-MA and methyl methacrylate (MMA) is carried out using varied comonomer ratios. Polymers are characterized by NMR spectroscopy to evaluate comonomer ratios and, if possible, the degree of polymerization (DP). Gel-permeation (size exclusion) chromatography (GPC, or SEC) is then carried out for polymer molecular weight determination.

Two points of variation in these multiQAC-MA monomer allow for the tuning of polymer hydrophobicity and potential for micelle formation: the length of the alkyl ester tail and the choice of amine ($NR_3$). Also, comonomer ratios are optimized. By tuning these parameters, multiQAC methacrylate/methyl methacrylate copolymers that are efficacious as antiseptics or as surfaces to which bacteria will not adhere may be identified. The copolymers are then biologically tested.

Polymers are characterized prior to antimicrobial testing. End-group analysis ($^1$H nuclear magnetic resonance, $^1$H NMR) and gel-permeation (size exclusion) chromatography (GPC, or SEC) is used for molecular weight determination; recent articles suggests end-group analysis is superior for analyzing polymers containing QACs when compared to more traditional GPC methods (Locock et al., 2014, Anal. Chem. 86:2131-2137; Li and Matyjaszewski, 2011, Macromolecules 44:5578-5585). In cases where end-group analysis suggests a low degree of polymerization, the identity of the RAFT agent is considered for subsequent antimicrobial activity and cytotoxicity testing; RAFT end groups may be cleaved from the polymers if deemed necessary Michl et al., 2014, Polym. Chem. 5:5813-5822). In addition, multinuclear NMR spectroscopy, infrared (IR) spectroscopy, elemental analysis, differential scanning calorimetry (DSC), and other methods are used for polymer characterization.

Post-Polymerization Modification to Append Multicationic QACs to Homopolymers and Copolymers Post-polymerization modification is an attractive strategy for the preparation of multiQAC polymers. In the event that monomers containing multicationic QACs give unfavorable polymerization kinetics, the option of post-polymerization modification may be used. For example, commercially available poly(4-vinyl-benzyl chloride) may be functionalized with QACs such as 12(2)0 or 12(3)0(3)12 to generate the desired QAC-containing polymers. If copolymers are desired, post-polymerization modification is an attractive synthetic method since copolymerization of styrene or methacrylate with multicationic QAC monomers in some cases may lead to low incorporation of the latter in the polymer backbone. Conventional free-radical polymerization may be used to prepare random copolymers of 4-vinylbenzyl chloride and styrene; nitroxide mediated polymerization (NMP, another type of CRP) may be used to prepare block copolymers of these (Li et al., 2014, Macromolecules 47:6757-6767). Bis- and tris-cationic QACs may be appended to these copolymers (FIG. 15) to form the desired QAC-containing polymers. Polymers are characterized using the methods described elsewhere herein.

The QACs may be appended to a surface, such as a surface composed of glass, metal, or a polymer. Glass and paper surfaces may be functionalized with monocationic QAC containing polymers using previously published methods (Ganewatta et al., 2014, Chem. Sci. 5:2011-2016); the QAC units may be established by post-polymerization modification. Characterization of these types of surfaces are performed using surface and bulk characterization techniques, such as attenuated total reflectance (ATR) IR spectroscopy and elemental analysis, and other methods. Post-polymerization modification is useful for appending multiQACs to a surface, whether that surface is composed of glass, metal, or a polymer. This concept may be useful to prepare antiseptic-coated surfaces for operating rooms.

Anticipated Results and Alternative Approaches

Approaches for the preparation of QAC-functionalized polymers have been described herein. In cases where homopolymerization of QAC-functionalized monomers leads to low conversion, copolymerization of QAC-functionalized monomers and also post-polymerization modification is attempted. All of these polymeric materials are tested for antimicrobial activity; the American Society for Testing and Materials (ASTM) has developed a standard method for the antimicrobial efficacy assessment of immobilized antimicrobials (ASTM E2149) (ASTM E 2149-01 Standard Test Method for Determining the Antimicrobial Activity of Immobilized Antimicrobial Agents Under Dynamic Contact Conditions American Society for Testing & Materials, West Conshohocken, Pa., 2001; Green et al., 2011, Biointerphases 6:MR13-28). It is hypothesized that these QAC-functionalized polymers will have activities that exceed those of their small-molecule QAC counterparts, though polymer aggregation and solubility may affect antimicrobial activity. Polyacrylamides and polycarbonates are used to expand the scope and enhance aqueous solubility of these materials. Polyacrylamides may be prepared by RAFT (Mertoglu et al., 2005, Macromolecules 38:3601-3614) using QAC-functionalized monomers or traditional free-radical polymerization followed by post-polymerization modification (Dizman et al., 2006, Macromolecules 39:5738-2746); polycarbonates may be prepared by ring-opening polymerization followed by post-polymerization modification (Ng et al., 2014, Macromolecules 47:1285-1291).

Example 4: Structure-Resistance Relationships: Interrogating Antiseptic Resistance in Bacteria with Multicationic Quaternary Ammonium Dyes The results described herein demonstrate a series of quaternary ammonium compounds (QACs) based on the motif of a polyaromatic structural core analogous to activators of QacR, a negative transcriptional regulator of the efflux pump QacA. Using commercially available dye scaffolds, 52 novel QACs bearing 1-3 quaternary ammonium centers were synthesized and their antimicrobial activity was evaluated. Striking differences in antimicrobial activity against bacteria bearing QAC resistance genes was observed, with up to a 125-fold increase in MIC for select structures against bacteria known to bear efflux pumps.

A series of compounds with varied cationic character as well as aromatic groups were investigated to determine whether aryl substrates are particularly prone to QacR recognition. A library of QACs featuring dye scaffolds known to permeate cellular membranes was rationally designed, taking advantage of the reported QacR binding of crystal violet and malachite green (Wilhelm et al., 2015, ACS Chem. Bio. 10:1711-1717). Akin to structure-activity relationship (SAR) assays ubiquitous in the pharmaceutical sector, a series of QAC structures were designed to investigate what structural features would trigger resistance in bacterial strains with known efflux pumps, herein referred to as a "structure-resistance relationship". The library focused on interrogating the role that permanent charge (+1 to +3) and alkyl length play on efficacy and susceptibility to resistance. Due to the presence of many conjugated ring systems in the dyes, it was hypothesized that an increased amount of recognition and efflux would be observed.

Synthesis of the QAC Library of Dye Hybrids

Figure 16:
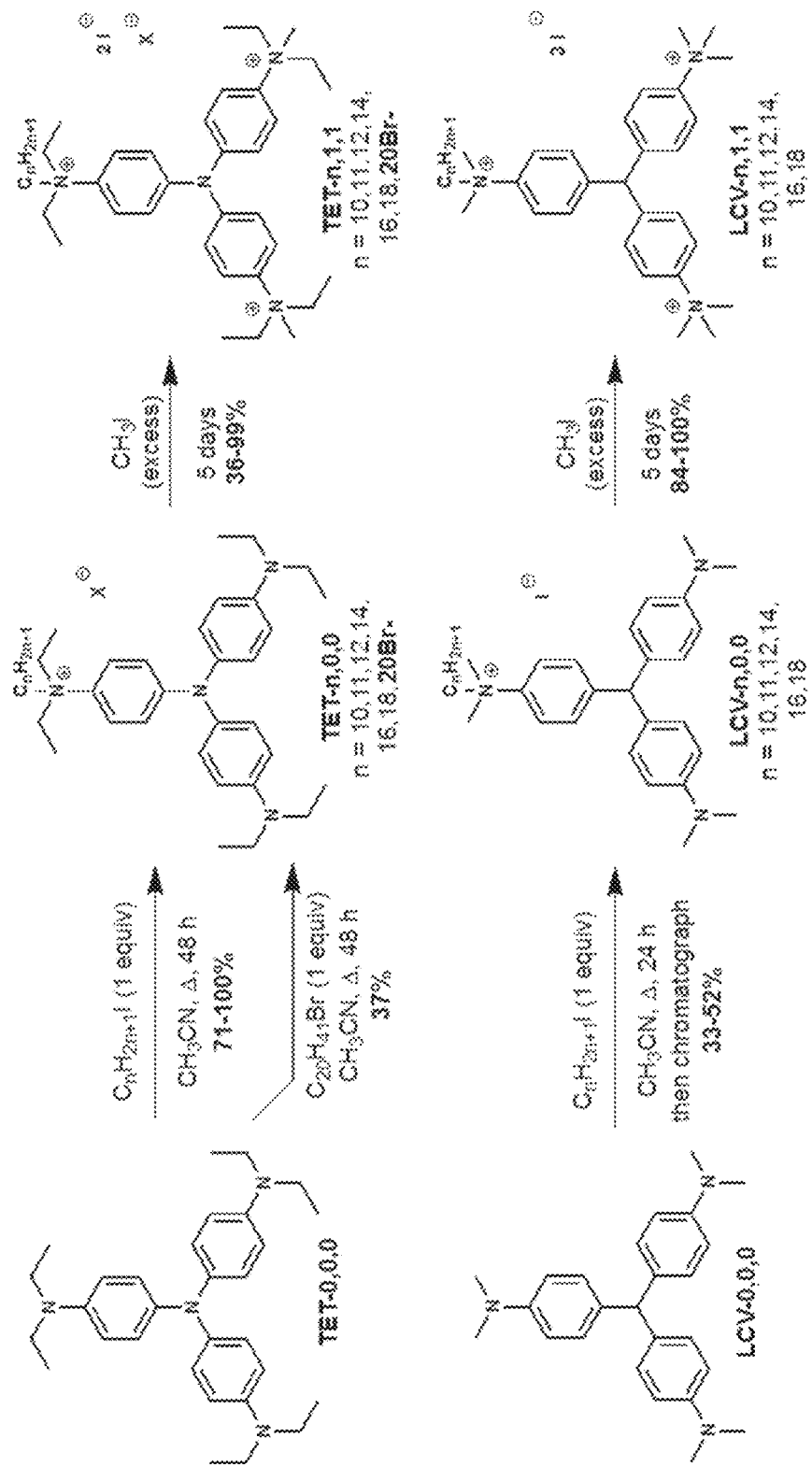
FIG. 16 is a scheme of syntheses of mono- and tris-quaternary ammonium compounds of the present invention by alkylation of dye-based scaffolds.
Figure 17:
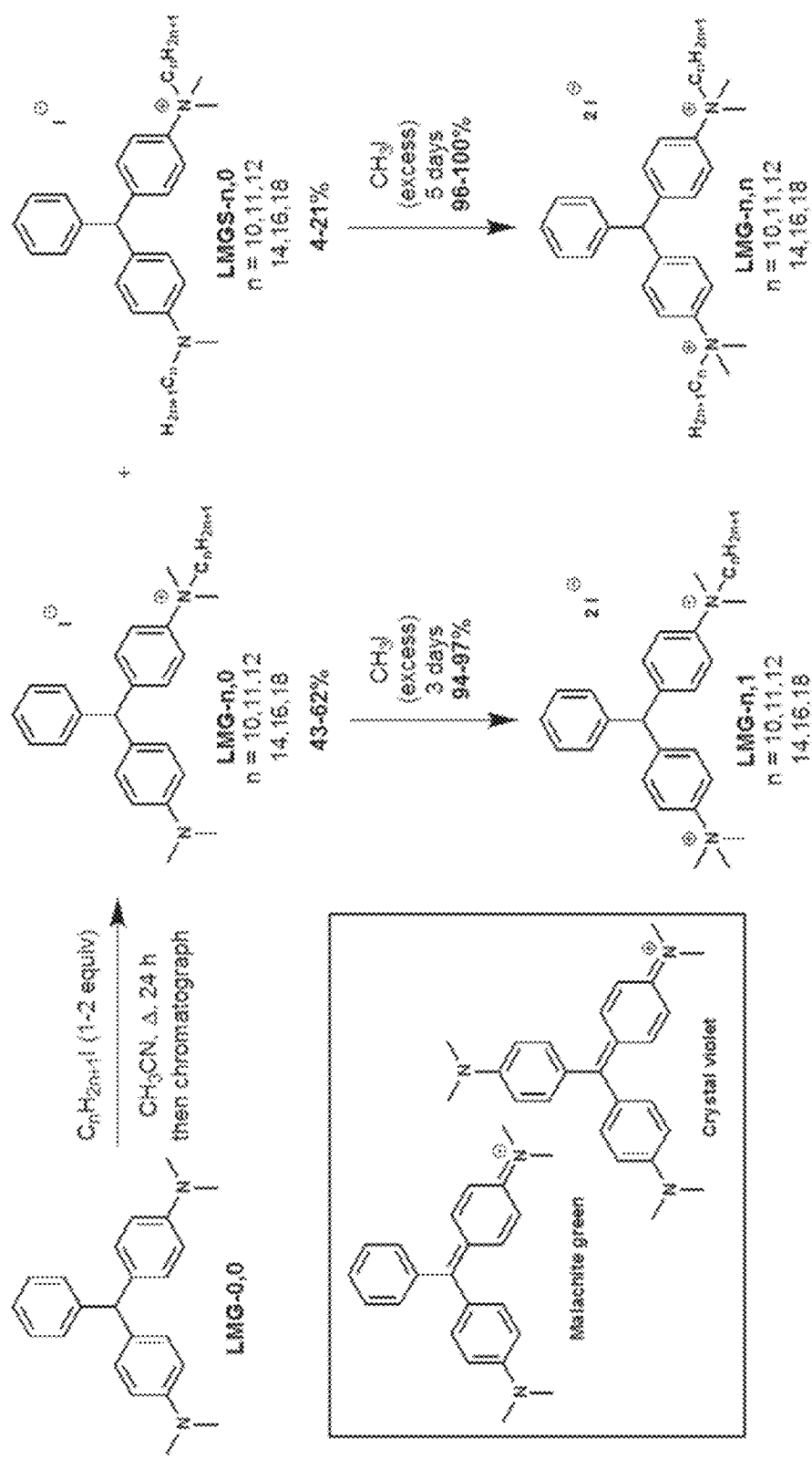
FIG. 17 is a scheme of syntheses of mono- and bis-quaternary ammonium compounds of the present invention by alkylation of dye-based scaffolds.

Synthesis of the dye-based QAC compounds began with two commercially available dye scaffolds in their reduced (and thus more nucleophilic) form—the bisamine leukomalachite green (LMG) and the trisamine leukocrystal violet (LCV) (FIGS. 16 and 17). Also readily available was the tetraamine analog shown (herein abbreviated as TET), whose aromatic rings are more electron rich due to a central nitrogen atom that was hypothesized to be unreactive to alkylation. Each polycyclic aromatic core system was subjected to an analogous synthetic sequence to generate a series of dye-based amphiphiles bearing varied ratios of tertiary amines, quaternary amines, and long alkyl chains. Thus each dye was first exposed to one equivalent of an alkyl iodide ($C_nH_{2n+1}I$) at reflux to furnish compounds abbreviated as TET-n,0,0, LCV-n,0,0, and LMG-n,0 bearing varying alkyl chain lengths, in moderate yields (FIGS. 16 and 17). The inaccessibility of 1-iodoeicosane led to the employment of the 20-carbon bromide analog, which resulted in diminished yields in the formation of TET-20,0,0 as the bromide salt. These singly-quaternized dyes were then exposed to neat methyl iodide over three to five days to provide fully quaternized tris-QACs (TET-n,1,1 and LCV-n,1,1) or bis-QACs (LMG-n,1) in moderate to high yields.

Initial exposure of each dye structure to an excess of the long chained alkyl halide led to complex mixtures, although in the case of the simpler LMG series, a byproduct was purified. Through NMR characterization, an unexpected reaction was observed. Although not wishing to be bound by any particular theory, the results suggested that some bis-alkylation of LMG was occurring, but under these conditions an iodide counterion reacted with the product, displacing one of the methyl groups to furnish a monocationic compound bearing two long-chain alkyl substituents. This monoQAC subset was termed a "swapped" series (i.e., LMGS) due to the net swap of one methyl group for a long-chained alkyl group. Recognizing that both an unexpected monoQAC series, as well as opened a route to prepare symmetrical bisQAC dye derivatives, had been accessed, the LMGS compounds were exposed to neat methyl iodide to fully quaternize the dye compound in high yields. This resulted in the LMG-n,n series bearing extended carbon chains on both nitrogens in the molecule.

Biological Evaluation of QAC Compounds

The complete set of MIC values against six bacteria [*Staphylococcus aureus* (SA), hospital-acquired methicillin-resistant SA (HA-MRSA), community-acquired methicillin-resistant SA (CA-MRSA), *Enterococcus faecalis* (EF), *Escherichia coli* (EC), and *Pseudomonas aeruginosa* (PA)] is presented in FIG. 66, wherein multiQACs are grouped with their monoQAC counterparts. The dye-based QACs with greatest inhibition of the complete range of Gram-positive and Gram-negative bacteria featured bis- or tris-quaternization, with the optimal alkyl total ranging from 17-24 carbons. For example, comparison of two biscationic series—LMG-n,1 and LMG-n,n—evaluates the effect of total alkyl chain length in retention of efficacy against the more challenging CA-MRSA and the Gram-negative strains EC and PA. LMG compounds bearing a single long-chain alkyl group exhibited some elevated MIC values against CA-MRSA and PA, while LMG-10,10, LMG-11,11, and LMG-12,12 showed virtual equipotency across the board (≤2 µM).

When tested against non-resistant SA, most of the 52 QAC structures displayed MIC values in the single-digit micromolar range. Very similar results were observed against two additional strains lacking the qacAB/R machinery, known to be susceptible to QAC compounds, namely HA-MRSA and EF. However, when testing against CA-MRSA, a strain known to contain efflux pump genes, increases in MIC were observed, albeit to greatly varying degrees. Marked differences in MIC values against the SA strains were observed for all monoQACs tested (FIG. 67). In fact, up to 125-fold increases in MIC values were noted (e.g., TET-14,0,0 and TET-16,0,0), even though the most active compounds (e.g., TET-16,1,1) showed no difference in activity. Although not wishing to be bound by any particular theory, these results suggest that the multiaromatic nature of dye scaffolds are unique in their ability to trigger bacterial resistance.

Additionally, antiseptics that display increased MIC values for CA-MRSA (as compared to SA) also show increased MIC values for PA; often the MIC values against PA were greatly elevated (500 µM). In has been hypothesized that the second membrane present in Gram-negative bacteria may be a significant factor in the decreased activity of monoQACs; however, while not wishing to be bound by any particular theory, these results suggest that a family of MDR efflux pumps (MexAB-OprM in PA and AcrAB-TolC in EC) is responsible. Therefore, it is hypothesized that this QAC resistance may not be solely attributed to the additional cell membrane but instead to multidrug efflux transporters present within the PAO1 strain.

Direct comparisons of dye-based monoQACs with their multiQAC analogs led to some of the most surprising observations. Enhanced activity of the multiQACs was expected, but the magnitude of the differences was not; for example, when comparing the MIC values of monocationic TET-16,0,0 with that of triscationic TET-16,1,1 against CA-MRSA (a species known to have QacR), a 500× difference (250 µM vs 0.5 µM) was observed. While the same differential was observed in a second case (LCV-18,0,0 vs LCV-18,1,1), the smallest monoQACs prepared (i.e., LMG-10,0 and LMG-11,0) were quite potent against CA-MRSA. It is hypothesized that these compounds were too small or too hydrophilic to evoke significant resistance. Additionally, analysis of the MIC values for the prepared trisQACs led to another unexpected observation: in the fully quaternized LCV series, the first triscationic QAC (LCV-10,1,1) that demonstrates a 32-fold decrease in antibacterial effectiveness against CA-MRSA was identified. In fact, dye-based multiQACs with alkyl chain substitution of less than 14 total carbons repeatedly displayed elevated MICs, suggesting bacterial resistance. This stands in complete contrast to dozens of previously reported non-aromatic tris-QAC structures which showed no notable difference in MIC against SA versus CA-MRSA.

Figure 18:
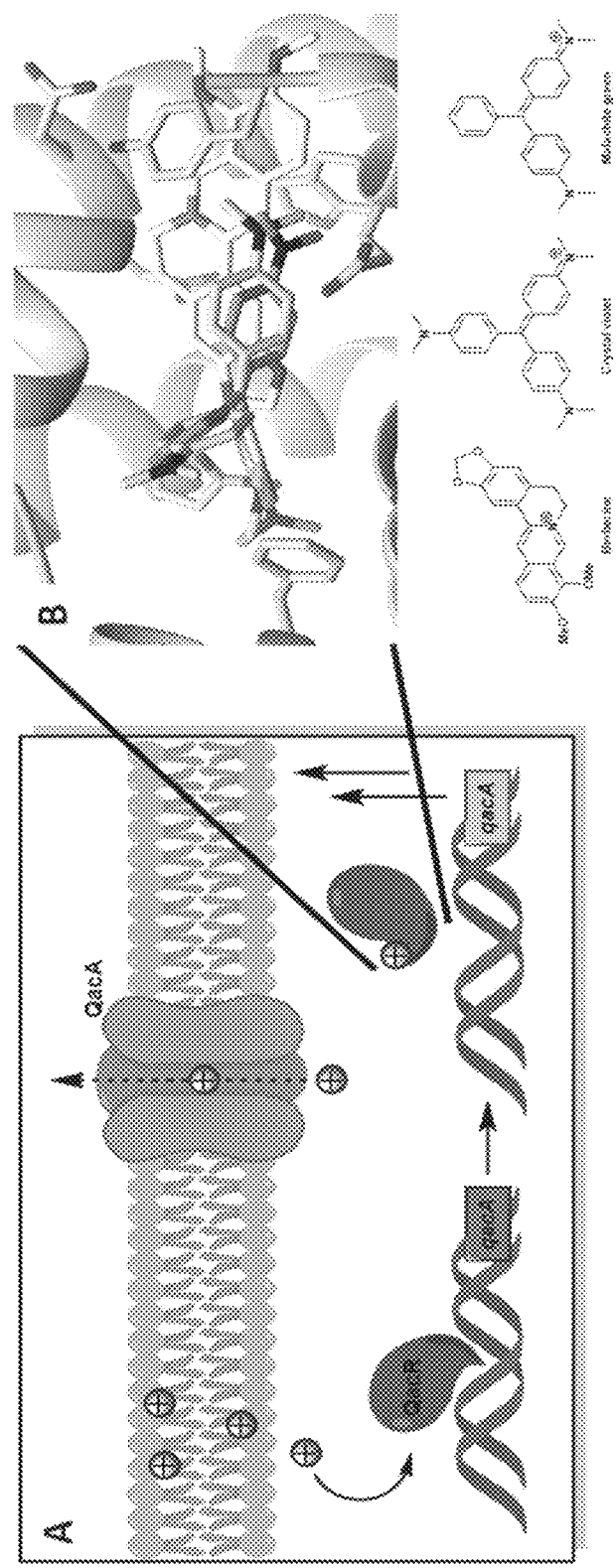
FIG. 18, comprising

Although not wishing to be bound by any particular theory, the drastic increase in bacterial tolerance of most dye-based monoQACs and other aromatic multiQACs may arise from one of three proposed modes of action (FIG. 18). The first possibility is that, in contrast to monoQACs (as well as other QACs with shorter alkyl lengths), multiQACs are less likely to traverse the cell membrane due to their increased cationic charge. This would prevent the intracellular buildup of QACs, and accordingly, the overexpression of QacA. A second possible mechanism involves recognition of the compounds by QacR, but an inability of multiQAC efflux by QacA resulting in the accumulation of QAC inside the cell ultimately leading to membrane association and eventual cell death. A third possible mechanism is based on the inability of QacR to recognize more complex substrates such as the multiQACs. This would result in a lack of overexpression of the QacA efflux pump, again resulting in the detrimental buildup of QAC substrate. With these possible mechanisms in mind, these QAC dyes were utilized as tool compounds to determine if QacR was responsible for the limited development of resistance.

It was hypothesized that by using a reactivation assay (essentially the inverse of a potentiation assay), the role QacR plays in monoQAC resistance could be better understood. Specifically, the CA-MRSA strain was dosed with sub-MIC concentrations of a compound known to be tolerated (i.e. TET-14,0,0), which was suggested to activate efflux pumps, causing an increase in MIC for a different QAC, such as trisQAC TET-14,1,1. However, dosing of the CA-MRSA strain with sub-MIC concentrations of TET-14,0,0 and varying concentrations of the triscationic variant did not result in any significant modification of observed MIC values. This result did not confirm the role of QacR in the resistance experienced by our monoQAC dye analogs. Without being bound by any particular theory, this results suggests that there is an inability of QacR to recognize these structural entities. Other possible hypotheses include that QacR may be activated by our monoQACs but that QacA cannot efflux the trisQACs or that the resistance mechanism implicated for TET-14,0,0 may be orthogonal to the Qac system.

As described herein, a series of 52 QACs were identified that exhibited excellent antimicrobial activity, as well as quite similar structures evoking markedly different MIC values in bacteria with or without efflux pumps (up to 125-fold change). Although not wishing to be bound by any particular theory, this variation in bacterial susceptibility suggests that the presence of efflux pumps is a greater protective factor than the second bacterial membrane of Gram-negative strains. These findings support the synthetic approach implemented to characterize the "structure-resistance relationship" of QAC-resistance in bacteria.

Example 5: Natural Product-Derived Quaternary Ammonium Compounds with Potent Antimicrobial Activity The results described herein demonstrate that natural products lacking a quaternary ammonium group can be converted into QACs, and thus gain antimicrobial activity. Amphiphilic properties were conferred to natural products that are not, in their own right, antibacterial agents. Further, an analogous series of structures that could bear one or two cationic residues were generated, as multicationic QACs (multiQACs) have been recently shown to exhibit strong antibacterial activity, and importantly, be able to evade the QAC resistance traits observed due to efflux pumps.

The materials and methods employed in these experiments are now described.

Biological Assays

For all biological assays, laboratory strains of methicillin-susceptible *Staphylococcus aureus* MSSA (SH1000), *Enterococcus faecalis* (OGIRF), *Escherichia coli* (MC4100), *Pseudomonas aeruginosa* (PAO1), community-acquired methicillin-resistant *Staphylococcus aureus* CA-MRSA (USA300-0114), and hospital-acquired methicillin-resistant *Staphylococcus aureus* HA-MRSA (ATCC 33591) were grown at 37° C. overnight from freezer stocks in 10 mL of Mueller-Hinton media. All cultures, with the exception of *E. faecalis*, were grown with shaking at 250 rpm.

Minimum Inhibitory Concentration (MIC) Determinations

Compounds were serially diluted two-fold from a 10% DMSO/aqueous stock solution to yield twelve test concentrations. Overnight *S. aureus, E. faecalis, E. coli, P. aeruginosa*, CA-MRSA, and HA-MRSA cultures diluted to ca. $10^6$ cfu/mL in Mueller-Hinton media and 100 μL were inoculated into each well of a U-bottom 96-well plate (BD Biosciences, BD351177) containing 100 μL of compound solution. Plates were incubated statically at 37° C. for 72 hours upon which time wells were evaluated visually for bacterial growth. The MIC was determined as the lowest concentration of compound resulting in no bacterial growth visible to the naked eye, based on the majority of three independent experiments. Positive and negative DMSO/aqueous solution and media controls were conducted for each trial. See Peng et al., 2011, Chem. Comm. 47:4896-4898.

General Chemical Information

Reagents and solvents were used from Sigma-Aldrich, Acros, TCI America, and Alfa Aesar without further purification. All melting points were obtained on a SRS DigiMelt apparatus. All reactions were carried out under ambient atmosphere with reagent grade solvents and magnetic stirring. All yields refer to spectroscopically pure compounds. $^1$H NMR spectra were measured with a 300 MHz Varian spectrophotometer, and chemical shifts were reported on a δ-scale (ppm) downfield from TMS. Coupling constants were calculated in hertz. $^{13}$C NMR spectra were obtained at 75 MHz, and results were reported on a δ-scale (ppm). Chloroform-d (CDCl$_3$) was the solvent used for most $^1$H NMR samples with an internal reference of 7.26 ppm. Deuterated methanol (CD$_3$OD) was used for other NMR samples with an internal reference of 3.35 ppm for $^1$H NMR and 49.3 for $^{13}$C NMR. High-resolution mass spectrometry was performed by the Mass Spectrometry Facility at Temple University.

Preparation of Q-10,0

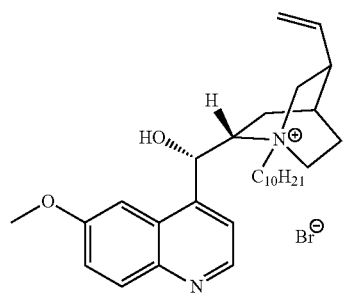

To a solution of quinine (0.500 g, 1.54 mmol) in acetonitrile (2 mL) was added 1-bromodecane (0.366 g, 1.65 mmol). The resulting yellow solution was stirred and heated at reflux for 26 h. The reaction was then concentrated under reduced pressure to afford Q-10,0 (0.834 g, 99%) as a dark brown solid; mp=169-178° C.; $^1$H NMR (300 MHz, CDCl$_3$) δ 8.77-8.73 (m, 1H), 8.08-8.05 (m, 1H), 7.71 (m, 1H), 7.41-7.38 (m, 1H), 6.43 (m, 1H), 6.33-6.31 (m, 1H), 5.66-5.54 (m, 1H), 5.09-5.27 (m, 2H), 4.94-4.87 (m, 1H), 4.27-4.21 (m, 1H), 4.18-4.01 (m, 1H), 3.97 (s, 3H), 3.83-3.72 (m, 1H), 3.62-3.40 (m, 2H), 3.12-3.00 (m, 1H), 2.86-2.71 (m, 1H), 2.33-2.23 (m, 2H), 2.17 (s, 1H), 2.00-1.87 (m, 2H), 1.65-1.48 (m, 1H), 1.41-1.26 (m, 16H), 0.88 (m, 3H); high resolution mass spectrum (ESI) m/z 465.3502 ([M]$^+$; calculated for [C$_{30}$H$_{45}$N$_2$O$_2$]$^+$: 465.3476).

Preparation of Q-11,0

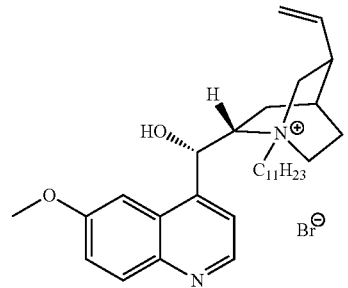

To a solution of quinine (0.503 g, 1.55 mmol) in acetonitrile (2 mL) was added 1-bromoundecane (0.365 g, 1.55 mmol). The resulting yellow solution was stirred and heated at reflux for 25 h. The reaction was then concentrated under reduced pressure to afford Q-11,0 (0.854 g, 98%) as a dark brown solid; mp=94-105° C.; $^1$H NMR (300 MHz, CDCl$_3$) δ 8.76-8.74 (m, 1H), 8.08-8.04 (d, 1H), 7.93-7.66 (m, 1H), 7.42-7.28 (d, 1H), 7.19 (m, 1H), 6.34 (m, 1H), 5.56 (m, 1H), 5.63-5.54 (m, 1H), 5.12-5.03 (m, 2H), 4.91-4.87 (m, 1H), 4.24-4.21 (m, 1H), 4.15-4.09 (m, 1H), 3.93 (s, 3H), 3.83-3.47 (m, 2H), 3.03-2.99 (m, 1H), 2.86-2.83 (m, 1H), 2.09 (m, 1H), 2.05-1.82 (m, 2H), 1.61-1.54 (m, 1H), 1.48-1.26 (m, 18H), 0.90-0.88 (m, 3H); high resolution mass spectrum (ESI) m/z 479.3657 ([M]$^+$; calculated for [C$_{31}$H$_{47}$N$_2$O$_2$]$^+$: 479.3632).

Preparation of Q-12,0

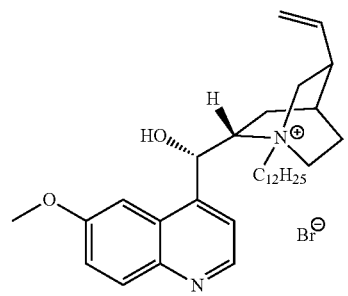

To a solution of quinine (0.500 g, 1.54 mmol) in acetonitrile (2 mL) was added 1-bromododecane (0.386 g, 1.55 mmol). The resulting yellow solution was stirred and heated at reflux for 25 h. The reaction was then concentrated under reduced pressure to afford Q-12,0 (0.806 g, 91%) as a dark brown solid; mp=164-174° C.; $^1$H NMR (300 MHz, CDCl$_3$)

δ 8.78-8.76 (m, 1H), 8.08-8.04 (m, 1H), 7.70-7.69 (m, 1H), 7.41-7.38 (d, 1H), 7.19 (s, 1H), 6.42 (m, 1H), 6.34 (m, 1H), 5.65-5.54 (m, 1H), 5.12-5.03 (m, 2H), 5.01-4.86 (m, 1H), 4.23-4.20 (m, 1H), 4.15-4.11 (m, 1H), 3.92 (s, 3H), 3.80-3.76 (m, 1H), 3.60-3.47 (m, 2H), 3.03-2.99 (m, 1H), 2.86 (m, 1H), 2.34-2.25 (m, 2H), 2.09 (m, 1H), 1.97-1.82 (m, 2H), 1.61-1.53 (m, 1H), 1.48-1.25 (m, 20H), 0.89-0.87 (m, 3H); high resolution mass spectrum (ESI) m/z 493.3812 ([M]$^+$; calculated for [C$_{32}$H$_{49}$N$_2$O$_2$]$^+$: 493.3789).

Preparation of Q-14,0

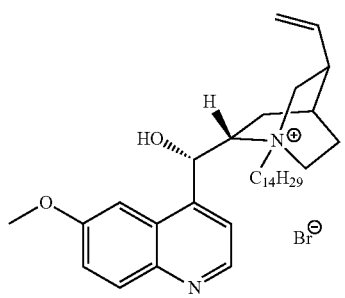

To a solution of quinine (0.504 g, 1.55 mmol) in acetonitrile (2 mL) was added 1-bromotetradecane (0.429 g, 1.54 mmol). The resulting yellow solution was stirred and heated at reflux for 25 h. The reaction was then concentrated under reduced pressure to afford Q-14,0 (0.844 g, 91%) as a dark brown solid; mp=74-84° C.; $^1$H NMR (300 MHz, CDCl$_3$) δ 8.78-8.77 (m, 1H), 8.08-8.05 (m, 1H), 7.71-7.69 (m, 1H), 7.42-7.38 (d, 1H), 7.19 (s, 1H), 6.45-6.44 (m, 1H), 6.35-6.33 (m, 1H), 5.66-5.54 (m, 2H), 5.13-5.07 (m, 2H), 5.01-4.98 (m, 1H), 4.26-4.16 (m, 1H), 4.15-4.06 (m, 1H), 3.92 (s, 3H), 3.81-3.73 (m, 1H), 3.59-3.47 (m, 2H), 3.04-2.99 (m, 1H), 2.86 (m, 1H), 2.37 (m, 2H), 2.24-2.16 (m, 2H), 2.10 (m, 1H), 1.96 (m, 2H), 1.62-1.59 (m, 1H), 1.54-1.25 (m, 24H), 0.89-0.87 (m, 3H); high resolution mass spectrum (ESI) m/z 521.4121 ([M]$^+$; calculated for [C$_{34}$H$_{53}$N$_2$O$_2$]$^+$: 521.4102).

Preparation of Q-16,0

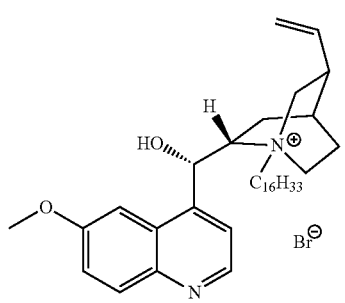

To a solution of quinine (0.500 g, 1.54 mmol) in acetonitrile (2 mL) was added 1-bromohexadecane (0.499 g, 1.63 mmol). The resulting yellow solution was stirred and heated at reflux for 26 h. The reaction was then concentrated under reduced pressure to afford Q-16,0 (0.967 g, 100%) as a dark brown solid; mp=74-84° C.; $^1$H NMR (300 MHz, CDCl$_3$) δ 8.78-8.76 (m, 1H), 8.08-8.03 (m, 1H), 7.70-7.69 (m, 1H), 7.41-7.38 (d, 1H), 7.19 (s, 1H), 6.42 (m, 1H), 6.34 (m, 1H), 5.65-5.54 (m, 1H), 5.12-5.03 (m, 2H), 5.01-4.89 (m, 1H), 4.23-4.18 (m, 1H), 4.15-4.12 (m, 1H), 3.91 (s, 3H), 3.85-3.77 (m, 1H), 3.59-3.50 (m, 2H), 3.04-3.00 (m, 1H), 2.86 (m, 1H), 2.34-2.25 (m, 2H), 2.09 (m, 1H), 2.01-1.82 (m, 2H), 1.69-1.48 (m, 1H), 1.41-1.25 (m, 28H) 0.87-0.86 (m, 3H); high resolution mass spectrum (ESI) m/z 549.4441 ([M]$^+$; calculated for [C$_{36}$H$_{57}$N$_2$O$_2$]$^+$: 549.4415).

Preparation of Q-18,0

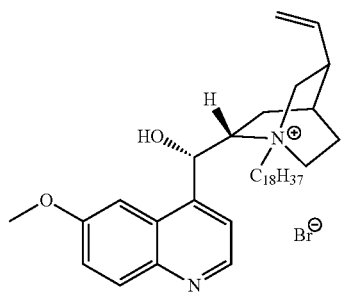

To a solution of quinine (0.502 g, 1.54 mmol) in acetonitrile (2 mL) was added 1-bromooctodecane (0.552 g, 1.65 mmol). The resulting yellow solution was stirred and heated at reflux for 26 h. The reaction was then concentrated under reduced pressure to afford Q-18,0 (1.01 g, 100%) as a dark brown solid; mp=74-84° C.; $^1$H NMR (300 MHz, CDCl$_3$) δ 8.77 (m, 1H), 8.07-8.04 (m, 1H), 7.70 (m, 1H), 7.41-7.38 (m, 1H), 7.19 (s, 1H), 6.41 (m, 1H), 6.33-6.31 (m, 1H), 5.56-5.54 (m, 2H), 5.12-5.03 (m, 2H), 5.01-4.85 (m, 1H), 4.23-4.20 (m, 1H), 4.16-4.08 (m, 1H), 3.92 (s, 3H), 3.89-3.78 (m, 1H), 3.62-3.60 (m, 1H), 3.56-3.47 (m, 1H), 3.04-3.00 (m, 1H), 2.34-2.25 (m, 2H), 2.09 (m, 1H), 1.97-1.79 (m, 2H), 1.61-1.56 (m, 1H), 1.41-1.11 (m, 32H), 0.89-0.84 (m, 3H); high resolution mass spectrum (ESI) m/z 577.4728 ([M]$^+$; calculated for [C$_{38}$H$_{61}$N$_2$O$_2$]$^+$: 577.4742).

Preparation of Q-10,1

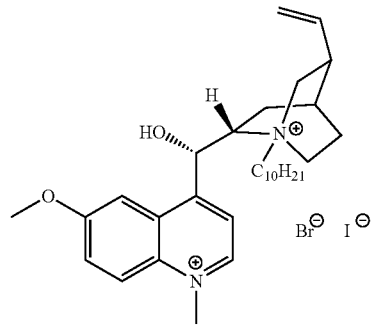

To a flask containing the viscous gel Q-10,0 (0.201 g, 0.369 mmol) was added iodomethane (2 mL, 40 mmol). The resulting solution was capped and stirred for 48 h. The resulting yellow solid was concentrated under reduced pressure resulting in Q-10,1 (0.244 g, 96%) as a yellow solid; mp=117-126° C.; $^1$H NMR (300 MHz, CDCl$_3$) δ 9.16 (m, 1H), 8.32 (m, 1H), 8.21-8.18 (m, 1H), 7.81 (m, 1H), 7.77 (m, 1H), 6.92 (m, 1H), 6.00 (m, 1H), 5.76 (m, 1H), 5.18-5.08 (m, 3H), 4.50 (m, 1H), 4.20-4.17 (m, 3H), 4.01-3.88 (m, 5H), 3.54 (m, 1H), 3.30 (m, 1H), 2.77 (m, 1H), 2.37 (m, 2H), 2.09 (m, 1H), 1.86 (m, 1H), 1.66 (m, 1H), 1.24 (m, 16H), 0.85 (m, 3H); high resolution mass spectrum (ESI) m/z 607.2746 ([M+I]$^+$; calculated for [C$_{31}$H$_{48}$N$_2$O$_2$I]$^+$: 607.2755).

Preparation of Q-11,1

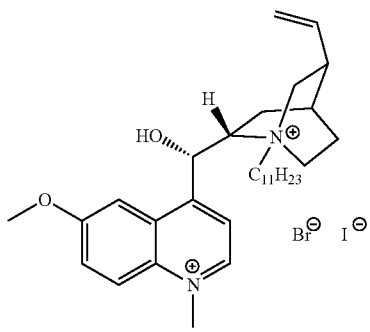

To a flask containing the viscous gel Q-11,0 (0.206 g, 0.368 mmol) was added iodomethane (2 mL, 40 mmol). The resulting solution was capped and stirred for 48 h. The resulting yellow solid was concentrated under reduced pressure resulting in Q-11,1 (0.2582 g, 100%) as a yellow solid; mp=118-126° C.; $^1$H NMR (300 MHz, CDCl$_3$) δ 9.03-9.01 (m, 1H), 8.36-8.34 (m, 1H), 8.18-8.15 (m, 1H), 7.94 (m, 1H), 7.80-7.77 (m, 1H), 6.95 (m, 1H), 6.12-6.00 (m, 1H), 5.84 (m, 1H), 5.22-5.10 (m, 3H), 4.61 (m, 1H), 4.21-4.17 (m, 3H), 4.08-3.51 (m, 5H), 3.27-3.24 (m, 1H), 2.75 (m, 1H), 2.39 (m, 1H), 2.23 (m, 2H), 2.11 (m, 1H), 1.94 (m, 1H), 1.61 (m, 1H), 1.25 (m, 18H), 0.88-0.86 (m, 3H); high resolution mass spectrum (ESI) m/z 621.2906 ([M+I]$^+$; calculated for [C$_{32}$H$_{50}$N$_2$O$_2$I]$^+$: 621.2911).

Preparation of Q-12,1

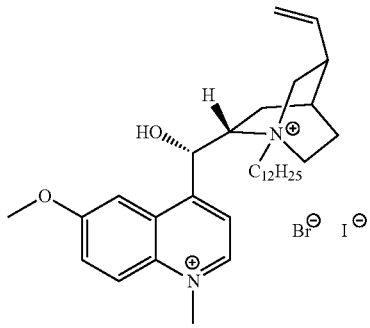

To the viscous gel Q-12,0 (0.202 g, 0.352 mmol) was added iodomethane (2 mL, 40 mmol). The resulting solution was capped and stirred for 48 h. The resulting yellow solid was concentrated under reduced pressure resulting in Q-12,1 (0.246 g, 97%) as a yellow solid; mp=117-124° C.; $^1$H NMR (300 MHz, CDCl$_3$) δ 9.16-9.14 (m, 1H), 8.34-8.32 (9m, 1H), 8.24-8.21 (m, 1H), 7.85 (m, 1H), 7.79-7.76 (m, 1H), 6.92 (m, 1H), 6.07-5.98 (m, 3H), 5.50-5.77 (m, 1H), 5.22-5.08 (m, 3H), 4.20-4.10 (m, 1H), 4.01 (m, 3H), 4.01-3.75 (m, 5H), 3.56-3.53 (m, 1H), 3.29-3.30 (m, 1H), 2.77 (m, 1H), 2.36 (m, 2H), 2.10 (m, 1H), 1.94-1.80 (m, 1H), 1.67 (m, 1H), 1.26-1.14 (m, 20H), 0.88-0.86 (m, 3H); high resolution mass spectrum (ESI) m/z 635.3055 ([M+I]$^+$; calculated for [C$_{33}$H$_{52}$N$_2$O$_2$I]$^+$: 635.3068).

Preparation of Q-14,1

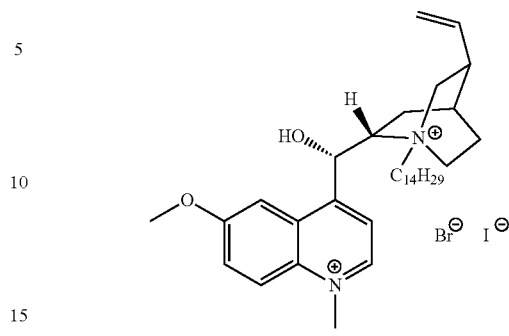

To a flask containing the viscous gel Q-14,0 (0.207 g, 0.344 mmol) was added iodomethane (2 mL, 40 mmol). The resulting solution was capped and stirred for 48 h. The resulting yellow solid was concentrated under reduced pressure resulting in Q-14,1 (0.254 g, 99%) as a yellow solid; mp=117-125 OC; $^1$H NMR (300 MHz, CDCl$_3$) δ 9.07 (m, 1H), 8.34-8.32 (m, 1H), 8.24-8.11 (m, 1H), 8.08-7.90 (m, 1H), 7.80-7.77 (m, 1H), 6.69 (m, 1H), 6.12-6.01 (m, 1H), 5.77 (m, 1H), 5.30-5.10 (m, 3H), 4.66-4.54 (m, 1H), 4.20-4.17 (m, 3H), 3.99-3.76 (m, 5H), 3.57-3.50 (m, 1H), 3.26-3.18 (m, 1H), 2.75 (m, 1H), 2.38 (m, 1H), 2.23-2.17 (m, 1H), 2.10-2.01 (m, 1H), 1.65 (m, 1H), 1.38-1.26 (m, 24H), 0.88-0.86 (m, 3H); high resolution mass spectrum (ESI) m/z 663.3379 ([M+I]$^+$; calculated for [C$_{35}$H$_{56}$N$_2$O$_2$I]$^+$: 663.3381).

Preparation of Q-16,1

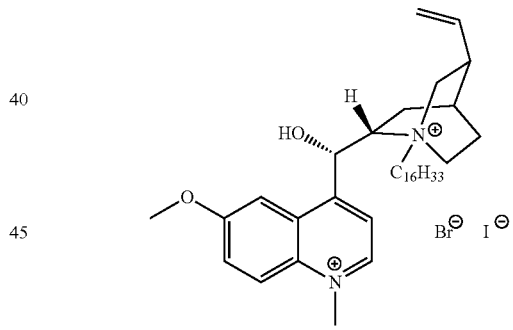

To a flask containing the viscous gel Q-16,0 (0.202 g, 0.320 mmol) was added iodomethane (2 mL, 40 mmol). The resulting solution was capped and stirred for 48 h. The resulting yellow solid was concentrated under reduced pressure resulting in Q-16,1 (0.248 g, 100%) as a yellow solid; mp=134-140 OC; $^1$H NMR (300 MHz, CDCl$_3$) δ 9.21-9.10 (m, 1H), 8.34-8.32 (m, 1H), 8.21-8.18 (m, 1H), 7.88 (m, 1H) m 7.79-7.76 (m, 1H), 6.93 (m, 1H), 6.08-6.02 (m, 1H), 5.77-5.76 (m, 1H), 5.22-5.12 (m, 3H), 4.62-4.56 (m, 1H), 4.20-4.16 (m, 3H), 4.01-3.75 (m, 5H), 3.53-3.50 (m, 1H), 3.27 (m, 1H), 2.76 (m, 1H), 2.21-2.17 (m, 2H), 2.10 (m, 1H), 1.94-1.81 (m, 1H), 1.64 (m, 1H), 1.37-1.25 (m, 28H), 0.87-0.85 (m, 3H); high resolution mass spectrum (ESI) m/z 691.3697 ([M+I]$^+$; calculated for [C$_{37}$H$_{60}$N$_2$O$_2$I]$^+$: 691.3694).

Preparation of Q-18,1

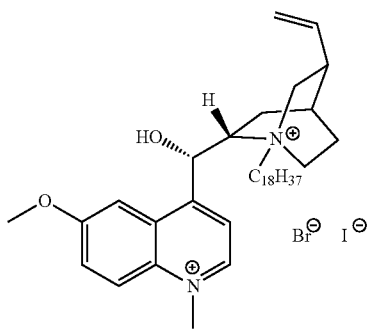

To a flask containing the viscous gel Q-18,0 (0.204 g, 0.311 mmol) was added iodomethane (2 mL, 40 mmol). The resulting solution was capped and stirred for 48 h. The resulting yellow solid was concentrated under reduced pressure resulting in Q-16,1 (0.248 g, 100%) as a yellow solid; mp=122-127° C.; $^1$H NMR (300 MHz, CDCl$_3$) δ 9.09-9.06 (m, 1H), 8.36-8.33 (m, 1H), 8.25-8.17 (m, 1H), 7.91-7.80 (m, 1H), 7.78-7.77 (m, 1H), 6.94 (m, 1H), 6.10-6.00 (m, 1H), 5.81 (m, 1H), 5.23-5.10 (m, 3H), 4.62-4.59 (m, 1H), 4.21-4.20 (m, 3H), 3.99-3.75 (m, 5H), 3.57-3.50 (m, 1H), 3.26-3.21 (m, 1H), 2.75 (m, 1H), 2.38 (m, 1H), 2.23 (m, 1H), 2.11 (m, 1H), 2.01-1.81 (m, 1H), 1.63 (m, 1H), 1.38-1.25 (m, 32H), 0.88-0.85 (m, 3H); high resolution mass spectrum (ESI) m/z 719.4009 ([M+I]$^+$; calculated for [C$_{39}$H$_{64}$N$_2$O$_2$I]$^+$: 719.4007).

Preparation of Q-1,1

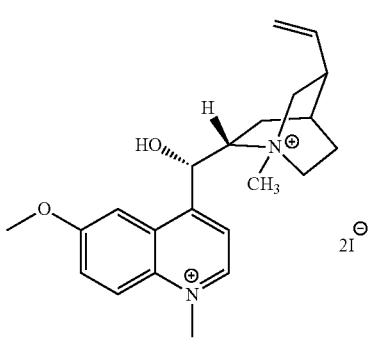 [SMILES: C=CC1C[N+]2(C)CCC1C[C@H]2[C@@H](O)c1cc[n+](C)c2ccc(OC)cc12 ; "2I"]

To quinine (0.211 g, 0.653 mmol) was added iodomethane (2 mL, 40 mmol). The resulting solution was capped and stirred for 48 h. The resulting yellow solid was concentrated under reduced pressure resulting in Q-1,1 (0.305 g, 77%) as a yellow solid; mp=224-226° C.; $^1$H NMR (300 MHz, CDCl$_3$) δ 8.78-8.76 (m, 1H), 8.08-8.05 (d, 1H), 7.75-7.73 (d, 1H), 7.41-7.38 (d, 1H), 7.02-7.01 (s, 1H), 6.54-6.52 (m, 1H), 5.60-5.49 (m, 1H), 5.15-5.04 (m, 3H), 4.75-4.67 (m, 1H), 4.25-4.17 (m, 1H), 3.96 (m, 3H), 3.90-3.72 (m, 5H), 3.38-3.33 (m, 1H), 3.18-3.13 (m, 1H), 2.89 (m, 1H), 2.31-2.20 (m, 2H), 2.12-2.11 (m, 1H), 2.05-2.02 (m, 1H), 1.69 (s, 1H), 1.45-1.37 (t, 1H).

Preparation of N-10,0

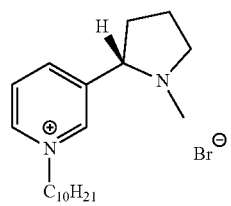

To a solution of nicotine (0.505 g, 3.11 mmol) in acetonitrile (1 mL) was added 1-bromodecane (0.680 g 3.07 mmol). The resulting tan solution was stirred and heated at reflux for 24 h. The reaction was then concentrated under reduced pressure to afford N-10,0 (1.18 g, 98%) as a dark viscous gel; $^1$H NMR (300 MHz, CDCl$_3$) δ 9.52-9.50 (d, 1H), 9.13 (s, 1H), 8.45-8.42 (d, 1H), 8.12-8.07 (m, 1H), 4.97-4.92 (t, 2H), 3.59-3.54 (m, 1H), 3.25-3.19 (m, 1H), 2.47-2.35 (m, 2), 2.22 (s, 3H), 1.93-1.79 (m, 2H), 1.68-1.58 (m, 1H), 1.58-1.19 (m, 16H), 0.85-0.83 (t, 3H); $^{13}$C NMR (75 MHz, CD$_3$OH) δ 145.9, 144.3, 143.5, 127.9, 67.2, 61.7, 56.5, 39.3, 34.9, 31.6, 31.2, 29.2, 29.1, 29.0, 28.7, 25.8, 22.6, 22.3, 13.1; high resolution mass spectrum (ESI) m/z 303.2803 ([M]$^+$; calculated for [C$_{20}$H$_{35}$N$_2$]$^+$: 303.2795).

Preparation of N-11,0

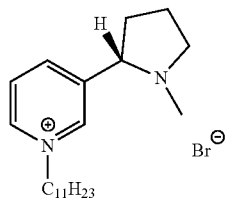

To a solution of nicotine (0.503 g, 3.10 mmol) in acetonitrile (1 mL) was added 1-bromoundecane (0.722 g, 3.06 mmol). The resulting tan solution was stirred and heated at reflux for 24 h. The reaction was then concentrated under reduced pressure to afford N-11,0 (1.23 g, 99%) as a dark viscous gel; $^1$H NMR (300 MHz, CDCl$_3$) δ 9.56-5.47 (m, 1H), 9.09 (s, 1H), 8.44-8.41 (d, 1H) 8.10-8.06 (m, 1H), 5.00-4.95 (t, 2H), 3.59-3.54 (t, 1H), 3.28-3.21 (m, 1H), 2.49-2.37 (m, 2H), 2.24 (s, 3H), 2.00-1.83 (m, 2H), 1.72-1.63 (m, 1H), 1.32-1.21 (m, 18H), 0.87-0.83 (t, 3H); $^{13}$C NMR (75 MHz, CDCl$_3$) δ 146.4, 143.9, 143.0, 128.5, 66.9, 62.1, 56.7, 40.5, 35.8, 32.0, 31.8, 29.5, 29.4, 29.3, 29.2, 29.0, 26.1, 23.1, 22.6, 14.1; high resolution mass spectrum (ESI) m/z 317.2968 ([M]$^+$; calculated for [C$_{21}$H$_{37}$N$_2$]$^+$: 317.2951).

Preparation on N-12,0

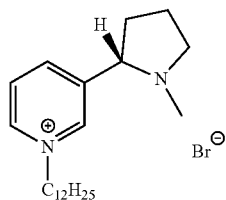

To a solution of nicotine (0.503 g, 3.10 mmol) in acetonitrile (1 mL) was added 1-bromododecane (0.769 g, 3.08 mmol). The resulting tan solution was stirred and heated at reflux for 24 h. The reaction was then concentrated under reduced pressure to afford N-12,0 (1.28 g, 99%) as a dark viscous gel; $^1$H NMR (300 MHz, CDCl$_3$) δ 9.52-9.51 (m, 1H), 9.13 (s, 1H), 8.45-8.42 (d, 1H), 8.11-8.07 (m, 1H), 4.97-4.92 (m, 2H) 3.59-3.53 (m, 1H), 3.26-3.19 (m, 1H), 2.47-2.35 (m, 2H), 2.21 (s, 3H), 1.96-1.82 (m, 2H), 1.68-1.61 (m, 1H), 1.60-1.19 (m, 21H), 0.85-0.83 (t, 3H); $^{13}$C NMR (75 MHz, CDCl$_3$) δ 146.3, 143.9, 143.0, 128.5, 66.9, 62.0, 56.7, 40.5, 35.7, 31.8, 29.5, 29.4, 29.3, 29.3, 29.0, 28.9, 26.1, 23.1, 22.6, 22.6, 14.1; high resolution mass spectrum (ESI) m/z 331.3130 ([M]$^+$; calculated for [C$_{22}$H$_{39}$N$_2$]$^+$: 331.3108).

Preparation of N-14,0

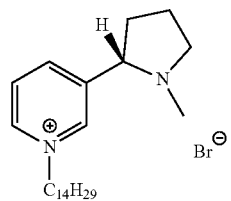

To a solution of nicotine (0.505 g, 3.11 mmol) in acetonitrile (1 mL) was added 1-bromotetradecane (0.858 g, 3.08 mmol). The resulting tan solution was stirred and heated at reflux for 24 h. The reaction was then concentrated under reduced pressure to afford N-14,0 (1.36 g, 99%) as a dark viscous gel; $^1$H NMR (300 MHz, CDCl$_3$) δ 9.53-9.51 (m, 1H), 9.14 (s, 1H), 8.45-8.42 (m, 1H), 8.11-8.07 (m, 1H), 4.97-4.92 (m, 2H), 3.60-3.54 (m, 1H), 3.23-3.19 (m, 1H), 2.47-2.35 (m, 2H), 2.05-1.93 (m, 3H), 1.93-1.80 (m, 2H), 1.70-1.59 (m, 1H), 1.30-1.12 (m, 24H), 0.85-0.80 (t, 3H); $^{13}$C NMR (75 MHz, CDCl$_3$) δ 146.3, 143.9, 143.0, 128.5, 66.9, 62.0, 56.7, 40.5, 35.7, 32.0, 31.9, 29.6, 29.6, 29.5, 29.3, 29.3, 29.0, 26.1, 23.1, 22.6, 14.1; high resolution mass spectrum (ESI) m/z 359.3443 ([M]$^+$; calculated for [C$_{24}$H$_{43}$N$_2$]$^+$: 359.3421).

Preparation of N-16,0

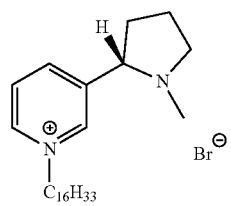

To a solution of nicotine (0.505 g, 3.10 mmol) in acetonitrile (1 mL) was added 1-bromohexadecane (0.940 g, 3.07 mmol). The resulting tan solution was stirred and heated at reflux for 24 h. The reaction was then concentrated under reduced pressure to afford N-16,0 (1.45 g, 99%) as a dark viscous gel; $^1$H NMR (300 MHz, CDCl$_3$) δ 9.56-9.54 (m, 1H), 9.10 (s, 1H), 8.44-8.41 (m, 1H), 8.10-8.06 (m, 1H), 5.00-4.95 (m, 2H), 3.57-3.54 (m, 1H), 3.28-3.21 (m, 1H), 2.49-2.39 (m, 2H), 2.04-1.95 (m, 3H), 1.94-1.85 (m, 2H), 1.67-1.64 (m, 1H), 1.32-1.21 (m, 28H), 0.87-0.83 (t, 3H); $^{13}$C NMR (75 MHz, CDCl$_3$) δ 146.3, 143.9, 143.0, 128.4, 66.9, 62.0, 56.6, 40.4, 35.7, 31.9, 31.8, 29.6, 29.6, 29.6, 29.5, 29.3, 29.0, 26.1, 23.1, 22.6, 14.1; high resolution mass spectrum (ESI) m/z 387.3751 ([M]$^+$; calculated for [C$_{26}$H$_{47}$N$_2$]$^+$: 387.3734).

Preparation of N-18,0

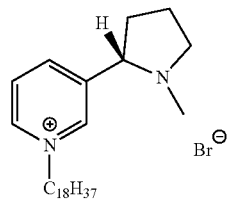

To a solution of nicotine (0.501 g, 3.09 mmol) in acetonitrile (1 mL) was added 1-bromooctadecane (1.02 g, 3.09 mmol). The resulting tan solution was stirred and heated at reflux for 24 h. The reaction was then concentrated under reduced pressure to afford N-18,0 (1.17 g, 77%) as a dark viscous gel; $^1$H NMR (300 MHz, CDCl$_3$) δ 9.56-9.55 (m, 1H), 9.07 (s, 1H), 8.43-8.40 (m, 1H), 8.08-8.04 (m, 1H), 5.01-4.96 (m, 2H), 3.57-3.54 (m, 2H), 3.29-3.24 (m, 1H), 2.48-2.38 (m, 2H), 2.06-1.90 (m, 3H), 1.89-1.82 (m, 2H), 1.69-1.67 (m, 1H), 1.33-1.22 (m, 32H), 0.89-0.85 (t, 3H); $^{13}$C NMR (75 MHz, CDCl$_3$) δ 146.3, 143.9, 143.0, 128.5, 66.9, 62.1, 56.7, 40.5, 35.7, 32.0, 31.9, 29.7, 29.6, 29.6, 29.5, 29.4, 29.3, 29.0, 26.1, 23.1, 22.6, 14.1; high resolution mass spectrum (ESI) m/z 415.4066 ([M]$^+$; calculated for [C$_{28}$H$_{51}$N$_2$]$^+$: 415.4047).

Preparation of N-20,0

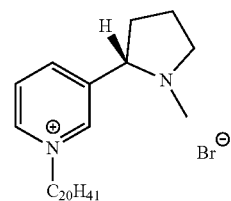

To a solution of nicotine (0.509 g, 3.14 mmol) in acetonitrile (1 mL) was added 1-bromoicosane (1.108 g, 3.06 mmol). The resulting tan solution was stirred and heated at reflux for 24 h. The reaction was then concentrated under reduced pressure to afford N-20,0 (1.64 g, 99%) as a dark vicious gel; mp=53-55° C.; $^1$H NMR (300 MHz, CDCl$_3$) δ 9.58-9.56 (m, 1H), 9.07 (s, 1H), 8.42-8.39 (m, 1H), 8.08-8.04 (m, 1H), 5.01-4.96 (m, 2H), 3.56-3.53 (m, 1H), 3.28-3.23 (m, 1H), 2.50-2.38 (m, 2H), 2.03-2.00 (m, 3H), 2.00-1.82 (m, 2H), 1.68 (s, 1H), 1.33-1.22 (m, 36H), 0.89-0.85 (t, 3H); $^{13}$C NMR (75 MHz, CDCl$_3$) δ 146.4, 144.0, 143.9, 143.0, 128.4, 66.9, 62.0, 56.7, 40.5, 35.8, 32.0, 31.9, 29.7, 29.6, 29.6, 29.5, 29.4, 29.3, 29.0, 26.1, 23.1, 22.7, 14.1; high resolution mass spectrum (ESI) m/z 443.4376 ([M]$^+$; calculated for [C$_{30}$H$_{55}$N$_2$]$^+$: 443.4360).

Preparation of N-10, 1

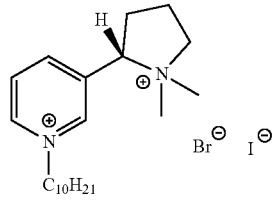

To a flask containing the viscous gel N-10,0 (0.199 g, 0.521 mmol) was added iodomethane (2 mL, 40 mmol). The resulting solution was capped and stirred for 48 h. The resulting dark gel was concentrated under reduced pressure resulting in N-10,1 (0.227 g, 83%) as a dark amorphous solid; $^1$H NMR (300 MHz, CD$_3$OD) δ 9.50 (s, 1H), 9.21 (s, 1H), 8.93-8.91 (m, 1H), 8.29 (s, 1H), 5.19-5.13 (t, 1H), 4.73 (m, 2H), 3.94-3.87 (m, 2H), 3.30 (s, 3H), 2.97 (s, 3H), 2.84-2.73 (m, 2H), 2.43 (m, 2H), 2.09 (m, 2H), 1.43-1.21 (m, 14H), 0.89 (m, 3H); $^{13}$C NMR (75 MHz, CD$_3$OD) δ 147.7, 146.9, 146.6, 131.0, 128.8, 74.5, 67.1, 62.3, 50.6, 45.5, 31.6, 31.2, 29.2, 29.2, 29.0, 28.8, 26.4, 25.9, 22.3, 19.0, 13.1; high resolution mass spectrum (ESI) m/z 445.2067 ([M+I]$^+$; calculated for [C$_{21}$H$_{38}$N$_2$I]$^+$: 445.2074).
Preparation of N-11,1

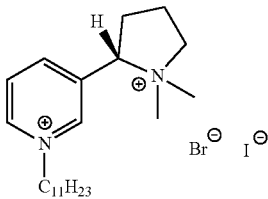

To a flask containing the viscous gel N-11,0 (0.210 g, 0.529 mmol) was added iodomethane (2 mL, 40 mmol). The resulting solution was capped and stirred for 48 h. The resulting dark gel was concentrated under reduced pressure resulting in N-11,1 (0.277 g, 97%) as a dark amorphous solid; $^1$H NMR (300 MHz, CD$_3$OD) δ 9.57 (s, 1H), 9.19 (m, 1H), 8.94-8.92 (m, 1H), 8.29 (m, 1H) 5.19 (t, 2H), 4.74 (m, 2H), 3.94-3.84 (m, 2H), 3.28 (s, 3H) 2.98 (m, 3H), 2.82-2.71 (m, 2H), 2.43 (m, 2H), 2.14-2.10 (m, 2H), 1.43-1.28 (m, 16H), 0.89 (m, 3H); $^{13}$C NMR (75 MHz, CD$_3$OD) δ 147.7, 146.9, 146.6, 131.1, 128.8, 74.6, 67.1, 62.4, 50.7, 45.6, 31.6, 31.1, 29.2, 29.1, 29.0, 28.7, 26.4, 25.9, 22.3, 19.1, 13.0; high resolution mass spectrum (ESI) m/z 459.2228 ([M+I]$^+$; calculated for [C$_{22}$H$_{40}$N$_2$I]$^+$: 459.2231).
Preparation of N-12,1

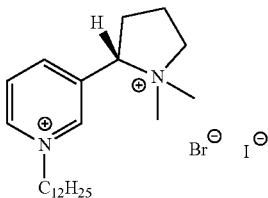

To a flask containing the viscous gel N-12,0 (0.218 g, 0.532 mmol) was added iodomethane (2 mL, 40 mmol). The resulting solution was capped and stirred for 48 h. The resulting dark gel was concentrated under reduced pressure resulting in N-12,1 (0.293 g, 99%) as a dark amorphous solid; $^1$H NMR (300 MHz, CD$_3$OD) δ 9.54 (s, 1H), 9.21 (s, 1H), 8.94-8.92 (m, 1H), 8.28 (m, 1H), 5.23-5.17 (t, 2H), 4.74 (m, 2H), 3.94-3.85 (m, 2H), 3.29 (s, 3H), 2.99 (s, 3H), 2.82-2.72 (m, 2H), 2.43 (m, 2H), 2.10 (m, 2H), 1.43-1.28 (m, 18H), 0.89 (m, 3H); $^{13}$C NMR (75 MHz, CD$_3$OD) δ 147.7, 147.0, 146.6, 131.0, 128.8, 74.5, 67.0, 62.3, 50.6, 45.5, 31.7, 31.2, 29.4, 29.1, 29.2, 28.8, 26.4, 26.0, 22.3, 19.0, 13.1; high resolution mass spectrum (ESI) m/z 473.2396 ([M+I]$^+$; calculated for [C$_{23}$H$_{42}$N$_2$I]$^+$: 473.2387).
Preparation of N-14,1

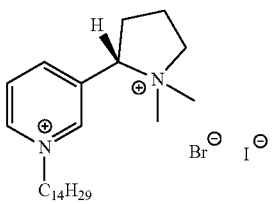

To a flask containing the viscous gel N-14,0 (0.211 g, 0.479 mmol) was added iodomethane (2 mL, 40 mmol). The resulting solution was capped and stirred for 48 h. The resulting dark gel was concentrated under reduced pressure resulting in N-14,1 (0.242 g, 87%) as a dark amorphous solid; $^1$H NMR (300 MHz, CD$_3$OD) δ 9.53 (s, 1H), 9.22-9.20 (m, 1H), 8.94-8.92 (m, 1H), 8.31-8.29 (t, 1H), 5.22-5.15 (m, 2H), 4.76-4.71 (m, 1H), 3.96-3.84 (m, 3H), 2.99 (s, 3H), 2.84-2.71 (m, 2H), 2.43 (m, 2H), 2.15-2.03 (m, 2H), 1.43-1.28 (m, 24H), 0.89-0.87 (m, 3H); $^{13}$C NMR (75 MHz, CD$_3$OD) δ 147.7, 146.9, 146.6, 131.0, 128.9, 74.5, 67.1, 62.4, 50.8, 45.7, 31.6, 31.1, 29.4, 29.3, 29.2, 29.1, 29.0, 28.7, 26.4, 25.9, 22.3, 19.1, 13.0; high resolution mass spectrum (ESI) m/z 501.2701 ([M+I]$^+$; calculated for [C$_{25}$H$_{42}$N$_2$I]$^+$: 501.2700).
Preparation of N-16,1

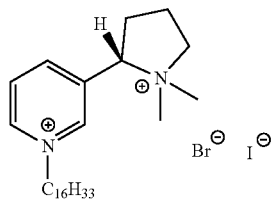

To a flask containing the viscous gel N-14,0 (0.253 g, 0.543 mmol) was added iodomethane (2 mL, 40 mmol). The resulting solution was capped and stirred for 48 h. The resulting dark gel was concentrated under reduced pressure resulting in N-16,1 (0.251 g, 76%) as a dark solid; mp=195-215 OC; $^1$H NMR (300 MHz, CD$_3$OD) δ 9.51-9.22 (s, 1H), 9.22-9.20 (m, 1H), 8.94-8.91 (m, 1H), 8.29-8.27 (m, 1H), 5.20-5.13 (m, 1H), 4.76-4.70 (m, 2H), 3.98-3.84 (m, 2H), 3.57 (s, 3H), 2.98 (s, 3H), 2.84-2.71 (m, 2H), 2.45-2.43 (m, 2H), 2.15-2.03 (m, 2H), 1.43-1.28 (m, 26H), 0.90-0.88 (m, 3H); $^{13}$C NMR (75 MHz, CD$_3$OD) δ 147.7, 147.9, 146.6, 130.9, 128.8, 74.5, 67.1, 62.3, 50.6, 45.6, 31.7, 31.2, 29.4, 29.3, 29.2, 29.1, 28.8, 26.4, 25.9, 22.4, 19.0, 13.1; high resolution mass spectrum (ESI) m/z 529.3010 ([M+I]$^+$; calculated for [C$_{27}$H$_{50}$N$_2$I]$^+$: 529.3013).
Preparation of N-18,1

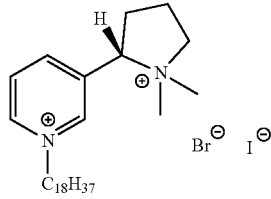

To a flask containing the viscous gel N-18,0 (0.176 g, 0.355 mmol) was added iodomethane (2 mL, 40 mmol). The resulting solution was capped and stirred for 48 h. The resulting dark gel was concentrated under reduced pressure resulting in N-18,1 (0.220 g, 97%) as a dark solid; $^1$H NMR (300 MHz, CD$_3$OD) δ 9.48 (s, 1H), 9.20 (m, 1H), 8.91 (m, 1H), 8.29 (m, 1H), 5.23-5.03 (m, 1H), 4.72 (m, 2H), 3.94-3.87 (m, 2H), 3.29 (s, 3H), 2.97 (m, 3H), 2.79 (m, 2H), 2.50-2.43 (m, 2H), 2.20-2.12 (m, 2H), 1.92-1.28 (m, 30H), 0.97-0.87 (m, 3H); $^{13}$C NMR (75 MHz, CD$_3$OD) δ 147.7, 146.9, 146.6, 131.0, 128.9, 74.5, 67.1, 62.4, 50.8, 45.7, 1.6, 31.2, 29.4, 29.3, 29.3, 29.1, 29.0, 28.7, 26.4, 25.9, 22.3, 19.1, 13.0; high resolution mass spectrum (ESI) m/z 557.3328 ([M+I]$^+$; calculated for [$C_{29}H_{54}N_2I$]$^+$: 557.3326).

Preparation of N-20,1

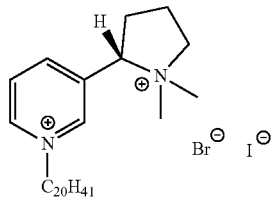

To a flask containing the viscous gel N-20,0 (0.224 g, 0.429 mmol) was added iodomethane (2 mL, 40 mmol). The resulting solution was capped and stirred for 48 h. The resulting dark gel was concentrated under reduced pressure resulting in N-20,1 (0.285 g, 99%) as a dark solid; mp=239-241 OC; $^1$H NMR (300 MHz, CD$_3$OD) δ 9.56 (s, 1H), 9.21 (m, 1H), 8.95-8.93 (m, 1H), 8.31-8.26 (m, 1H) 5.25-5.18 (m, 1H), 4.77-4.72 (m, 2H), 3.97-3.82 (m, 2H), 3.35 (s, 3H), 3.00 (s, 3H), 2.86-2.72 (m, 2H), 2.44-2.43 (m, 2H), 2.10 (m, 2H), 1.27 (m, 34H), 0.91-0.87 (m, 3H); high resolution mass spectrum (ESI) m/z 585.3636 ([M+I]$^+$; calculated for [$C_{31}H_{58}N_2I$]$^+$: 585.3639).

The results of the experiments are now described.

Figure 19:
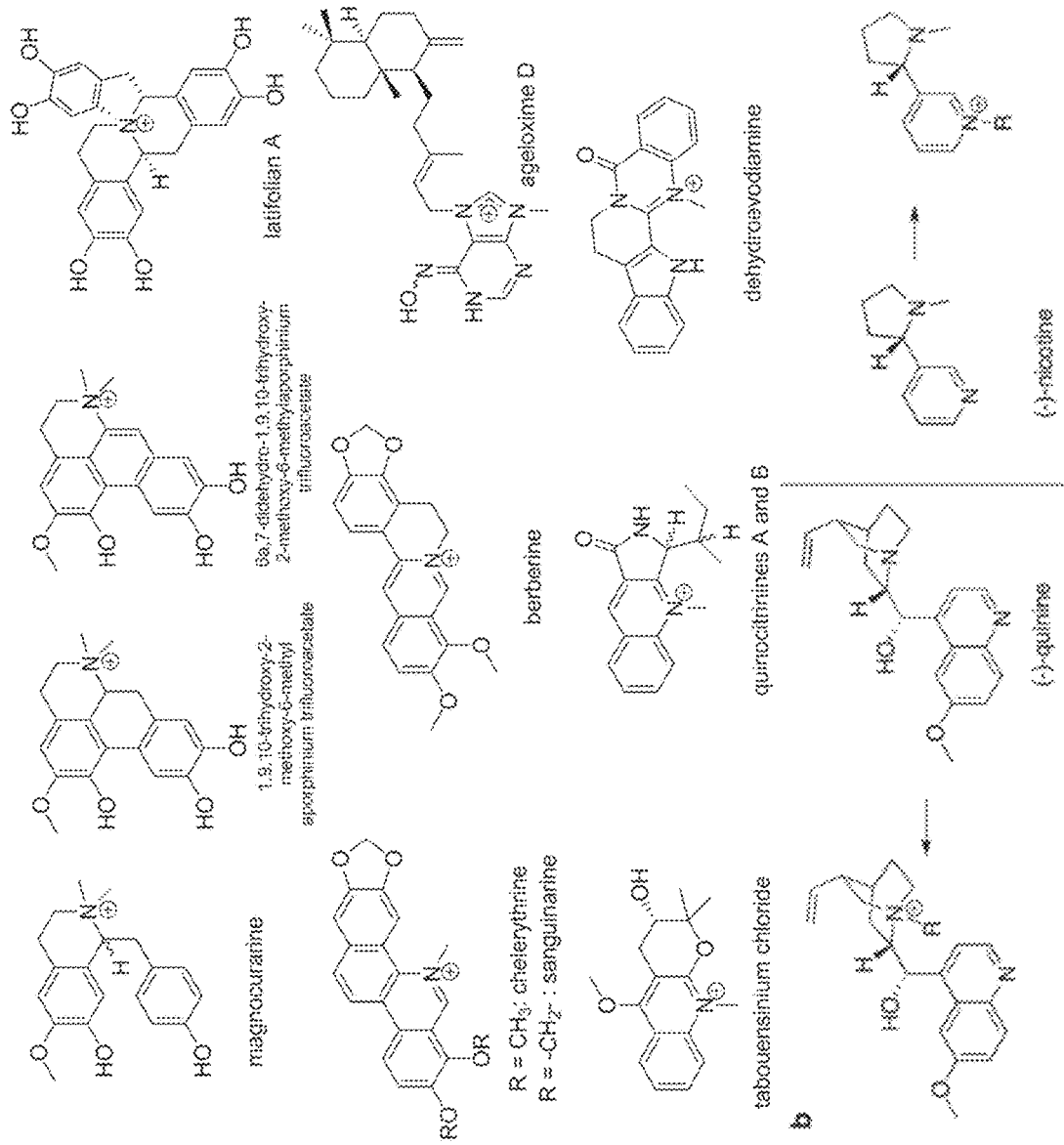
FIG. 19, comprising

Two natural products core structures that were examined were quinine and nicotine (FIG. 19B). Each presents a pyridine nitrogen, as well as a separate tertiary amine with only modest steric hindrance. Each compound is naturally abundant, therefore, making it inexpensive, and presents no significant reported antibacterial property as the unmodified natural product. Furthermore, although each has precedent to react as chiral bases (Palomo et al., 2009, Chem. Soc. Rev. 38:632-653) and nucleophiles, neither has been systematically investigated regarding their alkylation to form antimicrobial amphiphiles (Lv et al., 2007, Bioorg. Med. Chem. Lett. 17:4102-4106; WO 9937635).

Interestingly, these two natural products present opposite trends in their reported alkylation chemistry; nicotine is preferably alkylated at its pyridine nitrogen (Shibagaki et al., 1982, Heterocycles 19:1641-1645), and quinine is precedented to react at its tertiary aliphatic amine (FIG. 19B) (Badiya et al., 2009, J. Org. Chem. 74:7157-7164). For both compounds, however, little is known about the amphiphilic properties of long-chain alkylated derivatives, though some nicotine-based amphiphiles have been investigated for their effects on the central nervous system (US 2003/0225142) and applications as ionic liquids (Crooks et al., 2004, Bioorg. Med. Chem. Lett. 14:869-1874); quinine derivatives have served as phase-transfer catalysts (Sing and Arora, 1986, Indian J. Chem. Sect. B 25B:1034-1037) and substrates for phosphorylation (Gavrilov et al., 1996, Phosphorus Sulfur Silicon Relat. Elem. 108:285-287). A series of mono- and bis-alkylated derivatives of quinine and nicotine were synthesized for the purpose of evaluating their antimicrobial potential.

Figure 20:
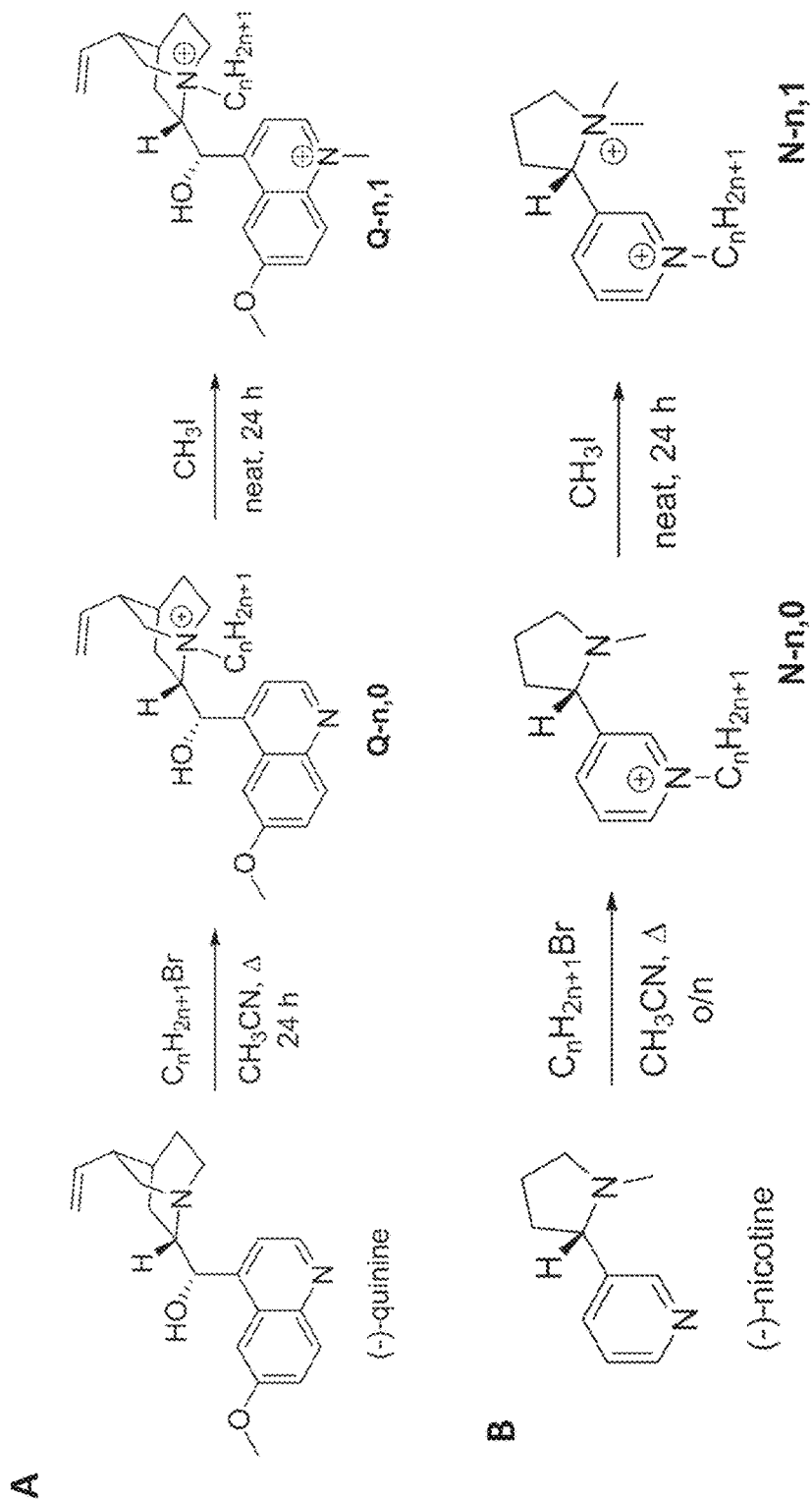
FIG. 20, comprising

To this end, the alkylation of quinine was first explored, and proceeded under high-concentration conditions (~1 m, CH$_3$CN) using a variety of alkyl bromide electrophiles (FIG. 20A). Yields were uniformly high, and led to a simple production of the monocationic compounds abbreviated as Q-n,0. Subsequent alkylation proved to be limited in scope; it was found that a second alkylation with a long-chained alkyl bromide or iodide was difficult to complete, resulting in a mixture of compounds. However, exposure to neat methyl iodide led to nearly quantitative alkylation overnight, affording the Q-n,1 series after simple evaporation.

Nicotine derivatives were alkylated in a highly analogous manner, again leading to alkylation in high yields (1 equiv RBr, CH$_3$CN, Δ, o/n), as illustrated in FIG. 20B. Alkylation was observed exclusively at the pyridine nitrogen. Subsequent alkylation, converting the N-n,0 series to the N-n,1 series, proceeded somewhat more slowly, completing in 48 h at high yield. Evaporation provided the final set of compounds abbreviated as N-n,1, setting the stage for biological investigation.

MIC values against Gram-positive *Staphylococcus aureus* (methicillin-susceptible *Staphyloccocus aureus* (MSSA) and two MRSA strains—USA300-0114 and ATCC33591) and *Enterococcus faecalis* and Gram-negative *Escherichia coli* and *P. aeruginosa* were determined according to standard, and results appear in FIG. 67.

The amphiphiles derived from both quinine and nicotine displayed strong antibacterial activity against a number of Gram-positive and Gram-negative strains. Control compounds, including the parent natural products as well as their bis-methylated derivatives (Q-1,1 and N-1,1) showed essentially no antimicrobial activity. Longer chain alkyl derivatives of these natural products showed clear correlations between alkyl chain length and antimicrobial activity. In the nicotine series, the strongest activity was observed for N-16,0 and N-18,1 for the mono- and bisQACs, respectively. Each showed low micromolar activity (4 μm) for all bacteria except for *P. aeruginosa*. For the monocationic quinine derivatives, the strongest activity was observed for Q-14,0; however, longer chains proved had improved properties for the bisQACs (Q-16,1 and Q-18,1), and in fact provided two amphiphiles with single-digit micromolar activity against all bacteria tested. The modest inconsistencies in chain length are somewhat unexpected, and although not wishing to be bound by any particular theory, these results may reflect a balance between polar and non-polar sections of the amphiphiles, as well as the markedly different core natural products.

It was unexpected to observe roughly comparable activity when comparing the mono- and bis-cationic compounds for most of this data set. BisQACs did not prove uniformly more potent than the singly cationic analogs, and in many cases proved inferior to the analogous monoQACs (for example, N-12,0 vs N-12,1). When comparing activity against MSSA and MRSA (shaded entries in Table 5), nearly every natural product-derived QAC showed significant levels of bacterial resistance, with up to a 32-fold higher MIC for MRSA strains. In fact, in only two of the 28 compounds prepared was comparable activity against MSSA and MRSA observed-only Q-16,1 and Q-18,1 were unaffected by QAC resistance. This stands in stark contrast to Q-18,0, which showed strong susceptibility to MRSA resistance, resulting in a 32-fold increase in MIC of MRSA as compared to MSSA. Although not wishing to be bound by any particular theory, these results support previous observations that MRSA resistance seems to be associated with monoQACs as well as bisQACs based on aromatic substrates, but it is possible that alkyl chain length should also be a consideration.

In summary, these results demonstrate that selected natural products can serve as the platform for amphiphile construction, and that such derivatization is capable of imparting significant levels of antibacterial activity. Further, these results support the hypothesis that monoQACs are susceptible to MRSA resistance, presumably through the effect of efflux pumps. Two longer chained bisQACs derived from quinine showed no resistance at all to two MRSA strains. The simplicity of synthesis, and observed potency of many of the compounds presented herein demonstrate that these compounds may be useful as antiseptics and antibiotics.

Example 6: Scaffold-Hopping of Multicationic Amphiphiles Yields Three New Classes of Antimicrobials The results herein describe a scaffold-hopping approach to develop alternative QAC architectures that display 1-3 long alkyl chains in specific projections from cyclic and branched core structures bearing 3-4 nitrogen atoms. The preparation of 30 QAC structures allowed for correlation of scaffold structure with antimicrobial activity. QACs with limited conformational flexibility that have improved bioactivity against planktonic bacteria as compared to their linear counterparts were identified. It was also found that resistance, as evidenced by an increased minimum inhibitory concentration (MIC) for methicillin-resistant *Staphylococcus aureus* (MRSA) compared to methicillin-susceptible *Staphylococcus aureus* (MSSA), can reduce efficacy up to 64-fold for monocationic QACs.

The materials and methods employed in these experiments are now described.

General Information

Reagents and solvents were used from Sigma-Aldrich, Acros, TCI America, Matrix Scientific, and Alfa Aesar without further purification. All melting points were obtained on a SRS DigiMelt apparatus. All reactions were carried out under ambient atmosphere with reagent grade solvents and magnetic stirring. All yields refer to spectroscopically pure compounds. $^1$H NMR spectra were measured with a 300 MHz Varian spectrophotometer, and chemical shifts were reported on a δ-scale (ppm) downfield from TMS. Coupling constants were calculated in hertz. $^{13}$C NMR spectra were obtained at 75 MHz, and results were reported on a δ-scale (ppm). Chloroform-d (CDCl$_3$) was the solvent used for most $^1$H NMR samples with an internal reference of 7.26 ppm. Deuterated methanol (CD$_3$OD) was used for other NMR samples with an internal reference of 3.35 ppm for $^1$H NMR and 49.3 for $^{13}$C NMR. High-resolution mass spectrometry was performed by the Mass Spectrometry Facility at Temple University.

Synthesis of Compounds

Preparation of P-10,0,10 (11)

Figure 26:
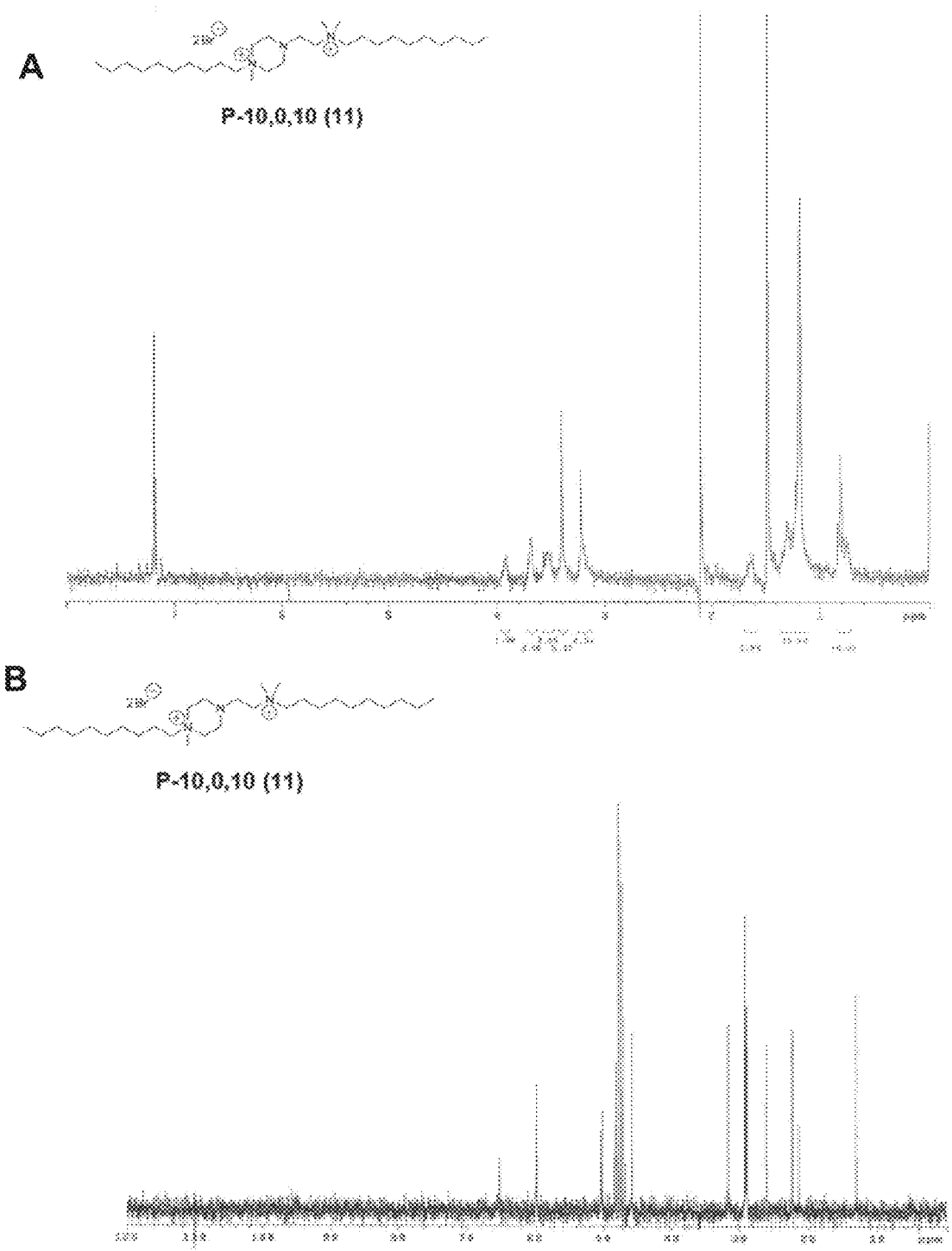
FIG. 26, comprising

To a solution of 1-(2-dimethylaminoethyl)-4-methylpiperazine (0.505 g, 2.95 mmol) in acetonitrile (2 mL) was added 1-bromodecane (1.31 g, 5.92 mmol). The resulting colorless solution was heated at reflux with stirring overnight, during which time a white precipitate with a brown top layer was observed. After cooling, and the addition of acetonitrile (1 mL), then a cold hexanes/acetone mixture (~15 mL, 1:1), to the reaction flask, the precipitate was filtered with a Büchner funnel, and rinsed with cold hexanes/acetone (~20 mL). The resulting crude product (a white powder with a slight brown hue) was triturated with hot acetone (~35 mL), then washed with a cold hexanes/acetone mixture (50 mL, 1:1), resulting in P-10,0,10 (1.40 g, 77%) as a white powder; mp>260° C.; $^1$H NMR (300 MHz, CDCl$_3$) δ 3.96-3.90 (m, 2H), 3.72-3.66 (m, 4H), 3.57-3.48 (m, 6H), 3.40 (s, 6H), 3.24-3.16 (m, 7H), 1.71-1.58 (m, 2H), 1.36-1.15 (m, 30H), 0.84-0.78 (m, 6H); $^{13}$C NMR (75 MHz, CD$_3$OD) δ 65.2, 59.9, 59.8, 50.5, 50.2, 45.8, 31.7, 29.2, 29.2, 29.0, 28.9, 28.9, 26.0, 22.3, 22.3, 21.4, 13.1; high resolution mass spectrum (ESI) m/z 226.7495 ([M]$^{2+}$; calculated for [C$_{29}$H$_{63}$N$_3$]$^{2+}$: 226.7506). $^1$H and $^{13}$C NMR spectra of compound P-10,0,10 can be found in FIG. 26.

Preparation of P-11,0,11 (12)

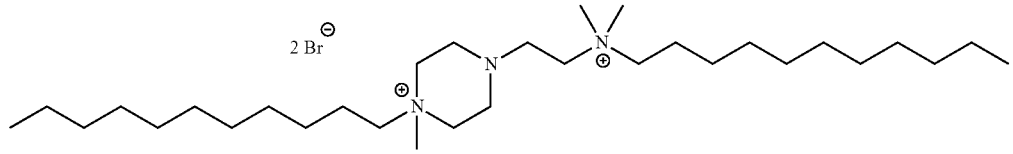

Figure 27:
FIG. 27, comprising
Figure 27:
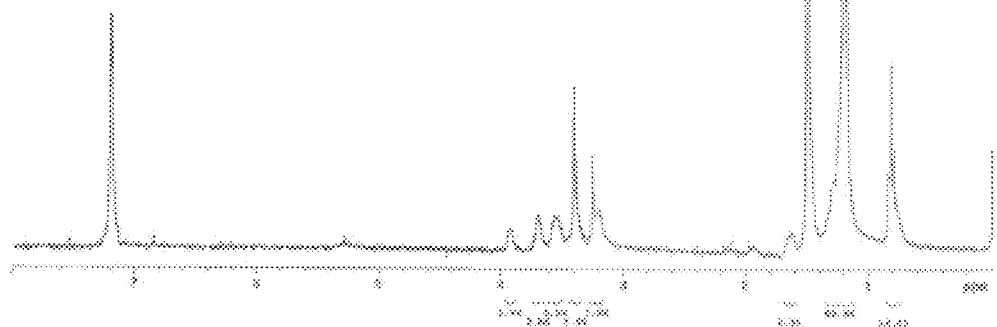
Figure 27:
Figure 27:
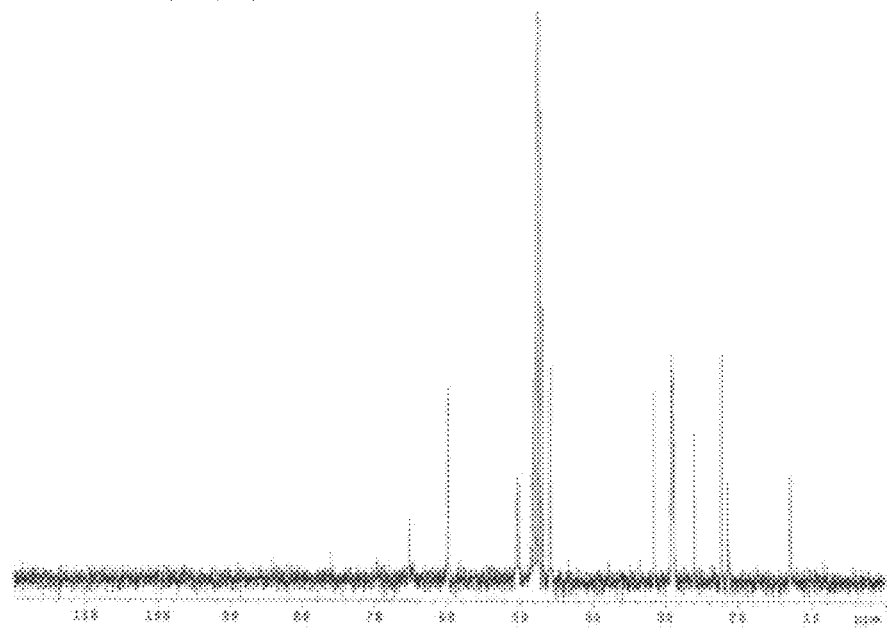

To a solution of 1-(2-dimethylaminoethyl)-4-methylpiperazine (0.539 g, 3.15 mmol) in acetonitrile (4 mL) was added 1-bromoundecane (1.51 g, 6.42 mmol). The resulting colorless solution was heated at reflux with stirring overnight, during which time a white precipitate with a brown top layer was observed. After cooling, and the addition of a cold hexanes/acetone mixture (~15 mL, 1:1), to the reaction flask, the precipitate was filtered with a Büchner funnel, and rinsed with cold hexanes/acetone (~20 mL). The resulting crude product (a white powder with a slight brown hue) was triturated with hot acetone (~35 mL), then washed with a cold hexanes/acetone mixture (50 mL, 1:1), resulting in P-11,0,11 (1.44 g, 71%) as a white powder; mp>260° C.; $^1$H NMR (300 MHz, CDCl$_3$) δ 3.96-3.89 (m, 2H), 3.73-3.64 (m, 4H), 3.61-3.48 (m, 6H), 3.40 (s, 6H), 3.27-3.17 (m, 7H), 1.70-1.58 (m, 2H), 1.37-1.12 (m, 34H), 0.85-0.78 (m, 6H); $^{13}$C NMR (75 MHz, CD$_3$OD) δ 65.3, 59.9, 50.5, 50.2, 45.9, 31.6, 29.2, 29.2, 29.1, 29.0, 28.9, 28.8, 26.0, 22.3, 21.4, 13.0; high resolution mass spectrum (ESI) m/z 240.7650 ([M]$^{2+}$; calculated for [C$_{31}$H$_{67}$N$_3$]$^{2+}$: 240.7662). $^1$H and $^{13}$C NMR spectra of compound P-11,0,11 can be found in FIG. 27.

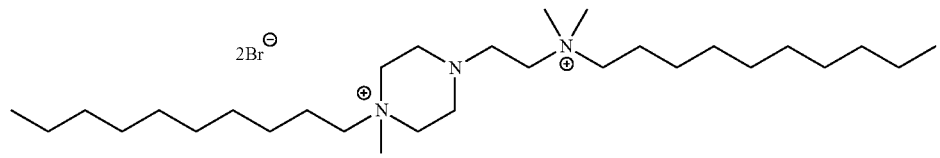 [SMILES: CCCCCCCCCC[N+](C)(C)CCN1CC[N+](C)(CCCCCCCCCC)CC1]

Preparation of P-12,0,12 (13)

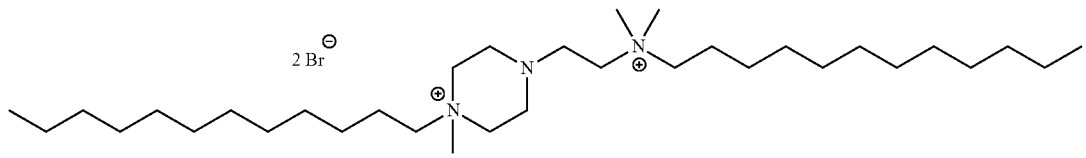 [SMILES: CCCCCCCCCCCC[N+](C)(C)CCN1CC[N+](C)(CCCCCCCCCCCC)CC1]

Figure 28:
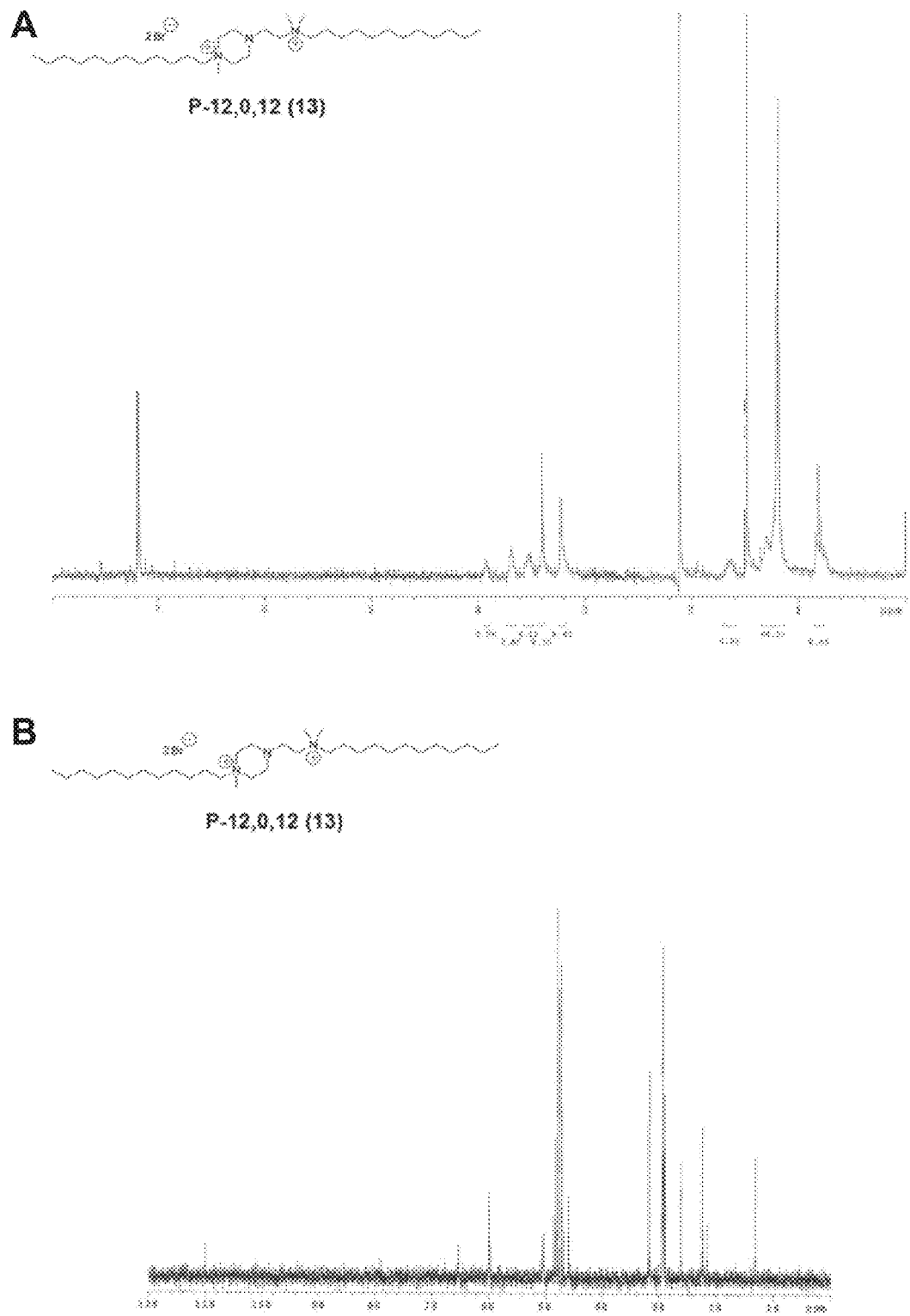
FIG. 28, comprising

To a solution of 1-(2-dimethylaminoethyl)-4-methylpiperazine (0.530 g, 3.09 mmol) in acetonitrile (2 mL) was added 1-bromododecane (1.55 g, 6.20 mmol). The resulting colorless solution was heated at reflux with stirring overnight, during which time a white precipitate with a brown top layer was observed. After cooling, and the addition of acetonitrile (1 mL), then a cold hexanes/acetone mixture (~15 mL, 1:1), to the reaction flask, the precipitate was filtered with a Büchner funnel, and rinsed with cold hexanes/acetone (~20 mL). The resulting crude product (a white powder with a slight brown hue) was triturated with hot acetone (~35 mL), then washed with a cold hexanes/acetone mixture (50 mL, 1:1), resulting in P-12,0,12 (1.33 g, 64%) as a white powder; mp>260° C.; $^1$H NMR (300 MHz, CDCl$_3$) δ 3.96-3.89 (m, 2H), 3.73-3.64 (m, 4H), 3.57-3.48 (m, 6H), 3.40 (s, 6H), 3.24-3.16 (m, 7H), 1.70-1.58 (m, 2H), 1.36-1.15 (m, 38H), 0.85-0.78 (m, 6H); $^{13}$C NMR (75 MHz, CD$_3$OD) δ 65.2, 59.9, 50.5, 50.2, 45.8, 31.7, 29.4, 29.3, 29.2, 29.2, 29.1, 28.9, 28.9, 26.0, 22.3, 21.4, 13.1; high resolution mass spectrum (ESI) m/z 254.7830 ([M]$^{2+}$; calculated for [C$_{33}$H$_{71}$N$_3$]$^{2+}$: 254.7819). $^1$H and $^{13}$C NMR spectra of compound P-12,0,12 can be found in FIG. 28.

Large Scale Preparation of P-12,0,12 (13)

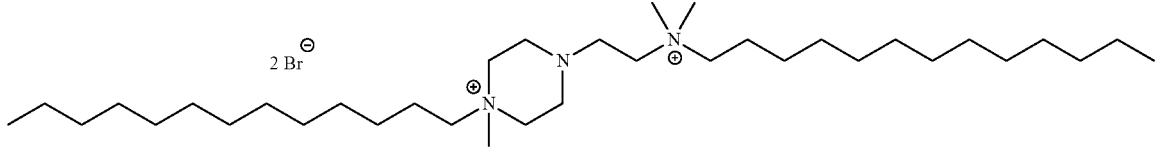

To a solution of 1-(2-dimethylaminoethyl)-4-methylpiperazine (20.00 mL, 17.90 g, 0.1045 mol) in acetonitrile (50 mL) in a 200-mL round-bottom flask was added 1-bromododecane (50.17 mL, 52.09 g, 0.209 mol). The resulting colorless solution was heated at reflux using a water-cooled condenser with magnetic stirring under ambient atmosphere. After 90 minutes at reflux, 20 mL of acetonitrile was added to the reaction mixture to facilitate stirring. The reaction was removed from heat after a total reaction time of 22 hours, during which time a beige slurry was observed. After cooling, the precipitate was filtered with a Büchner funnel, and rinsed with cold hexanes/acetone (1:1, ~150 mL). The resulting crude product was triturated with hot hexanes/acetone (1:1, ~150 mL), then filtered, resulting in P-12,0,12 (65.43 g, 93%) as a white solid; mp>260° C.; $^1$H NMR (300 MHz, CDCl$_3$) δ 3.96-3.89 (m, 2H), 3.73-3.64 (m, 4H), 3.57-3.48 (m, 6H), 3.40 (s, 6H), 3.24-3.16 (m, 7H), 1.70-1.58 (m, 2H), 1.36-1.15 (m, 38H), 0.85-0.78 (m, 6H); $^{13}$C NMR (75 MHz, CD$_3$OD) δ 65.2, 59.9, 50.5, 50.2, 45.8, 31.7, 29.4, 29.3, 29.2, 29.2, 29.1, 28.9, 28.9, 26.0, 22.3, 21.4, 13.1; high resolution mass spectrum (ESI) m/z 254.7830 ([M]$^{2+}$; calculated for [C$_{33}$H$_{71}$N$_3$]$^{2+}$: 254.7819).

Preparation of P-13,0,13 (14)

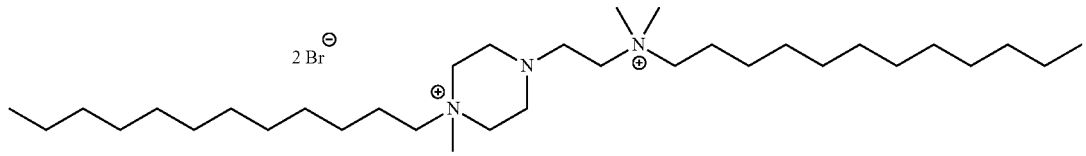 [SMILES: CCCCCCCCCCCC[N+](C)(C)CCN1CC[N+](C)(CCCCCCCCCCCC)CC1]

Figure 29:
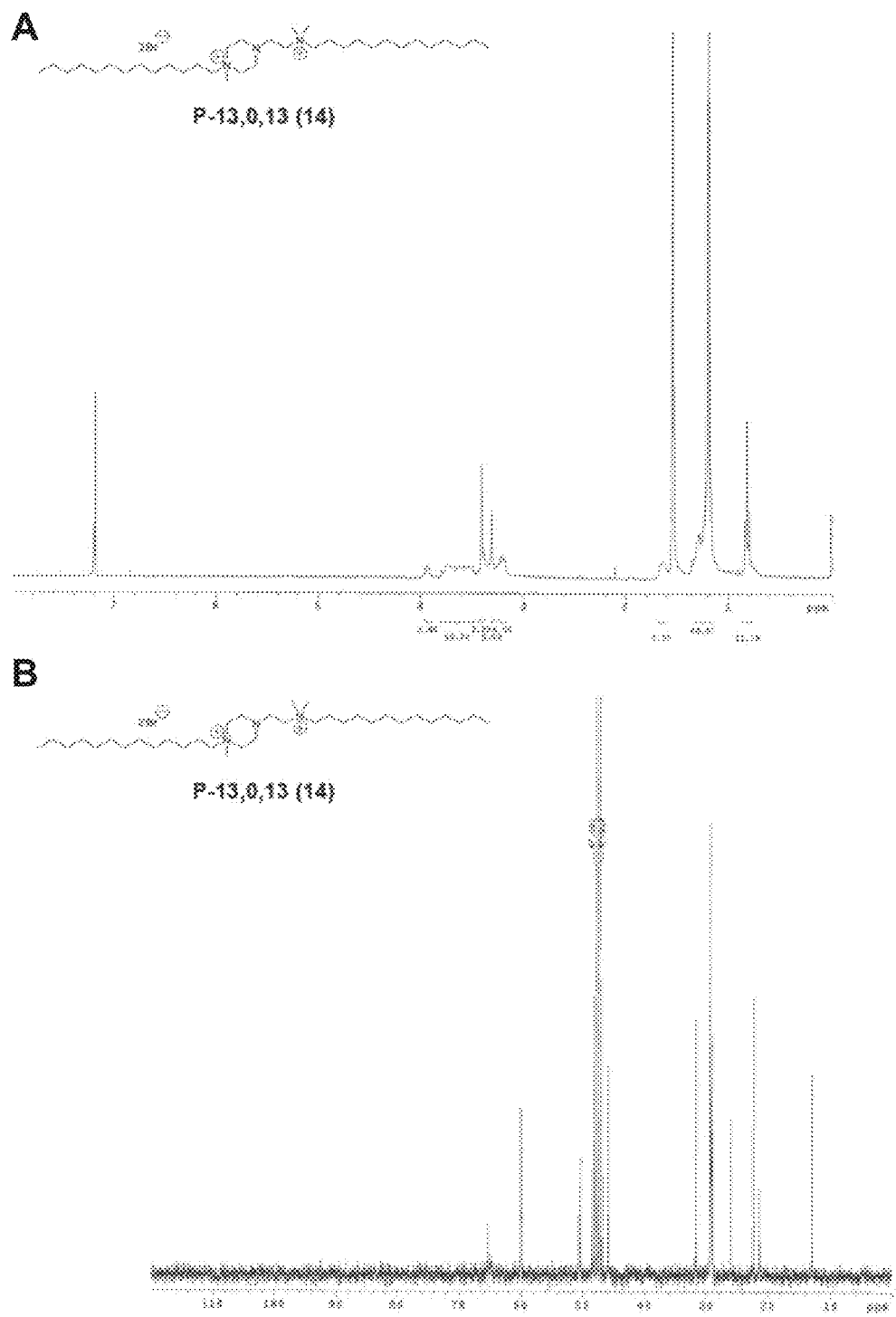
FIG. 29, comprising

To a solution of 1-(2-dimethylaminoethyl)-4-methylpiperazine (0.516 g, 3.01 mmol) in acetonitrile (4 mL) was added 1-bromotridecane (1.81 g, 6.87 mmol). The resulting colorless solution was heated at reflux with stirring overnight, during which time a white precipitate with a brown top layer was observed. After cooling, and the addition of a cold hexanes/acetone mixture (~15 mL, 1:1), to the reaction flask, the precipitate was filtered with a Büchner funnel, and rinsed with cold hexanes/acetone (~20 mL). The resulting crude product (a white powder with a slight brown hue) was triturated with hot acetone (~35 mL), then washed with a cold hexanes/acetone mixture (50 mL, 1:1), resulting in P-13,0,13 (1.89 g, 90%) as a white powder; mp>260° C.; $^1$H NMR (300 MHz, CDCl$_3$) δ 3.95-3.91 (m, 2H), 3.79-3.48 (m, 10H), 3.40 (s, 6H), 3.31 (s, 3H), 3.23-3.17 (m, 4H), 1.68-1.59 (m, 2H), 1.36-1.12 (m, 42H), 0.84-0.77 (m, 6H); $^{13}$C NMR (75 MHz, CD$_3$OD) δ 65.3, 59.9, 50.5, 50.2, 45.9, 31.6, 29.3, 29.3, 29.2, 29.2, 29.2, 29.1, 29.0, 28.9, 28.8, 26.0, 22.3, 21.4, 13.0; high resolution mass spectrum (ESI) m/z 268.7966 ([M]$^{2+}$; calculated for [C$_{35}$H$_{75}$N$_3$]$^{2+}$: 268.7975). $^1$H and $^{13}$C NMR spectra of compound P-13,0,13 can be found in FIG. 29.

Preparation of P-14,0,14 (15)

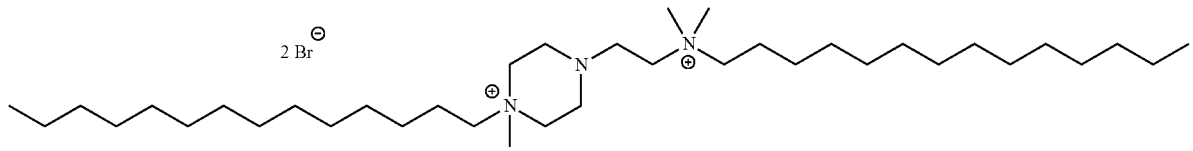 [SMILES: CCCCCCCCCCCCCC[N+](C)(C)CCN1CC[N+](C)(CCCCCCCCCCCCCC)CC1]

Figure 30:
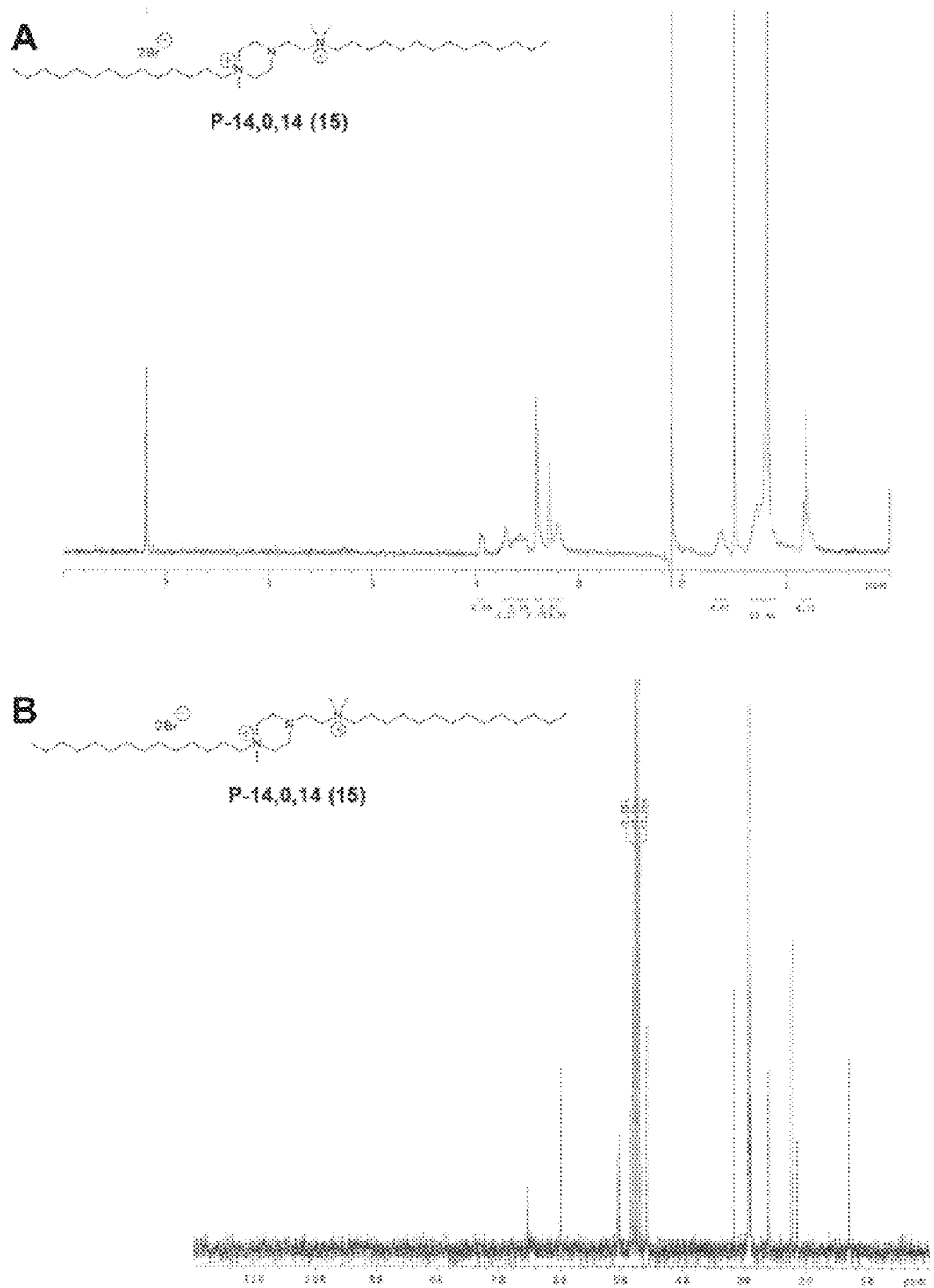
FIG. 30, comprising

To a solution of 1-(2-dimethylaminoethyl)-4-methylpiperazine (0.517 g, 3.02 mmol) in acetonitrile (2 mL) was added 1-bromotetradecane (1.69 g, 6.11 mmol). The resulting colorless solution was heated at reflux with stirring overnight, during which time a white precipitate with a brown top layer was observed. After cooling, and the addition of acetonitrile (1 mL), then a cold hexanes/acetone mixture (~15 mL, 1:1), to the reaction flask, the precipitate was filtered with a Büchner funnel, and rinsed with cold hexanes/acetone (~20 mL). The resulting crude product (a white powder with a slight brown hue) was triturated with hot acetone (~35 mL), then washed with a cold hexanes/acetone mixture (50 mL, 1:1), resulting in P-14,0,14 (1.65 g, 75%) as a white powder; mp>260° C.; $^1$H NMR (300 MHz, CDCl$_3$) δ 3.98-3.91 (m, 2H), 3.75-3.67 (m, 4H), 3.66-3.50 (m, 6H), 3.41 (s, 6H), 3.29 (s, 3H), 3.24-3.18 (m, 4H), 1.70-1.56 (m, 2H), 1.36-1.13 (m, 46H), 0.85-0.72 (m, 6H); $^{13}$C NMR (75 MHz, CD$_3$OD) δ 65.3, 59.9, 50.5, 50.2, 45.9, 31.6, 29.3, 29.3, 29.2, 29.2, 29.2, 29.1, 29.0, 28.9, 28.8, 26.0, 22.3, 21.4, 13.0; high resolution mass spectrum (ESI) m/z 282.8124 ([M]$^{2+}$; calculated for [C$_{37}$H$_{79}$N$_3$]$^{2+}$: 282.8132). $^1$H and $^{13}$C NMR spectra of compound P-14,0,14 can be found in FIG. 30.

Preparation of P-16,0,16 (16)

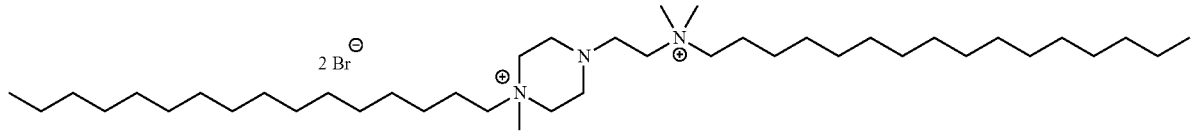 [SMILES: CCCCCCCCCCCCCCCC[N+](C)(C)CCN1CC[N+](C)(CCCCCCCCCCCCCCCC)CC1]

Figure 31:
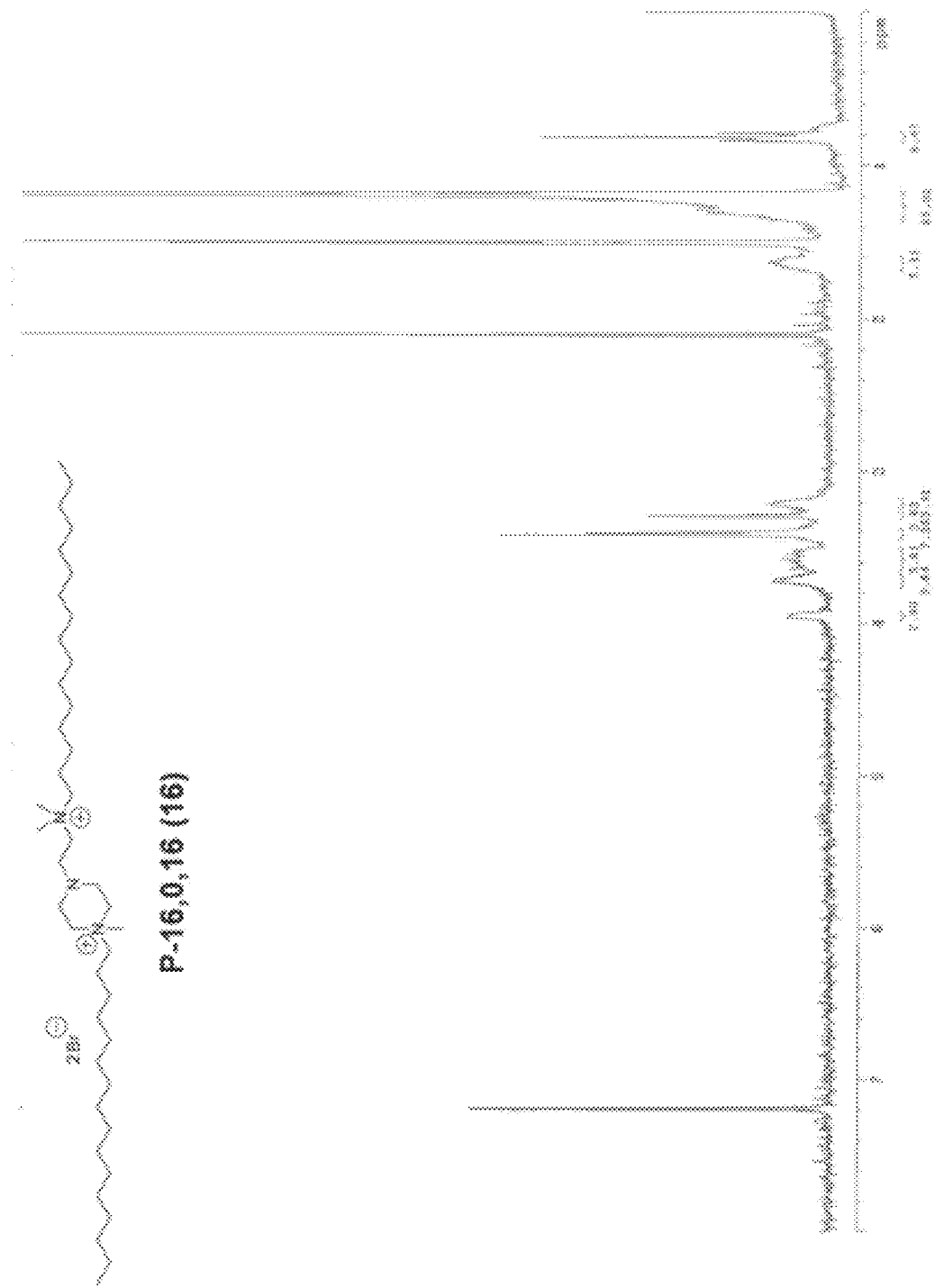
FIG. 31 depicts the $^1$H NMR spectrum of compound P-16,0,16.

To a solution of 1-(2-dimethylaminoethyl)-4-methylpiperazine (0.522 g, 3.05 mmol) in acetonitrile (2 mL) was added 1-bromohexadecane (1.87 g, 6.13 mmol). The resulting colorless solution was heated at reflux with stirring overnight, during which time a white precipitate with a brown top layer was observed. After cooling, and the addition of acetonitrile (1 mL), then a cold hexanes/acetone mixture (~15 mL, 1:1), to the reaction flask, the precipitate was filtered with a Büchner funnel, and rinsed with cold hexanes/acetone (~20 mL). The resulting crude product (a white powder with a slight brown hue) was triturated with hot acetone (~35 mL), then washed with a cold hexanes/acetone mixture (50 mL, 1:1), resulting in P-16,0,16 (1.97 g, 83%) as a white powder; mp>260° C.; $^1$H NMR (300 MHz, CDCl$_3$) δ 3.98-3.91 (m, 2H), 3.76-3.67 (m, 4H), 3.65-3.50 (m, 6H), 3.41 (s, 6H), 3.29 (s, 3H), 3.25-3.17 (m, 4H), 1.70-1.56 (m, 2H), 1.39-1.15 (m, 54H), 0.86-0.78 (m, 6H); high resolution mass spectrum (ESI) m/z 310.8431 ([M]$^{2+}$; calculated for [C$_{41}$H$_{87}$N$_3$]$^{2+}$: 310.8445). $^1$H spectrum of compound P-16,0,16 can be found in FIG. 31.

Preparation of P-18,0,18 (17)

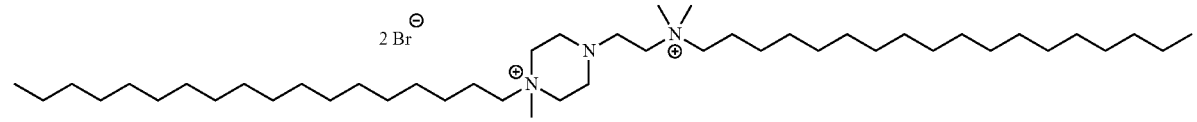 [SMILES: CCCCCCCCCCCCCCCCCC[N+](C)(C)CCN1CC[N+](C)(CCCCCCCCCCCCCCCCCC)CC1]

Figure 32:
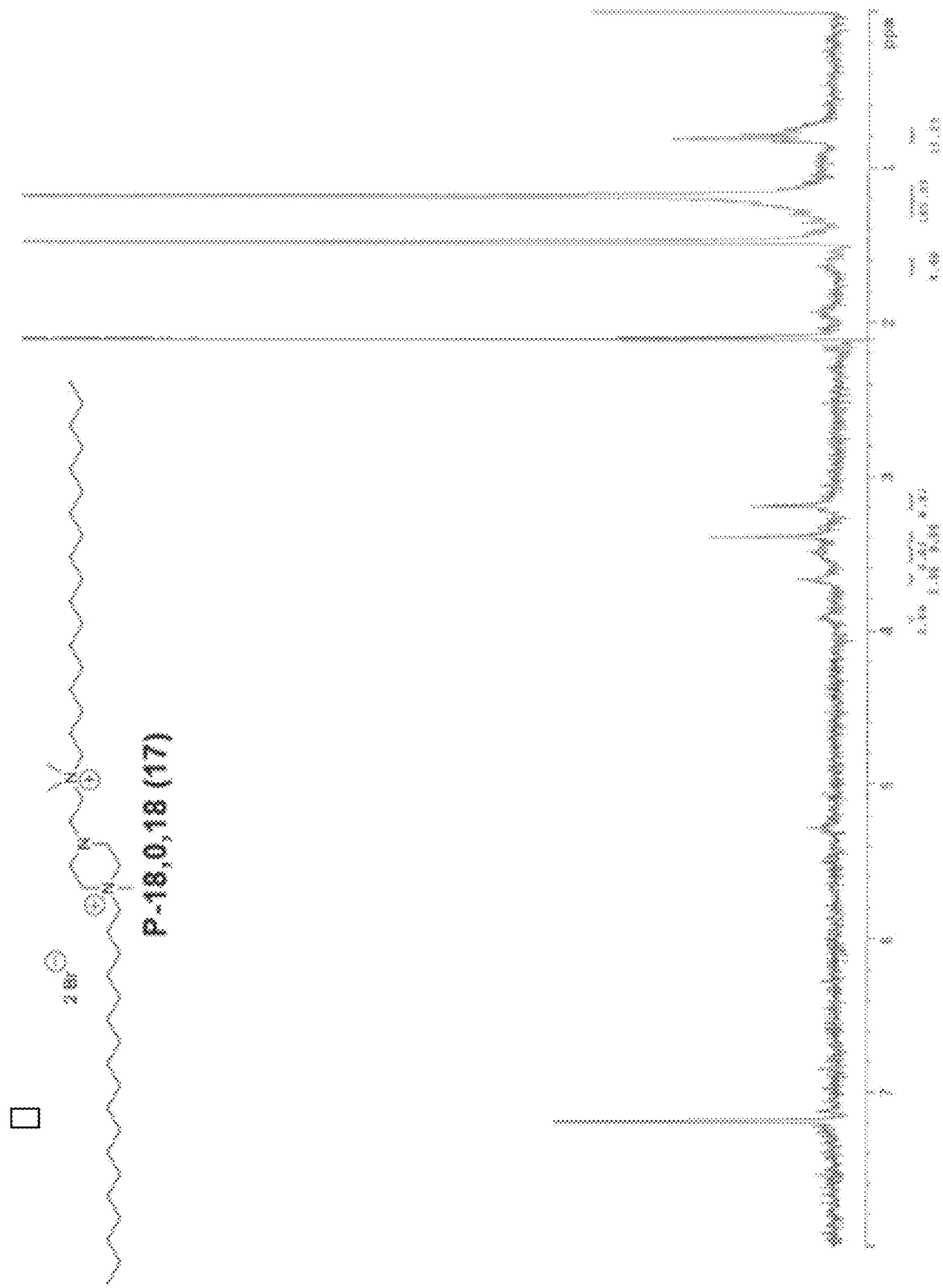
FIG. 32 depicts the $^1$H NMR spectrum of compound P-18,0,18.

To a solution of 1-(2-dimethylaminoethyl)-4-methylpiperazine (0.397 g, 2.32 mmol) in acetonitrile (4 mL) was added 1-bromooctadecane (1.57 g, 4.71 mmol). The resulting colorless solution was heated at reflux with stirring overnight, during which time a white precipitate with a brown top layer was observed. After cooling, and the addition of a cold hexanes/acetone mixture (~15 mL, 1:1), to the reaction flask, the precipitate was filtered with a Büchner funnel, and rinsed with cold hexanes/acetone (~20 mL). The resulting crude product (a white powder with a slight brown hue) was triturated with hot acetone (~35 mL), then washed with a cold hexanes/acetone mixture (50 mL, 1:1), resulting in P-18,0,18 (1.16 g, 60%) as a white powder; mp>260° C.; $^1$H NMR (300 MHz, CDCl$_3$) δ 3.95-3.88 (m, 2H), 3.71-3.64 (m 4H), 3.57-3.45 (m, 6H), 3.39 (s, 6H), 3.24-3.16 (m, 7H), 1.70-1.53 (m, 2H), 1.36-1.08 (m, 62H), 0.84-0.77 (m, 6H); high resolution mass spectrum (ESI) m/z 338.8752 ([M]$^{2+}$; calculated for [C$_{45}$H$_{95}$N$_3$]$^{2+}$: 338.8758). $^1$H spectrum of compound P-18,0,18 can be found in FIG. 32.

Preparation of C-10,0,0 (18)

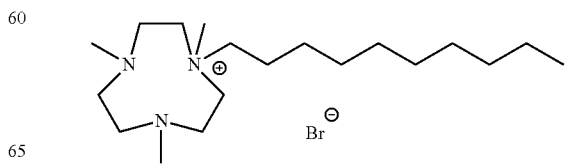

Figure 33:
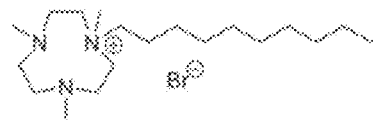
FIG. 33, comprising
Figure 33:
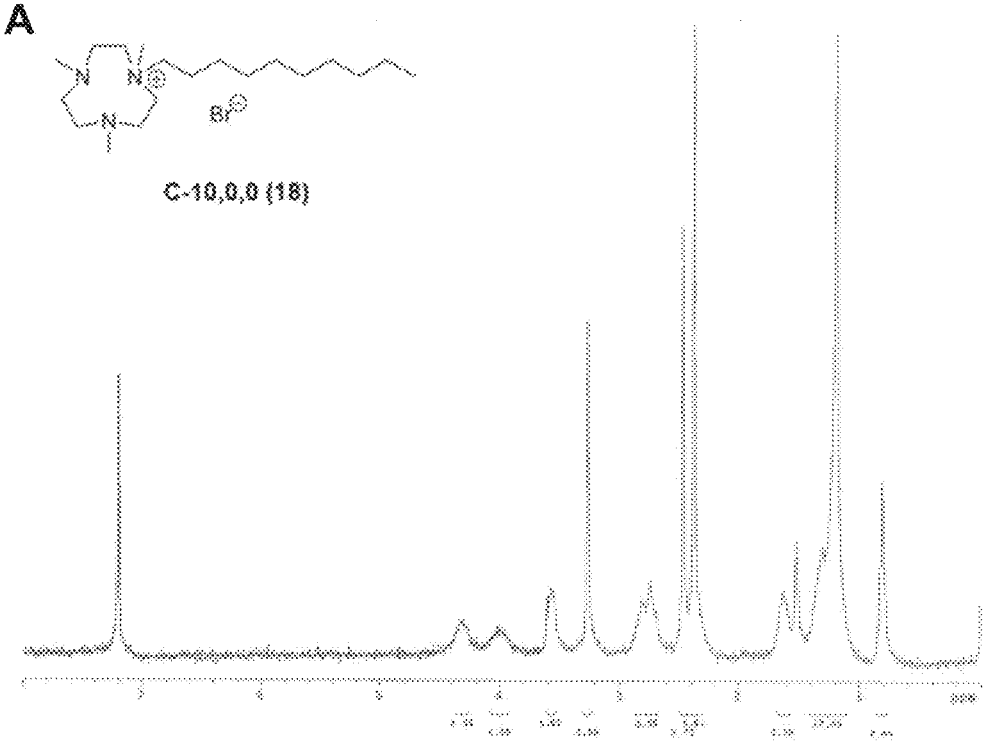
Figure 33:
Figure 33:
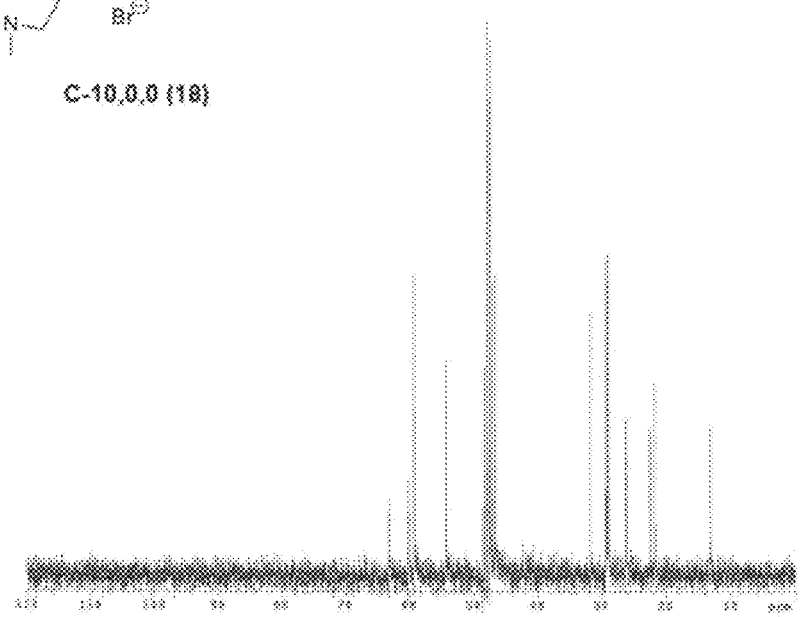

To a solution of 1,4,7-trimethyl-1,4,7-triazacyclononane (0.260 g, 1.52 mmol) in acetonitrile (4 mL) was added 1-bromodecane (0.387 g, 1.75 mmol). The resulting colorless solution was heated at reflux with stirring for 17 hours, during which time the solution turned yellow-brown. The reaction mixture was concentrated in vacuo, resulting in a yellow-white crude solid, which was triturated with hot hexanes (~35 mL), then washed with cold hexanes (50 mL), resulting in C-10,0,0 (0.520 g, 87%) as a white powder; mp=136-143° C.; $^1$H NMR (300 MHz, CDCl$_3$) δ 4.41-4.21 (m, 2H), 4.12-3.87 (m, 2H), 3.62-3.48 (m, 2H), 3.26 (s, 3H), 2.91-2.65 (m, 4H), 2.47 (s, 4H), 2.37 (s, 6H), 1.71-1.56 (m, 2H), 1.43-1.05 (m, 14H), 0.87-0.75 (m, 3H); $^{13}$C NMR (75 MHz, CD$_3$OD) δ 63.2, 63.1, 60.1, 59.2, 54.3, 47.5, 46.7, 31.6, 29.2, 29.2, 29.0, 28.9, 26.1, 22.3, 21.6, 13.1; high resolution mass spectrum (ESI) m/z 312.3368 ([M]$^+$; calculated for [C$_{19}$H$_{42}$N$_3$]$^+$: 312.3373). $^1$H and $^{13}$C NMR spectra of compound C-10,0,0 can be found in FIG. 33.

Preparation of C-11,0,0 (19)

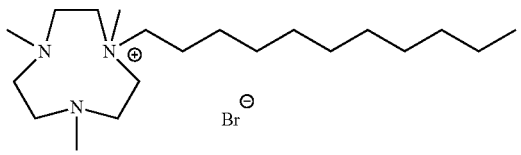 [SMILES: CCCCCCCCCCC[N+]1(C)CCN(C)CCN(C)CC1 ; [Br-]]

Figure 34:
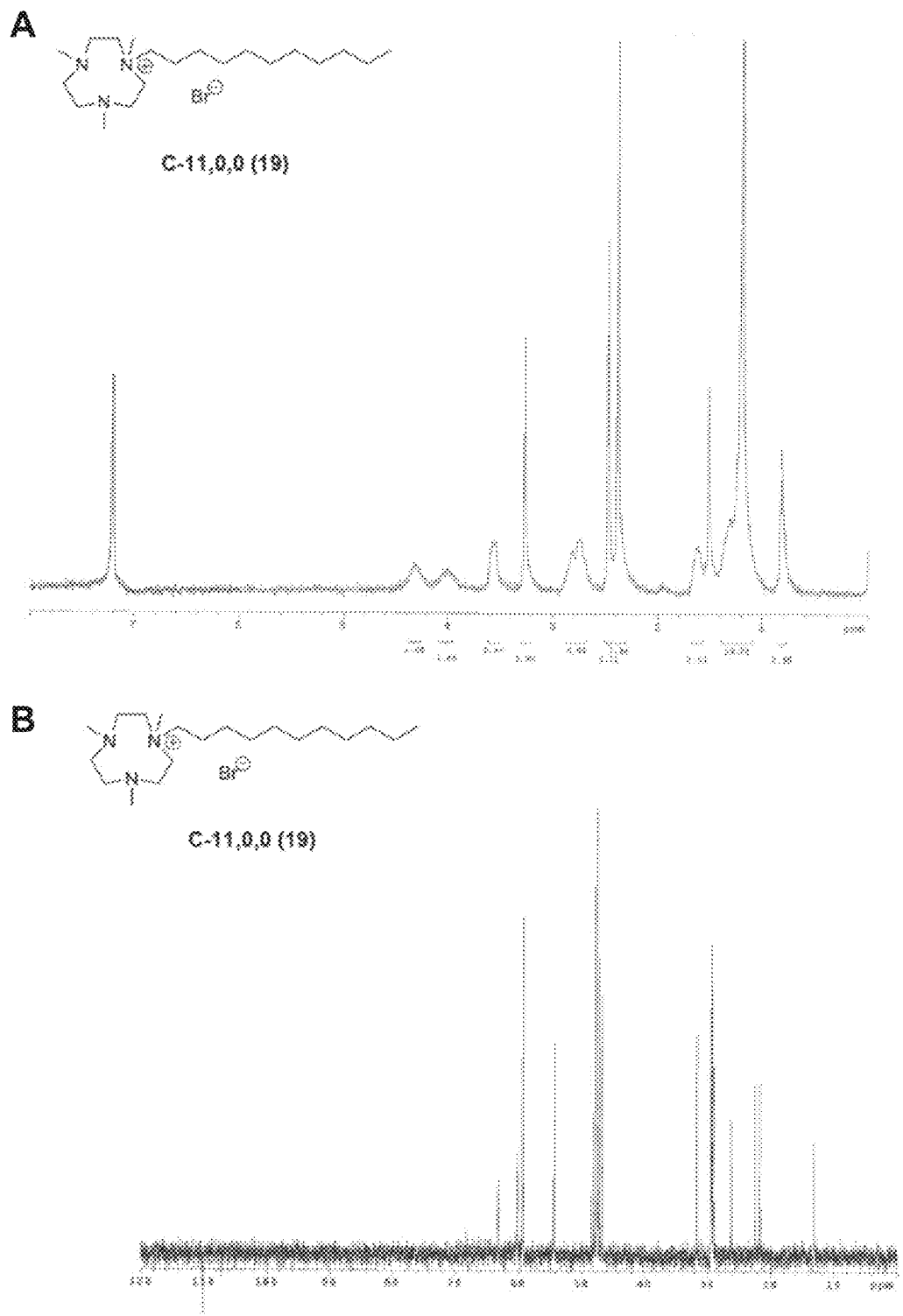
FIG. 34, comprising

To a solution of 1,4,7-trimethyl-1,4,7-triazacyclononane (0.209 g, 1.22 mmol) in acetonitrile (4 mL) was added 1-bromoundecane (0.293 g, 1.25 mmol). The resulting colorless solution was heated at reflux with stirring for 25 hours, during which time the solution turned yellow. The reaction mixture was concentrated in vacuo, resulting in a yellow-white crude solid, which was triturated with hot hexanes (~35 mL), then washed with cold hexanes (50 mL), resulting in C-11,0,0 (0.276 g, 56%) as a white powder; mp=139-151° C.; $^1$H NMR (300 MHz, CDCl$_3$) δ 4.38-4.25 (m, 2H), 4.06-3.94 (m, 2H), 3.61-3.52 (m, 2H), 3.26 (s, 3H), 2.88-2.66 (m, 4H), 2.47 (s, 4H), 2.38 (s, 6H), 1.67-1.58 (m, 2H), 1.39-1.12 (m, 16H), 0.85-0.78 (m, 3H); $^{13}$C NMR (75 MHz, CD$_3$OD) δ 3.2, 60.1, 59.3, 54.3, 47.5, 46.7, 31.7, 29.3, 29.3, 29.2, 29.1, 28.9, 26.1, 22.3, 21.6, 13.1; high resolution mass spectrum (ESI) m/z 326.3525 ([M]$^+$; calculated for [C$_{20}$H$_{44}$N$_3$]$^+$: 326.3530). $^1$H and $^{13}$C NMR spectra of compound C-11,0,0 can be found in FIG. 34.

Preparation of C-12,0,0 (20)

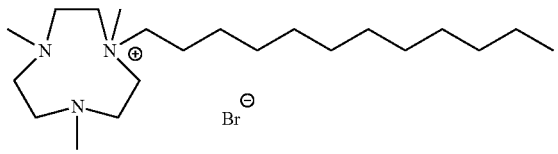 [SMILES: CCCCCCCCCCCC[N+]1(C)CCN(C)CCN(C)CC1 ; [Br-]]

Figure 35:
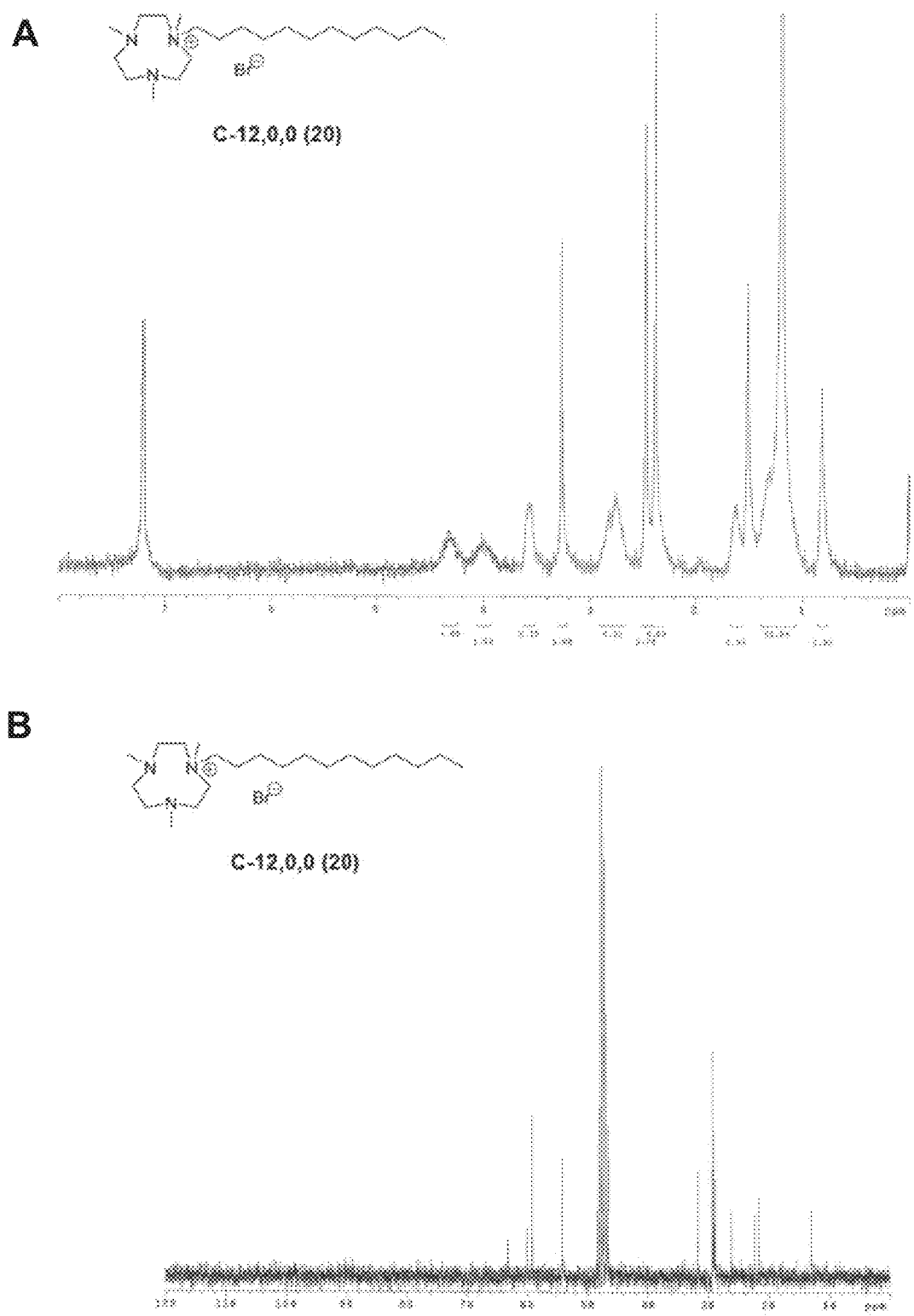
FIG. 35, comprising

To a solution of 1,4,7-trimethyl-1,4,7-triazacyclononane (0.206 g, 1.20 mmol) in acetonitrile (4 mL) was added 1-bromododecane (0.311 g, 1.25 mmol). The resulting colorless solution was heated at reflux with stirring for 26 hours, during which time the solution turned yellow. The reaction mixture was concentrated in vacuo, resulting in a yellow-white crude solid, which was triturated with hot hexanes (~35 mL), then washed with cold hexanes (50 mL), resulting in C-12,0,0 (0.331 g, 65%) as a white powder; mp=140-154° C.; $^1$H NMR (300 MHz, CDCl$_3$) δ 4.38-4.25 (m, 2H), 4.09-3.92 (m, 2H), 3.60-3.53 (m, 2H), 3.26 (s, 3H), 2.84-2.69 (m, 4H), 2.47 (s, 4H), 2.38 (s, 6H), 1.66-1.58 (m, 2H), 1.37-1.11 (m, 18H), 0.85-0.78 (m, 3H); $^{13}$C NMR (75 MHz, CD$_3$OD) δ 63.2, 60.1, 59.2, 54.3, 47.5, 46.6, 31.7, 29.3, 29.2, 29.2, 29.1, 28.9, 26.1, 22.3, 21.6, 13.0; high resolution mass spectrum (ESI) m/z 340.3693 ([M]$^+$; calculated for [C$_{21}$H$_{46}$N$_3$]$^+$: 340.3686). $^1$H and $^{13}$C NMR spectra of compound C-20,0,0 can be found in FIG. 35.

Preparation of C-13,0,0 (21)

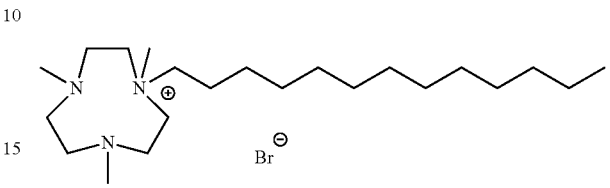

Figure 36:
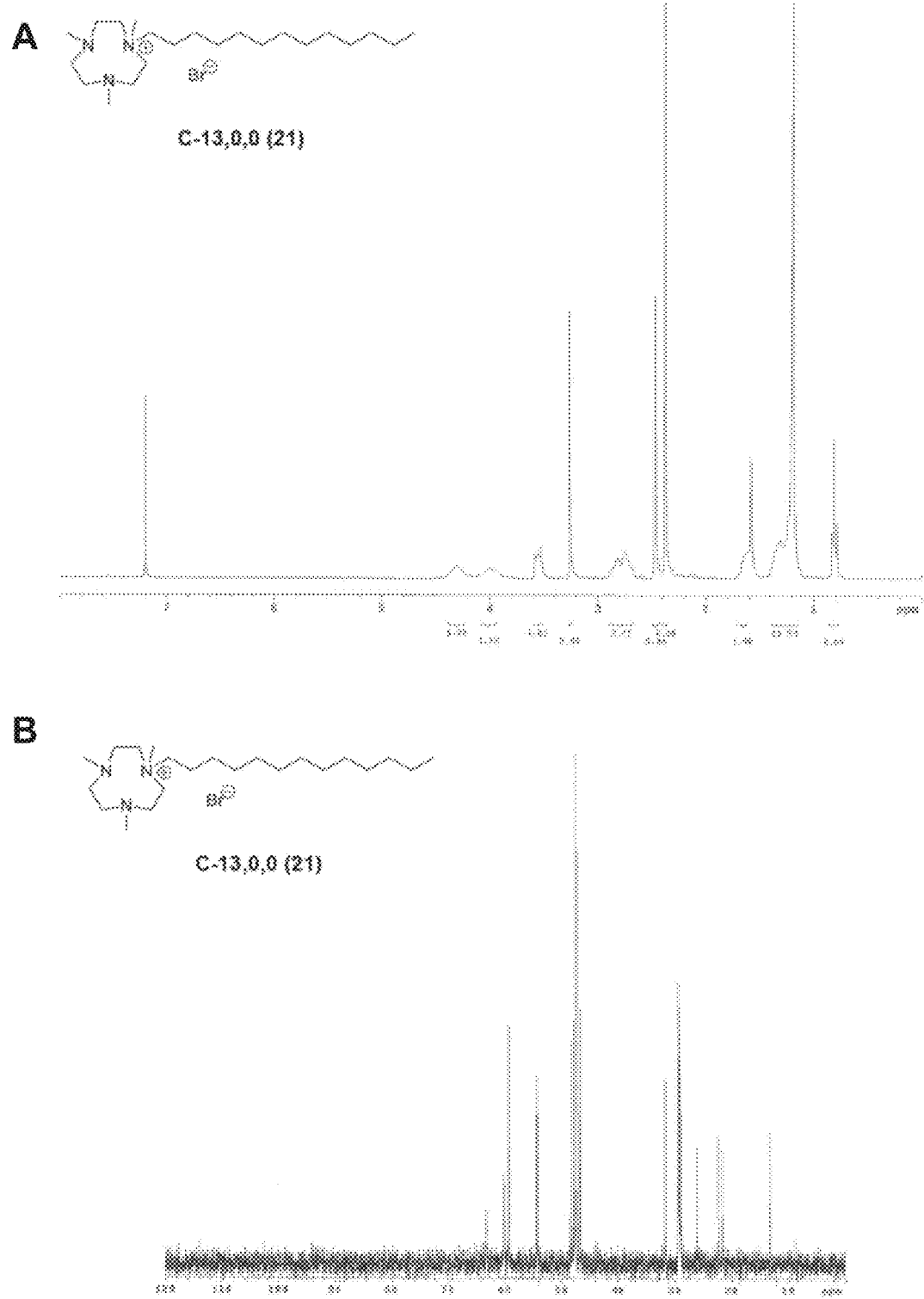
FIG. 36, comprising

To a solution of 1,4,7-trimethyl-1,4,7-triazacyclononane (0.259 g, 1.51 mmol) in acetonitrile (4 mL) was added 1-bromotridecane (0.469 g, 1.78 mmol). The resulting colorless solution was heated at reflux with stirring for 19 hours, during which time the solution turned yellow. The reaction mixture was concentrated in vacuo, resulting in a yellow-white crude solid, which was triturated with hot hexanes (~35 mL), then washed with cold hexanes (50 mL), resulting in C-13,0,0 (0.369 g, 56%) as a white powder; mp=161-168° C.; $^1$H NMR (300 MHz, CDCl$_3$) δ 4.37-4.24 (m, 2H), 4.07-3.94 (m, 2H), 3.59-3.51 (m, 2H), 3.26 (s, 3H), 2.88-2.67 (m, 4H), 2.47 (s, 4H), 2.38 (s, 6H), 1.68-1.60 (m, 2H), 1.38-1.14 (m, 20H), 0.84-0.78 (m, 3H); $^{13}$C NMR (75 MHz, CD$_3$OD) δ 3.2, 60.1, 59.3, 54.3, 47.5, 46.7, 31.7, 29.4, 29.3, 29.2, 29.1, 28.9, 26.1, 22.4, 21.6, 13.1; high resolution mass spectrum (ESI) m/z 354.3839 ([M]$^+$; calculated for [C$_{22}$H$_{48}$N$_3$]$^+$: 354.3843). $^1$H and $^{13}$C NMR spectra of compound C-13,0,0 can be found in FIG. 36.

Preparation of C-14,0,0 (22)

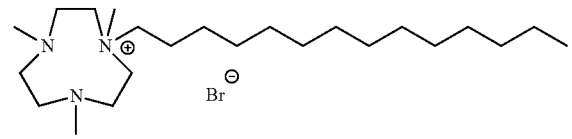 [SMILES: CCCCCCCCCCCCCC[N+]1(C)CCN(C)CCN(C)CC1 ; [Br-]]

Figure 37:
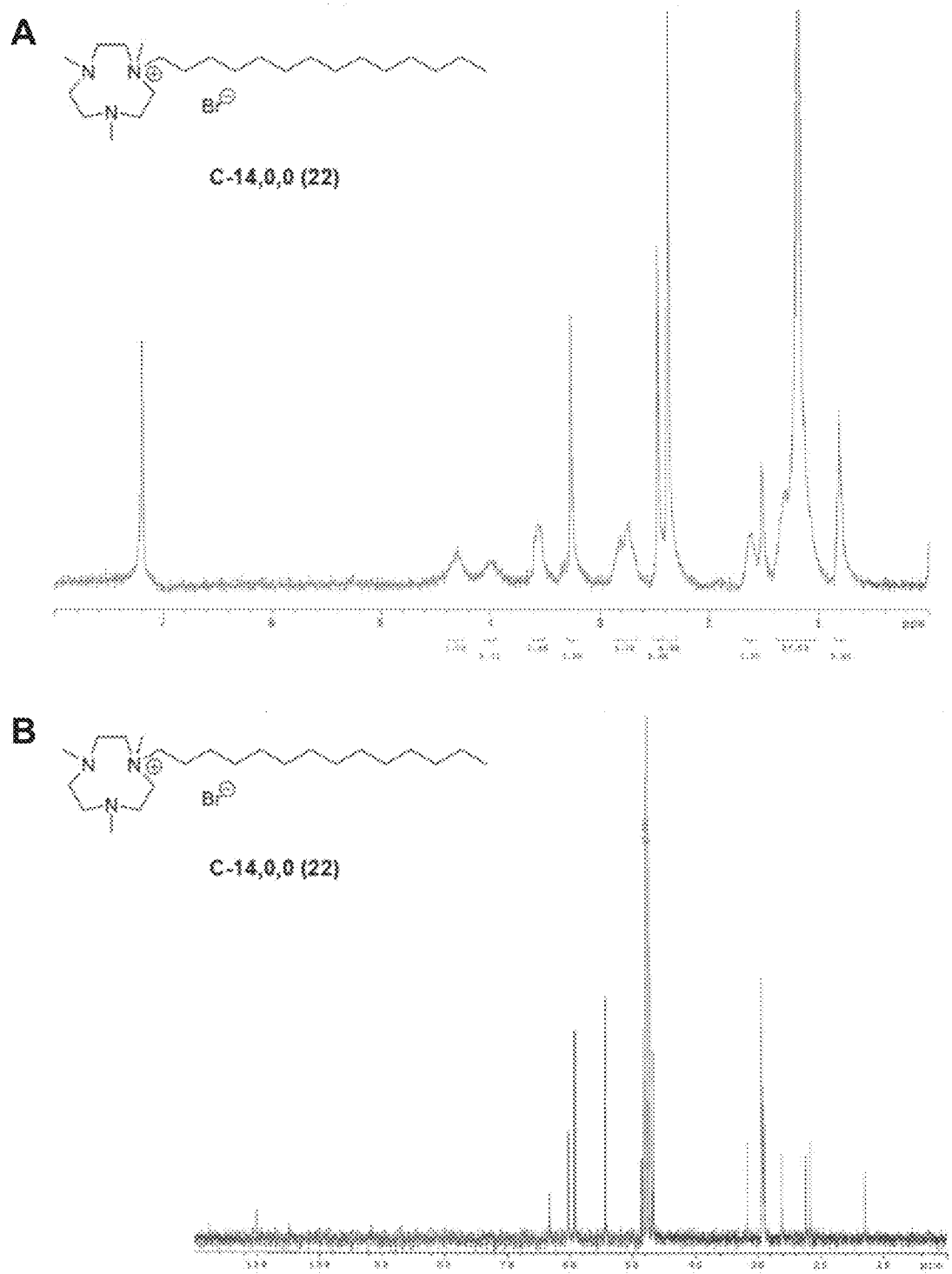
FIG. 37, comprising

To a solution of 1,4,7-trimethyl-1,4,7-triazacyclononane (0.203 g, 1.19 mmol) in acetonitrile (4 mL) was added 1-bromotetradecane (0.702 g, 2.53 mmol). The resulting colorless solution was heated at reflux with stirring for 19 hours, during which time the solution turned yellow. The reaction mixture was concentrated in vacuo, resulting in a yellow-white crude solid, which was triturated with hot hexanes (~35 mL), then washed with cold hexanes (50 mL), resulting in C-14,0,0 (0.382 g, 72%) as a white powder; mp=153-168° C.; $^1$H NMR (300 MHz, CDCl$_3$) δ 4.37-4.24 (m, 2H), 4.08-3.80 (m, 2H), 3.60-3.51 (m, 2H), 3.26 (s, 3H), 2.87-2.67 (m, 4H), 2.47 (s, 4H), 2.38 (s, 6H), 1.68-1.56 (m, 2H), 1.38-1.04 (m, 22H), 0.84-0.77 (m, 3H); $^{13}$C NMR (75 MHz, CD$_3$OD) δ 63.3, 60.2, 59.2, 54.3, 47.5, 46.6, 31.6, 29.3, 29.2, 29.1, 29.0, 28.8, 26.1, 22.3, 21.6, 13.0; high resolution mass spectrum (ESI) m/z 368.4000 ([M]$^+$; calculated for [C$_{23}$H$_{50}$N$_3$]$^+$: 368.3999). $^1$H and $^{13}$C NMR spectra of compound C-14,0,0 can be found in FIG. 37.

Preparation of C-16,0,0 (23)

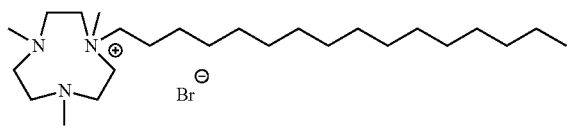 [SMILES: CCCCCCCCCCCCCCCC[N+]1(C)CCN(C)CCN(C)CC1 ; [Br-]]

Figure 38:
FIG. 38, comprising
Figure 38:
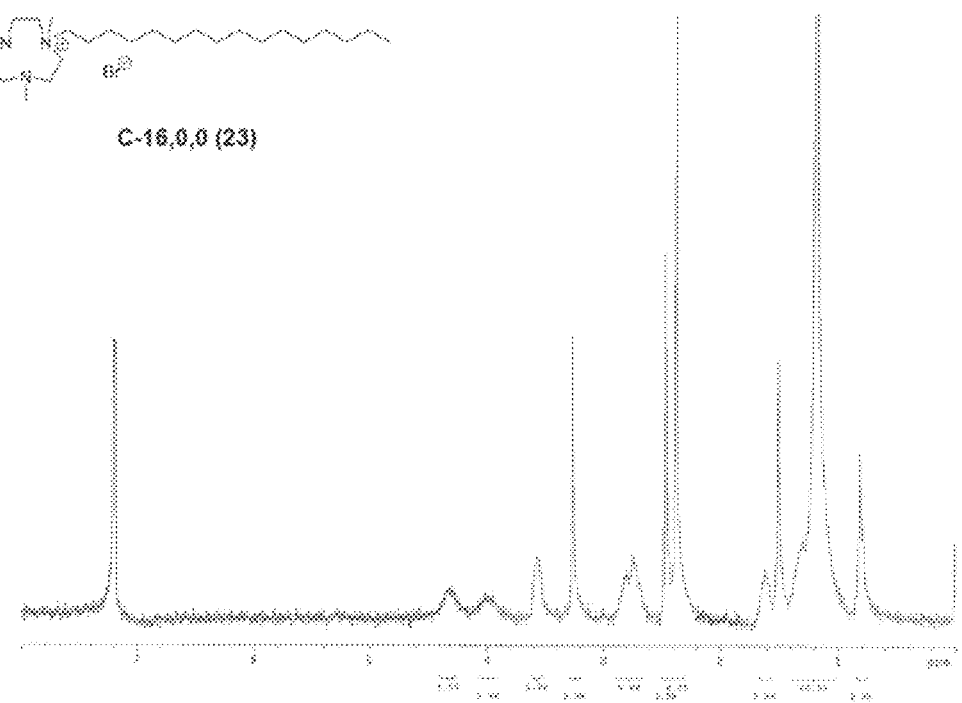
Figure 38:
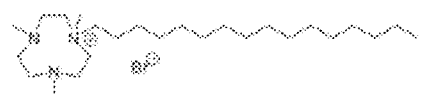
Figure 38:
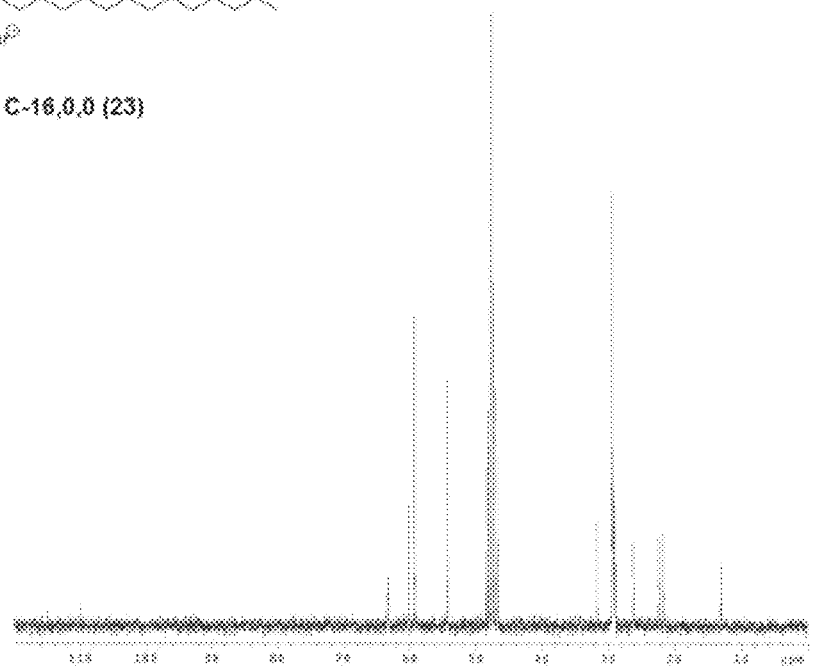

To a solution of 1,4,7-trimethyl-1,4,7-triazacyclononane (0.208 g, 1.22 mmol) in acetonitrile (4 mL) was added 1-bromohexadecane (0.413 g, 1.35 mmol). The resulting colorless solution was heated at reflux with stirring for 19 hours, during which time the solution turned yellow. The reaction mixture was concentrated in vacuo, resulting in a yellow-white crude solid, which was triturated with hot hexanes (~35 mL), then washed with cold hexanes (50 mL), resulting in C-16,0,0 (0.502 g, 86%) as a white powder; mp=155-170° C.; $^1$H NMR (300 MHz, CDCl$_3$) δ 4.38-4.26 (m, 2H), 4.07-3.91 (m, 2H), 3.61-3.53 (m, 2H), 3.26 (s, 3H), 2.88-2.67 (m, 4H), 2.47 (s, 4H), 2.38 (s, 6H), 1.67-1.57 (m, 2H), 1.38-1.05 (m, 26H), 0.85-0.78 (m, 3H); $^{13}$C NMR (75 MHz, CD$_3$OD) δ 63.3, 60.2, 59.2, 54.3, 47.5, 46.6, 31.6, 29.3, 29.2, 29.1, 29.0, 28.8, 26.1, 22.3, 21.6, 13.0; high resolution mass spectrum (ESI) m/z 396.4305 ([M]$^+$; calculated for [C$_{25}$H$_{54}$N$_3$]$^+$: 396.4312). $^1$H and $^{13}$C NMR spectra of compound C-16,0,0 can be found in FIG. 38.

Preparation of C-18,0,0 (24)

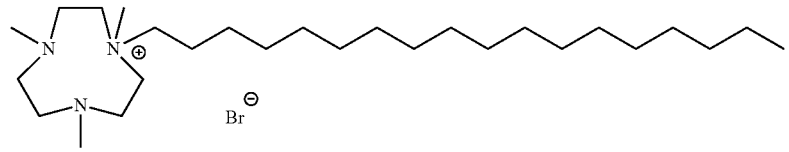 [SMILES: CCCCCCCCCCCCCCCCCC[N+]1(C)CCN(C)CCN(C)CC1 ; [Br-]]

Figure 39:
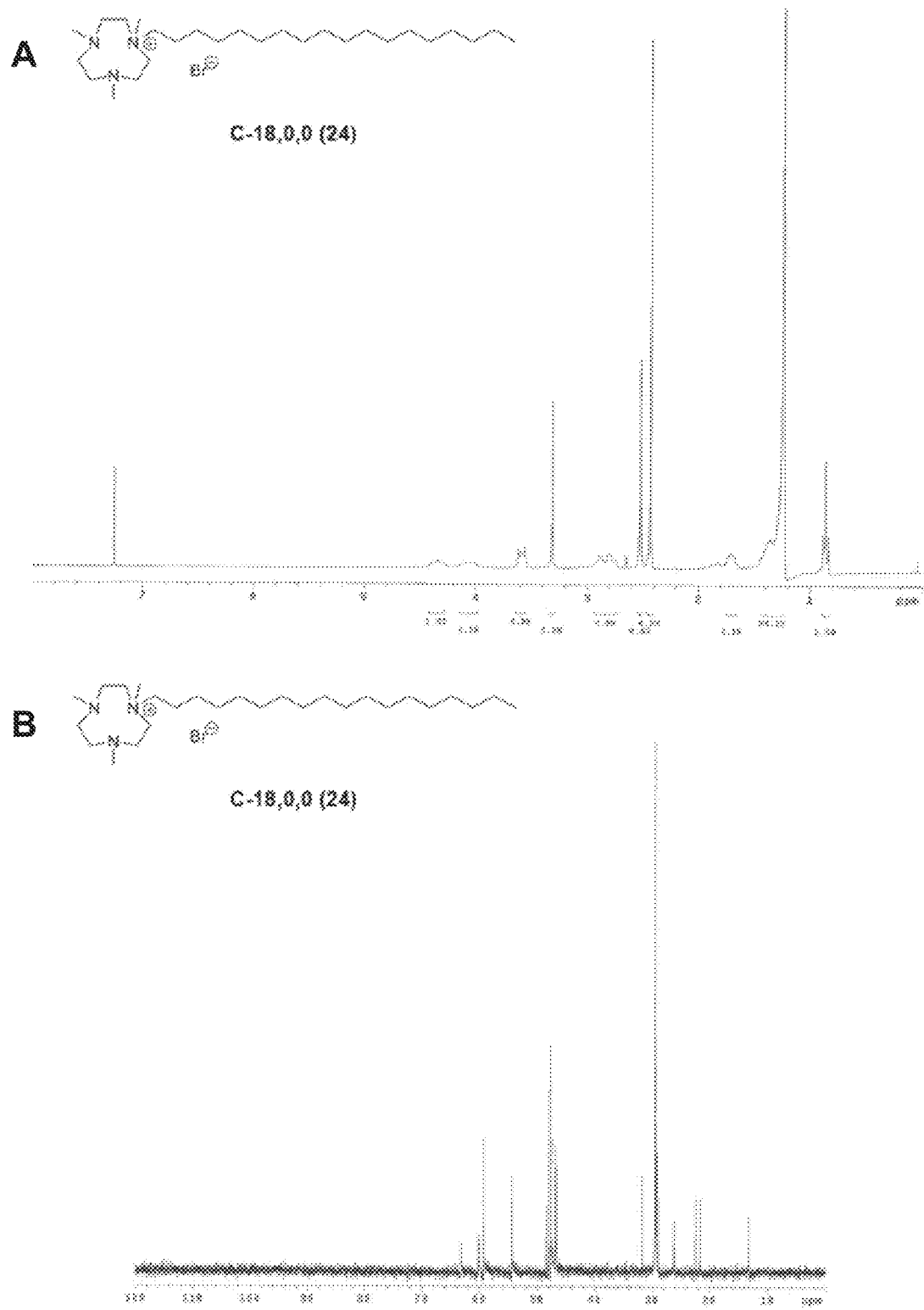
FIG. 39, comprising

To a solution of 1,4,7-trimethyl-1,4,7-triazacyclononane (0.214 g, 1.25 mmol) in acetonitrile (4 mL) was added 1-bromooctadecane (0.435 g, 1.30 mmol). The resulting colorless solution was heated at reflux with stirring for 22 hours, during which time the solution turned yellow. The reaction mixture was concentrated in vacuo, resulting in a yellow-white crude solid, which was triturated with hot hexanes (~35 mL), then washed with cold hexanes (50 mL), resulting in C-18,0,0 (0.490 g, 78%) as a white powder; mp=161-172° C.; $^1$H NMR (300 MHz, CDCl$_3$) δ 4.40-4.28 (m, 2H), 4.13-3.99 (m, 2H), 3.62-3.55 (m, 2H), 3.32 (s, 3H), 2.95-2.72 (m, 4H), 2.52 (s, 4H), 2.43 (s, 6H), 1.78-1.64 (m, 2H), 1.42-1.22 (m, 30H), 0.89-0.83 (m, 3H); $^{13}$C NMR (75 MHz, CD$_3$OD) δ 63.2, 60.1, 59.3, 54.3, 47.5, 46.7, 31.7, 29.4, 29.3, 29.2, 29.1, 28.9, 26.1, 22.4, 21.6, 13.1; high resolution mass spectrum (ESI) m/z 424.4622 ([M]$^+$; calculated for [C$_{27}$H$_{58}$N$_3$]$^+$: 424.4625). $^1$H and $^{13}$C NMR spectra of compound C-18,0,0 can be found in FIG. 39.

Preparation of C-20,0,0 (25)

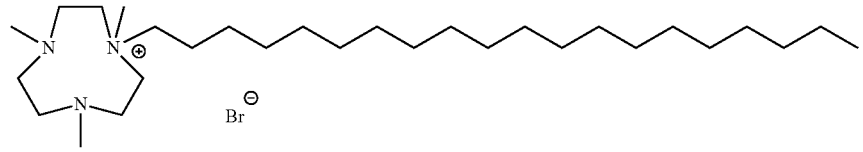 [SMILES: CCCCCCCCCCCCCCCCCCCC[N+]1(C)CCN(C)CCN(C)CC1 ; [Br-]]

Figure 40:
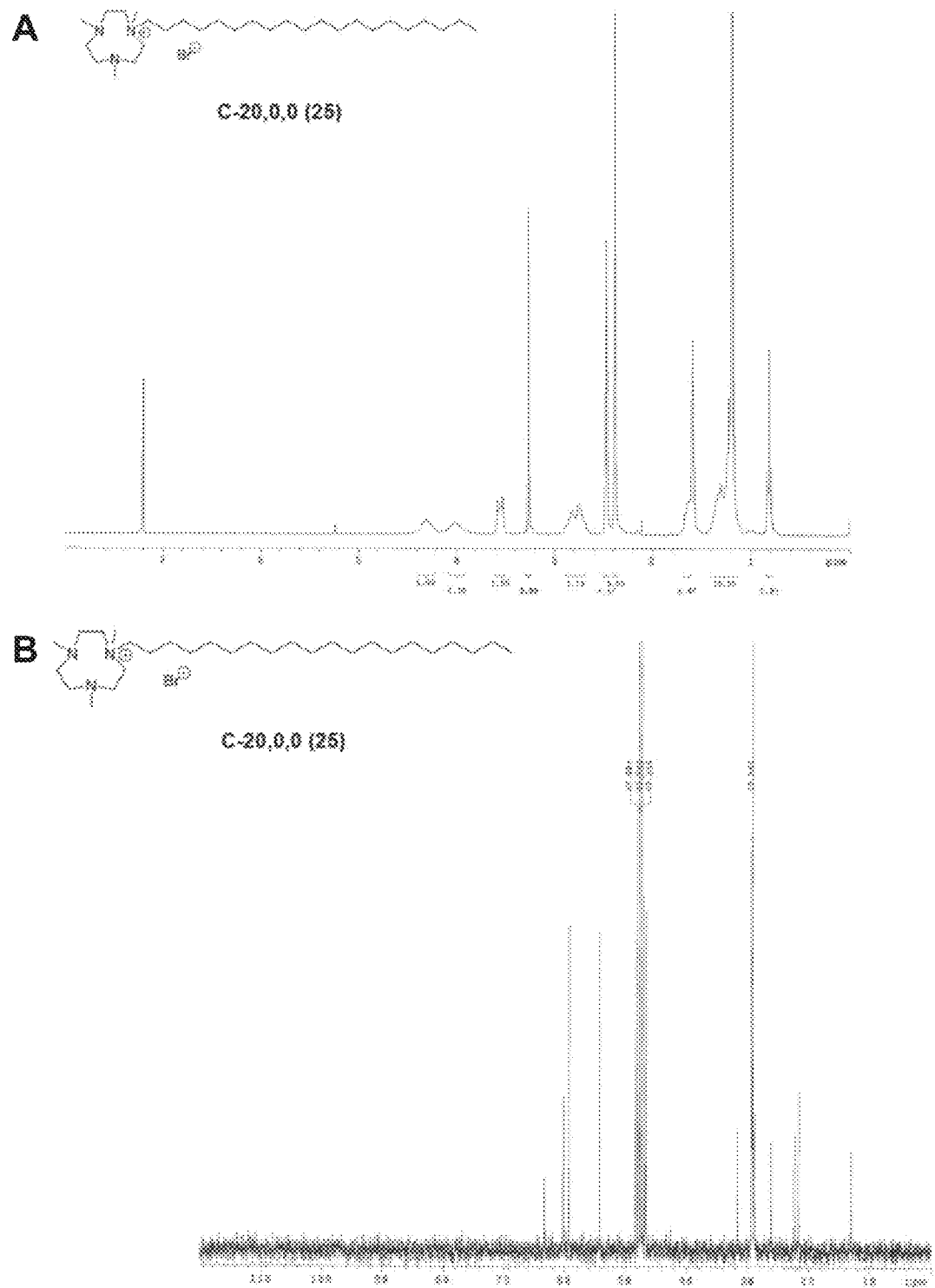
FIG. 40, comprising

To a solution of 1,4,7-trimethyl-1,4,7-triazacyclononane (0.318 g, 1.86 mmol) in acetonitrile (4 mL) was added 1-bromoeicosane (0.778 g, 2.15 mmol). The resulting colorless solution heated at reflux with stirring for 22 hours, during which time the solution turned yellow. The reaction mixture concentrated in vacuo, resulting in a yellow-white crude solid, which was triturated with hot hexanes (~35 mL), then washed with cold hexanes (50 mL), resulting in C-20,0,0 (0.744 g, 74%) as a white powder; mp=167-186° C.; $^1$H NMR (300 MHz, CDCl$_3$) δ 4.36-4.24 (m, 2H), 4.07-3.95 (m, 2H), 3.59-3.51 (m, 2H), 3.26 (s, 3H), 2.89-2.67 (m, 4H), 2.47 (s, 4H), 2.38 (s, 6H), 1.69-1.63 (m, 2H), 1.39-1.14 (m, 34H), 0.84-0.78 (m, 3H); $^{13}$C NMR (75 MHz, CD$_3$OD) δ 63.3, 60.2, 59.2, 54.3, 47.5, 46.6, 31.6, 29.3, 29.2, 29.1, 29.0, 28.9, 26.1, 22.3, 21.6, 13.0; high resolution mass spectrum (ESI) m/z 452.4936 ([M]$^+$; calculated for [C$_{29}$H$_{62}$N$_3$]$^+$: 452.4938). $^1$H and $^{13}$C NMR spectra of compound C-20,0,0 can be found in FIG. 40.

Preparation of C-10,1,1 (26)

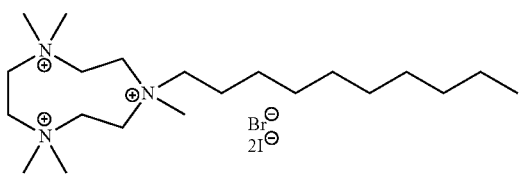 [SMILES: CCCCCCCCCC[N+]1(C)CC[N+](C)(C)CC[N+](C)(C)CC1]

Figure 41:
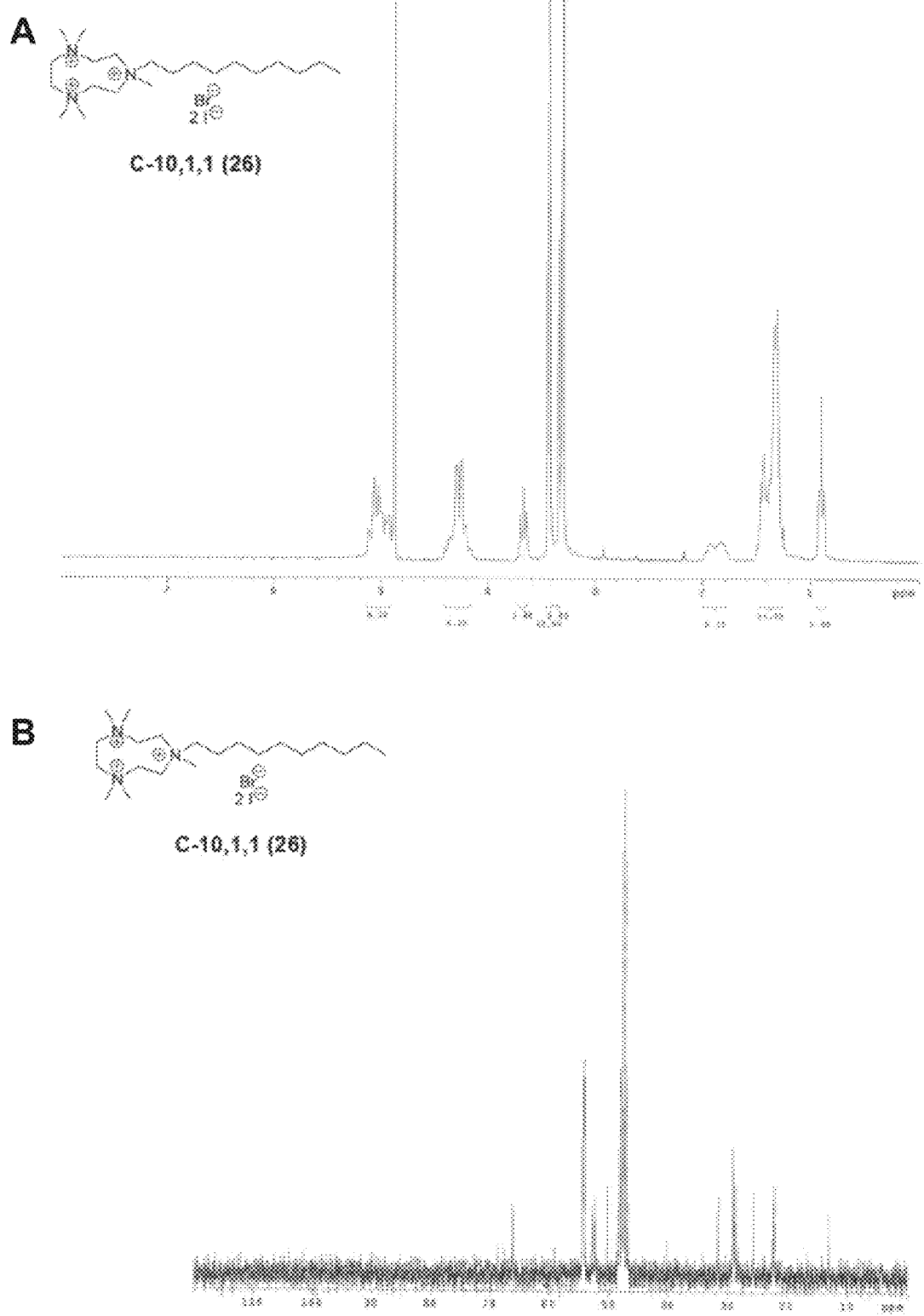
FIG. 41, comprising

To a flask containing C-10,0,0 (0.106 g, 0.270 mmol) was added iodomethane (~1.5 mL, 24 mmol). The resulting yellow solution with white solid was capped and stirred for 19 hours. The reaction flask was uncapped and the solvent was allowed to evaporate, resulting in C-10,1,1 (0.186 g, ~100%) as a yellow-orange solid; mp=152-173° C.; $^1$H NMR (300 MHz, CD$_3$OD) δ 5.15-4.98 (m, 6H), 4.42-4.18 (m, 6H), 3.74-3.63 (m, 2H), 3.51-340 (m, 12H), 3.35 (s, 3H), 2.00-1.77 (m, 2H), 1.49-1.26 (m, 14H), 0.95-0.86 (m, 3H); $^{13}$C NMR (75 MHz, CD$_3$OD) δ 66.1, 54.4, 54.2, 54.1, 52.8, 52.4, 50.3, 31.6, 29.1, 28.9, 28.7, 25.6, 22.3, 22.1, 13.0; high resolution mass spectrum (ESI) m/z 596.1921 ([M+2I]$^+$; calculated for [C$_{21}$H$_{48}$N$_3$I$_2$]$^+$: 596.1932). $^1$H and $^{13}$C NMR spectra of compound C-10,1,1 can be found in FIG. 41.

Preparation of C-11,1,1 (27)

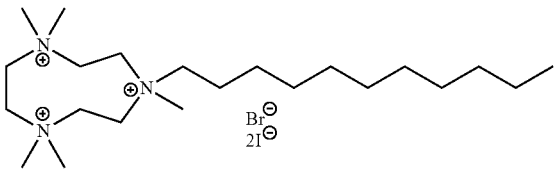 [SMILES: CCCCCCCCCCC[N+]1(C)CC[N+](C)(C)CC[N+](C)(C)CC1]

Figure 42:
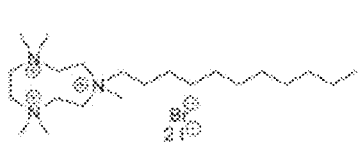
FIG. 42, comprising
Figure 42:
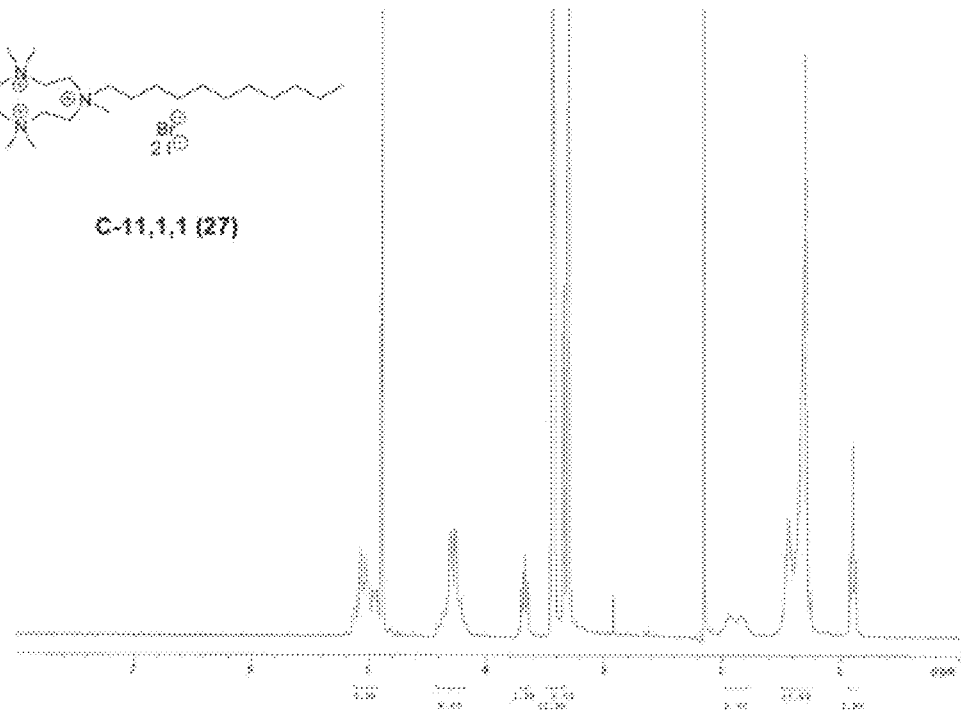
Figure 42:
Figure 42:
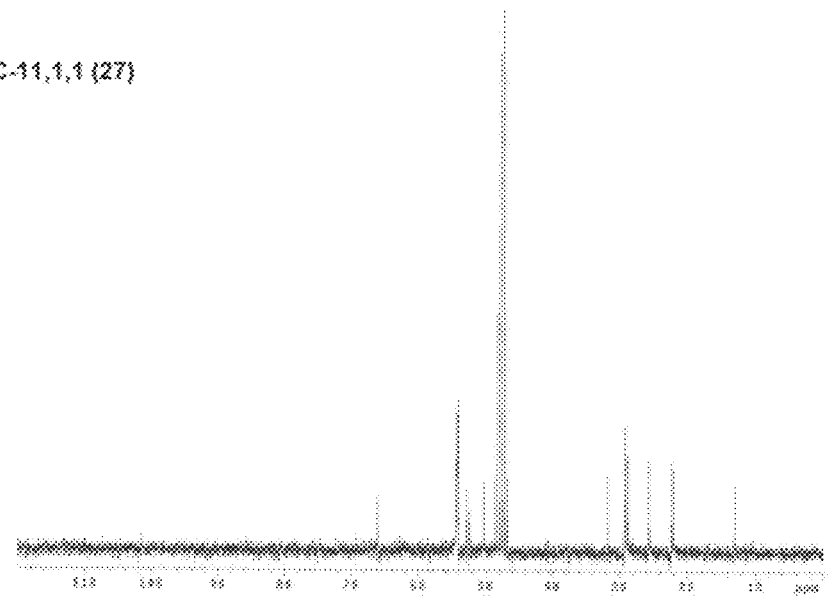

To a flask containing C-11,0,0 (0.0914 g, 0.225 mmol) was added iodomethane (~1.5 mL, 24 mmol). The resulting yellow solution with white solid was capped and stirred for 21 hours. The reaction flask was uncapped and the solvent was allowed to evaporate, resulting in C-11,1,1 (0.113 g, 73%) as a yellow-orange solid; mp=162-174 OC; $^1$H NMR (300 MHz, CD$_3$OD) δ 5.14-4.91 (m, 6H), 4.42-4.16 (m, 6H), 3.71-3.63 (m, 2H), 3.46-3.40 (m, 12H), 3.34 (s, 3H), 1.99-1.77 (m, 2H), 1.48-1.24 (m, 16H), 0.93-0.86 (3H); $^{13}$C NMR (75 MHz, CD$_3$OD) δ 66.1, 54.4, 54.2, 54.1, 52.8, 52.4, 50.3, 31.6, 29.3, 29.2, 29.1, 29.0, 28.7, 25.6, 22.3, 22.1, 13.0; high resolution mass spectrum (ESI) m/z 610.2089 ([M+2I]$^+$; calculated for [C$_{22}$H$_{50}$N$_3$I$_2$]$^+$: 610.2089). $^1$H and $^{13}$C NMR spectra of compound C-11,1,1 can be found in FIG. 42.

Preparation of C-12,1,1 (28)

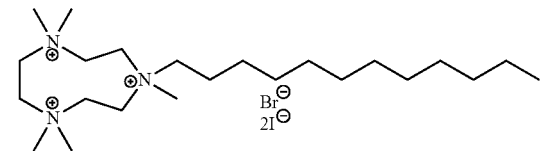

Figure 43:
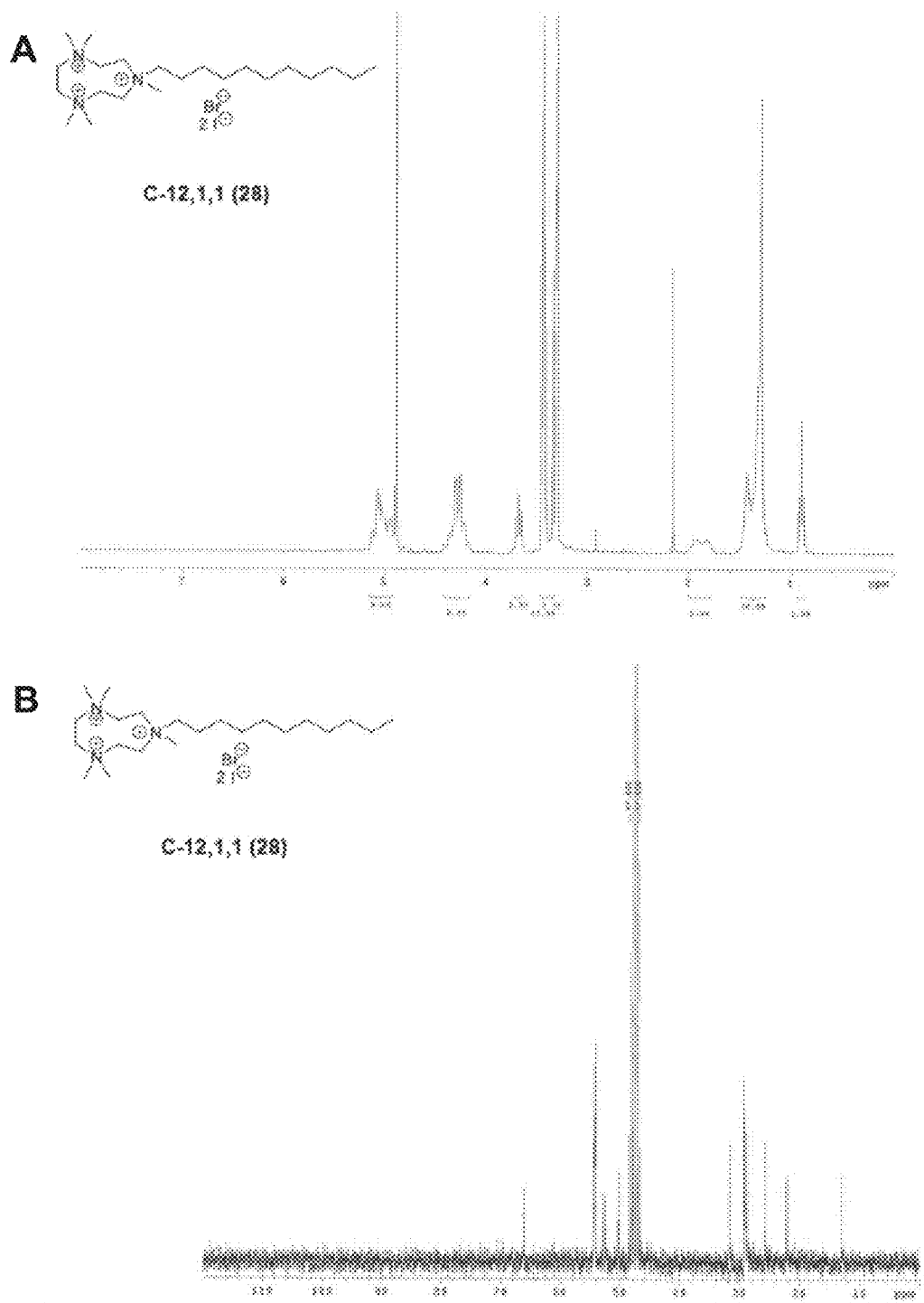
FIG. 43, comprising

To a flask containing C-12,0,0 (0.0800 g, 0.190 mmol) was added iodomethane (~1.5 mL, 24 mmol). The resulting yellow solution with white solid was capped and stirred for 21 hours. The reaction flask was uncapped and the solvent was allowed to evaporate, resulting in C-12,1,1 (0.112 g, 84%) as a yellow-orange solid; mp=169-178° C.; $^1$H NMR (300 MHz, CD$_3$OD) δ 5.12-4.91 (m, 6H), 4.43-4.16 (m, 6H), 3.71-3.63 (m, 2H), 3.47-3.39 (m, 12H), 3.34 (s, 3H), 1.99-1.76 (m, 2H), 1.48-1.24 (m, 18H), 0.93-0.86 (m, 3H); $^{13}$C NMR (75 MHz, CD$_3$OD) δ 66.1, 54.4, 54.2, 54.1, 52.8, 52.4, 50.2, 31.6, 29.3, 29.2, 29.1, 29.0, 28.7, 25.6, 22.3, 22.1, 13.0; high resolution mass spectrum (ESI) m/z 624.2223 ([M+2I]$^+$; calculated for [C$_{23}$H$_{52}$N$_3$I$_2$]$^+$: 624.2245). $^1$H and $^{13}$C NMR spectra of compound C-12,1,1 can be found in FIG. 43.

Preparation of C-13,1,1 (29)

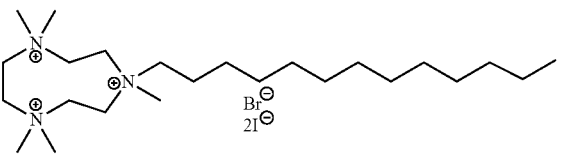

Figure 44:
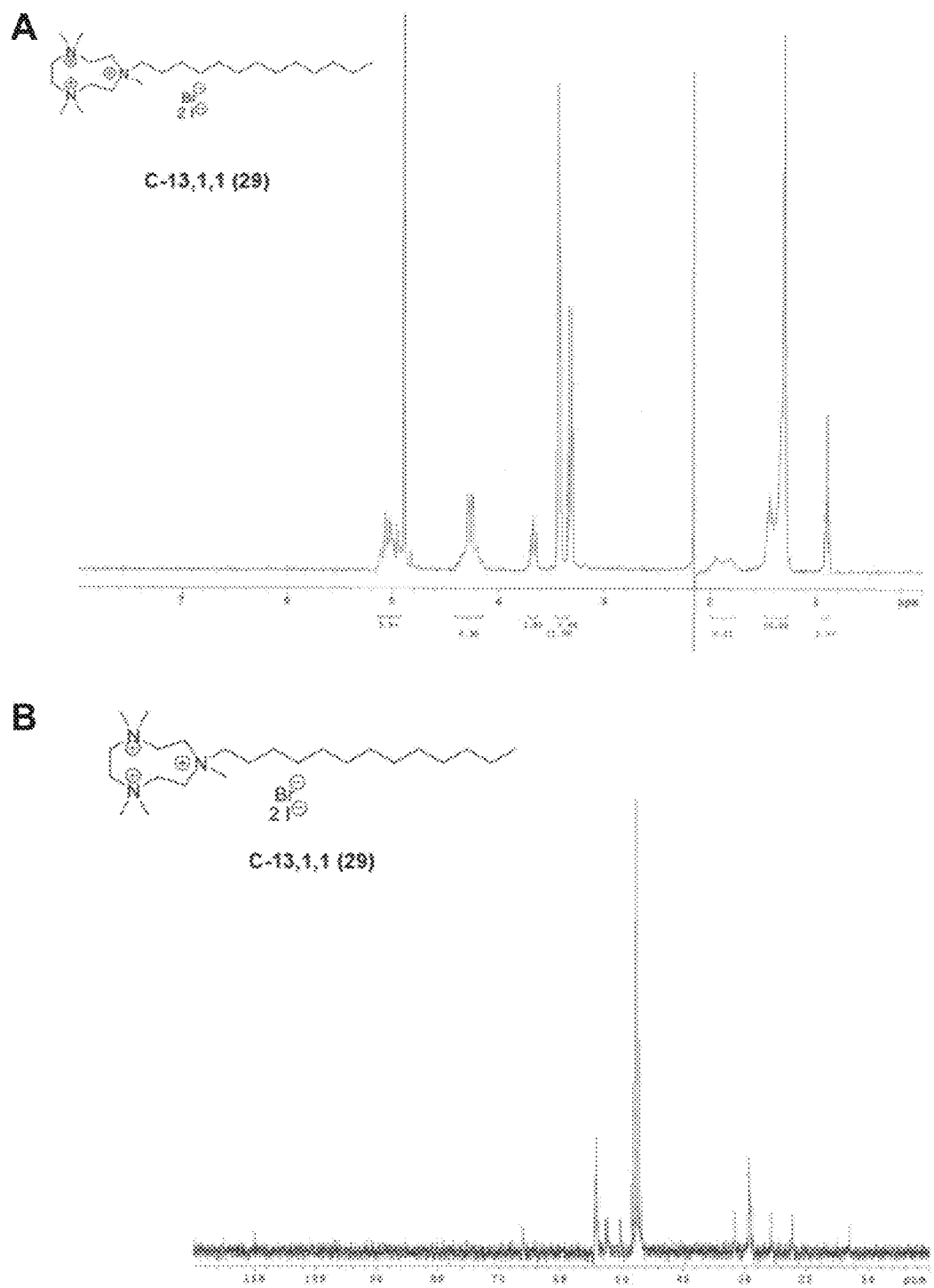
FIG. 44, comprising

To a flask containing C-13,0,0 (0.0912 g, 0.210 mmol) was added iodomethane (~1.5 mL, 24 mmol). The resulting yellow solution with white solid was capped and stirred for 25 hours. The reaction flask was uncapped and the solvent was allowed to evaporate, resulting in C-13,1,1 (0.154 g, ~100%) as a yellow solid; mp=173-177° C.; $^1$H NMR (300 MHz, CD$_3$OD) δ 5.13-4.93 (m, 6H), 4.40-4.13 (m, 6H), 3.71-3.63 (m, 2H), 3.45-3.40 (m, 12H), 3.33 (s, 3H), 1.99-1.76 (m, 2H), 1.48-1.25 (m, 20H), 0.93-0.87 (m, 3H); $^{13}$C NMR (75 MHz, CD$_3$OD) δ 66.1, 54.5, 54.4, 54.2, 54.1, 52.8, 52.4, 50.3, 31.6, 29.3, 29.2, 29.1, 29.0, 28.7, 25.6, 22.3, 22.1, 13.0; high resolution mass spectrum (ESI) m/z 638.2407 ([M+2I]$^+$; calculated for [C$_{24}$H$_{54}$N$_3$I$_2$]$^+$: 638.2402). $^1$H and $^{13}$C NMR spectra of compound C-13,1,1 can be found in FIG. 44.

Preparation of C-14,1,1 (30)

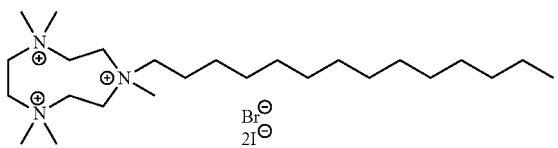 [SMILES: CCCCCCCCCCCCCC[N+]1(C)CC[N+](C)(C)CC[N+](C)(C)CC1]

Figure 45:
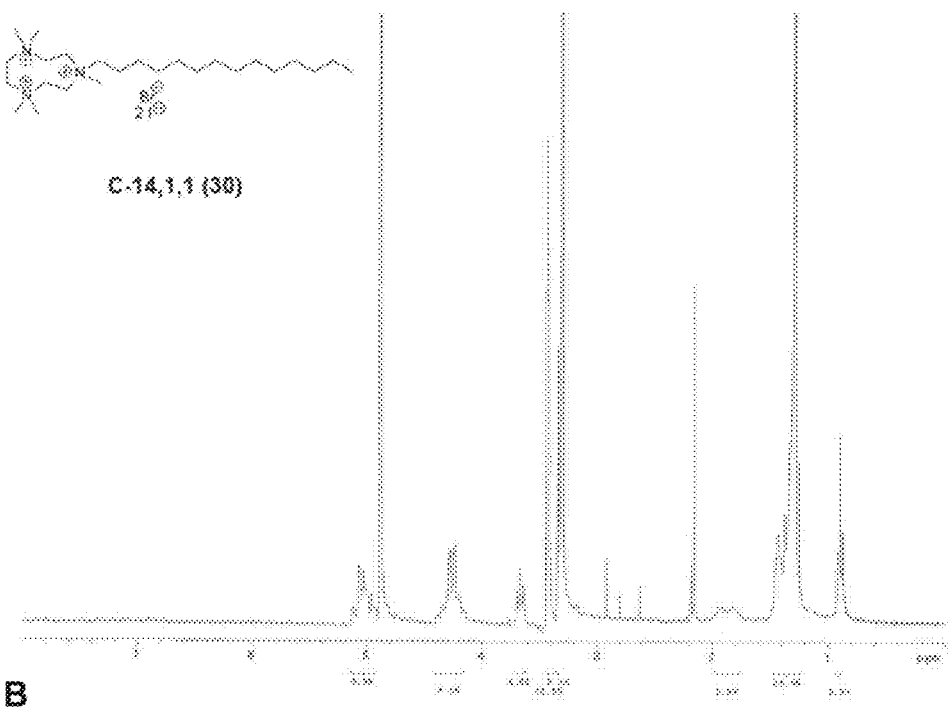
FIG. 45, comprising
Figure 45:
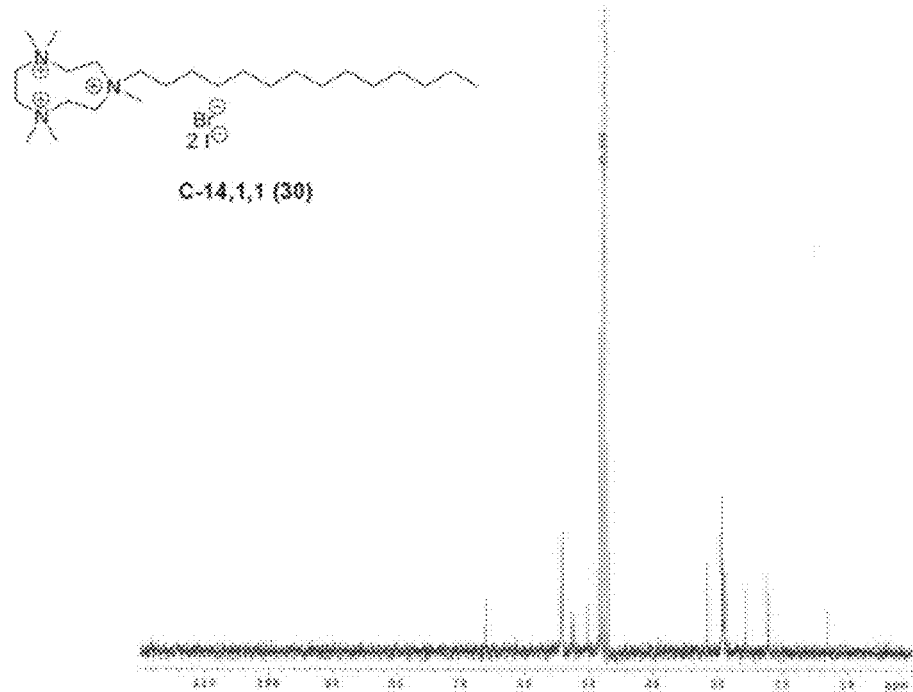

To a flask containing C-14,0,0 (0.0815 g, 0.182 mmol) was added iodomethane (~1.5 mL, 24 mmol). The resulting yellow solution with white solid was capped and stirred for 21 hours. The reaction flask was uncapped and the solvent was allowed to evaporate, resulting in C-14,1,1 (0.119 g, 89%) as a yellow-orange solid; mp=173-180° C.; $^1$H NMR (300 MHz, CD$_3$OD) δ 5.13-4.91 (m, 6H), 4.40-4.14 (m, 6H), 3.71-3.62 (m, 2H), 3.45-3.39 (m, 12H), 3.33 (s, 3H), 1.97-1.74 (m, 2H), 1.47-1.24 (m, 22H), 0.93-0.87 (m, 3H); $^{13}$C NMR (75 MHz, CD$_3$OD) δ 66.1, 54.4, 54.2, 54.1, 52.8, 52.3, 50.2, 31.6, 29.4, 29.3, 29.2, 29.1, 29.0, 28.7, 25.6, 22.3, 22.0, 13.0; high resolution mass spectrum (ESI) m/z 652.2571 ([M+2I]$^+$; calculated for [C$_{25}$H$_{56}$N$_3$I$_2$]$^+$: 652.2558). $^1$H and $^{13}$C NMR spectra of compound C-14,1,1 can be found in FIG. 45.

Preparation of C-16,1,1 (31)

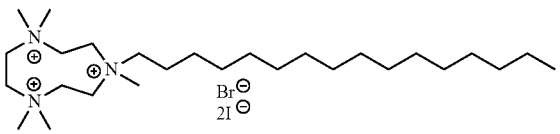 [SMILES: CCCCCCCCCCCCCCCC[N+]1(C)CC[N+](C)(C)CC[N+](C)(C)CC1]

Figure 46:
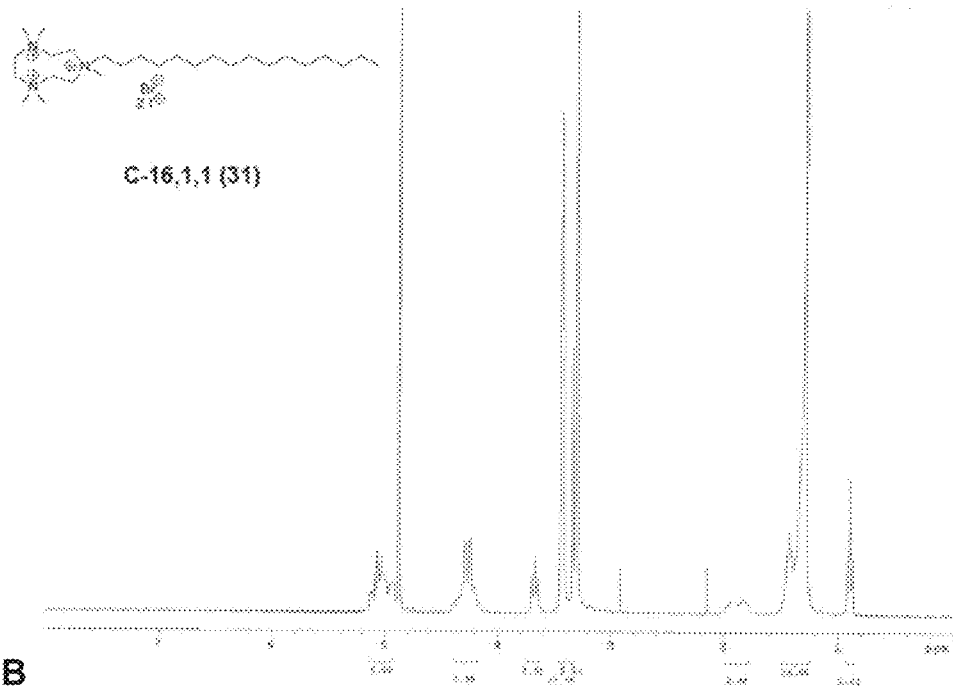
FIG. 46, comprising
Figure 46:
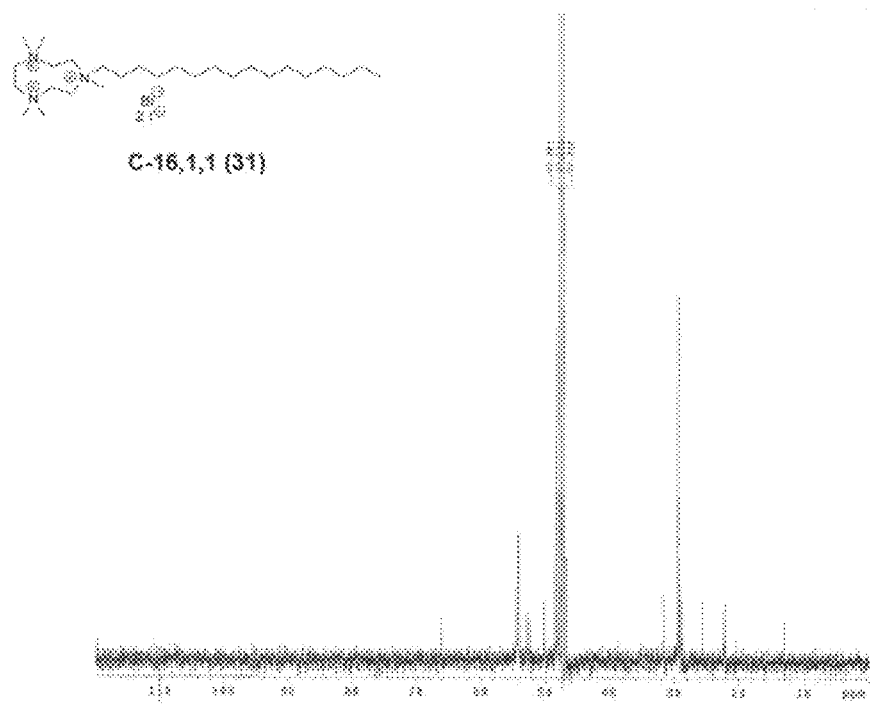

To a flask containing C-16,0,0 (0.0884 g, 0.186 mmol) was added iodomethane (~1.5 mL, 24 mmol). The resulting yellow solution with white solid was capped and stirred for 24 hours. The reaction flask was uncapped and the solvent was allowed to evaporate, resulting in C-16,1,1 (0.138 g, 98%) as a yellow-orange solid; mp=174-182° C.; $^1$H NMR (300 MHz, CD$_3$OD) δ 5.14-4.91 (m, 6H), 4.41-4.15 (m, 6H), 3.71-3.63 (m, 2H), 3.46-3.40 (m, 12H), 3.34 (s, 3H), 1.98-1.77 (m, 2H), 1.48-1.25 (m, 26H), 0.93-0.87 (m, 3H); $^{13}$C NMR (75 MHz, CD$_3$OD) δ 66.1, 54.4, 54.2, 54.1, 52.8, 52.3, 50.2, 31.6, 29.4, 29.3, 29.3, 29.2, 29.1, 29.0, 28.7, 25.6, 22.3, 22.0, 13.0; high resolution mass spectrum (ESI) m/z 680.2850 ([M+2I]$^+$; calculated for [C$_{27}$H$_{60}$N$_3$I$_2$]$^+$: 680.2871). $^1$H and $^{13}$C NMR spectra of compound C-16,1,1 can be found in FIG. 46.

Preparation of C-18,1,1 (32)

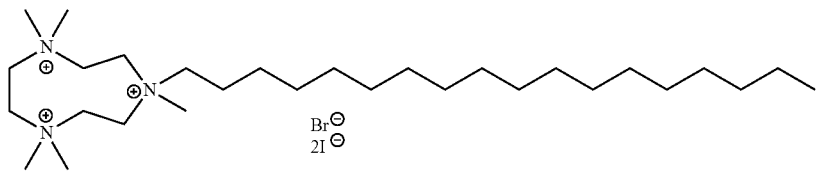 [SMILES: CCCCCCCCCCCCCCCCCC[N+]1(C)CC[N+](C)(C)CC[N+](C)(C)CC1]

Figure 47:
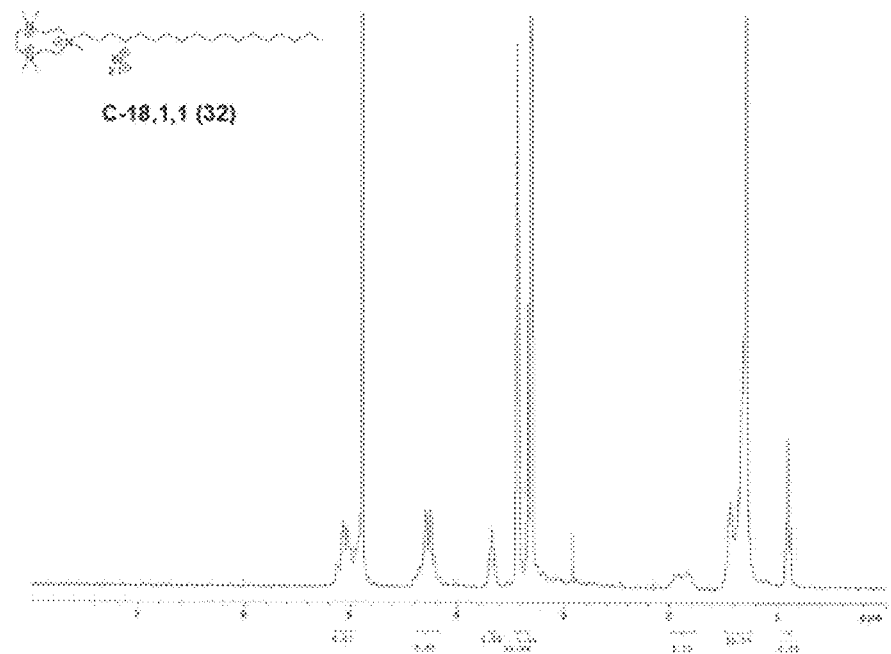
FIG. 47, comprising
Figure 47:
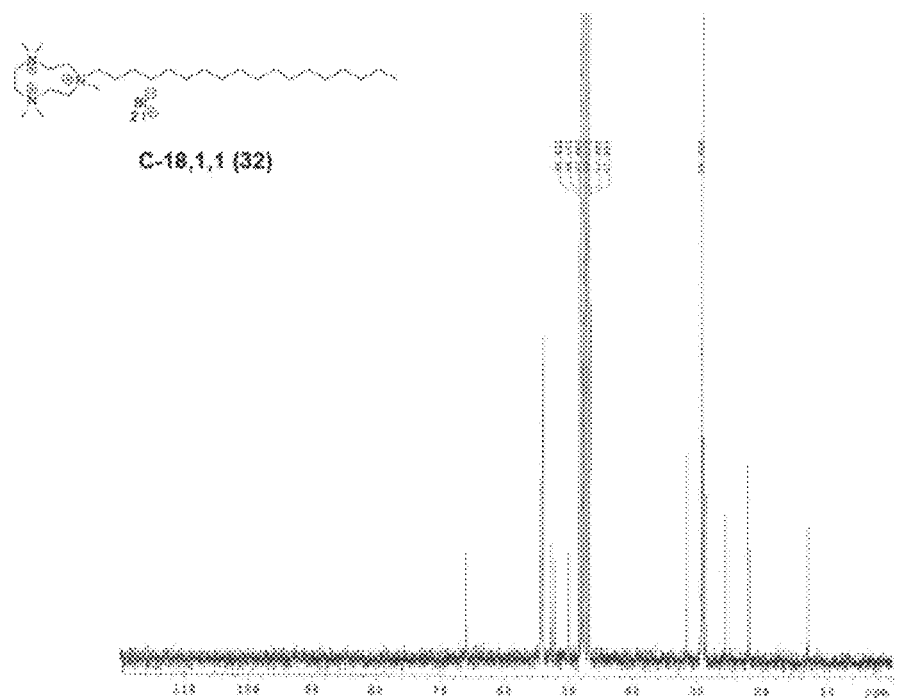

To a flask containing C-18,0,0 (0.0893 g, 0.177 mmol) was added iodomethane (~1.5 mL, 24 mmol). The resulting yellow solution with white solid was capped and stirred for 20 hours. The reaction flask was uncapped and the solvent was allowed to evaporate, resulting in C-18,1,1 (0.126 g, 91%) as a yellow-orange solid; mp=176-201° C.; $^1$H NMR (300 MHz, CD$_3$OD) 5.12-4.94 (m, 6H), 4.41-4.15 (m, 6H), 3.72-3.63 (m, 2H), 3.46-3.40 (m, 12H), 3.33 (s, 3H), 1.98-1.73 (m, 2H), 1.48-1.23 (m, 30H), 0.93-0.87 (m, 3H); $^{13}$C NMR (75 MHz, CD$_3$OD) δ 66.1, 54.4, 54.1, 54.1, 52.8, 52.3, 50.1, 31.6, 29.3, 29.3, 29.1, 29.1, 29.0, 28.7, 25.6, 22.3, 22.0, 13.0; high resolution mass spectrum (ESI) m/z 708.3157 ([M+2I]$^+$; calculated for [C$_{29}$H$_{64}$N$_3$I$_2$]$^+$: 708.3184). $^1$H and $^{13}$C NMR spectra of compound C-18,1,1 can be found in FIG. 47.

Preparation of C-20,1,1 (33)

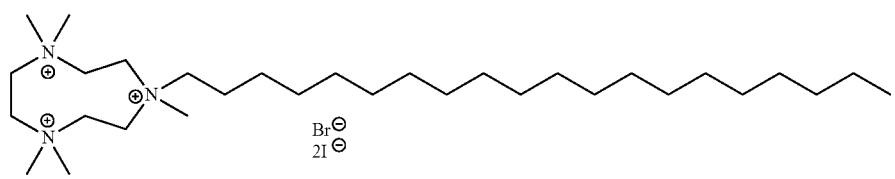 [SMILES: CCCCCCCCCCCCCCCCCCCC[N+]1(C)CC[N+](C)(C)CC[N+](C)(C)CC1]

Figure 48:
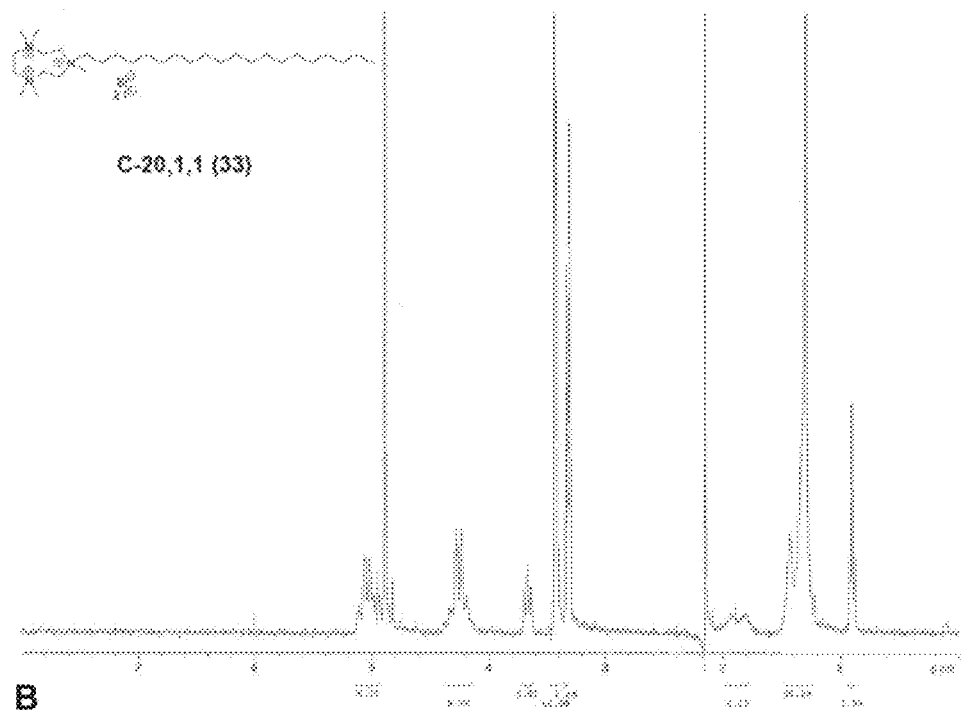
FIG. 48, comprising
Figure 48:
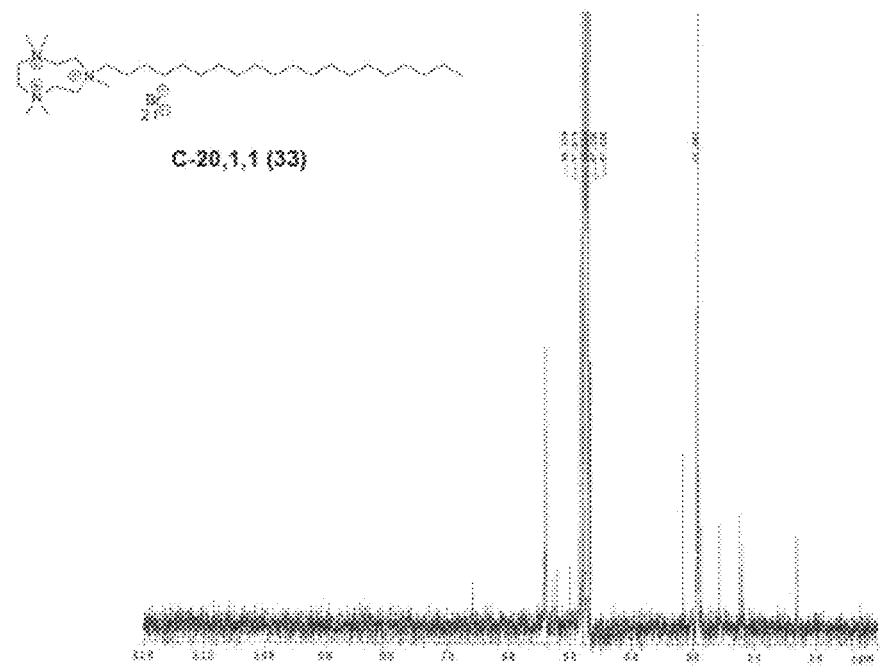

To a flask containing C-20,0,0 (0.0992, 0.186 mmol) was added iodomethane (~1.5 mL, 24 mmol). The resulting yellow solution with white solid was capped and stirred for 25 hours. The reaction flask was uncapped and the solvent was allowed to evaporate, resulting in C-20,1,1 (0.156 g, ~100%) as a yellow solid; mp=183-202 OC; $^1$H NMR (300 MHz, CD$_3$OD) δ 5.12-4.92 (m, 6H), 4.35-4.17 (m, 6H), 3.71-3.62 (m, 2H), 3.45-3.39 (m, 12H), 3.33 (s, 3H), 1.97-1.77 (m, 2H), 1.47-1.25 (m, 34H), 0.93-0.87 (m, 3H); $^{13}$C NMR (75 MHz, CD$_3$OD) δ 66.0, 54.3, 54.0, 53.9, 52.7, 52.2, 50.0, 31.7, 29.4, 29.2, 29.1, 29.1, 28.8, 25.6, 22.3, 21.9, 13.1; high resolution mass spectrum (ESI) m/z 736.3438 ([M+2I]$^+$; calculated for [C$_{31}$H$_{68}$N$_3$I$_2$]$^+$: 736.3458). $^1$H and $^{13}$C NMR spectra of compound C-20,1,1 can be found in FIG. 48.

Preparation of T-8,8,8 (34)

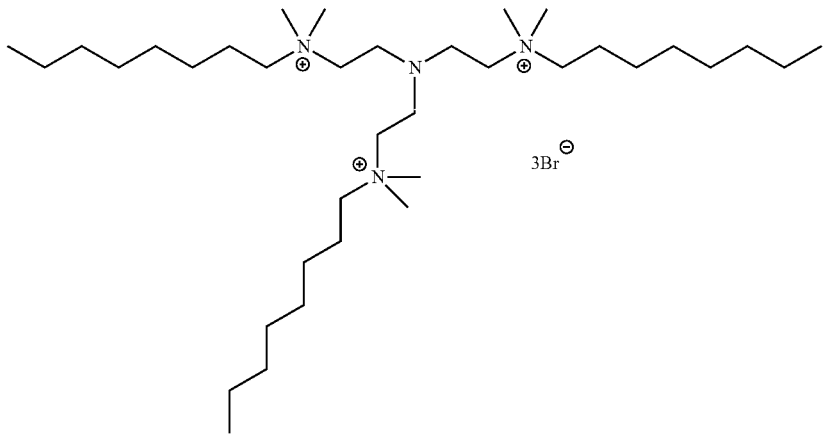 [SMILES: CCCCCCCC[N+](C)(C)CCCN(CC[N+](C)(C)CCCCCCCC)CC[N+](C)(C)CCCCCCCC]

Figure 49:
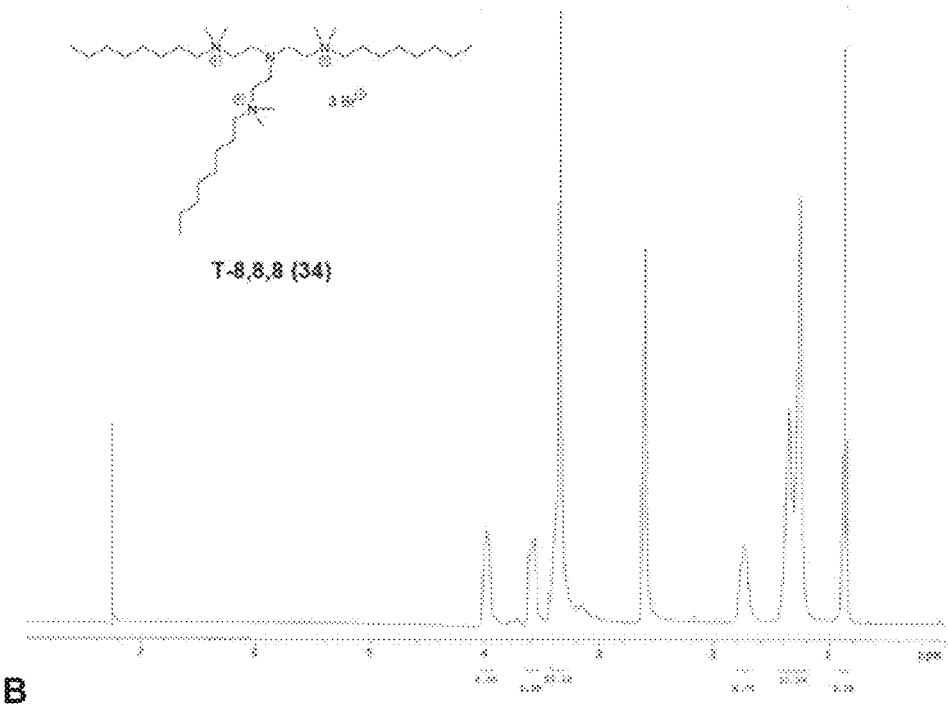
FIG. 49, comprising
Figure 49:
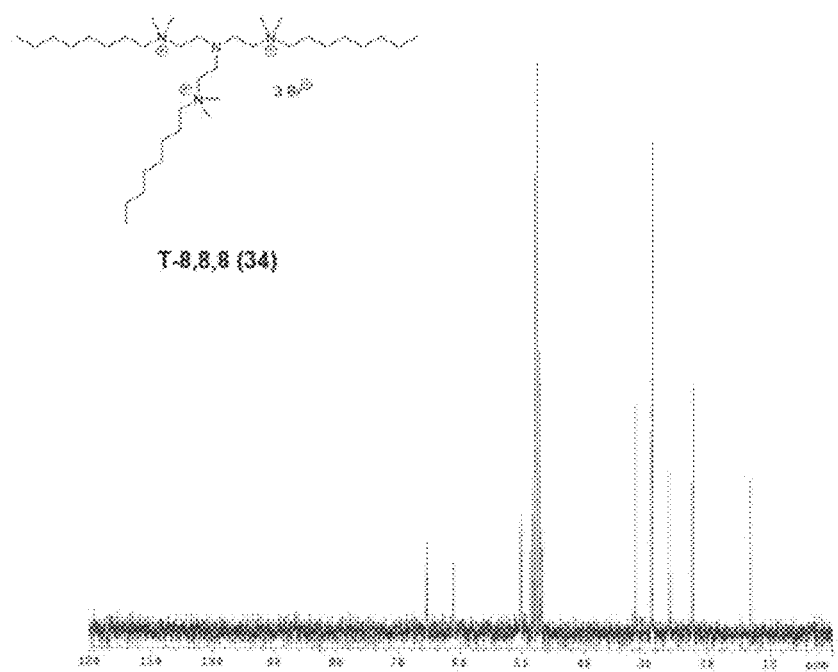

To a solution of tris(2-dimethylaminoethyl)amine (0.436 g, 1.89 mmol) in acetonitrile (4 mL) was added 1-bromooctane (1.20 g, 6.22 mmol). The resulting mixture was heated at reflux with stirring for 18 hours, during which time a white solid was observed. After cooling, and the addition of a cold hexanes/acetone mixture (~15 mL, 1:1), to the reaction flask, the precipitate was filtered with a Büchner funnel, and rinsed with a cold hexanes/acetone mixture (~20 mL, 1:1), resulting in T-8,8,8 (1.45 g, 95%) as a yellow-white wax; $^1$H NMR (300 MHz, CDCl$_3$) δ 4.02-3.94 (m, 6H), 3.63-3.54 (m, 6H), 3.42-3.30 (m, 24H), 1.79-1.67 (m, 6H), 1.41-1.19 (m, 30H), 0.90-0.83 (m, 9H); $^{13}$C NMR (75 MHz, CD$_3$OD) δ 65.3, 61.0, 50.1, 46.8, 31.5, 28.9, 26.1, 22.4, 22.3, 13.1; high resolution mass spectrum (ESI) m/z 189.8823 ([M]$^{3+}$; calculated for [C$_{36}$H$_{81}$N$_4$]$^{3+}$: 189.8815). See also Yoshimura et al., 2012, Langmuir 28:9322-9331. $^1$H and $^{13}$C NMR spectra of compound T-8,8,8 can be found in FIG. 49.

Preparation of T-10,10,10 (35)

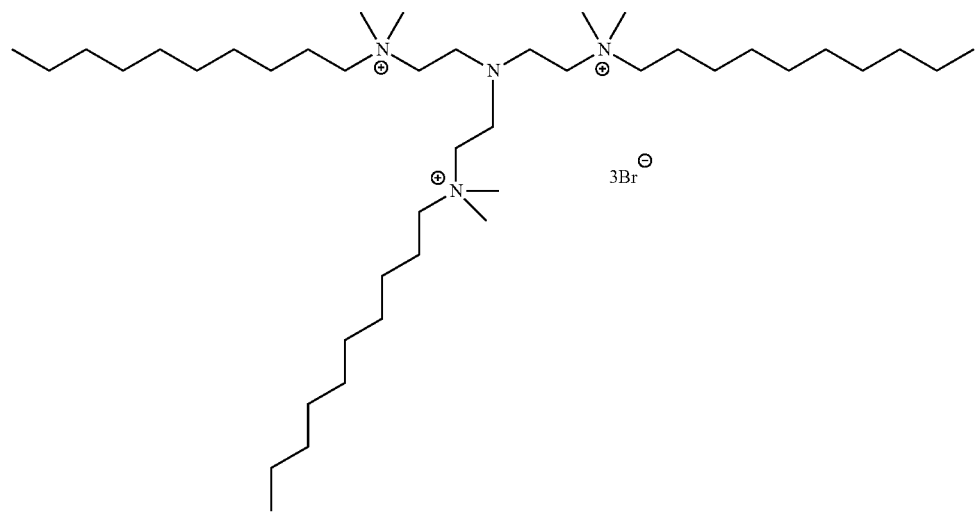 [SMILES: CCCCCCCCCC[N+](C)(C)CCCN(CC[N+](C)(C)CCCCCCCCCC)CC[N+](C)(C)CCCCCCCCCC]

Figure 50:
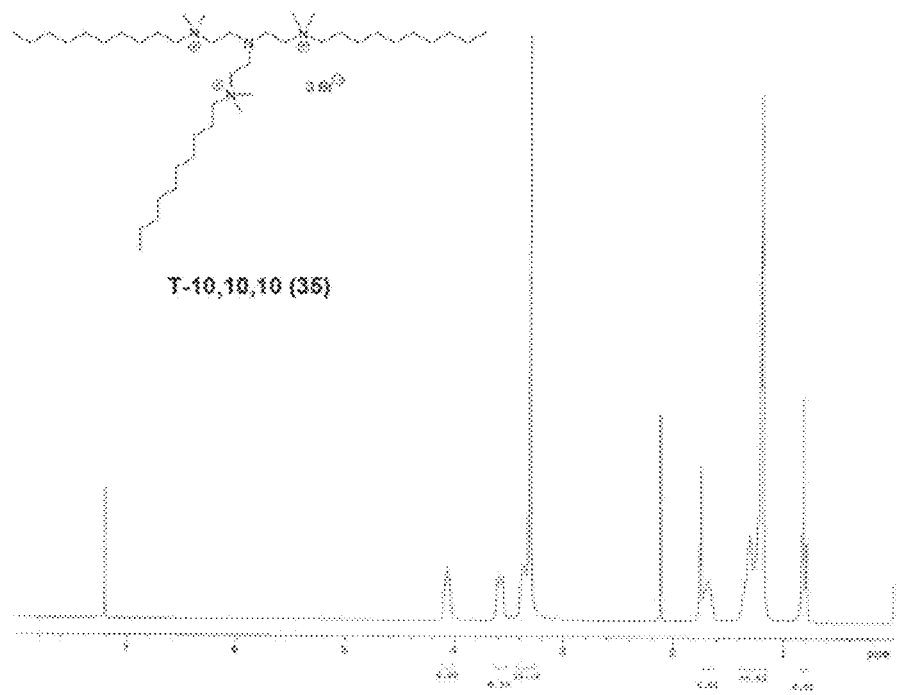
FIG. 50, comprising
Figure 50:
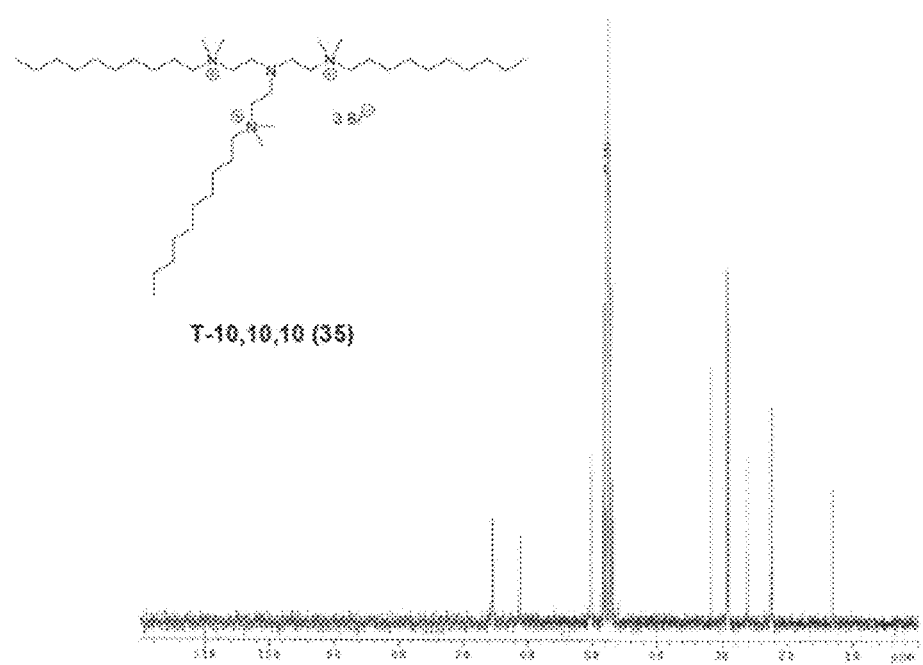

To a solution of tris(2-dimethylaminoethyl)amine (0.426 g, 1.85 mmol) in acetonitrile (4 mL) was added 1-bromodecane (1.27 g, 5.73 mmol). The resulting mixture was heated at reflux with stirring for 18 hours. After cooling, and the addition of hexanes (5 mL), a white solid precipitated, which was filtered with a Büchner funnel, transferring with a cold hexanes/acetone mixture (~15 mL, 1:1). The solid was rinsed with a cold hexanes/acetone mixture (~20 mL, 1:1), resulting in T-10,10,10 (1.16 g, 70%) as a white powder; mp=223-248° C.; $^1$H NMR (300 MHz, CDCl$_3$) δ 4.11-4.02 (m, 6H), 3.62-3.53 (m, 6H), 3.41-3.27 (m, 24H), 1.72-1.62 (m, 6H), 1.38-1.14 (m, 42H), 0.85-0.78 (m, 9H); $^{13}$C NMR (75 MHz, CD$_3$OD) δ 65.4, 61.1, 50.2, 46.9, 31.6, 29.2, 29.0, 28.9, 26.1, 22.4, 22.3, 13.0; high resolution mass spectrum (ESI) m/z 217.9095 ([M]$^3$; calculated for [C$_{42}$H$_{93}$N$_4$]$^{3+}$: 217.9128). See also Yoshimura et al., 2012, Langmuir 28:9322-9331. $^1$H and $^{13}$C NMR spectra of compound T-10,10,10 can be found in FIG. 50.

Preparation of T-11,11,11 (36)

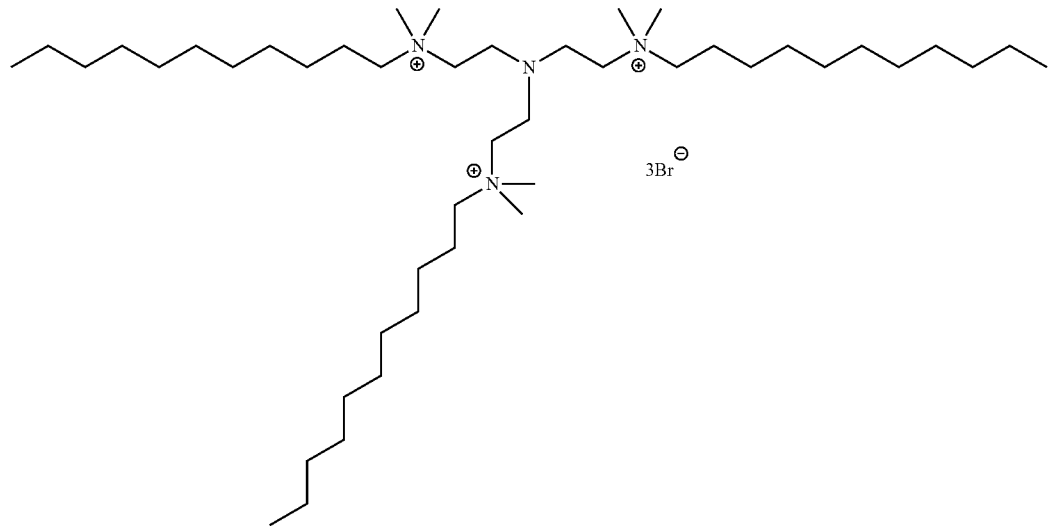 [SMILES: CCCCCCCCCCC[N+](C)(C)CCCN(CC[N+](C)(C)CCCCCCCCCCC)CC[N+](C)(C)CCCCCCCCCCC]

Figure 51:
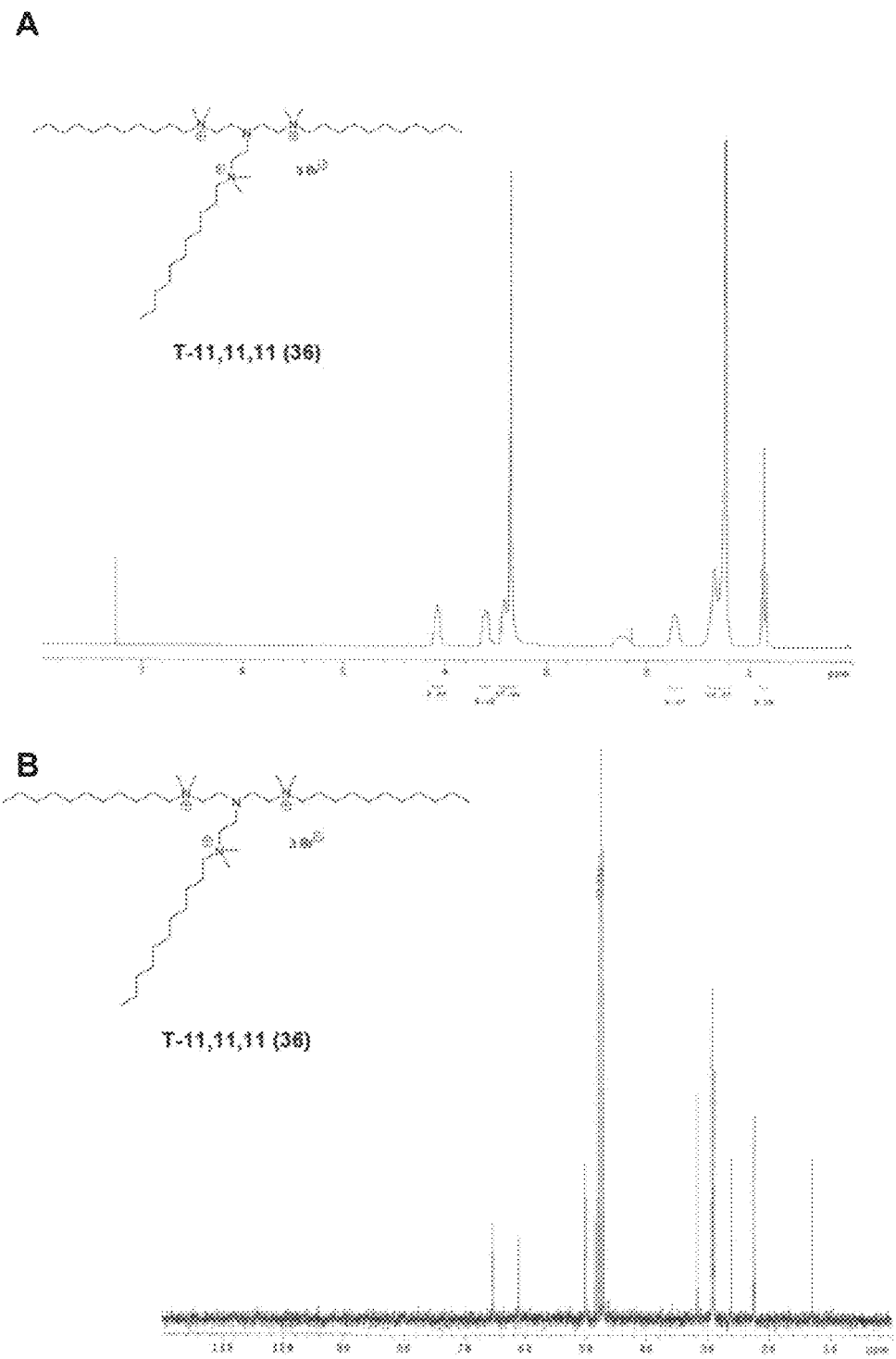
FIG. 51, comprising

To a solution of tris(2-dimethylaminoethyl)amine (0.486 g, 2.11 mmol) in acetonitrile (4 mL) was added 1-bromoundecane (1.55 g, 6.57 mmol). The resulting mixture was heated at reflux with stirring for 19 hours. After cooling, and the addition of hexanes (5 mL), a white solid precipitated, which was filtered with a Büchner funnel, transferring with a cold hexanes/acetone mixture (~15 mL, 1:1). The solid was rinsed with a cold hexanes/acetone mixture (~20 mL, 1:1), resulting in T-11,11,11 (1.62 g, 82%) as a white powder; mp=224-253° C.; $^1$H NMR (300 MHz, CDCl$_3$) δ 4.12-4.03 (m, 6H), 3.65-3.56 (m, 6H), 3.45-3.37 (m, 6H), 3.34 (s, 18H), 1.79-1.66 (m, 6H), 1.41-1.18 (m, 48H), 0.89-0.82 (m, 9H); $^{13}$C NMR (75 MHz, CD$_3$OD) δ 5.4, 61.1, 50.1, 46.9, 31.6, 29.3, 29.3, 29.2, 29.0, 28.9, 26.1, 22.4, 22.3, 13.0; high resolution mass spectrum (ESI) m/z 231.9281 ([M]$^{3+}$; calculated for [C$_{45}$H$_{99}$N$_4$]$^{3+}$: 231.9284). $^1$H and $^{13}$C NMR spectra of compound T-11,11,11 can be found in FIG. 51.

Preparation of T-12,12,12 (37)

Figure 52:
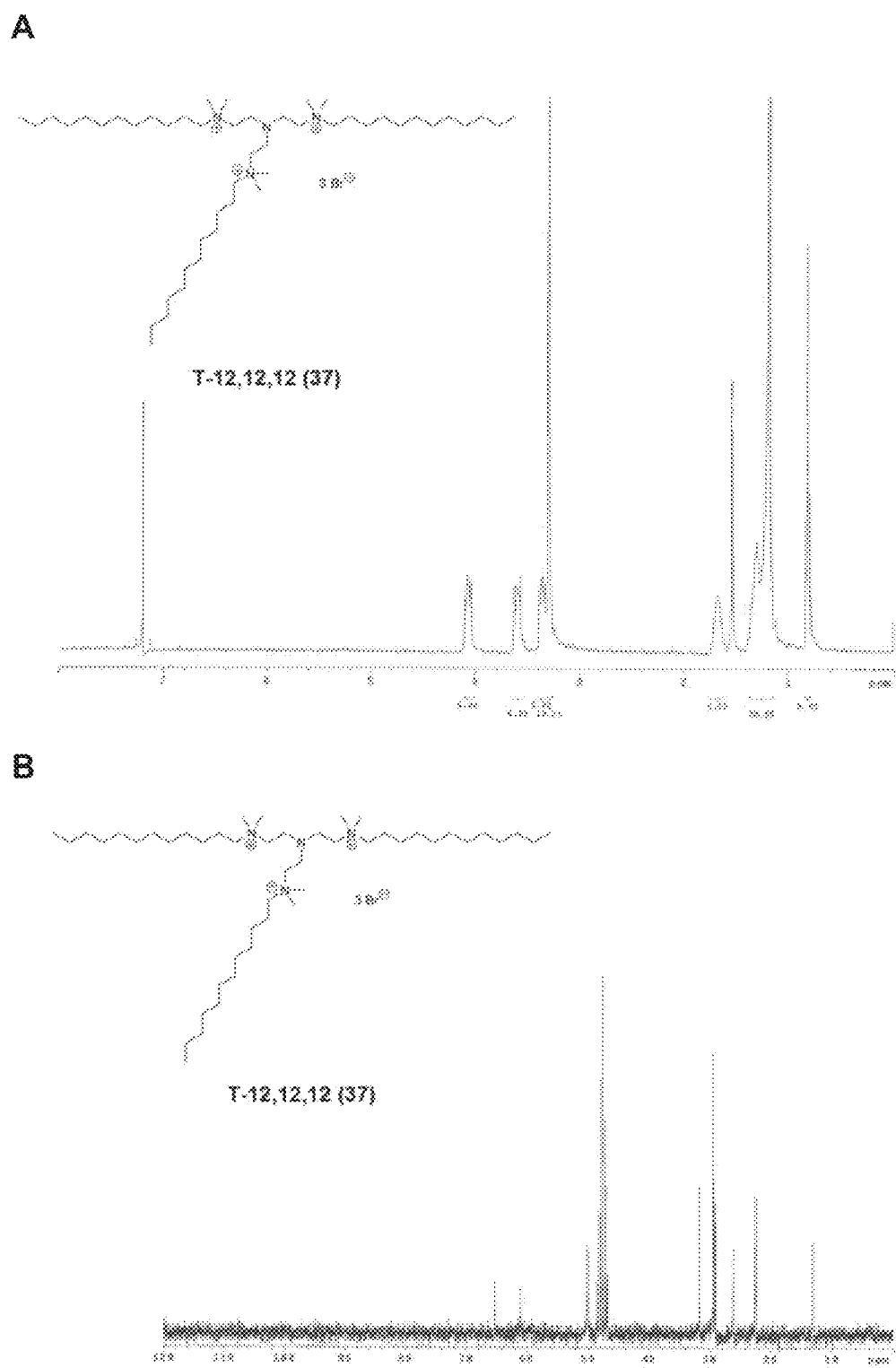
FIG. 52, comprising

To a solution of tris(2-dimethylaminoethyl)amine (0.401 g, 1.74 mmol) in acetonitrile (4 mL) was added 1-bromododecane (1.34 g, 5.38 mmol). The resulting mixture was heated at reflux with stirring for 22 hours, during which time a white solid was observed. After cooling, and the addition of a cold hexanes/acetone mixture (~15 mL, 1:1), to the reaction flask, the precipitate was filtered with a Büchner funnel, and rinsed with a cold hexanes/acetone mixture (~20 mL, 1:1), resulting in T-12,12,12 (1.39 g, 82%) as a white powder; mp=225-254 OC; $^1$H NMR (300 MHz, CDCl$_3$) δ 4.11-4.03 (m, 6H), 3.63-3.55 (m, 6H), 3.39-3.32 (m, 6H), 3.30 (s, 18H), 1.72-1.62 (m, 6H), 1.37-1.14 (m, 54H), 0.84-0.78 (m, 9H); $^{13}$C NMR (75 MHz, CD$_3$OD) δ 65.3, 61.0, 50.1, 46.8, 31.7, 29.4, 29.3, 29.3, 29.1, 29.0, 26.1, 22.4, 22.4, 13.1; high resolution mass spectrum (ESI) m/z 245.9435 ([M]$^{3+}$; calculated for [C$_{48}$H$_{105}$N$_4$]$^{3+}$: 245.9441). See also Yoshimura et al., 2012, Langmuir 28:9322-9331. $^1$H and $^{13}$C NMR spectra of compound T-12,12,12 can be found in FIG. 52.

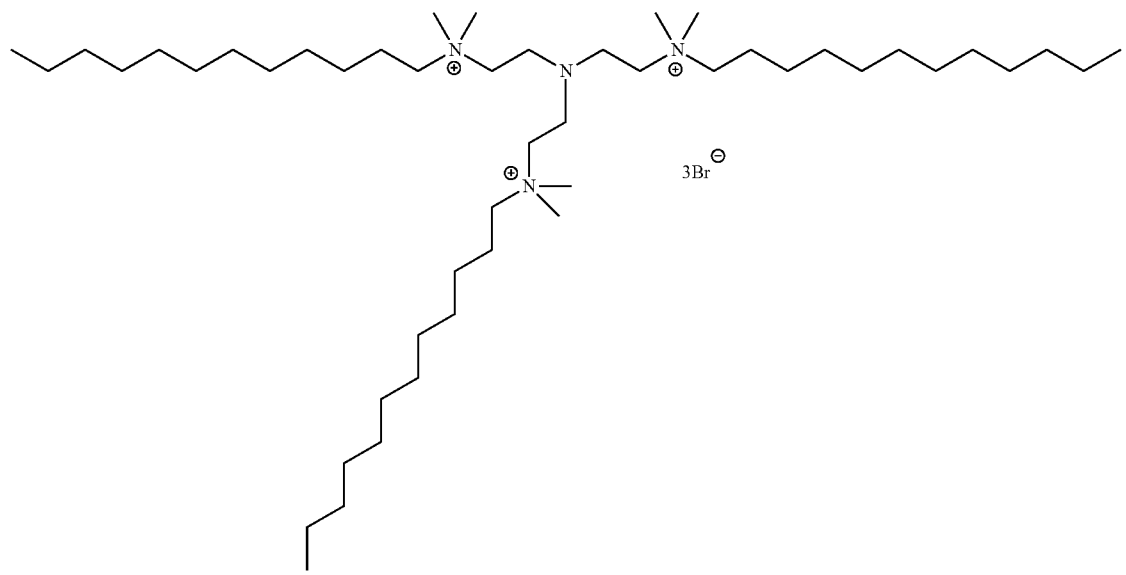 [SMILES: CCCCCCCCCCCC[N+](C)(C)CCCN(CC[N+](C)(C)CCCCCCCCCCCC)CC[N+](C)(C)CCCCCCCCCCCC]

Preparation of T-14,14,14 (38)

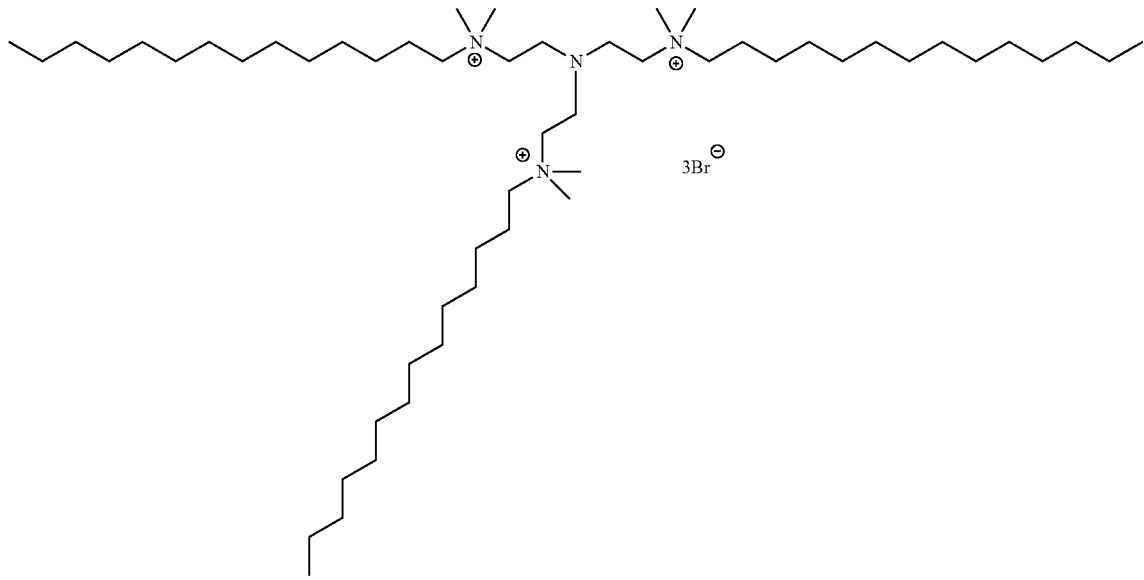 [SMILES: CCCCCCCCCCCCCC[N+](C)(C)CCCN(CC[N+](C)(C)CCCCCCCCCCCCCC)CC[N+](C)(C)CCCCCCCCCCCCCC]

Figure 53:
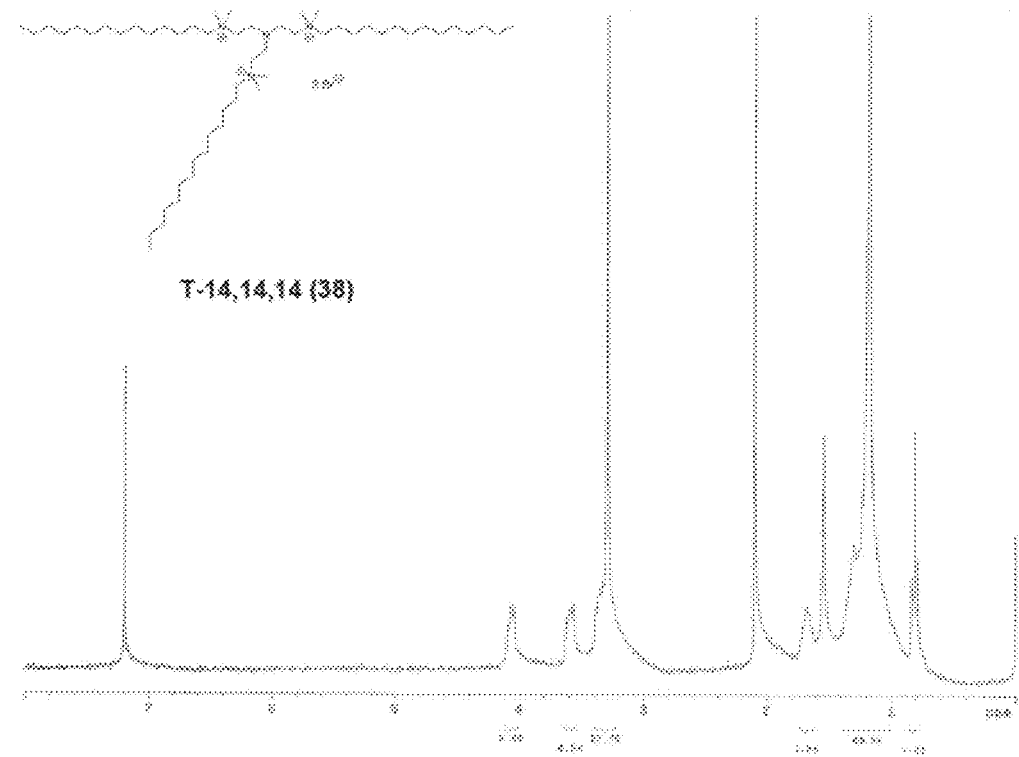
FIG. 53, comprising
Figure 53:
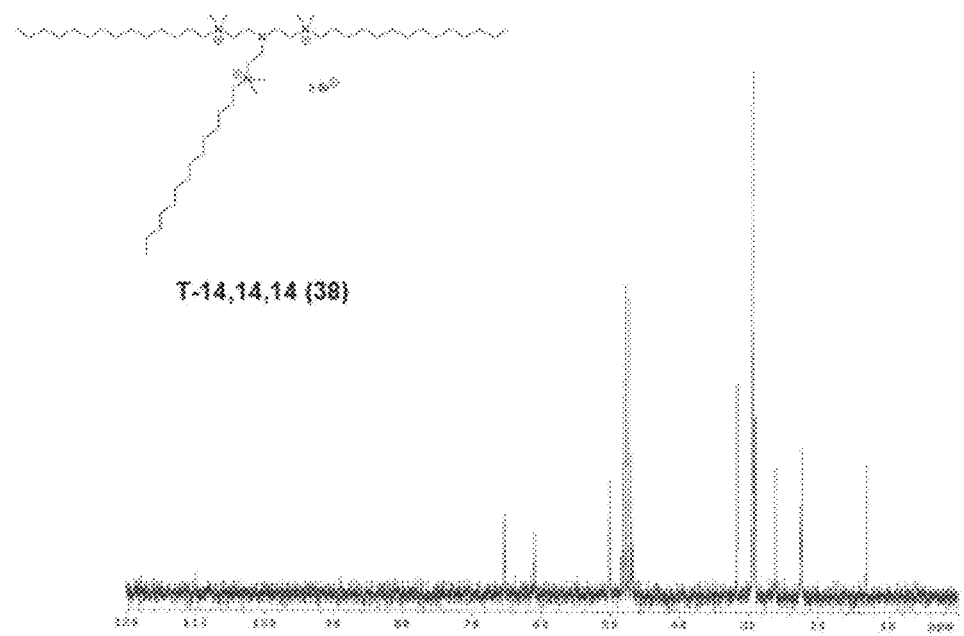

To a solution of tris(2-dimethylaminoethyl)amine (0.404 g, 1.75 mmol) in acetonitrile (4 mL) was added 1-bromotetradecane (1.47 g, 5.32 mmol). The resulting mixture was heated at reflux with stirring for 23 hours, during which time a white solid was observed. After cooling, and the addition of a cold hexanes/acetone mixture (~15 mL, 1:1), to the reaction flask, the precipitate was filtered with a Büchner funnel, and rinsed with a cold hexanes/acetone mixture (~20 mL, 1:1), resulting in T-14,14,14 (1.31 g, 70%) as a white powder; mp=229-258° C.; $^1$H NMR (300 MHz, CDCl$_3$) δ 4.10-4.02 (m, 6H), 3.63-3.54 (m, 6H), 3.39-3.22 (m, 24H), 1.73-1.61 (m, 6H), 1.36-1.06 (m, 66H), 0.84-0.77 (m, 9H); $^{13}$C NMR (75 MHz, CD$_3$OD) δ 65.3, 61.0, 50.1, 46.9, 31.7, 29.4, 29.4, 29.3, 29.3, 29.1, 29.0, 26.1, 22.5, 22.4, 13.1; high resolution mass spectrum (ESI) m/z 273.9766 ([M]$^{3+}$; calculated for [C$_{54}$H$_{117}$N$_4$]$^{3+}$: 273.9754). See also Yoshimura et al., 2012, Langmuir 28:9322-9331. $^1$H and $^{13}$C NMR spectra of compound T-14,14,14 can be found in FIG. 53.

Preparation of T-16,16,16 (39)

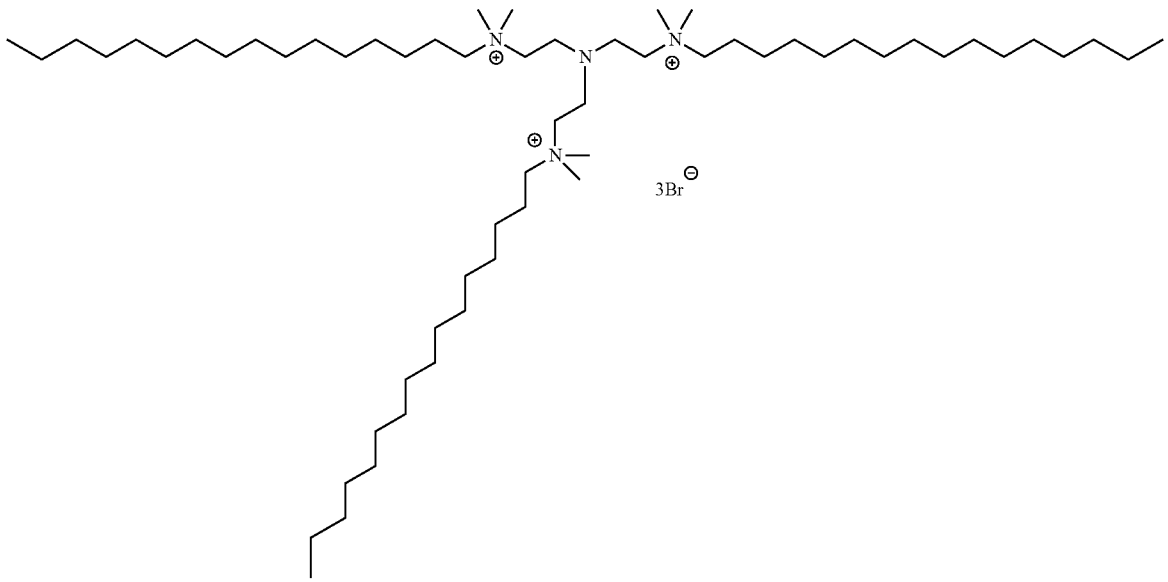 [SMILES: CCCCCCCCCCCCCCCC[N+](C)(C)CCCN(CC[N+](C)(C)CCCCCCCCCCCCCCCC)CC[N+](C)(C)CCCCCCCCCCCCCCCC]

Figure 54:
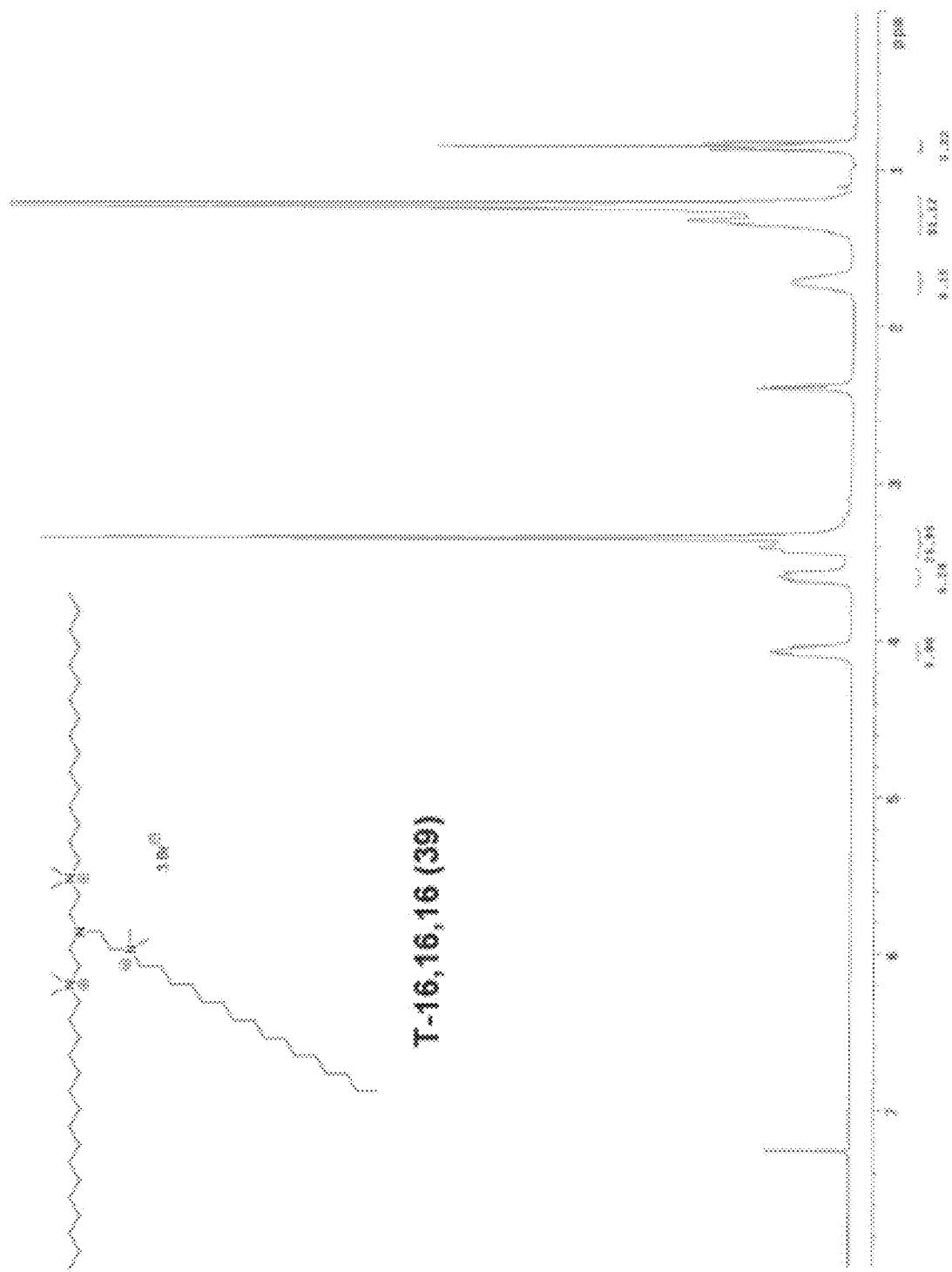
FIG. 54 depicts the $^1$H NMR spectrum of compound T-16,16,16.

To a solution of tris(2-dimethylaminoethyl)amine (0.403 g, 1.75 mmol) in acetonitrile (4 mL) was added 1-bromohexadecane (1.63 g, 5.35 mmol). The resulting mixture was heated at reflux with stirring for 18 hours, during which time a white solid was observed. After cooling, and the addition of a cold hexanes/acetone mixture (~15 mL, 1:1), to the reaction flask, the precipitate was filtered with a Büchner funnel, and rinsed with a cold hexanes/acetone mixture (~20 mL, 1:1), resulting in T-16,16,16 (1.67 g, 84%) as a white powder; mp=229-258° C.; $^1$H NMR (300 MHz, CDCl$_3$) δ 4.11-4.02 (m, 6H), 3.64-3.55 (m, 6H), 3.45-3.37 (m, 6H), 3.35 (s, 18H), 1.78-1.66 (m, 6H), 1.40-1.18 (m, 78H), 0.88-0.81 (m, 9H); high resolution mass spectrum (ESI) m/z 302.0073 ([M]$^{3+}$; calculated for [C$_{60}$H$_{129}$N$_4$]$^{3+}$: 302.0067). $^1$H spectrum of compound T-16,16,16 can be found in FIG. 54.

Preparation of T-18,18,18 (40)

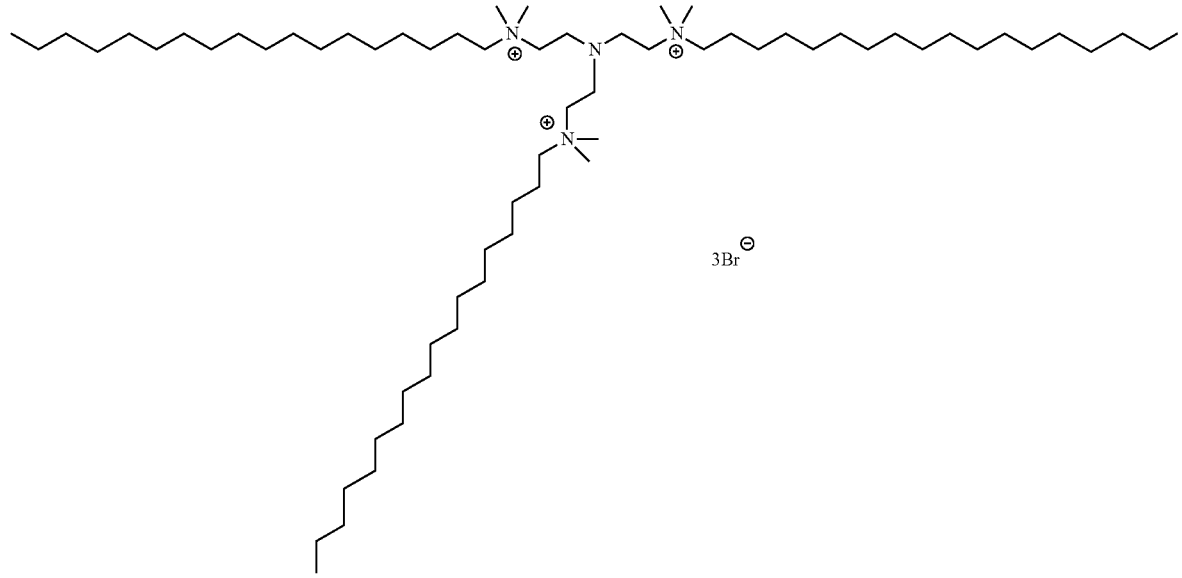 [SMILES: CCCCCCCCCCCCCCCCCC[N+](C)(C)CCCN(CC[N+](C)(C)CCCCCCCCCCCCCCCCCC)CC[N+](C)(C)CCCCCCCCCCCCCCCCCC]

Figure 55:
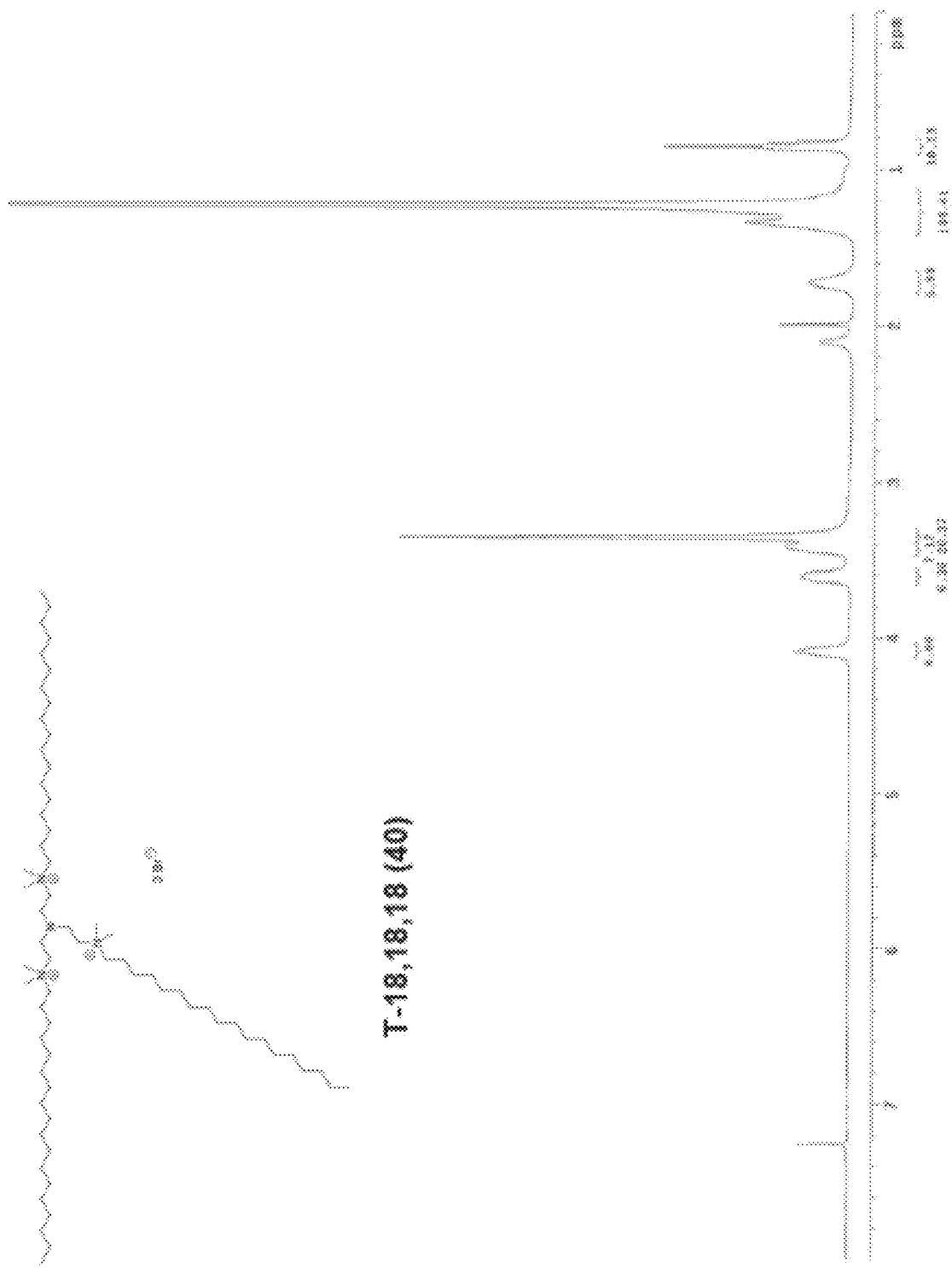
FIG. 55 depicts the $^1$H NMR spectrum of compound T-18,18,18.

To a solution of tris(2-dimethylaminoethyl)amine (0.326 g, 1.41 mmol) in acetonitrile (4 mL) was added 1-bromooctadecane (1.41 g, 4.23 mmol). The resulting mixture was heated at reflux with stirring for 23 hours, during which time a white solid was observed. After cooling, and the addition of a cold hexanes/acetone mixture (~15 mL, 1:1), to the reaction flask, the precipitate was filtered with a Büchner funnel, and rinsed with a cold hexanes/acetone mixture (~20 mL, 1:1), resulting in T-18,18,18 (1.48 g, 85%) as a white powder; mp=227-259° C.; $^1$H NMR (300 MHz, CDCl$_3$) δ 4.13-4.02 (m, 6H), 3.65-3.58 (m, 6H), 3.46-3.38 (m, 6H), 3.35 (s, 18H), 1.78-1.66 (m, 6H), 1.41-1.37 (m, 90H), 0.89-0.82 (m, 9H); high resolution mass spectrum (ESI) m/z 330.0376 ([M]$^{3+}$; calculated for [C$_{66}$H$_{141}$N$_4$]$^{3+}$: 330.0380). $^1$H spectrum of compound T-18,18,18 can be found in FIG. 55.

Biological Assays

For all biological assays, laboratory strains of methicillin-susceptible *Staphylococcus aureus* MSSA (SH1000), *Enterococcus faecalis* (OG1RF), *Escherichia coli* (MC4100), *Pseudomonas aeruginosa* (PAO1), community-acquired methicillin-resistant *Staphylococcus aureus* CA-MRSA (USA300-0114), and hospital-acquired methicillin-resistant *Staphylococcus aureus* HA-MRSA (ATCC 33591) were grown at 37° C. overnight from freezer stocks in 10 mL of the media indicated for each assay. All cultures, with the exception of *E. faecalis*, were grown with shaking at 250 rpm.

(i) Minimum Inhibitory Concentration (MIC)

Compounds were serially diluted two-fold from a 10% DMSO/aqueous stock solution to yield twelve test concentrations. Overnight *S. aureus*, *E. faecalis*, *E. coli*, *P. aeruginosa*, CA-MRSA, and HA-MRSA cultures diluted to ca. 106 cfu/mL in Mueller-Hinton media and 100 μL were inoculated into each well of a U-bottom 96-well plate (BD Biosciences, BD351177) containing 100 μL of compound solution. Plates were incubated statically at 37° C. for 72 hours upon which time wells were evaluated visually for bacterial growth. The MIC was determined as the lowest concentration of compound resulting in no bacterial growth visible to the naked eye, based on the majority of three independent experiments. Positive and negative DMSO/aqueous solution and media controls were conducted for each trial.

(ii) Minimum Biofilm Eradication Concentration (MBEC)

To each well of a flat-bottomed 96-well plate (Corning 3370), 8 μL of overnight bacterial culture was brought to a volume of 200 μL with fresh media (BHI for MSSA and MRSA). Plates were incubated statically for 24 hours at 37° C. to establish biofilms. After 24 hours, the wells were carefully emptied by inverting the plate and gently shaking. A pre-mixed solution of media and compound stock solution was added to each well and plates were incubated at 37° C. 16 hours after pre-established biofilms were treated with compound, the media from each well was removed, biofilms were washed three times with 200 μL PBS to remove planktonic cells, and biofilms were incubated overnight at 37° C. in 200 μL of fresh media to allow any viable cells to continue growing. The wells were then vigorously pipetted to resuspend the biofilm cells and the OD at 595 nm was measured using a plate reader (POLARstar Omega, BMG Labtech). Biofilms reaching a final OD of less than 0.1 were considered eradicated and the lowest concentration of antibiotic corresponded to the MBEC. Four replicates were completed for each concentration of compound as well as positive and negative controls.

(iii) Hemolysis Assay (Lysis20)

Hemolysis assays were performed according to a known method (Peng et al., 2011, Chem. Comm. 47:4896-4898). Defibrinated sheep blood was purchased from Hemostat Labs (DSB030). Compounds representative of each class were serially diluted in sterile PBS from stock solutions and incubated with resuspended blood cells. The OD of the final suspensions were measured directly using plate reader. TritonX (1% by volume) served as a positive control (100% lysis marker) and sterile PBS served as a negative control (0% lysis marker).

The results of the experiments are now described.

As described herein, synthetic efforts focused on the preparation of aliphatic amphiphilic structures with at least three nitrogen atoms and 2-4 permanent cationic charges. It was postulated that a scaffold-hopping approach, similar to that used broadly in medicinal chemistry, would yield potent antimicrobials with improved selectivity, potency, and anti-biofilm properties (Bohm et al., 2004, Drug Discovery Today Technol. 1:217-224; Scaffold Hopping in Medicinal Chemistry (Ed.: N. Brown), Wiley-VCH, Weinheim, 2014). It was hypothesized that if the display of the alkyl side chains and cationic charges could be subtly altered, improved toxicity profiles could be obtained while retaining significant antimicrobial/anti-biofilm activity. Furthermore, QAC resistance was examined by determining if the alternative architectures would trigger such a defense.

Figure 21:
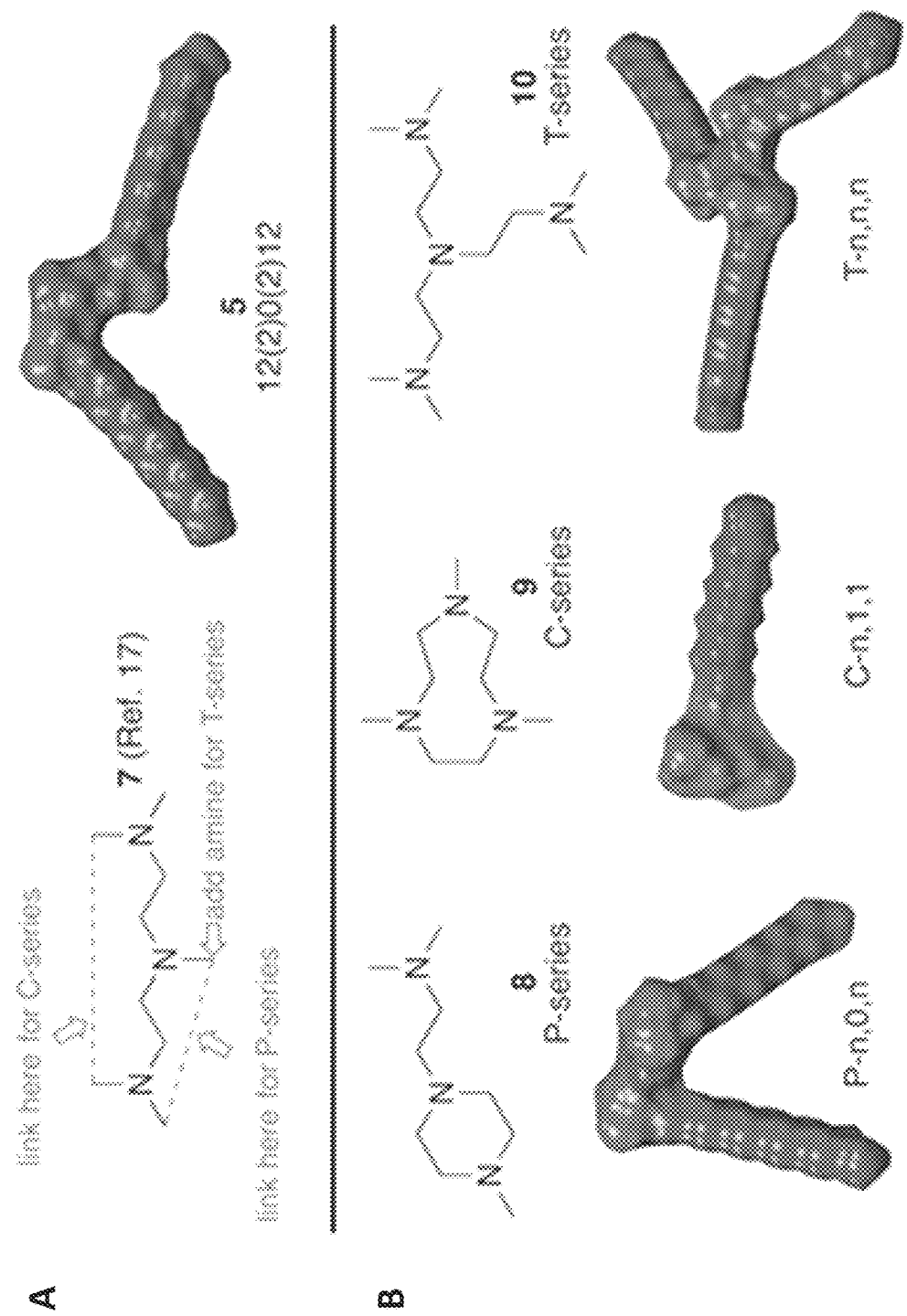
FIG. 21, comprising

Toward this end, alternative polyamine scaffolds that provided access to three structural classes of QACs for biological testing were identified. The architectures are illustrated in FIG. 21. Starting with previously utilized core compound 7, commercially available alternative launch points were identified (8-10) that represented two intramolecular linkages, forming a piperazine or a cyclononyl ring (the P-series and C-series, respectively), as well as a branched tetramine core (the T-series). Restricted rotation of the cyclic structures, and in turn the projection of the alkyl chains, was expected to impart different three-dimensional architecture, allowing for fine-tuning of bioactivity; Chimera-modeled structures are illustrated. Scaffold 9 was particularly interesting, as this compound would possess an increased local density of positive charge, somewhat akin to compounds 3 and 4, but without the benefit of delocalization. Earlier hypotheses suggested that the π system and not necessarily the charge density was responsible for triggering QacR; however, these studies were limited solely to aryl systems. Finally, this investigation was extended to biofilms. Previous studies with charged polyamine derivatives have shown that the specific chemical architecture is relevant to dispersing established biofilms (Bottcher et al., 2013, J. Am. Chem. Soc. 135:2927-2930). Therefore, it was hypothesized that particular scaffolds might elicit specific biofilm eradication properties that do not necessarily correlate to the inhibition of planktonic growth. However, little is known about the specific mechanisms that promote biofilm dispersion and/or eradication.

Figure 22:
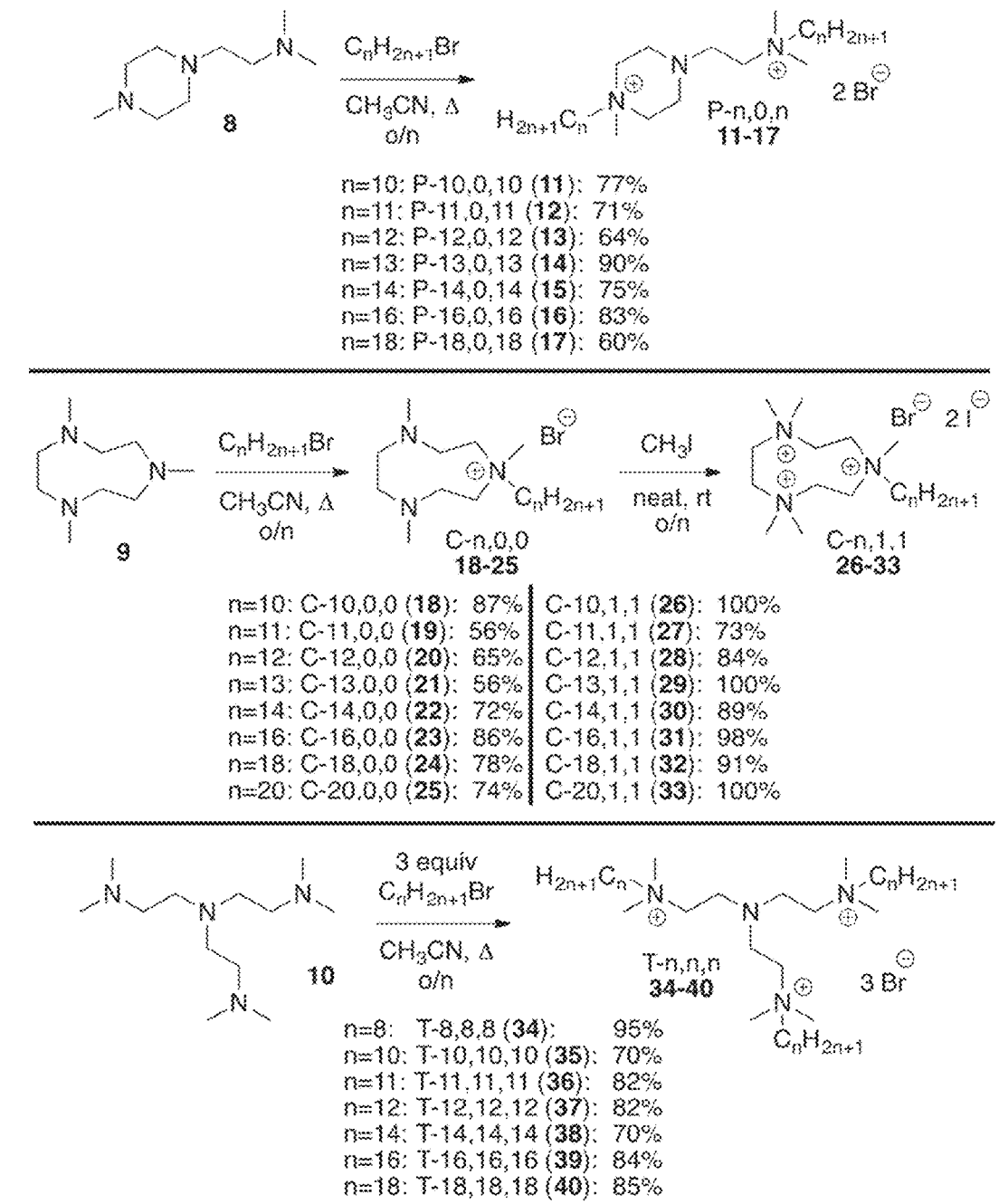
FIG. 22 depicts synthetic schemes for the synthesis of amphiphiles of the present invention including the P-series (top), C-series (middle), and T-series (bottom).
Figure 24:
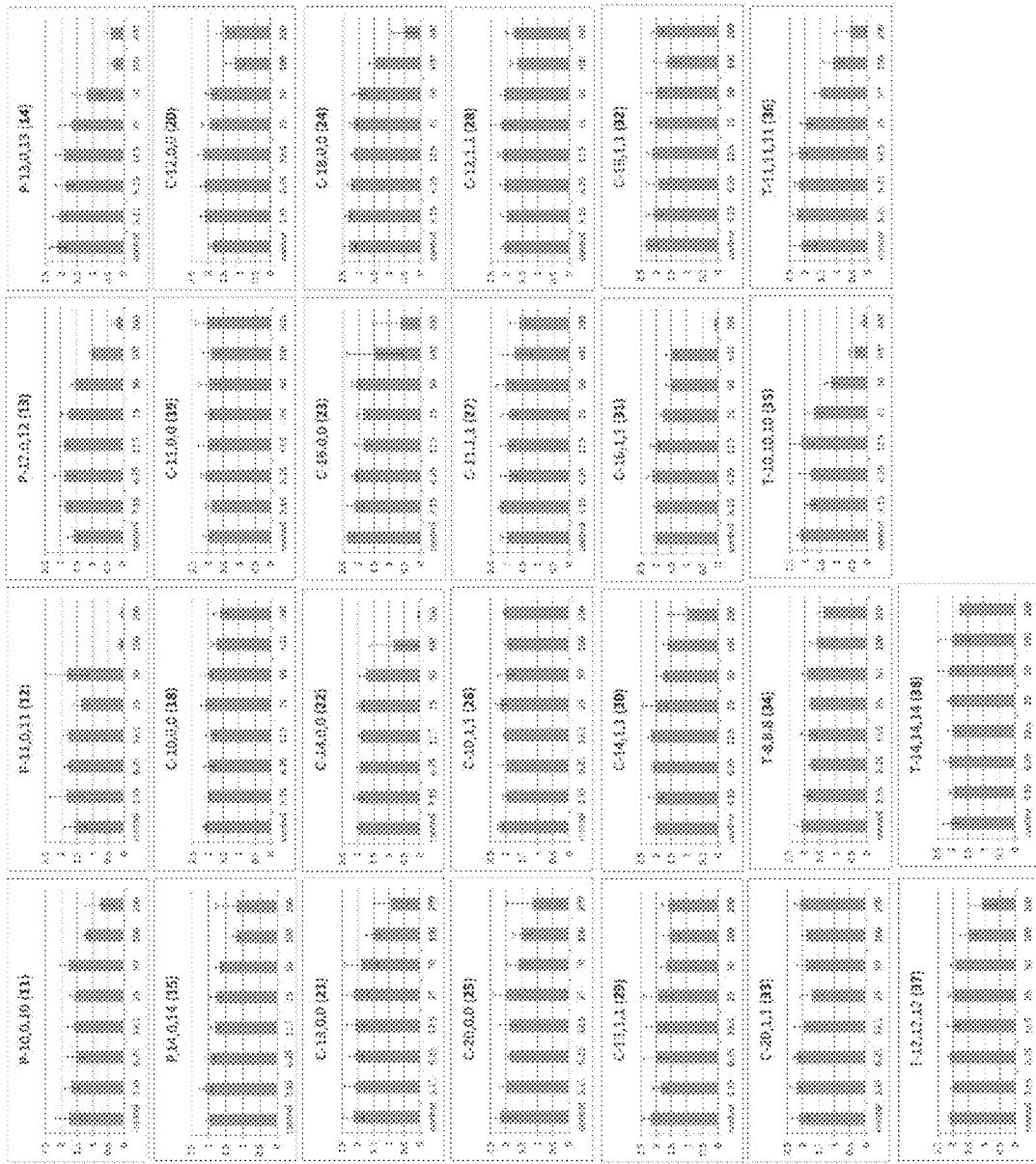
FIG. 24 depicts experimental data of OD of regrown QAC-treated MSSA biofilms versus concentration of QAC with which biofilm was treated. MBEC, or complete eradication, is defined by regrowth assays that result in OD values under 0.1, significant eradication corresponds to OD values under 0.5. Error bars represent the standard deviation among four replicates.
Figure 25:
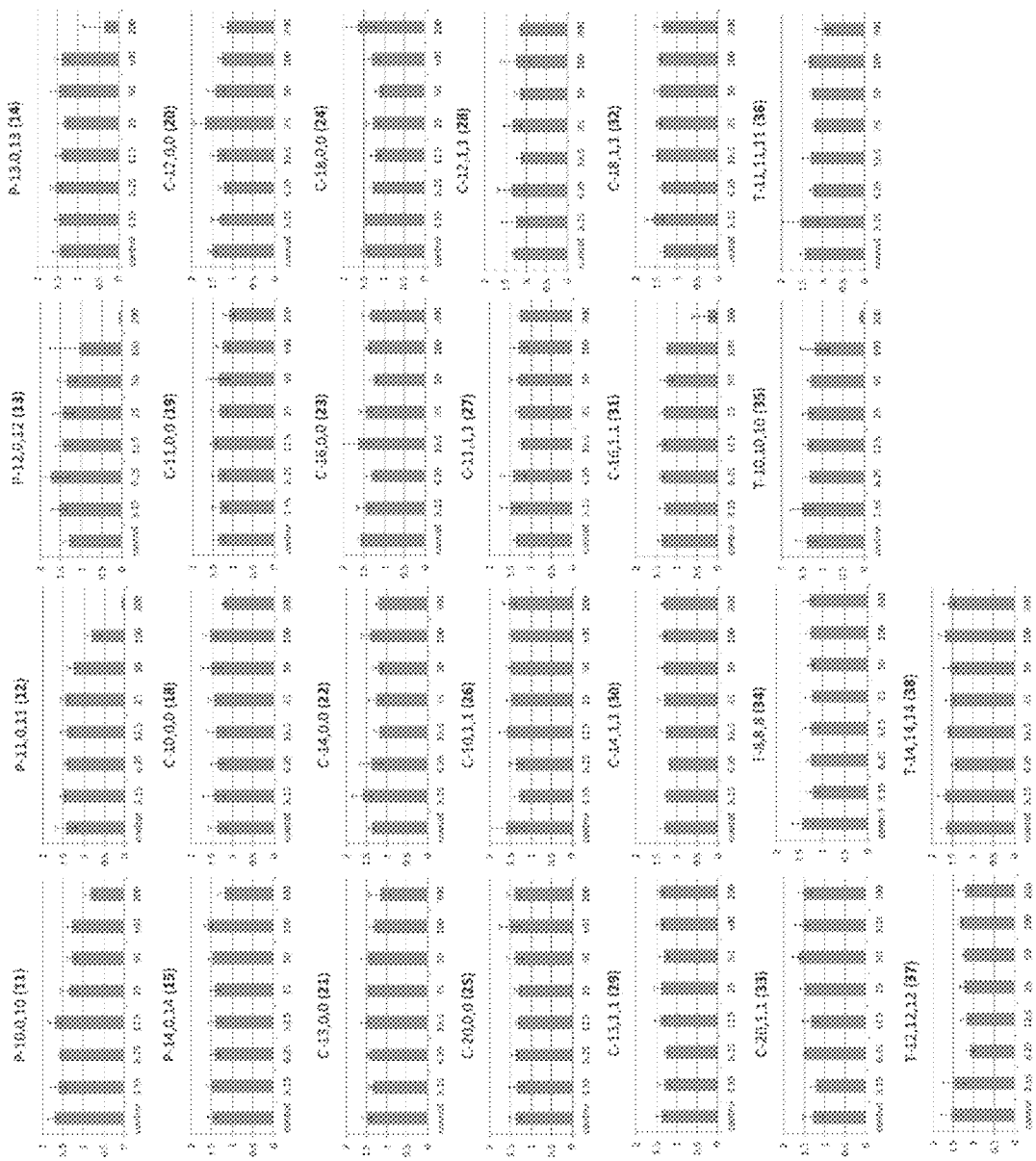
FIG. 25 depicts experimental data of OD of regrown QAC-treated MRSA biofilms versus concentration of QAC with which biofilm was treated. MBEC, or complete eradication, is defined by regrowth assays that result in OD values under 0.1, significant eradication corresponds to OD values under 0.5. Error bars represent the standard deviation among four replicates.

Synthesis of the 4-piperazine core structure (P-series) began with the alkylation of inexpensive 1-(2-dimethylaminoethyl)-4-methylpiperazine (8, FIG. 22). Accordingly, exposure to two equivalents of the requisite primary alkyl bromide at reflux in acetonitrile (overnight), followed by simple trituration, led to pure compounds 11-17 (60-90%). Unexpectedly, the resulting compounds (dubbed P-n,0,n) were inert to further alkylation at the central nitrogen under a variety of conditions ($CH_3I$; $CH_3OTs/DMF/150°$ C.).

The larger cyclic series (C-series) was prepared from the nine-membered ring, 1,4,7-trimethyl-1,4,7-triazacyclononane (9). Alkylation of this compound with the corresponding alkyl bromide (1 equiv $C_nH_{2n+1}Br$, acetonitrile, reflux, overnight) led only to monoalkylation, furnishing the C-n,0,0 series (18-25) in 56-87% yield after trituration. Although a second alkylation reaction with a long-chain alkyl halide was not observed, methylation proceeded in neat iodomethane (overnight, room temperature) to afford the triscationic series C-n,1,1 (26-33) in 73-98% yields as the diode/monobromide salts.

Finally, the branched tetramine series was explored, starting from 10. Selective alkylation of the terminal tertiary amines was exclusively observed (Yoshimura et al., 2012, Langmuir 28:9322-9331). Thus, alkylation with the corresponding alkyl bromide (3 equiv $C_nH_{2n+1}Br$, acetonitrile, reflux, overnight) led strictly to trisalkylation, furnishing the T-n,n,n series (34-40) in 70-95% yield after trituration. Again, there was no subsequent reactivity observed for the resultant tertiary amine in the T-n,n,n series, which reflects the electronic environment of three neighboring quaternary ammonium residues, as well as significant steric hindrance. In summary, we were able to prepare a library of 30 QACs comprised of three unique chemical scaffolds in a concise, high-yielding fashion with minimal purification needed, highlighting the utility of our method.

Figure 23:
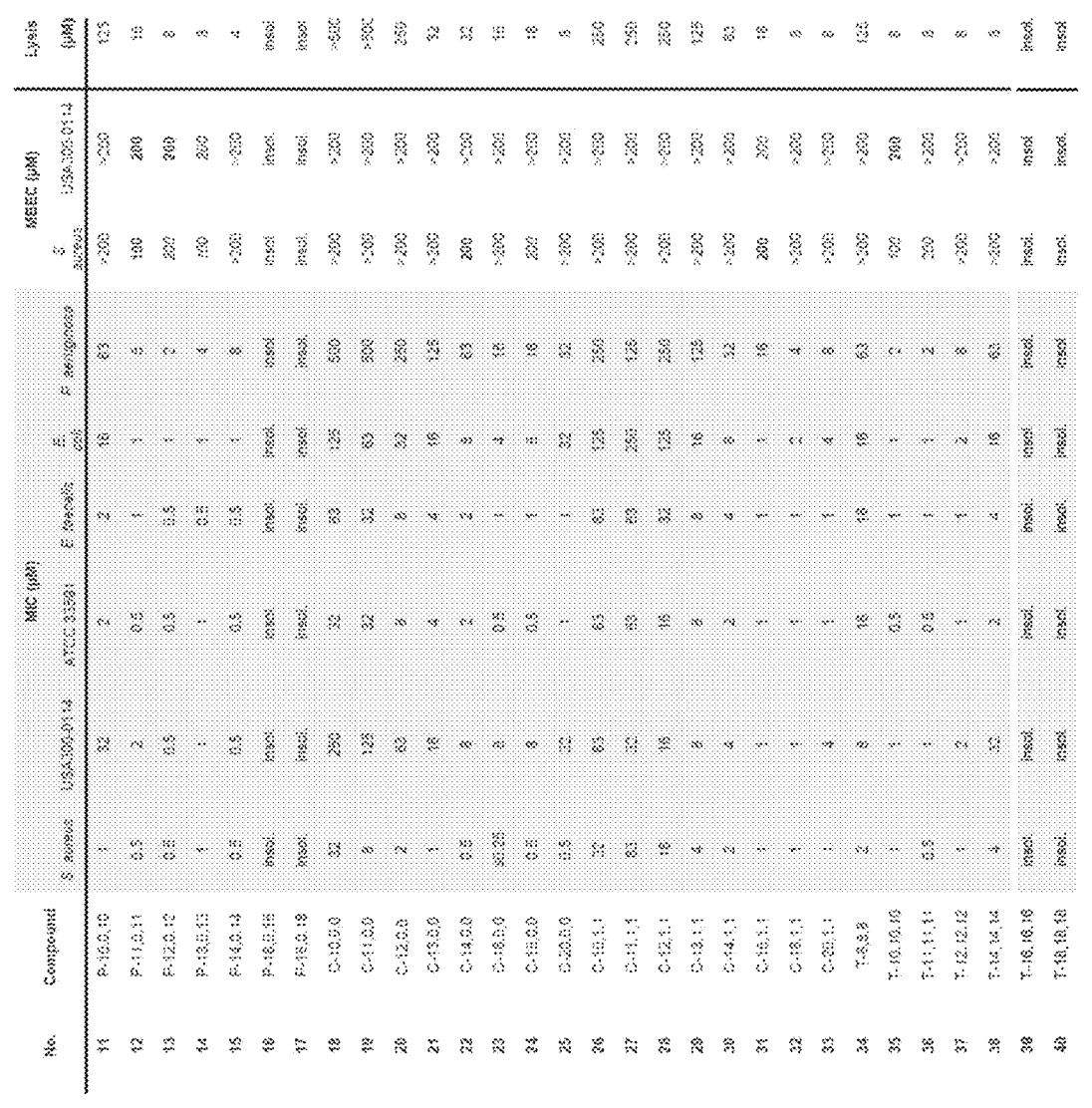

With a series of mono-, bis-, and trisQACs varying in structure and cationic nature in hand, MIC values against Gram-positive *Staphylococcus aureus* (MSSA and MRSA) and *Enterococcus faecalis* and Gram-negative *Escherichia coli* and *Pseudomonas aeruginosa* were determined according to standard methods (Wayne, Methods for Dilution Antimicrobial Tests for Bacteria that Grow Aerobically; Approved Standard, 9th ed., 2012, CLSI Document M07A9, Vol. 32, No. 2), as previously reported; toxicity, as measured by red blood cell lysis, was also assessed. Complete biological results are depicted in FIG. 23; key results appear in Table 5.

TABLE 5

MIC and MBEC values of select compounds against various bacteria.

| | MIC [mm] | | | | MBEC [mm] | |
|---|---|---|---|---|---|---|
| Compound | MSSA | MRSA | EC | PA | MSSA | MRSA |
| P-11,0,11 (12) | 0.5 | 2 | 1 | 8 | 100 | 200 |
| P-12,0,12 (13) | 0.5 | 0.5 | 1 | 2 | *200* | 200 |
| C-16,0,0 (23) | .0.25 | 8 | 4 | 16 | >200 | >200 |
| C-18,0,0 (24) | 0.5 | 8 | 8 | 16 | *200* | >200 |
| C-20,0,0 (25) | 0.5 | 32 | 32 | 32 | >200 | >200 |
| C-16,1,1 (31) | 1 | 1 | 1 | 16 | 200 | 200 |
| C-18,1,1 (32) | 1 | 1 | 2 | 4 | >200 | >200 |
| C-20,1,1 (33) | 1 | 4 | 4 | 8 | >200 | >200 |
| T-10,10,10 (35) | 1 | 1 | 1 | 2 | *100* | 200 |
| T-11,11,11 (36) | 0.5 | 1 | 1 | 2 | *200* | >200 |

MBEC values were defined by regrowth assays that result in OD values under 0.1 (in bold).
MBEC values in italics denote significant eradication (OD < 0.5).
MSSA = *S. aureus* SH1000,
MRSA = *S. aureus* USA300-0114,
EC = *E. coli* MC4100,
PA = *P. aeruginosa* PAO1.

Example 7: Multicationic Quaternary Ammonium Cations (multiQACs): Simple Amphiphile Scaffolds with Antimicrobial, Anti-Biofilm, and Anti-Resistance Properties The results described herein demonstrate the synthesis of 24 novel QACs using a commercially available tetraamine scaffold, N,N-bis[3-(dimethylamino)propyl]-N',N'-dimethylpropane-1,3-diamine (Super T); these compounds are prepared in high yield with simple procedures. The antimicrobial activity of these novel amphiphiles was also been evaluated, and MICs for Super T multiQACs with alkyl chain substitution of 11 carbons were ≤1 µM for all of the bacteria tested. Further identification of structure-activity relationships can be deduced based on these findings in order to better understand how multiQACs are able to combat resistance. As described elsewhere herein, multicationic structures have been found to be effective in their ability to kill bacteria and eradicate biofilms. It has been found that these "multiQACs" show little or no susceptibility to bacterial resistance, which is capable of reducing the efficacy of many quaternary ammonium compounds.

Figure 56:
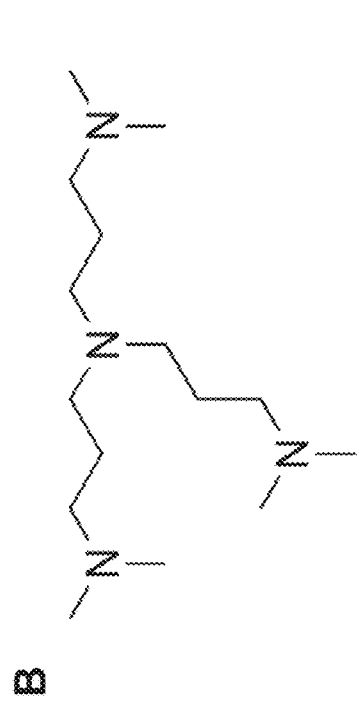
FIG. 56, comprising
Figure 56:
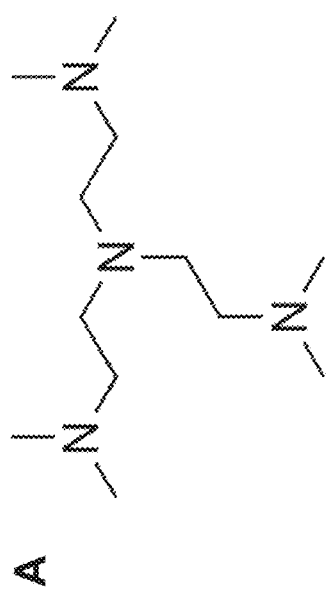

As described elsewhere herein, a T-shaped tetraamine starting material, tris(2-dimethylaminoethyl)amine (FIG. 56A), has been employed. After evaluating the antimicrobial activity of the triscationic derivatives, strong antimicrobial activity was observed, but with little ability to derivatize the central nitrogen, for steric and electronic reasons. However, another readily available tetramine starting material, N,N-bis[3-(dimethylamino)propyl]-N',N'-dimethylpropane-1,3-diamine, referred to as Super T, has been derivatized in order to explore the structure-activity relationships of this similar compound bearing an additional carbon in the linker to each of the terminal tertiary amines (FIG. 56B), to explore the role that the number and disposition of cationic charges plays in antimicrobial activity.

Figure 57:
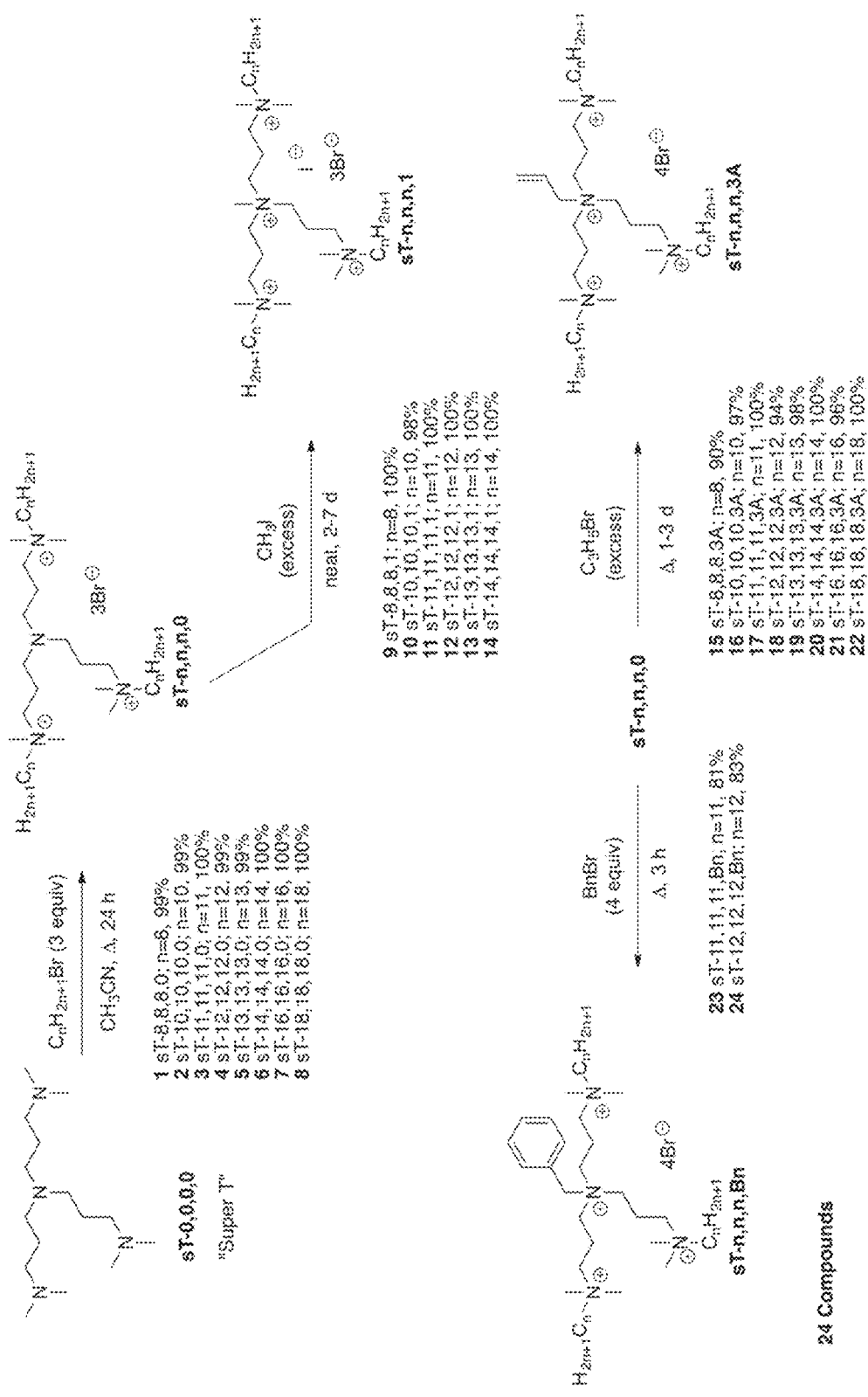
FIG. 57 depicts schemes of a synthesis of compounds of the invention based on the N,N-bis[3-(dimethylamine)propyl]-N,N'-dimethylpropane-1,3-diamine scaffold.

Twenty-four multiQACs were prepared using a tetraamine starting material, "Super T" or sT-0,0,0,0; numbers in this abbreviation indicate the number of carbons of appended alkyl chains, if any. Selective alkylation of the terminal tertiary amines was readily achieved. Thus alkylation with the corresponding alkyl bromide (3 equiv., $C_nH_{2n+1}Br$) furnished the sT-n,n,n,0 series after trituration. The resulting scaffold was then exposed to neat methyl iodide for 2-7 days to provide fully quaternized tetra-QACs dubbed sT-n,n,n,1, in high yields. The alkylated Super T series was also exposed to excess allyl bromide at reflux for 1-3 days, resulting in high yields of the sT-n,n,n,3A series after trituration. Finally, exposure to four equivalents of the corresponding benzyl bromide at reflux for 3 hours provided the final set of Super T compounds abbreviated as sT-n,n,n,Bn. Moderate yields of the sT-n,n,n,Bn series were observed after trituration. The reaction schemes for the Super T Compounds exemplified herein are illustrated in FIG. 57.

Minimum inhibitory concentration (MIC) values in mM of Super T compounds against six bacteria [Staphylococcus aureus (SA), hospital-acquired methicillin-resistant SA (HA-MRSA), community-acquired methicillin-resistant SA (CA-MRSA), Enterococcus faecalis (EF), Escherichia coli (EC), and Pseudomonas aeruginosa (PA)] were determined (FIG. 68). The Super T amphiphiles showed equipotent activity against MSSA (SH1000) and CA-MRSA (USA300-0114). MICs for Super T multiQACs with alkyl chain substitution of 11 total carbons were under 1 uM for all of the bacteria tested, providing considerably potent compounds. Tetracationic compounds showed improved activity over their triscationic counterparts. However, Super T multiQACs with short (8 carbons) or long (14+ carbons) alkyl chain substitution displayed elevated MICs in HA-MRSA as compared to SA.

These series of QACs with varied cationic character were synthesized in order to investigate what structural features would optimally inhibit growth of bacterial strains. It was observed that permanent charge (up to 4+) as well as alkyl length may have had an effect on efficacy and susceptibility to resistance. With the expectation that these scaffolds are likely to bind in a similar manner to previously synthesized compounds known to trigger QAC resistance, Super T scaffolds were prepared in high yields and with simple operation, generating series of novel amphiphiles. With multiple amphiphiles displaying sub-micromolar MICs, a novel set of potent antiseptics was thus prepared.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of formula VII:

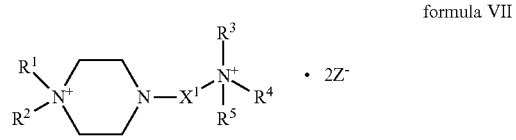

formula VII wherein:
$R^1$, $R^2$, $R^3$ and $R^5$ are each independently $C_{1-25}$ alkyl, optionally substituted with a substituent selected from the group consisting of halogen, phenyl, benzyl, o-vinylbenzyl, m-vinylbenzyl, p-vinylbenzyl, —CH₂—CH═CH₂, —CF₃, —OR', —OCF₃, —SR', —C(O)R', —C(O)OR', —C(O)N(R')₂, —N(R')₂, —NR'C(O)R', —NR'C(O)CR'═C(R')₂ and —OC(O)R';

$R^4$ is H or $C_{1-25}$ alkyl, where $C_{1-25}$ alkyl is optionally substituted with a substituent selected from the group consisting of halogen, phenyl, benzyl, o-vinylbenzyl, m-vinylbenzyl, p-vinylbenzyl, —CH₂—CH═CH₂, —CF₃, —OR', —OCF₃, —SR', —C(O)R', —C(O)OR', —C(O)N(R')₂, —N(R')₂, —NR'C(O)R', —NR'C(O)CR'═C(R')₂ and —OC(O)R';

R', at each occurrence, is independently selected from the group consisting of H and $C_{1-4}$ alkyl;

$X^1$ is $C_{1-6}$ alkylene, optionally substituted with a substituent selected from the group consisting of halogen, phenyl, —CF₃, —OR', —OCF₃, —SR', —C(O)R', —C(O)OR', —C(O)N(R')₂, —N(R')₂, —NR'C(O)R', —NR'C(O)CR'═C(R')₂ and —OC(O)R'; and Z⁻, at each occurrence, is independently selected from the group consisting of F⁻, Br⁻, Cl⁻, I⁻, $CH_3S(O)_2O^-$, p-$CH_3$-Ph-$S(O)_2O^-$, $CF_3S(O)_2O^-$, $CH_3C(O)O^-$, $CH_3CH_2C(O)O^-$ and $CH_3(CH_2)_{16}C(O)O^-$;

with the proviso that at least one of $R^1$ and $R^2$ is a $C_{10}$ alkyl, a $C_{11}$ alkyl, a $C_{12}$ alkyl, a $C_{13}$ alkyl, a $C_{14}$ alkyl, a $C_{16}$ alkyl or a $C_{18}$ alkyl and at least one of $R^3$, $R^4$ and $R^5$ is a $C_{10}$ alkyl, a $C_{11}$ alkyl, a $C_{12}$ alkyl, a $C_{13}$ alkyl, a $C_{14}$ alkyl, a $C_{16}$ alkyl or a $C_{18}$ alkyl.

2. The compound of claim 1, wherein at least one of $R^1$, $R^2$, $R^3$, $R^4$ and $R^5$ is selected from the group consisting of $C_{10}$ alkyl, $C_{12}$ alkyl and benzyl.

3. The compound of claim 1, wherein $X^1$ is selected from the group consisting of optionally substituted $C_2$ alkylene and optionally substituted $C_3$ alkylene.

4. The compound of claim 1, wherein the compound is a compound of formula XVII:

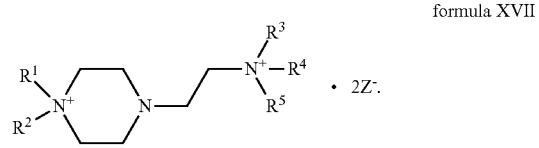

formula XVII

5. The compound of claim 4, wherein the compound is of the following formula:

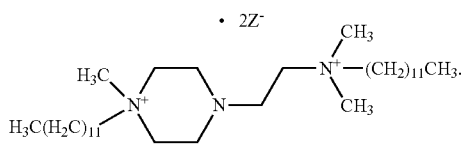

6. The compound of claim 1, wherein the compound is of a formula selected from the group consisting of:

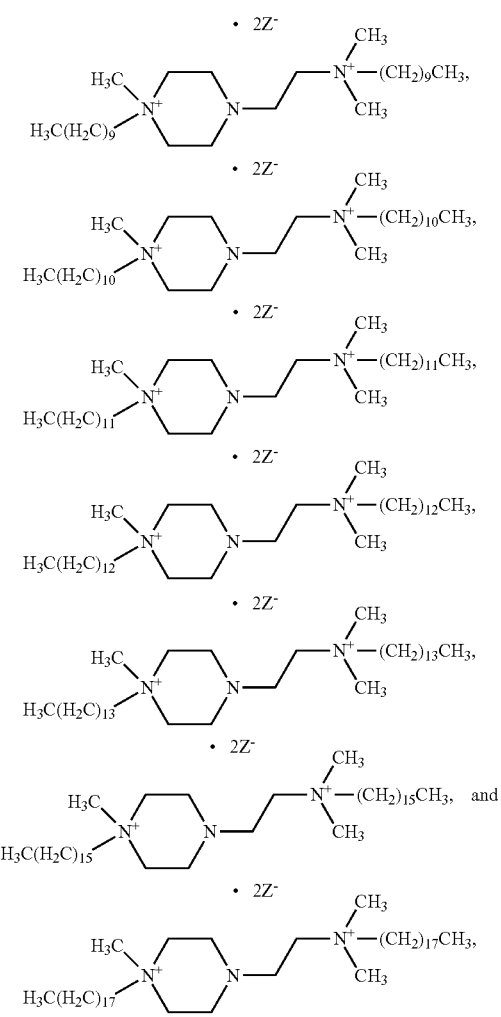

wherein:
each occurrence of Z is independently selected from the group consisting of Br⁻ and I⁻.

7. A method for preventing the growth or proliferation of microorganisms on at least one surface or reducing the growth or proliferation of microorganisms on at least one surface, wherein the method comprises the steps of:
   (i) providing at least one surface;
   (ii) providing a pharmaceutical composition comprising a pharmaceutically acceptable carrier and at least one compound of formula VII:

formula VII

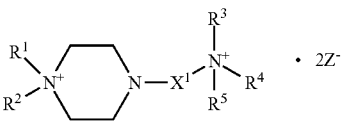

wherein:
$R^1$, $R^2$, $R^3$ and $R^5$ are each independently $C_{1-25}$ alkyl, optionally substituted with a substituent selected from the group consisting of halogen, phenyl, benzyl, o-vinylbenzyl, m-vinylbenzyl, p-vinylbenzyl, —$CH_2$—CH=$CH_2$, —$CF_3$, —OR', —$OCF_3$, —SR', —C(O)R', —C(O)OR', —C(O)N(R')$_2$, —N(R')$_2$, —NR'C(O)R', —NR'C(O)CR'=C(R')$_2$ and —OC(O)R';

$R^4$ is H or $C_{1-25}$ alkyl, where $C_{1-25}$ alkyl is optionally substituted with a substituent selected from the group consisting of halogen, phenyl, benzyl, o-vinylbenzyl, m-vinylbenzyl, p-vinylbenzyl, —$CH_2$—CH=$CH_2$, —$CF_3$, —OR', —$OCF_3$, —SR', —C(O)R', —C(O)OR', —C(O)N(R')$_2$, —N(R')$_2$, —NR'C(O)R', —NR'C(O)CR'=C(R')$_2$ and —OC(O)R';

R', at each occurrence, is independently selected from the group consisting of H and $C_{1-4}$ alkyl;

$X^1$ is $C_{1-6}$ alkylene, optionally substituted with a substituent selected from the group consisting of halogen, phenyl, —$CF_3$, —OR', —$OCF_3$, —SR', —C(O)R', —C(O)OR', —C(O)N(R')$_2$, —N(R')$_2$, —NR'C(O)R', —NR'C(O)CR'=C(R')$_2$ and —OC(O)R'; and Z⁻, at each occurrence, is independently selected from the group consisting of F⁻, Br⁻, Cl⁻, I⁻, $CH_3S(O)_2O^-$, p-$CH_3$-Ph-S(O)$_2$O⁻, $CF_3S(O)_2O^-$, $CH_3C(O)O^-$, $CH_3CH_2C(O)O^-$ and $CH_3(CH_2)_{16}C(O)O^-$;

with the proviso that at least one of $R^1$ and $R^2$ is a $C_{10}$ alkyl, a $C_{11}$ alkyl, a $C_{12}$ alkyl, a $C_{13}$ alkyl, a $C_{14}$ alkyl, a $C_{16}$ alkyl or a $C_{18}$ alkyl and at least one of $R^3$, $R^4$ and $R^5$ is a $C_{10}$ alkyl, a $C_{11}$ alkyl, a $C_{12}$ alkyl, a $C_{13}$ alkyl, a $C_{14}$ alkyl, a $C_{16}$ alkyl or a $C_{18}$ alkyl and (iii) contacting the at least one surface with a therapeutically effective amount of the pharmaceutical composition.

8. The method of claim 7, wherein the pharmaceutical composition further comprises a base material.

9. The method of claim 7, wherein the contacting of the at least one surface with a therapeutically effective amount of the pharmaceutical composition forms a coating of the pharmaceutical composition on the at least one surface.

* * * * *